US010105448B2

(12) United States Patent
Guerry et al.

(10) Patent No.: US 10,105,448 B2

(45) Date of Patent: Oct. 23, 2018

(54) COMBINED ENTEROPATHOGEN RECOMBINANT CONSTRUCT

(71) Applicants: Patricia Guerry, Silver Spring, MD (US); Mario Artur Monteiro, Guelph (CA); Stephen Savarino, Kensington, MD (US)

(72) Inventors: Patricia Guerry, Silver Spring, MD (US); Mario Artur Monteiro, Guelph (CA); Stephen Savarino, Kensington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 201 days.

(21) Appl. No.: 14/721,656

(22) Filed: May 26, 2015

(65) Prior Publication Data

US 2015/0258201 A1 Sep. 17, 2015
US 2017/0266300 A9 Sep. 21, 2017

Related U.S. Application Data

(63) Continuation-in-part of application No. 11/340,003, filed on Jan. 10, 2006, now Pat. No. 9,079,945, and a continuation-in-part of application No. 11/524,057, filed on Sep. 20, 2006, now Pat. No. 9,084,809, and a continuation-in-part of application No. 14/048,264, filed on Oct. 8, 2013, now Pat. No. 9,328,150.

(60) Provisional application No. 60/642,771, filed on Jan. 11, 2005, provisional application No. 62/075,399, filed on Nov. 5, 2014, provisional application No. 62/034,436, filed on Aug. 7, 2014, provisional application No. 60/722,086, filed on Sep. 21, 2005, provisional application No. 62/054,454, filed on Sep. 24, 2014, provisional application No. 62/127,927, filed on Mar. 4, 2015, provisional application No. 62/165,301, filed on May 22, 2015, provisional application No. 61/727,943, filed on Nov. 19, 2012, provisional application No. 62/127,935, filed on Mar. 4, 2015.

(51) Int. Cl.

| | |
|---|---|
| ***C07K 14/245*** | (2006.01) |
| ***A61K 39/02*** | (2006.01) |
| ***A61K 39/385*** | (2006.01) |
| ***A61K 39/108*** | (2006.01) |
| ***A61K 47/64*** | (2017.01) |
| ***C07K 16/12*** | (2006.01) |
| ***A61K 39/112*** | (2006.01) |
| ***C07K 16/44*** | (2006.01) |
| *A61K 39/00* | (2006.01) |

(52) U.S. Cl.

CPC ........ *A61K 47/646* (2017.08); *A61K 39/0258* (2013.01); *A61K 39/0283* (2013.01); *A61K 39/105* (2013.01); *A61K 47/6415* (2017.08); *C07K 14/245* (2013.01); *C07K 16/1232* (2013.01); *C07K 16/1267* (2013.01); *C07K 16/44* (2013.01); *A61K 39/00* (2013.01); *A61K 2039/55505* (2013.01); *A61K 2039/6037* (2013.01); *A61K 2039/70* (2013.01); *C07K 2317/55* (2013.01); *C07K 2317/76* (2013.01); *C07K 2319/35* (2013.01); *Y02A 50/47* (2018.01); *Y02A 50/474* (2018.01); *Y02A 50/476* (2018.01)

(58) Field of Classification Search

CPC . A61K 47/646; A61K 39/0258; A61K 39/105
See application file for complete search history.

(56) References Cited

U.S. PATENT DOCUMENTS

| | | | |
|---|---|---|---|
| 2011/0097357 A1 | 4/2011 | Fernandez et al. |
| 2011/0300173 A1 | 12/2011 | Guerry et al. |
| 2012/0321658 A1 | 12/2012 | Biemans et al. |
| 2015/0258201 A1 | 9/2015 | Guerry et al. |

OTHER PUBLICATIONS

Ihssen et al., Microbial Cell Factories, 2010; 9(61): 1-13.*
Bowie et al. (Science, 1990, 257:1306-1310).*
Anatha et al., Infection and Immunity, 2004; 72(12): 7190-7201.*

* cited by examiner

*Primary Examiner* — Gary B Nickol
*Assistant Examiner* — Lakia J Jackson-Tongue
(74) *Attorney, Agent, or Firm* — Albert Churilla; Ning Yang; Diane Tso

(57) ABSTRACT

The inventive subject matter relates to a construct comprising antigens derived from multiple enterobacteria including *Campylobacter jejuni* capsule polysaccharide polymer, enterotoxigenic *Escherichia coli* recombinant polypeptide construct and lipopolysaccharide from *Shigella* spp. The subject invention also relates to a method of inducing an immune response utilizing the inventive composition.

20 Claims, 12 Drawing Sheets

Specification includes a Sequence Listing.

A.

B.

COMBINED ENTEROPATHOGEN RECOMBINANT CONSTRUCT

CROSS-REFERENCES TO RELATED APPLICATIONS

This application is a Continuation-in-Part to U.S. Nonprovisional application Ser. No. 11/340,003, filed Jan. 10, 2006, which claims priority to U.S. Provisional application 60/642,771 filed Jan. 11, 2005, and a Continuation-in-Part to U.S. Nonprovisional application Ser. No. 11/524,057 filed Sep. 20, 2006, which claims priority to U.S. Provisional application 60/722,086, filed Sep. 21, 2005, and a Continuation-in-Part to U.S. Nonprovisional application Ser. No. 14/048,264, filed Oct. 8, 2013, which claims priority to U.S. Provisional application 61/727,943, filed Nov. 19, 2012, the contents of which are herein incorporated by reference. This application also claims priority to U.S. Provisional application 62/054,454, filed 24 Sep. 2014, U.S. Provisional application 62/127,927, filed Mar. 4, 2015, U.S. Provisional application 62/165,301, filed May 22, 2015, U.S. Provisional application 62/127,935, filed Mar. 4, 2015, and U.S. Provisional application 62/075,399, filed Nov. 5, 2014, the contents of which are herein incorporated by reference.

BACKGROUND OF INVENTION

Field of the Invention

The inventive subject matter relates to a recombinant construct against enterotoxigenic *Escherichia coli* and *Campylobacter jejuni* comprising a combined anti-ETEC recombinant polypeptide construct and *C. jejuni* campsule polysaccharide.

Description of Related Art

Enterotoxigenic *Escherichia coli* (ETEC), *Shigella*, spp. and *Campylobacter jejuni* (CJ) are major causes of bacterial diarrhea worldwide. Both pathogens are a serious health threat to western travelers and young children in resource-limited countries, making them apt target populations for a single or dual pathogen vaccine against ETEC and CJ. No FDA-licensed vaccines are available for either pathogen.

ETEC causes an estimated 210 million cases of diarrhea and 380,000 deaths annually among infants and young children. Moreover, ETEC is the most common cause of travelers' diarrhea. ETEC causes diarrhea ranging in severity from mild illness to severe cholera-like purging. There are two major virulence factors, adhesive fimbriae, dubbed colonization factors (CFs), and enterotoxins. Surface-expressed CFs, consisting of complex protein heteropolymers, mediate adherence to the small intestinal epithelium to initiate colonization within this privileged host niche. ETEC produce one or both of two different enterotoxins, a heat-labile (LT) and a heat-stable enterotoxin (STI). LT and STI intoxicate epithelial cells, resulting in fluid and electrolyte secretion and clinical diarrhea. LT is highly immunogenic and a potent adjuvant, while STI is a small, poorly immunogenic peptide.

Prevalent CFs and a non-toxic form of the LT (or its congener cholera toxin (CT)) have been the focus for several strategies to develop an ETEC vaccine. Such antigens have been used individually or bundled as components of a whole-cell killed vaccine, live vaccines vectored by attenuated ETEC or other enterobacterial species (e.g., *Shigella* and *Vibrio cholerae* 01), and purified protein vaccines. None has yet been shown to confer sufficiently high and broad levels of protection. The weight of evidence from clinical trials indicates that anti-LT immunity confers short-term protection against LT-producing ETEC. There is also evidence to show that certain CFs function as protective antigens. There are, however, significant challenges for ETEC vaccine development. For one, about half of all ETEC express only STI, for which anti-LT immunity is not thought to be effective, thus necessitating anti-CF or anti-bacterial immunity. Also, the diversity of ETEC CFs poses issues for achievement of sufficiently broad coverage with inclusion of a realistic number of CFs.

SUMMARY OF THE INVENTION

The invention relates to an immunogenic construct comprising a polypeptide construct expressing enterotoxigenic *Escherichia coli* (ETEC) fimbrial subunits combined with a *Campylobacter jejuni* capsule polysaccharide or *Shigella* spp lipopolysaccharide (LPS).

In a preferred embodiment, one or more *Campylobacter jejuni* capsule polysaccharides are conjugated to one or more *Escherichia coli* enterotoxigenic recombinant polypeptide constructs. In another embodiment, *Shigella* LPS is conjugated to the ETEC polypeptide construct.

*Campylobacter jejuni* is associated with induction of Guillain-Barré Syndrome (GBS), a post-infectious polyneuropathy that can result in paralysis. The association is due to molecular mimicry between the sialic acid containing-outer core of the lipooligosaccharide (LOS) and human gangliosides (5, 6, 89, 91). Thus, antibodies generated against LOS cores result in an autoimmune response to human neural tissue. Use of capsule polysaccharide from *C. jejuni* can induce an immune response without the possible induction of Guillain-Barré Syndrome.

In a preferred embodiment, the composition comprises an ETEC recombinant polypeptide construct design wherein major or minor subunits, derived from the same ETEC fimbrial type, are connected, via polypeptide linkers, and stabilized by donor strand complementation. The C-terminal most ETEC major subunit is connected, via a linker, to a donor strand region from an ETEC major subunit, which can be either homologous or heterologous to the C-terminal major subunit. The immunogenic composition can comprise a whole or an immunogenic fragment, containing a donor β strand region, of the ETEC fimbrial major or minor subunits. In some construct examples, in order to avoid inadvertent association of subunits, especially in CS6 subunits to each other, major ETEC fimbrial subunits can contain an N-terminal deletion of 14 to 18 amino acids.

In another embodiment one or more of the above constructs are connected, via a polypeptide linker, to form a multipartite fusion construct, wherein the subunits derived from multiple fimbrial types are expressed. In this embodiment, the fimbrial subunits can be derived from any ETEC fimbrial type, including, but not limited to: ETEC class 5 fimbriae type, including class 5a, 5b or 5c; ETEC CS3; and ETEC CS6.

The embodied multipartite construct can contain a deletion of the N-terminal region of one or more fimbrial subunits to avoid undesirable associations with other monomers or multimers and to remove reduce amino acid sequence length between polypeptides to reduce the protease cleavage.

DNA encoding the ETEC recombinant polypeptide construct can be used to express a polypeptide for attachment to *C. jejuni* or *Shigella* LPS. As such, an object of the invention also includes a use of a construct for immunizing mammals, including humans, by a composition comprising antigens from multiple bacterial species, including ETEC, *C. jejuni* and *Shigella* strains. The embodied use comprises one or more priming administrations of the combination construct. The priming dose can be subsequently followed by one or more boosting doses.

DETAILED DESCRIPTION OF PREFERRED EMBODIMENTS

Figure 1:
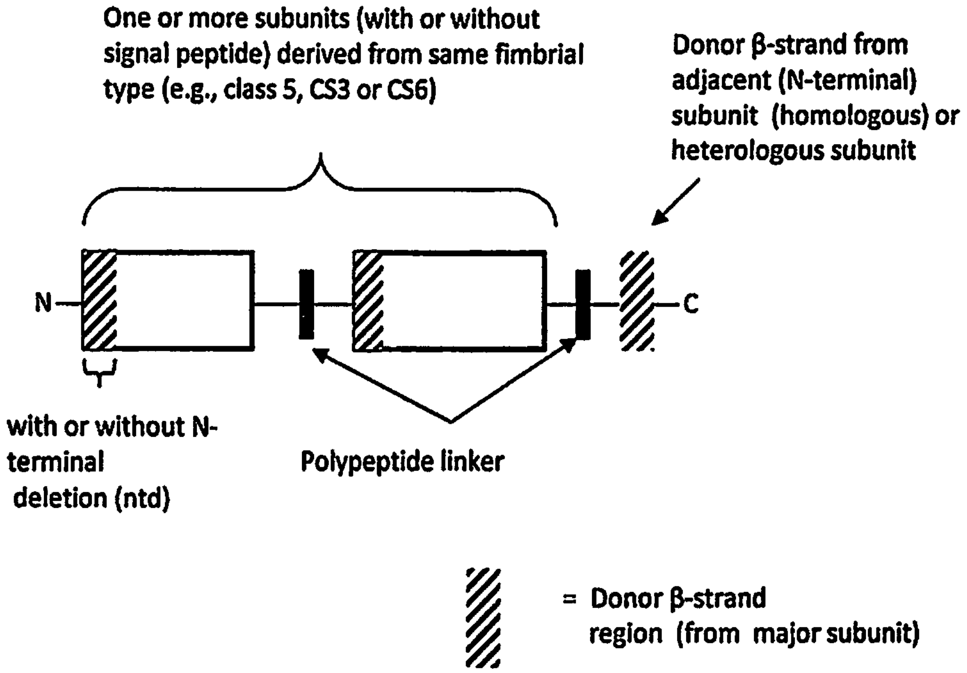
FIG. 1. Illustration of inventive construct design wherein major or minor subunits, derived from the same ETEC fimbrial type are connected, via polypeptide linkers and stabilized by donor strand complementation. The construct can contain a deletion of the N-terminal region of the N-terminal subunit. This feature prevents undesirable association with other monomers or multimers. The C-terminal subunit is stabilized by a donor β strand, connected to the subunit via a polypeptide linker, wherein the donor β strand is either derived from a homolgous subunit, which is defined as a subunit that is the same as the subunit the donor strand is stabilizing or from a heterologous subunit, defined as derived from a subunit that is different still from the same fimbrial type.

The term enterobacteria, as used herein, refers to enterotoxigenic *Escherichia coli* (ETEC), *Campylobacter jejuni* or *Shigella* spp., which include: *Shigella dysenteriae, Shigella flexneri, Shigella Boydii* or *Shigella sonnei*. As used herein, an enterobacteria polysaccharide polymer is a polysaccharide polymer derived from enterobacteria. The term "polysaccharide antigen" as used herein refers to a capsule polysaccharide derived from *Campylobacter jejuni* (*C. jejuni* or *Campylobacter jejuni* capsule) or a lipopolysaccharide derived from *Shigella* spp. As used herein, "polysaccharide" refers to two or more monosaccharide units composing a carbohydrate polymer molecule. A "polysaccharide polymer" refers to two or more polysaccharide molecules connected together.

The terms "polypeptide," "peptide," and "protein" as used herein can be interchangeably used, and refer to a polymer formed of two or more amino acid residues, wherein one or more amino acid residues are naturally occurring amino acids. The term "amino acid sequence" refers to the order of the amino acids within a polypeptide. As used, herein, "oligomer" are polypeptides sequences comprising relatively few amino acids.

The term "recombinant polypeptide", "recombinant polypeptide construct", or "recombinant protein", as used herein, refers to polypeptides or proteins produced by recombinant DNA techniques, i.e., produced from cells transformed by an exogenous DNA construct encoding the desired polypeptide or the desired protein. The term "recombinant construct" refers to the DNA encoding the recombinant polypeptide, recombinant polypeptide construct or recombinant protein.

The term "donor strand" or "donor β strand" refers to the N-terminal region of an ETEC fimbrial subunit that associates with another ETEC fimbrial subunit in donor strand complementation.

The term "immunogenic composition" refers to a formulation containing proteins or polypeptides or polysaccharides or polysaccharide polymers that induce a humoral and/or cellular immune response. The term "immunogenic coverage" or "spectrum of coverage" refers to the induction of humoral and/or cellular immune response against specific strains of bacteria under the "coverage." The term "immunogenic fragment" refers to a polypeptide containing one or more B- or T-cell epitopes and is of sufficient length to induce an immune response or to be recognized by T- or B-cells. The term "derivative" refers to a polypeptide or nucleic acid sequence with at least 80% identity with sequence of the identified gene. In this context, "identity"

refers to two or more sequences or subsequences that are the same or have a specified percentage of amino acid residues that are the same, when aligned for maximum correspondence. Where some sequences differ in conservative substitutions, i.e., substitution of residues with identical properties, the percent sequence identity may be adjusted upwards to correct for the conservative nature of the substitution. Percent similarity refers to proportion of identical and similar (conserved change) residues.

"Fimbriae" are defined as projections or filaments on ETEC bacteria and are composed of major subunits, as in the case of CS3 and CS6 fimbriae or major and minor subunits, as in the case of class 5a, 5b and 5c ETEC. "Fibrillae" are narrow projections from a bacteria. CS3 and CS6 fimbriae can also be termed fibrillae due to their narrow characteristic. The term "fimbrial subunit" refers to the proteins that comprise ETEC fimbriae and is used interchangeably with "pilin." "Pilin", therefore, can refer to a "major" or "minor" "fimbrial subunit" that comprise ETEC fimbriae. A "minor fimbrial subunit" refers to the adhesin protein at the tip of class 5 ETEC fimbriae and is expressed in stoichiometrically low amounts compared to "major" subunits. The "minor fimbrial subunits" include, but are not limited to, CfaE, CsfD, CsuD, CooD, CosD, CsdD, CsbD and CotD. "Major fimbrial subunits" refers to the ETEC fimbrial proteins represented in stoichiometrically larger amounts in ETEC fimbriae, compared to "minor fimbrial subunits." "Major fimbrial subunits" include the ETEC class 5 proteins: CfaB, CsfA, CsuA2, CsuA1, CooA, CosA, CsdA, CsbA, CotA; the ETEC CS3 proteins: CstH, CstG; and the ETEC CS6 proteins: CssA, and CssB.

The pathogenesis of *Campylobacter jejuni* remains poorly understood in comparison with ETEC and the organism shares few virulence factors with better-characterized pathogens. *C. jejuni* is unusual, however, among enteric pathogens in that it expresses a polysaccharide capsule (CPS) that is one of its few confirmed virulence factors.

Because of the importance of ETEC and *C. jejuni* as pathogenic agents, a combined ETEC-CJ composition was constructed in order to afford protection against both agents. In one embodiment, a recombinant polypeptide construct, comprising fimbrial subunits from Class 5 ETEC strains is fused to a capsule polysaccharided from the *C. jejuni* strain 18-176.

In a preferred embodiment, one or more recombinant polypeptide ETEC constructs, comprising the ETEC fimbrial adhesion, are conjugated to isolated *C. jejuni* capsule polysaccharide (CPS). One or more of a number of ETEC recombinant constructs can be conjugated to one or more of a number of *C. jejuni* capsule polysaccharide structures. In the inventive construct, the ETEC recombinant construct operates both as an immunogen against ETEC and as a protein carrier molecule, presenting the *C. jejuni* polysaccharide. Examples of ETEC recombinant polypeptides and *C. jejuni* capsule polysaccharides that can be incorporated into a combined structure are given in the following examples.

In a preferred embodiment, the ETEC polypeptide construct can not only serve as antigen against ETEC but also serve as a protein carrier for polysaccharide antigens, such as *C. jejuni* capsule polysaccharide.

Example 1: Conjugation of ETEC Polypeptides to *C. jejuni* Capsule Polysaccharide (CPS)

In a preferred embodiment, ETEC recombinant polypeptides or polypeptide constructs are conjugated to *C. jejuni* CPS. The CPS can be derived from a number of *C. jejuni* strains. In the embodiment, any CPS of any *C. jejuni* strain is envisioned to be conjugated to ETEC recombinant polypeptide constructs. Alternatively, *Shigella* LPS can be conjugated to ETEC recombinant polypeptide constructs.

The overall method of conjugating includes oxidizing *C. jejuni* CPS, for example, with $NaIO_4$ in sodium acetate (pH 4.0). Oxidized CPSs were desalted with a 5 kDa cutoff membrane by stirred ultrafiltration, which is subsequently lypholized. ETEC proteins are then added. The stoichiometery protein to CPS can vary, however, a typical ratio is 1:2 protein to CPS by mass. The concentration of components can be by any method. However, for example, polysaccharide concentration was determined by antrhone assay and protein concentration was determined. $NaCNBH_3$ is then added. The conjugates are subsequently desalted by ultrafiltration and lyophilized. CPS (or *Shigella* LPS), ETEC proteins and conjugates were analyzed, for example by SEC-HPLC. Conjugates were also analyzed by SDS polyacrylaminde gel electrophoresis (PAGE) and Gel Code® Blue (Pierce, Biotechnology, Inc, Lombard, Ill.) staining. Conjugates were detected by antibody-based assay using anti-CPS and anti-ETEC protein.

As an example of ETEC recombinant polypeptide and *C. jejuni* conjugation, the CPS from the *C. jejuni* strain 81-176 was conjugated to ETEC recombinant polypeptide construct CfaE (class 5 ETEC adhesin) or to the recombinant polypeptide construct CfaE linked, via a polypeptide linker, to the major subunit CfaB.

CPS *C. jejuni* capsule was purified from *Campylobacter jejuni* strain 81-176 (PG3208). This mutant, in which the galT gene was insertionally inactivated by chloramphenicol cassette, lacks all ganglioside mimicry in its lipooligosaccharide (LOS) core.

The cells were grown in porcine Brain-Heart Infusion (BHI) broth and sonicated to inactivate the cells. The CPS was extracted by hot water/phenol method previously employed for the same organism (Chen, et al., Carbohyd. Res. 243: 1034 (2008)). Cells were immersed in a water/phenol mixture (3:2 ratio by volume), which was heated to 67° C. with stirring for 4 hours. The suspension was cooled and separation of the mixture into two separate layers (the aqueous layer and the phenol layer) and extraction of the aqueous layer was performed. The aqueous layer was removed and the phenol/water extraction was repeated on residue, to maximize the yield. Aqueous layers from two extractions were pooled and boiled fro 1.5 hours with the addition of acetic acid to a pH of 3.5. The aqueous layer was dialyzed against running water for 2 days and concentrated using a Millipore concentrator cell with a 5 kDa cutoff membrane. Trace amounts of residual RNA were removed by digestion with benzonase enzyme at 90 u/ml in 50 mM Tris-CCl/1 mM $MgCl_2$, pH 8 overnight at 37° C. Benzonase was removed from CPS, then desalted and concentrated using stirred ultrafiltration with 30 and 5 kDa MWCO disc membranes, respectively.

The isolated CPS was oxidized with adding 40 mg of CPS to 40 mM $NaIO_4$ in sodium acetate pH 4 in the dark at 4° C. for 2 days. Oxidized CPS was desalted with 5 kDa cutoff membrane by stirred ultrafiltration and was subsequently lyophilized.

Prior to conjugation the ETEC proteins, for example dscCfaE and dscCfaEB, were transferred to 0.1M borate buffer at pH 9.0. Oxidized CPS was added to each ETEC protein at a ratio of 1:2, protein to CPS by mass, and then $NaCNBH_3$ was added at 2 times mass equivalent to CPS. The reaction was incubated 1 day at room temperature and 6 days at 37° C. in the dark with continuous stirring. The conjugates were desalted by stirred ultrafiltration with 30 kDa membrane and lyophilized. Conjugates of the CPS to dscCfaE and dscCfaEB was conducted by SEC-HPLC. and polyacrylamide gel (PAGE) (12.5%) electrophoresis.

Figure 3:
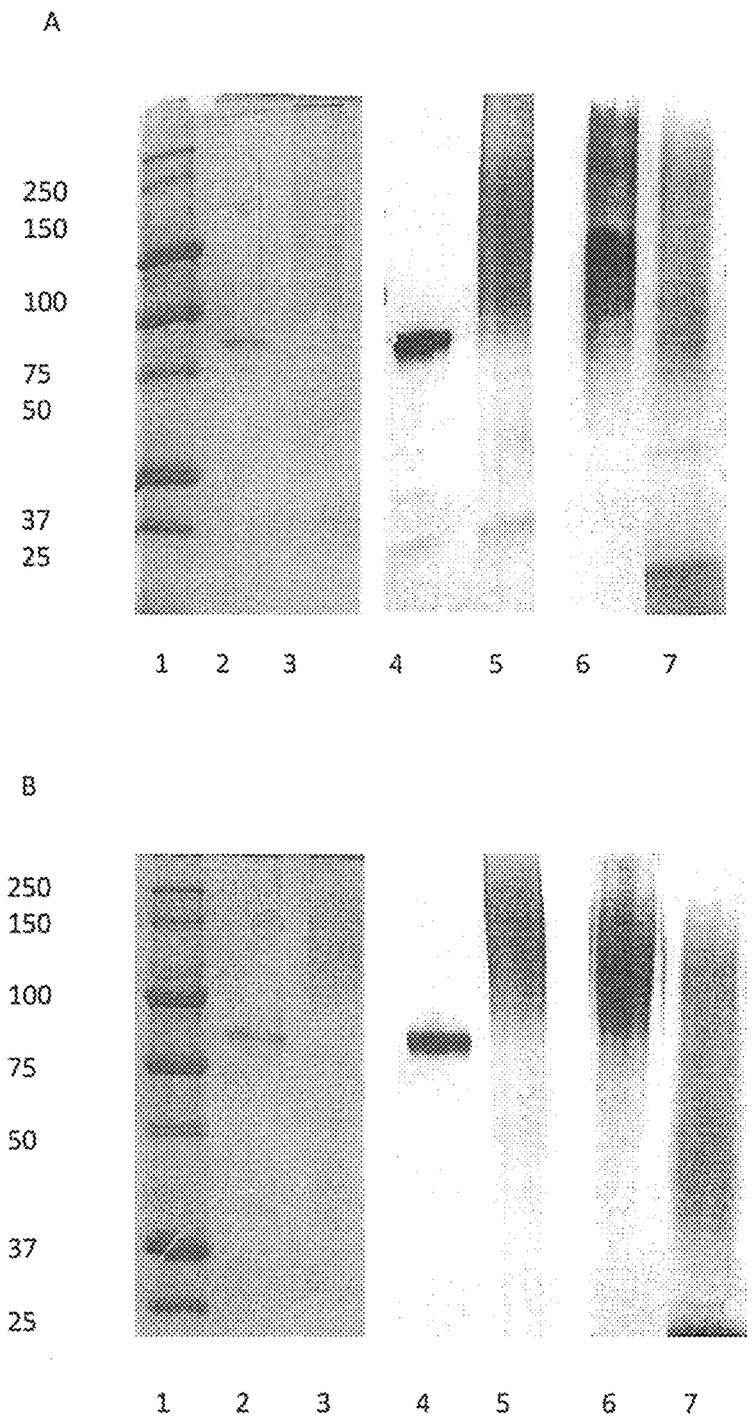
FIG. 3. SDS-PAGE and immunoblots of conjugate vaccines. A. Analyses of CfaE-HS36 conjugate. Lane 1-3 are stained with Gel Code Blue. Lane 1, Precision Plus Protein standards (BioRad); lane 2, CfaE; lane 3, CfaE-HS36 conjugate. Lanes 4-5 are immunodetected with anti-CfaE antibodies. Lane 4, CfaE; lane 5, CfaE-HS36 conjugate. Lanes 6-7 are immunodetected with antibodies to whole cells of 81-176 (HS36). Lane 6, CfaE-HS36 conjugate; lane 7, proteinase K digested whole cells of 81-176. B. Analyses of CfaEB-HS36 conjugate. Lane 1-3 are stained with Gel Code Blue. Lane 1, Precision Plus Protein standards (BioRad); lane 2, CfaEB lane 3, CfaEB-HS36 conjugate. Lanes 4-5 are immunodetected with anti-CfaE antibodies. Lane 4, CfaEB; lane 5, CfaEB-HS36 conjugate. Lanes 6-7 are immunodetected with antibodies to whole cells of 81-176 (HS36). Lane 6, CfaEB-HS36 conjugate; lane 7, proteinase K digested whole cells of 81-176. The molecular weights of the protein markers are shown on the left.

In PAGE analysis, immunodetected with rabbit polyclonal antibodies to whole cells of 81-176 was used to detect CPS and to CfaE. The results of this study are shown in FIG. 3. Immunoblotting of both conjugates with anti-CfaE antisera confirmed that the proteins ran as high molecular weight conjugates with conjugates with apparent masses ranging from just higher than the mass of each respective protein to >250 kDa. Immunoblotting with antisera to formalin fixed whole cells of *C. jejuni* 81-176 confirms that capsular polysaccharide was conjugated to the proteins. As illustrated in FIG. 3, no unconjugated protein remained in either conjugation.

The results of FIG. 3 were confirmed in SEC-HPLC. In the SEC-HPLC, unoxidized and oxidized CPSs, ETEC proteins and conjugates were analyzed using SEC-HPLC with a TSKgel-G2000SW$_{xl}$ column (30 cm×7.8 mm ID) and TSKgel SW guard column run on an ICS-5000 Dionex system with 0.1 M phosphate at pH 6.8, 0.1 M sodium sulfate and 5% acetonitrile at 0.6 ml/min flow rate. Samples were monitored at 214 nm with Ultimate 3000 variable wavelength detector and RI detector, both from Dionex.

Figure 4:
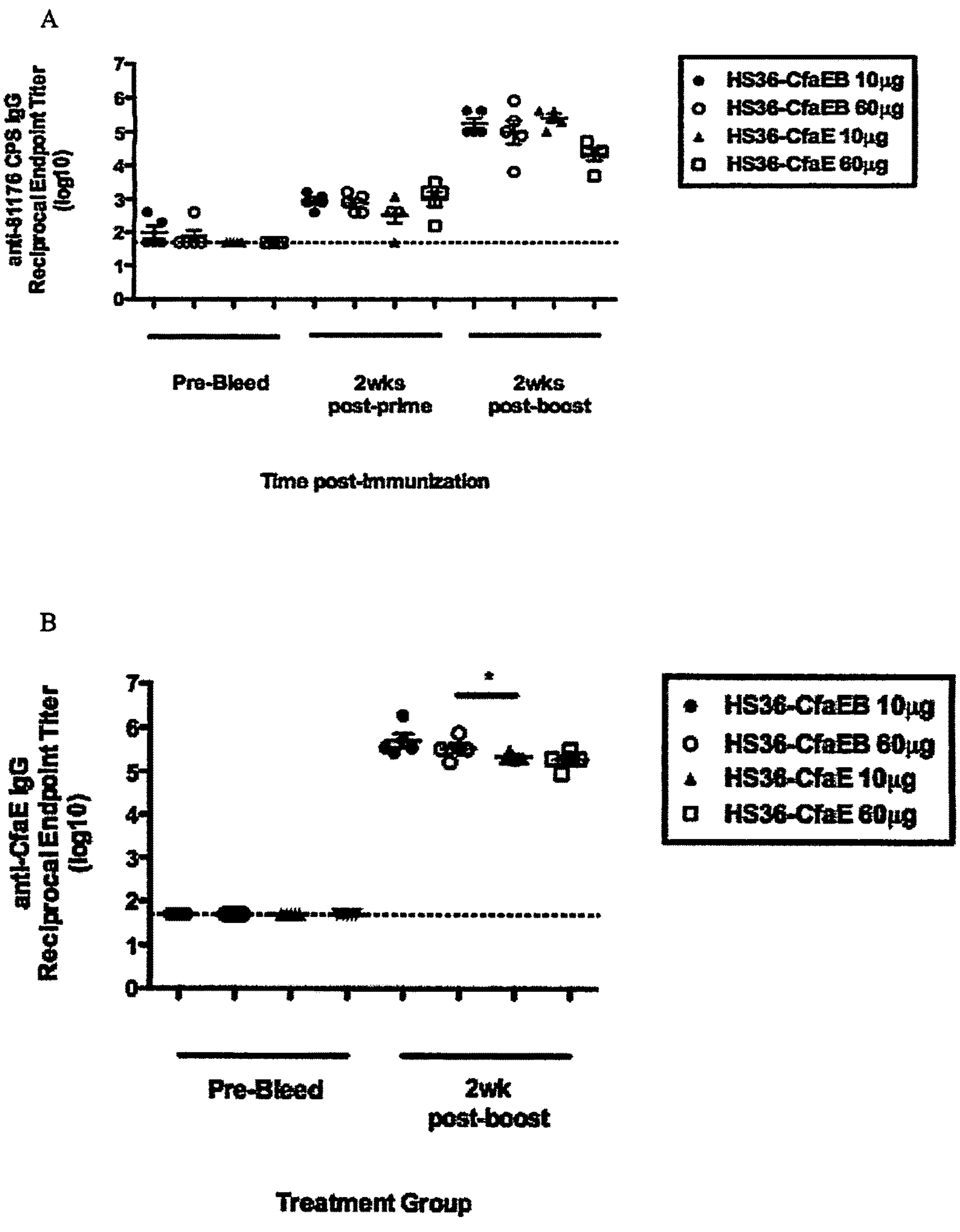
FIG. 4. *C. jejuni* anti-CPS (A) or ETEC anti-CfaE (B) induced by HS36 conjugated to CfaE or CfaEB in mice.
Figure 5:
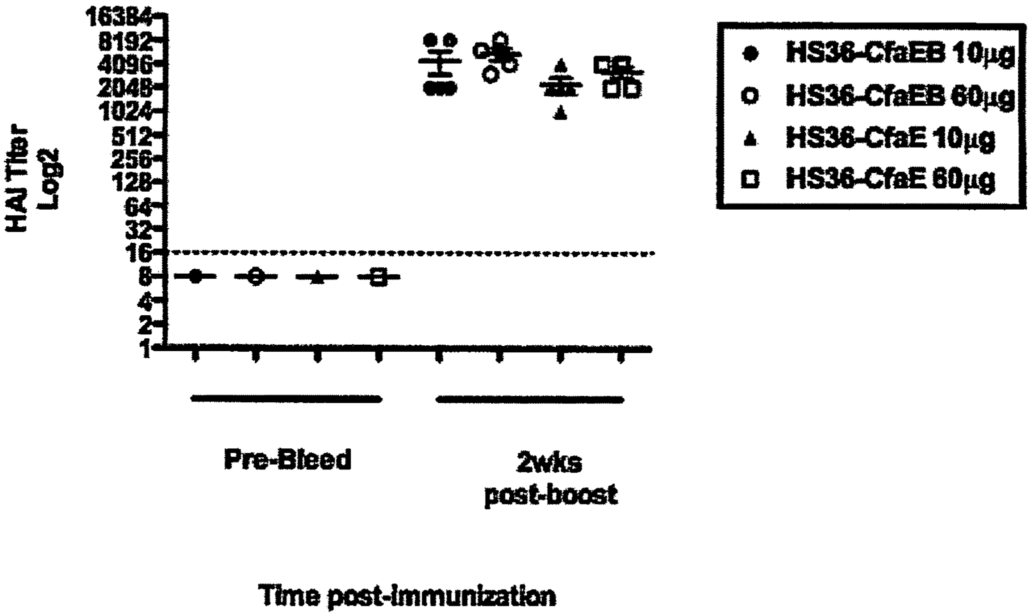
FIG. 5. Functional antibodies, evidenced by HAI titer, induced in mice immunized with HS36 conjugate vaccines.
Figure 6:
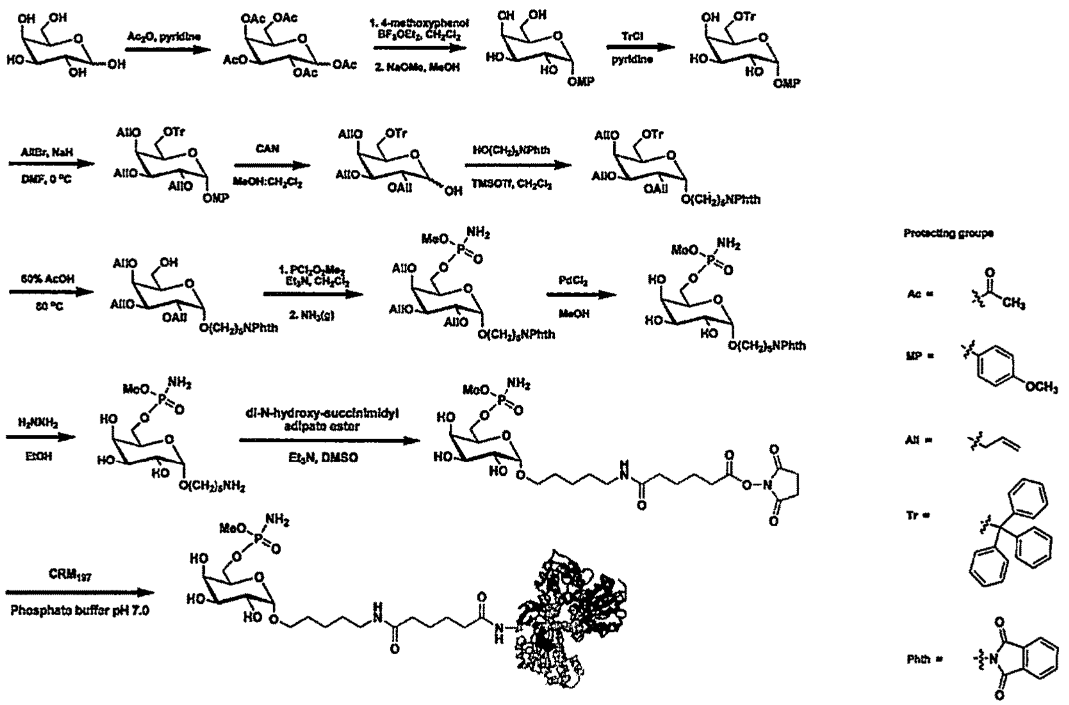
FIG. 6. Summary of synthesis of polysaccharide construct and conjugation to $CRM_{197}$.

The results of the SEC-HPLC are shown in FIG. 4 for dscCfaEB and in FIG. 5 for dscCfaE. Analysis by matrix-assisted laser desorption/ionization (MALDI) is shown in FIG. 6, for dscCfaEB and FIG. 7 for CfaE.

Detection of the conjugates by refractive index (RI) on SEC-HPLC revealed that 45% and 50% of the polysaccharide remained unconjugated with the CfaE and CfaEB conjugates respectively. This is summarized in Table 1, which also illustrates that the conjugated molar ratio of CPS to CfaE was 4.8:1 and that of CPS to CfaEB was 4.4:1.

TABLE 1

| | CfaE conjugate | | CfaEB conjugate | |
|---|---|---|---|---|
| | CPS | CfaE | CPS | CfaEB |
| Final product (includes unconjugated CPS) % yield | 49% | | 63% | |
| Sugar:protein mass ratio in final product | 2 | 1 | 1.85 | 1 |
| % unconjugated with respect to final product by SEC-HPLC RI detection | 45% | | 50% | |
| Conjugated mass ratio | 1 | 1.5 | 1 | 2.3 |
| Molecular weight | 5.5 kDa | 41 kDa | 5.5 kDa | 57 kDa |
| Conjugated molar ratio | 4.8 | 1 | 4.4 | 1 |

Example 2: Anti-Class 5 ETEC, CS3 or CS6 Constructs

Figure 2:
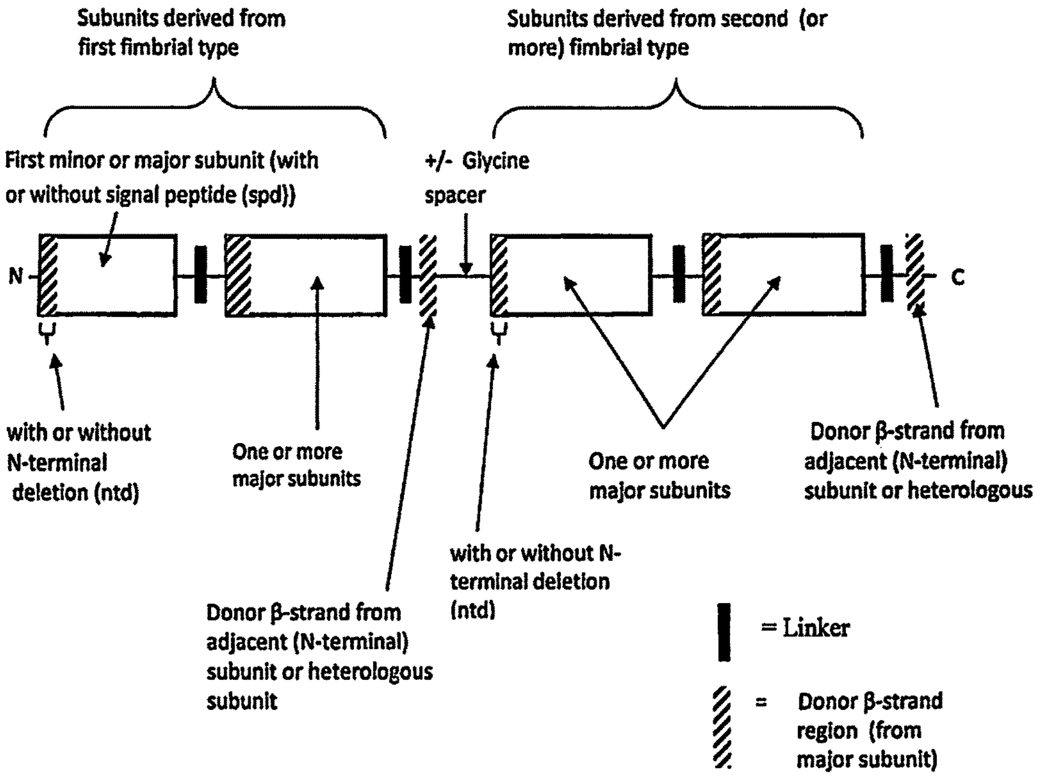
FIG. 2 illustrates a multipartite construct wherein multiple compositions, illustrated in FIG. 1, are connected via a polypeptide linker. The first subunit, is a major or minor (e.g. ETEC class 5 adhesin) ETEC fimbrial subunit. One or more major ETEC fimbrial subunits are then connected to the first subunit and to each other via a linker, wherein the subunits are stabilized by donor strand complementation. The C-terminal most ETEC major subunit is connected, via a linker, to a donor strand region from an ETEC major subunit, which can be either homologous or heterologous to the terminal major subunit. In some construct examples, in order to avoid inadvertent association of subunits, especially in CS6 subunits to each other, major ETEC fimbrial subunits can contain an N-terminal deletion of 14 to 18 amino acids.

Anti-ETEC constructs that are contemplated to be conjugated to *C. jejuni* polysaccharide comprise the structures as illustrated in FIG. 1 and FIG. 2. FIG. 1 illustrates the basic recombinant construct design. As diagrammed in FIG. 1 the construct design comprises one, or more ETEC major or minor fimbrial subunits or fragments of major fimbrial subunits, containing the donor strand, derived from the same ETEC fimbrial type, which are connected, via polypeptide linkers and stabilized by donor strand complementation. The construct can contain a deletion of the N-terminal region of the N-terminal subunit. This feature prevents undesirable associations with other monomers or multimers. The C-terminal subunit is connected to and stabilized by a donor β strand, connected to the subunit via a polypeptide linker, wherein the donor β strand is either derived from the adjacent subunit (i.e., homologous) or from a different subunit of the same fimbrial type (i.e., heterologous).

FIG. 2 illustrates the basic multipartite construct, wherein multiple constructs as in FIG. 1, are connected forming a recombinant construct comprising two or more fimbrial types. As illustrated in FIG. 1, major or minor subunits from the same fimbrial type are connected via a polypeptide linker sequence. In the multipartite construct, two or more constructs, as in FIG. 1, are connected, via a linker polypeptide.

In the multipartite construct design, as in the basic design (compare FIG. 1 with FIG. 2), the first subunit (N-terminal) is a major or minor ETEC fimbrial subunit. Each additional subunit is connected to adjacent subunits via a polypeptide linker that enables rotary freedom of the molecular components. The subunits are associated with and stabilized via a donor strand complementation from a C-terminally adjacent subunit via a donor β strand, connected via a linker polypeptide, to the C-terminus of the stabilized subunit. In some embodiments, subunits can contain a deletion of 14 to 18 amino acids from its N-terminal end. Additionally, specific constructs can be constructed with or without signal peptides of 18 to 22 amino acids and with or without histidine tags at the C-terminus.

In the multipartite construct, subunits from the same fimbrial type are directly connected. Groupings of subunits from the same fimbrial type are then connected to other groupings of subunits from other fimbrial types. Fimbrial types include, but are not limited to ETEC class 5a, 5b, 5c, CS3 and CS6. For example a single construct can include subunits derived from any two or more of class 5a, 5b, 5c, CS3 and CS6 fimbrial types.

Multiple linker sequences can be utilized in connecting the individual subunits. Examples of specific linkers include the tetrapeptide of SEQ ID No. 5. Another example is a tri-glycine linker (i.e., G-G-G). In the inventive construct, in cis donor strand complementation is used to stabilize adhesins and adhesin-pilin fusions for representative Class 5a, 5b, and 5c adhesins.

The contemplated composition is designed to enable as wide a range of coverage of ETEC strains as possible. As such, in one embodiment, the contemplated composition and use is aimed at inducing immunogenic response against class 5a, 5b, 5c ETEC, as well as ETEC strains expressing CS3 or CS6 fimbrial components.

In a preferred embodiment, recombinant polypeptide ETEC constructs are conjugated to *C. jejuni* capsule polysaccharide (CPS). One or more of a number of ETEC recombinant constructs can be conjugated to one or more of a number of *C. jejuni* capsule polysaccharide structures. Examples of Class 5 ETEC recombinant polypeptides are listed in Table 2. In Table 2, minor subunits are stabilized by connection, via a polypeptide linker, to associated major subunits. Alternatively, a 12-16 amino acid donor strand, derived from the associated major subunit is connected to the minor subunit via a polypeptide linker. These polypeptides can also be linked as per FIG. 1 and FIG. 2 to lead to the example constructs listed in Table 3. These examples can then be conjugated to isolated *C. jejuni* capsule polysaccharide, as in Example 1.

TABLE 2

| Immune coverage (fimbrial types) | Subunit | SEQ ID No. Full length sequences including spd[1] (DNA/polypeptide)) | SEQ ID No. Mature sequences (DNA/polypeptide)[2] |
|---|---|---|---|
| Class 5a | CfaE | 56/57 | 115/58 |
| | CfaB | 59/60 | 116/61 |
| | CsfD | 64/65 | 117/88 |
| | CsfA | 62/63 | 118/89 |
| | CsuD | 70/71 | 119/90 |
| | CsuA2 | 68/69 | 120/91 |
| | CsuA1 | 66/67 | 121/92 |
| Class 5b | CooD | 74/75 | 122/93 |
| | CooA | 72/73 | 123/94 |
| | CsdD | 78/79 | 124/95 |
| | CsdA | 76/77 | 125/96 |
| | CosD | 82/83 | 133/97 |
| | CosA | 80/81 | 126/98 |
| | CsbD | 44/45 | 127/46 |
| | CsbA | 47/48 | 128/49 |
| Class 5c | CotD | 50/51 | 129/52 |
| | CotA | 53/54 | 130/55 |
| CS3 | CstH | 84/85 | 131/99 |
| | CstG | 86/87 | 132/101 |
| CS6 | CssA | 134/135 | 1/2 |
| | CssB | 136/137 | 3/4 |

[1]"spd" refers to signal peptide. The mature polypeptide sequence, therefore, would be the full length minus the signal peptide.
[2]DNA sequence encodes mature protein.

TABLE 3

| Fimbriae class represented | Construct (adhesin-pilin) example[1] | SEQ ID No. DNA/ Protein[3] |
|---|---|---|
| Class 5a | $dsc_{14CsfA}$CfaE-CfaB-CsuA2-CsfA | 103/104 |
| Class 5b | $dsc_{14CsbA}$CsbD-CsbA-$ntd_{15}dsc_{14CooA}$CooA[2] | 105/106 |
| Class 5b | $dsc_{15CooA}$CsbD-CsbA-CooA[2] | 107/108 |
| Class 5c | $dsc_{14CotA}$CotD-CotA | 109/110 |

[1]dsc refers to donor strand complementation. The number and subunit refers to the N-terminal amino acids of length represented by the number from the subunit indicated that is connected at the C-terminus of the construct and is serving to stabilize the C-terminal construct. For example, "$dsc_{14CsfA}$" refers to the N-terminal 14 amino acids of CsfA connect to the C-terminus of the construct.
[2]Linkers polypeptides are GGG rather than DNKQ.
[3]Sequence in example contains a Leu-Glu-$His_6$ at the C-terminus.

An important feature of the anti-ETEC construct is the enhanced immune recognition of the fimbrial adhesion. The minor subunits (i.e., ETEC adhesin) of ETEC Class 5 fimbriae are stoichiometrically represented in very low numbers relative to the major subunit. Therefore, an important feature of the recombinant constructs is the vastly improved stoichiometric representation of the minor subunit in order to enhance immune recognition of the minor subunit. Additionally, since fimbrial subunits, such as CfaE, are relatively susceptible to proteolytic degradation outside of the fimbrial structure, stabilization of the adhesin is also important. Therefore, constructs are designed to express ETEC subunits stabilized from misfolding and degradation by donor strand complementation.

The donor β strand is provided by the major fimbrial subunit. For example, in the case of CfaE, stabilization is provided by the N-terminal region of CfaB. Engineering of dscCfaE by incorporation of a donor peptide strand from the N-terminus of the CFA/I major subunit CfaB at its C-terminus transformed an insoluble, unwieldy native, recombinant protein into a stable immunogenic composition (Savarino, U.S. Patent application publication no. 20060153878 (13 Jul. 2006)), which is incorporated by reference, herein.

Based on its atomic structure, dscCfaE is folded into a native, β-sandwich conformation, consisting of two half-barrels, comprising the N-terminal adhesin domain (CfaEad) a short α-helical connector, and the C-terminal pilin domain (CfaEpd). The molecule is functional in that it directly mediates MRHA of bovine and human erythrocytes, and generates neutralizing antibodies that act to inhibit MRHA and decorate the tips of CFA/I fimbriae on immunoelectron microscopy.

A fusion protein was engineered by genetic insertion of the coding sequence for mature major structural subunit of ETEC adhesin, such as CfaB, to the 3'-end of the minor subunit, such as CfaE. This concept was disclosed in Savarino, U.S. patent application (Ser. No. 11/340,003, filed Jan. 10, 2006), which is incorporated, herein. This molecule contains all three domains of the CFA/I fimbriae (i.e., ad, pd, and major subunit) in a ratio of 1:1:1, rather than that found in native fimbriae (ca. 1:1:1000).

A number of observations indicate the suitability of dscCfaE (cloned from ETEC strain E7473) as a vaccine antigen. First, sequencing of 31 different wild type alleles of cfaE from ETEC isolates of varying geographic origin and serotypes, show that the gene and predicted polypeptide sequence are nearly invariant, with three different nonsynonymous nucleotide changes at one site each in only five of these 31 alleles (Chattopadhyay, et al., J. Biol. Chem., 287(9): 6150-6158 (2012)). Hence, the target protein shows uniformity in natural ETEC bacterial populations.

Additionally, CfaE, a Class 5a fimbrial adhesin, is 80-81% identical with the other Class 5a minor subunits proteins adhesins CsuD of CS14 fimbriae and CsfD of CS4 fimbriae. CsuD and CsfD share 94% identity. This is considerably higher than the average identity with other Class 5b and 5c fimbrial adhesins (mean 50% identity).

Moreover, rabbit anti-dscCfaE serum cross-neutralizes CS4- and CS14-ETEC in the hemagglutination assay (HAI). A number of vaccination studies have been performed in small (rabbit and mice) and large (monkeys and cows) animals with various routes of administration and adjuvant combinations showing that dscCfaE is a potent immunogen that can elicit systemic and mucosal antibodies which recognize dscCfaE and CFA/I and are neutralizing (as measured by HAI assay).

An embodiment includes anti-class 5 ETEC constructs based on the construct design illustrated in FIG. 1, whereby the N-terminal subunit is an ETEC class 5 minor (i.e., adhesin) subunit, listed in Table 2, including CfaE, CsfD, CsuD, CooD, CsdD, CosD, CsbD and CotD, connected, via a polypeptide linker, to one or more ETEC major subunits, from the same ETEC class 5 type, listed in Table 2. The polypeptide linker can be any of a number of polypeptide sizes. In a preferred embodiment, the linker is a tetrapeptide with the polypeptide sequence of SEQ ID No. 5. The C-terminal class 5 subunit is connected to a donor β strand, derived from a homologous subunit and is typically 12-19 amino acids. In alternative embodiments, one or more major subunit can include a deletion of 12 to 16 amino acids from the N-terminal region of the subunit.

The design in FIG. 1, utilizes the concepts disclosed in Savarino, U.S. patent application (Ser. No. 11/340,003, filed Jan. 10, 2006)), including donor strand complementation to provide stabilized class 5 ETEC adhesin. Due to the homology of ETEC class 5 minor subunits and major subunits, FIG. 1 further contemplates multiple constructs incorporating the fimbrial subunits of Table 2, or derivatives of these polypeptides or DNA sequences.

The construct design, illustrated in FIG. 1, incorporates the donor strand complementation stabilization features of Savarino (U.S. patent application (Ser. No. 11/340,003, filed Jan. 10, 2006)), and furthers it by incorporating multiple major subunits, from a specific ETEC type, into a single adhesin-pilin construct. For example, multiple class 5b major subunits can be connected to a class 5b adhesin (i.e, minor subunit). Embodiments include adhesin-pilin constructs containing Csb D (ETEC Class 5b fimbrial adhesin) and Cot D (ETEC Class 5c fimbrial adhesin). Examples, for illustration, of embodiments of adhesin-pilin ETEC class 5 adhesin-pilin constructs, representing Class 5a, 5b and 5c are shown in Table 3.

CS6 and CS3

Rabbit model (RITARD) studies suggest the colonization factor CS6 and CS3 has immune-protective potential (Svennerholm, et al., Infect. Immun. 56: 523-528 (1988); Svennerholm, et al., Infect. Immun. 58: 341-346 (1990)). As such, an important technical goal is to reproduce a stabilized CS6 expressing recombinant structure expressing CS6 antigens that maximally elicits antibody responses inhibitory to CS6-directed adhesion.

Unlike class 5 ETEC fimbriae, the fimbrial structures may function as polyadhesins rather than monadhesins (Zavialov, et al., FEMS Microbiol. Rev. 31: 478-514 (2007)). Extrapolation from related fimbriae, assembly of ETEC CS6 and CS3 may be mediated bra donor strand complementation mediated process through association of a CS6 or CS3 subunit with the N-terminal donor strand region of an adjacent subunit. Additionally, protection against misfolding and proteolytic degradation may also be afforded through donor strand complementation.

Association of monomers of CS3 and CS6 was evaluated by visualization of the subunit proteins under denaturing and non-denaturing conditions in polyacrylamide gel electrophoresis (PAGE). For both CS3 and CS6 monomers, under denaturing conditions the proteins migrating at the expected sizes. Under non-denaturing conditions multiple size (i.e., ladders) are seen formed by multimeric association of the subunits.

CS6 Fimbriae

CS6 fimbriae comprise CssA and CssB. Whereas the two CS3 major subunits show little to no variation in polypeptide sequences, modest variation in CS6 proteins is observed. For example, greater than 90% identity is found in CS6 protein CssA and greater than 95% identity is found in CssB allotypes. Both CS6 structural proteins exhibit a relatively low level of variation (i.e., greater than 90% amino acid conservation), with greater variation in CssA and the mutations randomly distributed along the CssA polypeptide.

In order to design an effective immunogenic composition that would be suitable for inclusion in a vaccine formulation a number of criteria were devised for determination of suitable constructs. These included the ability to maintain a structure without unwanted self-association or assembly; thermostability; and ability to generate anti-CS6 IgG and IgA antibody levels similar to those elicited by immunization with CS6.

Monomeric CS6 subunit assembly appears to be mediated by donor strands from adjacent CS6 subunits, as discussed above. It is hypothesized that interaction to form these stable structures is mediated by inter-subunit interaction through donor strand complementation. Donor strand complementation also affords protection against misfolding and proteolytic degradation. Therefore, in a preferred embodiment, multimeric CS6 constructs were developed to take advantage of these attributes of donor strand complementation. Additionally, multimeric expression provides more efficient manufacture over production of monomers.

In one embodiment, a construct conjugated to *C. jejuni* comprises a multimeric CS6 with one or more of the CS6 subunits, CssA and CssB, or allelic variation or derivatives, with the construct design configuration illustrated in FIG. 1. In a preferred embodiment, the construct comprises a dimer of CssB and CssA with CssB N-terminal to CssA (i.e., CssB-CssA).

As illustrated in FIG. 1, or FIG. 2, CS6 subunit association is stabilized by in cis donor β strand complementation. Donor strand complementation is afforded by linking a CS6 subunit at its C-terminus, to the donor β strand region of another CS6 subunit, via a tetrapeptide linker. The linker can be any of a number of polypeptide regions. However, in a preferred embodiment, the linker is either as in SEQ ID No. 5 or a triglycine linker. In the case of a terminal CS6 subunit, stabilization is provided by donor β strand, connected at its C-terminus, from a homologous or heterologous CS6 subunit. Homologous subunit is defined as two subunits of the same form (e.g., CssA OR CssB). Heterologous subunits are of different forms (e.g., one is derived from CssA the other from CssB. The CS6 donor β strand is typically the N-terminal 14-16 amino acid region of CS6 subunit. The recombinant protein can be constructed with or without hexahistidine affinity tags, which are typically on the C-terminus.

Additionally, to prevent recombinant polypeptide constructs forming molecular associations resulting in un-desirable non-covalent oligomer formation, in a preferred embodiment, the N-terminal 14-16 amino acids of the N-terminal CS6 subunit is deleted. As an illustration, "$dsc_{B14}$CssBA" would contain a heterologous donor strand (i.e., "dsc"), from CS6 CssB, inserted at the C-terminus of the construct. In this case, the donor strand is 14 amino acids in length, as indicated by the "14." Similarly, a constructed designated "$ntd_{15}dsc_{A}$CssBA" would contain a homologous donor strand at the C-terminus of the construct and also comprises a deletion of the N-terminal amino acid region (termed "ntd").

Examples of constructs comprise one or more CS6 subunits with amino acid sequences selected from the group consisting of SEQ ID No. 2 (CssA) or SEQ ID No. 4 (CssB), or derivatives of these polypeptides. The DNA sequence for CssA is SEQ ID No. 1 and for CssB, SEQ ID No. 3. The subunits are connected by a polypeptide linker sequences. In a preferred embodiment, the linker is a tetrapeptide with the amino acid sequence of SEQ ID No. 5.

CS3 Fimbriae

Savarino (U.S. patent application Ser. No. 11/340,003 (2006)) discloses donor strand complementation stabilized ETEC constructs. Embodiments of this application incorporate the donor strand stabilization of CstH and adds the second CS3 subunit, CstG. Embodiments herein add additional features found to be important for stabilization of the CS3 subunits and immunogenicity against CS3. CS3 comprises CstH and CstG. The CS3 structural protein CstH is invariant. CstG is also highly conserved, showing 99-100% identity in polypeptide sequence for 39 wildtype CS3 genes sequenced. Similarly, although some variation CstG is observed, it is also relatively invariant, with 99-100% amino acid conservation.

CS3 contains both CstG and CstH, in near equal amounts. Therefore, dimeric constructs were devised incorporating CstG and CstH, according to the template construct design of FIG. 1.

In one embodiment a polypeptide construct conjugated to *C. jejuni* capsule polysaccharide comprises a CS3 s construct designed according to FIG. 1. In FIG. 1, CS3 constructs comprise one or more CS3 fimbrial subunits connected via a polypeptide linker. The C-terminal fimbrial subunit is connected, via a polypeptide linker, to a donor β strand region of a CS3 fimbrial subunit. The C-terminal donor β strand can be derived from the same CS3 subunit to which it is connect (i.e., homologous) or derived from a different subunit (i.e., heterologous). The polypeptide linker can be any number of polypeptide regions, however, in a preferred embodiment, the linker is a tetrapeptide of the sequence of SEQ ID No. 5, or a triglycine (i.e., G-G-G). The donor β strand region is the N-terminal 14-16 amino acids of the mature CstH or CstG protein. In alternatives of this embodiment, the first 14-18 amino acids of the N-terminal region of the N-terminal most subunit is deleted to avoid undesirable associations.

In a preferred embodiment, the CS3 construct is a dimer. Although other examples are contemplated using the design of FIG. 1, as an illustrative example, the recombinant polypeptide construct can be configured as "$dsc_{16CstH}$CstG-(linker)-CstH". In this example, the mature CstG polypeptide (SEQ ID No. 101) or full length polypeptide sequence (SEQ ID No. 87) is connected at its C-terminus to CstH polypeptide (SEQ ID No. 99), via a polypeptide linker. In this example, the CstH polypeptide, is connected, at its C-terminus, to a donor β strand region of 16 amino acids derived from CstH via a polypeptide linker.

Other examples can include constructs, according to FIG. 1. In other examples, the C-terminal donor β strand can be either homologous (derived from the same subunit) or heterologous (derived from a different subunit) to the C-terminal most CS3 fimbrial subunit.

Construction of Multipartite Fusion Constructs

Immunity to multiple strains of ETEC is important to obtain the greatest extent of anti-ETEC immunity. Toward this goal, recombinant polypeptide constructs were developed comprising two or more subunits derived from different ETEC fimbrial types according to the design illustrated in FIG. 2 to form multipartite fusion constructs. As used, herein, multipartite fusion or multipartite fusion constructs are recombinant polypeptide constructs according to FIG. 2. In this design, different ETEC fimbrial types are defined as fimbrial proteins derived from fimbriae of different strain ETEC types, as listed in Table 4 or 5, or derivates of these polypeptides or DNA sequences. For example, the fimbrial type "CS3" comprises CstH and CstG. The fimbrial type "CS6" comprises CssA and CssB. The fimbrial types of Class 5 ETEC include the fimbrial types Class 5a, Class 5b and Class 5c.

In a preferred embodiment, major and/or minor subunits, derived from the same ETEC fimbrial type are connected, via polypeptide linkers, and stabilized by donor β strand complementation, as illustrated in FIG. 1. A multipartite fusion comprises one or more fimbrial subunits of the same fimbrial type, as in FIG. 1, connected to one or more fimbrial subunits derived from a different fimbrial type as illustrated in FIG. 2.

In one embodiment, the multipartite fusion construct can include a deletion of the N-terminal region of one or more fimbrial subunits, but is preferably on the N-terminal most fimbrial subunit for a given ETEC fimbrial type, as illustrated in FIG. 2. This feature prevents undesirable associations with other monomers or multimers. The size of the deletion of the N-terminal region is 14 to 18 amino acids. In other embodiments, multipartite fusion constructs comprising Class 5 adhesins do not contain a deletion of the N-terminal region.

As illustrated in FIG. 2, the C-terminal subunit, for an ETEC fimbrial type, is connected to and stabilized by a donor β strand, connected to the subunit via a polypeptide linker, wherein the donor β strand is either that derived from the adjacent subunit (i.e., homologous) or from a different subunit of the same fimbrial type (i.e., heterologous). The size of the N-terminal donor strand depends on the fimbrial type and subunit stabilized. In preferred embodiments, for class 5 fimbrial subunits, the donor β strand, derived from the N-terminal region of the class 5 subunit stabilized, is 12 to 16 amino acids. For CS3 and CS6 subunits, the donor β strand is 14 to 16 amino acids. As mentioned above, the construct can contain a deletion of the N-terminal region of the N-terminal subunit. This feature prevents undesirable associations with other monomers or multimers. The size of the deletion of the N-terminal region is 14 to 18 amino acids.

As illustrated in FIG. 2 multiple constructs as in FIG. 1 are connected forming a recombinant polypeptide construct comprising two or more ETEC fimbrial types. In this way, one or more major or minor subunits, derived from the same ETEC fimbrial type, are connected via polypeptide linkers and stabilized by donor strand complementation. In another embodiment, one or more glycine residues separates different ETEC fimbrial types, acting as a "swivel" means between the ETEC types. The glycine residue, due to its small, unbranched molecular characteristics, enables rotary freedom of the molecular components. Subunits derived from the same fimbrial type (as in FIG. 1) are connected by a polypeptide linker, with the subunits stabilized by donor strand complementation. As shown in FIG. 2, the C-terminal subunit of each ETEC fimbrial type is stabilized by a donor strand that is homologous or heterologous to the C-terminal subunit of that fimbrial type.

In other embodiments, the construct can contain an N-terminal deletion at the N-terminus of the entire construct as well as an additional deletion, of 14 to 18 amino acids, at the N-terminus of the first "internal" subunit that is of a different fimbrial type. This is illustrated in FIG. 2. In the case of the deletion on the N-terminus of the "internal" subunit, the deletion serves to shorten the length between subunits, thus reducing the likelihood of misfolding and proteolytic cleavage. In another embodiment, a donor β strand, derived from a homologous or heterologous subunit, is inserted at the C-terminus of the C-terminal CS6 or CS3 subunit. For class 5 fimbrial subunits, the donor β strand, derived from the N-terminal region of the class 5 subunit that is stabilized, is 12 to 16 amino acids. For example, in preferred embodiments, CfaB is stabilized by a 14 amino acid donor β strand; CsfA by a 14 amino acid donor β strand; CsbA by a 15 amino acid donor β strand, CooA by a 14 amino acid donor β strand and CotA by a 14 amino acid donor β strand. For CS3 and CS6 subunits, the donor β strand is 14 to 16 amino acids, with preferred embodiments of CS3 fimbrial subunits (i.e., CstH or CstG) stabilized by a 16 amino acid donor β strand derived from CstH or CstG; and CS6 fimbrial subunits (i.e., CssA or CssB) stabilized with a 16 amino acid donor β strand derived from CssA or CssB. However, other donor β strand lengths are envisioned.

The inventive compositions can utilize different linker sequences. In a preferred embodiment, the linker contains the amino acid sequence of SEQ ID No. 5. In another embodiment, the linker is a tri-glycine linker. In other embodiments, the C-terminal end of the construct contains a histidine tag for purification of the construct.

In the inventive construct, in cis donor strand complementation is used to stabilize adhesins and adhesin-pilin fusions for representative Class 5a, 5b, and 5c adhesins. For each adhesin target group, in a preferred embodiment, the compositions are constructed with the intent of eliciting anti-adhesive immune responses. Further towards this goal, Class 5 multipartite fusions comprising Class 5 adhesin minor subunits are typically construct such that the adhesin (i.e., minor fimbrial subunit) is located at the N-terminus of the constructed with the minor fimbrial subunit linked at its C-terminus to one or more major subunits, followed at the terminal end of the construct with the donor β-strand of the last major subunit.

Other embodiments include constructs comprising Class 5a adhesin CfaE tandemly linked at its C-terminus to one or more of CfaB (CFA/I major subunit), CsuA2 (CS14 major subunit) and CsfA (CS4 major subunit); Class 5b adhesin CsbD tandemly linked at its C-terminus to one or more of CsbA (CS17 major subunit), which shares high identity to the CS19 pilin subunit CsdA, and CooA (CS1 major subunit), which shares high identity to the PCFO71 pilin subunit CosA; and Class 5c adhesin CotD tandemly linked at its C-terminus to CotA (CS2 major subunit).

Embodiments of ETEC multipartite fusion constructs are illustrated in Table 4 and 5. In this embodiment, constructs comprise any major or minor ETEC fimbrial subunit from Table 2 in multiple combinations, connected by linker polypeptides and stabilized from proteolytic degradation by donor strand complementation utilizing the design illustrated in FIG. 2. Table 2 lists the ETEC fimbrial subunits (major and minor subunits) than can be used and incorporated into the multipartite fusion construct design of FIG. 2, which can then be conjugated to *C. jejuni* capsule polysaccharide or *Shigella* LPS. Any subunit, therefore, is combined with one or more other ETEC major subunits from any ETEC fimbrial phenotypic type, including Class 5a, 5b, 5c, CS3 and CS6.

The recombinant polypeptide construct motif comprises a whole or immunogenic fragment of a minor or major ETEC fimbrial subunit connected at its C-terminal end to a linker. The linker is connected at its C-terminus to a whole major ETEC fimbrial subunit or a polypeptide donor strand of an ETEC major structural subunit, derived from the same fimbrial type. The whole ETEC major subunit or donor strand polypeptide is then connected, via a linker at its C-terminal end, to one or more additional major structural fimbrial subunits, derived from the same fimbrial type, from Table 2.

The strategy for selecting and developing specific genetic fusion constructs is guided, in part, by the phylogenetic and antigenic relatedness of subunits. For example, constructs containing Class 5a, 5b and 5c pilin subunits are selected based on the relatedness of minor and major subunits within a particular ETEC fimbrial class (i.e., class 5a, 5b or 5c). As such, adhesin (i.e., minor fimbrial subunit) from a specific fimbrial type (e.g., Class 5a) are linked to Class 5a major subunits. Further selection of subunits is guided and based on epidemiological study analysis in order to achieve optimum immunogenic coverage of ETEC strains. What *C. jejuni* capsule polysaccharide to conjugate is predicated primarily on epidemiological data suggesting pathogenicity of the strain providing the capsule polysaccharide. Although many *C. jejuni* strains exist, most are not pathogenic.

In the multipartite constructs listed in Table 4 and 5 the linker polypeptide, depending on the example construct, can comprise a four (4) amino acid sequence (tetrapeptide) or a tri-glycine. Also, as illustrated in FIG. 2, the subunits are interconnected and stabilized by donor strand complementation, which is denoted by "dsc". In this nomenclature, the fimbrial subunit derivation is also indicated. For example, in the construct "dsc$_{16CstH}$CstG-CstH-(G)-ntd$_5$dsc$_{16CssA}$CssA-CssB", the N-terminal CS3 subunit "CstG" is connected, via a linker, to the CS3 subunit "CstH", which is connected, via a linker, to a donor strand of 16 amino acids derived from "CstH." Similarly, the N-terminal CS6 subunit "CssB" is connected, via a linker, as illustrated in FIG. 2, to a 16 amino acid donor strand derived from "CssA." In this example, donor strand complementation of the "CssB" subunit is via a heterologous donor strand (i.e., derived from "CssA)."

In Table 4 and 5 the examples contain a "G" (i.e., glycine) to provide a "swivel." Also, in some examples, the N-terminal region of N-terminal CS6 subunit is deleted (delineated by "ntd") to avoid undesirable association with other CS6 subunits, as described above. It should be noted that, in addition to the examples illustrated in Table 4 or 5 (or Table 3), other combinations of major and minor subunits are contemplated utilizing the construct design illustrated in FIG. 2 and the fimbrial subunits of Table 2. In some sequences listed, a six (6) histidine (i.e., His$_6$) tag is inserted. The constructs can be designed to include the histidine (i.e., His$_6$) tag or designed without this tag region. Additionally, some sequences contain the signal peptide (designated "spd" in Table 2 and 3) region. Constructs can be constructed with or without this region, as well, which may be added to improve manufacturing efficiency of the multipartite fusion construct.

TABLE 4

| Fimbrial type (SEQ ID No. DNA/Protein) | Examples of CS3 containing constructs[1,2,4,5] |
|---|---|
| Class 5a/CS3 (6/7) | dsc$_{14CfaB}$-CfaE-CfaB-(G$^3$)-ntd$_{18}$dsc$_{16CstH}$CstG-CstH |
| Class 5a/CS3 (8/9) | dsc$_{14CsfA}$CfaE-CfaB-CsuA2-CsfA-(G)-ntd$_{18}$dsc$_{16CstH}$CstG-CstH |
| Class 5b/CS3 (10/11) | dsc$_{14csbA}$CsbD-CsbA-ntd$_{15}$dsc$_{14CooA}$CooA-(G)-ntd$_{18}$dsc$_{16CstH}$CstG-CstH |
| Class 5c/CS3 (12/13) | dsc$_{14CotA}$CotD-CotA-(G)-ntd$_{18}$ dsc$_{16CstH}$CstG-CstH |
| CS3/toxin fusion (36/37) | dsc$_{16CstH}$CstG-CstH-sCTA2 |
| LTB multimeric composition (38/39) | LTB$_5$ |
| CS3/CS6 (14/15) | dsc$_{16CstH}$CstG-CstH-(G)-ntd$_{15}$dsc$_{16CssA}$CssA-CssB |
| CS6/CS3 (34/35) | ntd$_{14}$dsc$_{16CssB}$CssB-CssA-(G)-ntd$_{18}$dsC$_{16CstH}$CstG-CstH |

[1]All combinations can include a histidine (i.e., His$_6$) at the C-terminal end.

[2]Subunits can be linked via either DNKQ or tri-glycine linker.

[3](G) refers to glycine residue introduced to provide a "swivel."

[4]"ntd" refers to N-terminal deletion (excised from mature protein) with extent of deletion (i.e., amino acids) indicated.

[5]"dsc" refers to span of N-terminal residues from donor β-strand, its amino acid length and its source.

TABLE 5

| Fimbrial type (SEQ ID No. DNA/Protein) | Examples of CS6 containing constructs |
|---|---|
| CS6/CS3 (34/35) | ntd$_{14}$dsc$_{16CssB}$CssB-CssA-(G)-ntd$_{18}$dsc$_{16CstH}$CstG-CstH |
| CS3/CS6 (32/33) | dsc$_{16}$CstG-CstH-(G)-ntd$_{14}$dsc$_{16CssB}$CssB-CssA |
| Class 5b/CS6 (28/29) | spd$_{19}$dsc$_{14CotA}$CotD-CotA-(G)-ntd$_{14}$dsc$_{16CssB}$-CssB-CssA |
| Class 5b/CS6 (30/31) | dsc$_{14CotA}$CotD-CotA-(G)-ntd$_{14}$dsc$_{16CssB}$-CssB-CssA |
| Class5b/CS6 (24/25) | spd$_{19}$dsc$_{15CsbA}$CsbD-(GGG)-CsbA-(GGG)-ntd$_{14}$dsc$_{14CooA}$CooA-(G)-(GGG)-ntd$_{14}$dsc$_{16CssB}$CssB-CssA |
| Class 5b/CS6 (26/27) | dsc$_{15CsbA}$CsbD-(GGG)-CsbA-(GGG)-ntd$_{14}$dsc$_{14CooA}$CooA-(G)-(GGG)-ntd$_{14}$dsc$_{16CssB}$CssB-CssA |
| Class 5a/CS6 (16/17) | dsc$_{14CfaB}$CfaE-CfaB-(G)-ntd$_{16}$dsc$_{16CssA}$CssB-CssA |
| Class 5a/CS6 (113/114) | dsc$_{14CfaB}$CfaE-CfaB-(G)-ntd$_{16}$dsc$_{16CssB}$CssB-CssA |
| Class 5a/CS6 (18/19) | dsc$_{14CfaB}$CfaE-CfaB-(G)-ntd$_{16}$dsc$_{16CssB}$CssA-CssB |
| Class 5a/CS6 (111/112) | dsc$_{14CfaB}$CfaE-CfaB-(G)-ntd$_{16}$dsc$_{16CssA}$CssA-CssB |
| CS3/CS6 (101/102) | dsc$_{16CssA}$CssA-CssB-(G)-ntd$_{18}$dsc$_{16CstH}$CstG-CstH |
| Class 5a/CS6 (22/23) | dsc$_{14CsfA}$CfaE-CfaB-CsuA2-CsfA-(G)-ntd$_{14}$dscCssB-CssA |
| Class 5a/CS6 (20/21) | spd$_{22}$dsc$_{14CsfA}$CfaE-CfaB-CsuA2-CsfA-(G)-ntd$_{14}$dscCssB-CssA |
| CS6-chimera (40/41) | ntd$_{14}$dsc$_{16CssB}$CssB-CssA-sCTA2 |
| CS6-chimera (42/43) | ntd$_{15}$dsc$_{16Cssa}$CssA-CssB-sCTA2 |

[1]All combinations can include a histidine (i.e., $His_6$) at the C-terminal end.

[2]Subunits can be linked via either DNKQ or tri-glycine (GGG) linker. In preferred embodiments, DNKQ is used, except where indicated with (GGG).

[3](G) refers to glycine residue introduced to provide a "swivel."

[4]"spd" refers signal peptide. Number indicates number of amino acids.

[5]"ntd" refers to N-terminal deletion (excised from mature protein) with extent of deletion (i.e., amino acids) indicated.

[6]"dsc" refers to span of N-terminal residues from donor β-strand, its amino acid length and its source.

In another embodiment, recombinant polypeptide constructs can contain a C-terminal toxin A subunit, such as cholera toxin A2 (CTA) to form a chimeric molecule. In this embodiment, a full-length or truncated CTA2 is connected to CS6 or CS3 multimeric recombinant polypeptide construct, such as a CS6 or CS3 dimer.

Examples of these toxin constructs are illustrated in Table 4 and 5. In these constructs, the LTB gene and the CS3 or CS6-toxin chimera are separately expressed. LTB, once expressed, would self assemble to form a pentameric structure. The ensuing LTB multimeric composition (i.e., $LTB_5$) and CS3 or CS6-toxin chimera then non-covalently associate to form a holotoxin-like heterohexamer.

Although other examples are contemplated, the sequences of examples of illustrative chimeric constructs, containing a C-terminal toxin component, are illustrated in Table 4 (for CS3) and Table 5 (for CS6).

For CS3-chimeric molecules, one or more CS3 fimbrial subunits are connected, as in FIG. 1, via a polypeptide linker, preferably a tetrapeptide or triglycine. The C-terminal most CS3 fimbrial subunit is then connected to a donor β strand, via a polypeptide linker. The donor strand can be homologous or heterologous to the C-terminal fimbrial subunit. The donor strand is then connected to a toxin fragment, such as CTA2. The CS3-chimera example shown in Table 4, comprise the polypeptide sequence of SEQ ID No. 37, which is encoded by the DNA sequence of SEQ ID No. 36. In this example, the N-terminal fimbrial subunit is CstG with a pelB leader (22 amino acids) connected at its N-terminal end (see FIG. 13). However, different ordering of CS3 fimbrial subunit units is contemplated. Also, in this example, the CstH is connected, via a polypeptide linker, to a 16 amino acid donor strand derived from the N-terminal 16 amino acids of CstH, which is connected to an A2 toxin fragment (i.e., CTA2). In a preferred embodiment, LTB is also expressed. LTB comprises the amino acid sequence of SEQ ID No. 39 and is encoded by the nucleotide sequence of SEQ ID No. 38. Once expressed, the LTB sequence would self assemble into a pentamer and associate, non-covalently, with the CS3-chimera to form a hetero-hexameric holotoxin-like structure.

CS6 toxin chimera examples are also illustrated in Table 5. For CS6 chimeras, as in CS3, one or more CS6 fimbrial subunits are connected via a polypeptide linker, preferably a tetrapeptide or triglycine. The C-terminal most CS6 fimbrial subunit is then connected to a donor β strand, via a polypeptide linker. The donor strand can be homologous or heterologous to the C-terminal fimbrial subunit. The donor strand is then connected to a toxin component (e.g., CTA2). In a preferred embodiment, like for CS3, the chimera is co-expressed, with LTB, which self assembles into a pentamer to form a non-covalent association with the chimeric adhesion-toxoid fusion molecule.

Although many additional combinations are possible, in the examples shown in Table 5, the constructs are dimers of CS6 subunits, connected via a tetrapeptide linker, with the C-terminal fimbrial subunit connected, via a tetrapeptide linker to a donor β strand. The donor β strand can be homologous or heterologous to the C-terminal most fimbrial subunit. However, in the examples in Table 5 the donor strands are heterologous to the C-terminal fimbrial subunit. The donor strand is then connected to a cholera toxin A2 (CTA2) subunit. The polypeptide sequences of one of the examples is as in SEQ ID No. 43, which is encoded by the nucleotide sequence of SEQ ID Nos. 42. In this example, the N-terminal subunit is CssA, with the N-terminal 15 amino acids of the mature CssA sequence deleted. In this example, a pelB leader sequence (22 amino acids) was also added, which is illustrated in FIG. 14.

Example 3: *C. jejuni* Capsule Polysaccharides

Recent development of a molecular CPS typing system re-enforced the strong correlation between CPS and Penner types (Poly, et al., J. Clin. Microbiol. 49: 1750 (2011)). Both Penner serotyping and molecular CPS typing have revealed the predominance of a handful of CPS types worldwide. Also, despite over 60 Penner serotypes having been identified, most *Campylobacter* diarrheal disease is caused by *C. jejuni* expressing only a limited number of serotypes. Therefore, only selected strains of *C. jejuni*, predicated on epidemiological studies, provides suitable candidate strains for development of vaccine compositions. However, despite the importance of this organism to human disease, there are no licensed vaccines against *C. jejuni*.

*C. jejuni* capsule polysaccharide (CPS) was extracted from *C. jejuni* strains selected based on their association with diarrheal disease. CPS from bacteria was extracted by hot water-phenol extraction for 2 h at 70° C. The aqueous layer was dialyzed (1000 Da) against water followed by 3ultracentrifugation to separate the CPS from the LOS. The supernatant material containing the CPS was subjected to size-exclusion chromatography (Sephadex G50) for further purification to yield the intact CPSs. Monosaccharide composition was performed using a procedure amenable to the alditol acetate method (Chen, et al., Carbohydr. Res. 343: 1034 (2008)) with the alditol acetates being analyzed in a ThermoFinnigan POLARIS™-Q (Thermo Fisher Scientific, Inc, Waltham, Mass.) gas chromatograph/mass spectrometer (GC/MS) using a DB-17 capillary column. The sugar linkage types were characterized by characterization of the permethylated alditol acetates by GC/MS as previously described (Chen, et al., Carbohydr. Res. 343: 1034 (2008)). The NMR experiments were performed on a Bruker 400 MHz spectrometer (Bruker Corporation, Billeria, Mass.) equipped with a Bruker cryo platform at 295 K with deuterated trimethylsilyl propanoic acid and orthophosphoric acid as external standards. The structures of important pathogenic *C. jejuni* capsule polysaccharides are shown in Table 6.

TABLE 6

| Capsule type | Polysaccharide structure |
|---|---|
| HS1 | →4)-a-D-Galp-(1→2)-Gro-(1→P→<br>3 2<br>↑ ↑<br>1 1<br>[MeOPN]→3)-Fruf Fruf-(3←[MeOPN] |
| HS44 | →4)-a-D-Galp-(1→2)-Gro-(1→P→ |
| HS3 | →4)-[P→3]-alpha-D-Gal-(1→3)-[P→2/7]-6-d-alpha-D-ido-Hep-(1→; or<br>→4)-[P→3]-alpha-D-Gal-(1→3)-[P→2]-L-glycero-alpha-D-ido-Hep-(1→<br>(where P represents O-methyl-phosphoramidate) |
| HS4/13/64 | →3)-6-deoxy-beta-D-ido-Heptose-(1→4)-beta-D-GlcNAc-(1→. |
| HS23/36 | →3)-α-D-Gal-(1→2)-6d-α-D-altro-Me-Hep-(1→3)-β-D-GlcNAc-(1→]$_n$ |
| HS15 | [→3)-α-Araf-(1→3)-6-d-α-gulo-Hepp-(1→]$_n$ |
| HS10 | [→3-β-GalpNAc-(1→]$_n$;<br>4<br>↑<br>6-d-α-gal-Hep<br>3<br>↑<br>MeOPN |
| HS13 | MeOPN<br>↓<br>7<br>[→4)-β-Glcp-(1→3)-6-d-α-ido-Hepp]$_n$ |
| HS13 | MeOPN<br>↓<br>7<br>[→4)-β-Glcp-(1→3)-LD-ido-Hepp]$_n$ |
| HS2 | [MeOPN]<br>↓<br>4<br>(3,6,-O—Me)-D-glycero-α-L-glc-Hepp<br>1<br>↓<br>[→2)-β-D-Ribf-(1→5)-β-D-GalfNAc-(1→4-α-D-GlcpA6-(1→]$_n$<br>3 5<br>↑ ↑<br>[MeOPN] [MeOPN] |

Additionally, the capsule polysaccharide from the HS5 strain of *C. jejuni* can be attached. HS 5 contains a complex of variations of polysaccharides. These include the following structures:

i

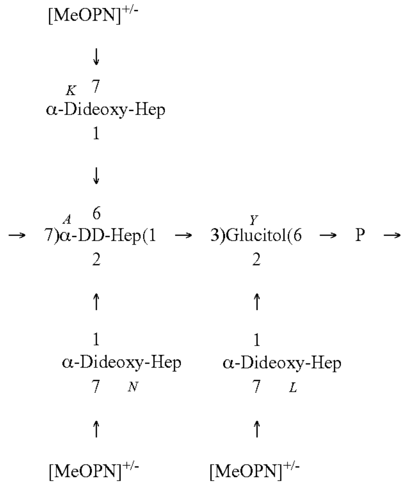

ii

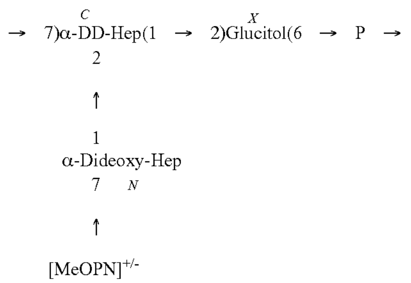

iii

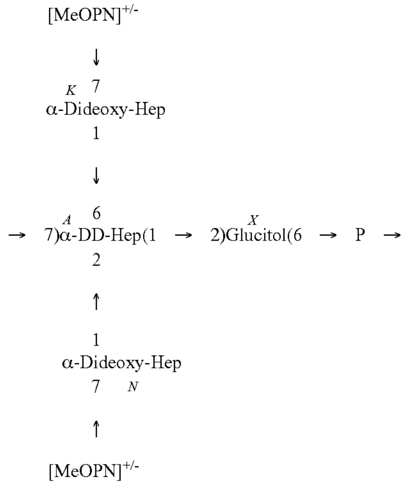

iv

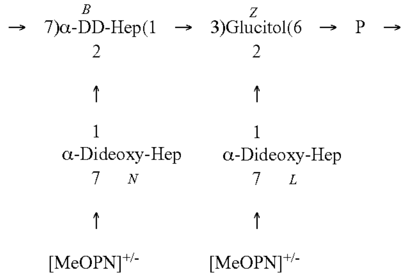

Example 4: Induction of Immune Response by ETEC-*Campylobacter* Capsule Conjugates Induction of an immune response by the conjugates was evaluated. In these studies, BALB/c mice were immunized with escalating amounts of vaccines administered with Alhydrogel® (Sergent Adjuvants, Clifton, N.J.). Mice received a total of two immunization at a 4-week interval.

The results of these studies is illustrated in FIG. 4. As shown in FIG. 4, two weeks following the first immunization, mice immunized with HS36-CfaEB (10 μg, 60 μg) and HS36-CfaE (60 μg) exhibited significant levels of serum IgG antibodies specific against HS36 CPS ($p<0.05$) (see FIG. 4 (A)), compared to pre-immune sera. Following two immunizations all groups of immunized animals had antibody levels that were significant increased ($p<0.05$) compared to levels observed after only one immunization. This effect was not dose dependent at the vaccine doses tested.

Furthermore, as illustrated in FIG. 4 (B), antibodies against CfaE was also determined by ELISA. As shown in FIG. 4(B), all mice immunized with the conjugate vaccine possessed significant levels of anti-CfaE IgG ($p<0.05$) for CPS-CfaE or CPS CfaEB. No dose dependent effects were observed and all groups displayed similar levels of CfaE-specific IgG.

The data shown in FIG. 4 illustrates that the conjugate vaccine comprising an ETEC adhesin-based carrier protein conjugated to a *C. jejuni* CPS is capable of inducing an immune response against both bacterial components, i.e., *C. jejuni* CPS and ETEC CfaE.

To determine the levels of functional anti-adhesive antibody generated by HS36 conjugate vaccines, serum samples were tested by hemagglutination inhibition assay (HAI) assay in order to measure functional anti-adhesive antibodies present in the immune mouse serum.

The HAI assays were conducted by evaluating samples from each animal. The samples were initially diluted 1:8, then diluted two-fold over a wide range of dilutions. Each serum dilution was incubated with an equal volume of $CFA/I^+$ ETEC bacteria (strain H10407), which further diluted the serum 1:2. The final lowest dilution tested dwas 1:16, which was the limit of detection (LOD). The pre-incubated mixture was subsequently mixed with bovine erythrocytes in the presence of 0.5% mannose in U-bottom 96-well plates. In the absence of anti-adhesive antibodies, the erythrocytes formed visible agglutinated "buttons" of cells. In the presence of anti-adhesive antibodies, agglutination was inhibited. The HAI titer was the highest serial dilution that completely inhibited agglutination. If there was not detectable inhibition at the lowest serum dilution of 1:16, the samples were assigned a value of one-half of the detection limit (i.e., 8) for computational purposes.

The results of the HAI analysis are illustrated in FIG. 5. Prior to immunization, pooled serum contained HAI titers below the assay's level of detection. Following immunization, all groups of mice displayed significantly ($p<0.05$) higher levels of anti-adhesive antibodies in their sera compared to pre-immune titers. Generally, mice immunized with HS36-CfaEB conjugate vaccine exhibited higher HAI titers. However, the only significance difference ($P<0.05$) observed was between mice immunized with an HS36-CfaEB (60 μg) and HS36-CfaE (10 μg).

Example 5: Immune Response Against Multiple MeOPN-6-Gal

Synthesis of Polysaccharide Construct

A polysaccharide constructed was synthesized as shown in FIG. 6. Starting from a previously reported compound 4-methoxyphenyl-α-D-galactopyranoside (see also FIG. 7, structure 1) (Comfort, et al., Biochem. 46: 3319-3330 (2007)), trityl group was selectively introduced to C-6. Originally, benzoylation was performed on compound (FIG. 7, structure 2), however extensive migration observed during the introduction of MeOPN lead us to look for a more suitable protecting group. Therefore, allyl groups were selected to protect the C-2, C-3 and C-4 positions which were resistant to migration. Allyl groups were later deprotected with catalytic hydrogenolysis which proved to be compatible with the MeOPN modification.

Figure 7:
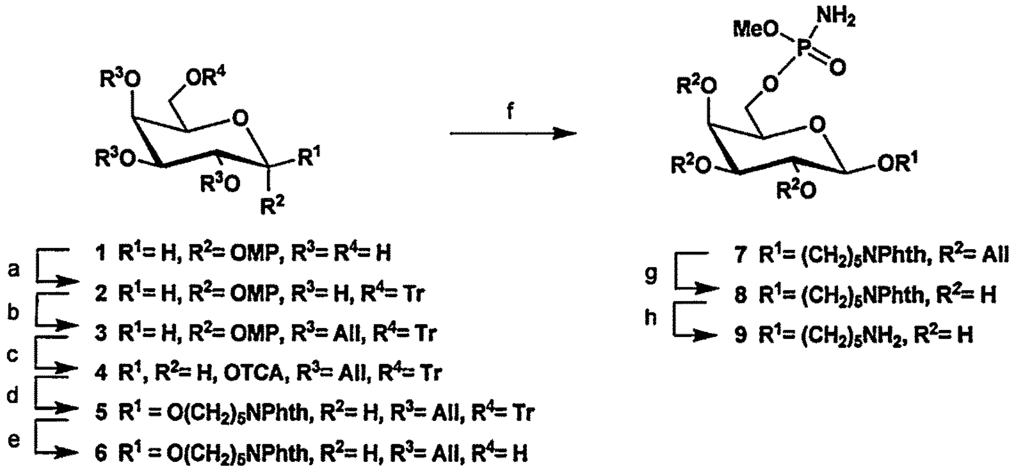
FIG. 7. Synthesis of aminopentanyl OMe-phosphoramidate galactoside. Reagent and conditions: (a) TrCl, pyridine, 95%; (b) AllBr, NaH, DMF, 0° C., 89%; (c) CAN, $CH_3CN$, $H_2O$, 0° C.; then $CCl_3CN$, $K_2CO_3$, $CH_2Cl_2$, 57% over 2 steps; (d) $HO(CH_2)_5NPhth$, TMSOTf, $CH_2Cl_2$, 65%; (e) 80% AcOH, 80° C., 78%; (f) $PCl_2O_2Me_2$, $Et_3N$, $CH_2Cl_2$, then $NH_3(g)$, 27%; (g) $PdCl_2$, MeOH, 75%, (h) $H_2NNH_2$, EtOH, 82%.

As shown in FIG. 6 and FIG. 7, after allyl groups were installed, an aminopentanyl linker was introduced to the anomeric position as a site for conjugation. Starting from galactoside (FIG. 7, structure 3), 4-methoxyphenyl group (OMP) was first removed with cerium ammonium nitrate (CAN). The corresponding hemiacetal was then converted into trichloroacetimidate donor. 5-Amino-N-phthalimido-pentanyl linker was then introduced with TMSOTf as activator at 0° C. Compound 5 (FIG. 7) was collected with 65% as the β anomer and 29% as the α anomer. The removal of trityl group gave a free 6-hydroxyl group for modification.

The strategy for the introduction of MeOPN group was inspired by a similar reaction initially proposed by C. Mara et al, Bioorg. Med. Chem. Lett. 6180-6183 (2011). Compound 6 (FIG. 6 and FIG. 7) was treated with commercially available methyl dichlorophosphate in the presence of triethyl amine, followed by ammonolysis. Due to the chirality nature of the newly introduced MeOPN (R and S), product 7 (FIG. 7, structure 7) was collected as a mixture of two diastereoisomers. $^{1}$H NMR was able to confirm that product 7 (FIG. 7) was indeed a 1:1 mixture of two diastereoisomers, revealing two sets of signals throughout the spectrum, such can be seen for anomeric and O-Me signals. The reaction yielded a mixture of side products, the most abundant being the O-Me group being replaced by a second $NH_2$, accounting for the poor yield of this reaction.

Allyl and phthalimido protecting groups were removed with palladium (II) chloride and hydrazine respectively, generating product 9 (FIG. 7, structure 9). Similar to compound 7 (FIG. 7), a mixture of diastereoisomers is apparent in NMR. Although not optically pure, the $^{31}$P NMR result agrees with native MeOPN-containing polysaccharides, having a phosphorous signals around 14 ppm. $^{31}$H-$^{31}$P HMBC NMR experiment was able to confirm that the MeOPN was introduced to the O-6 position, showing correlation signal with O-Me as well as the H-6 signals.

Induction of Immunity Against MeOPN-6-Gal

Figure 8:
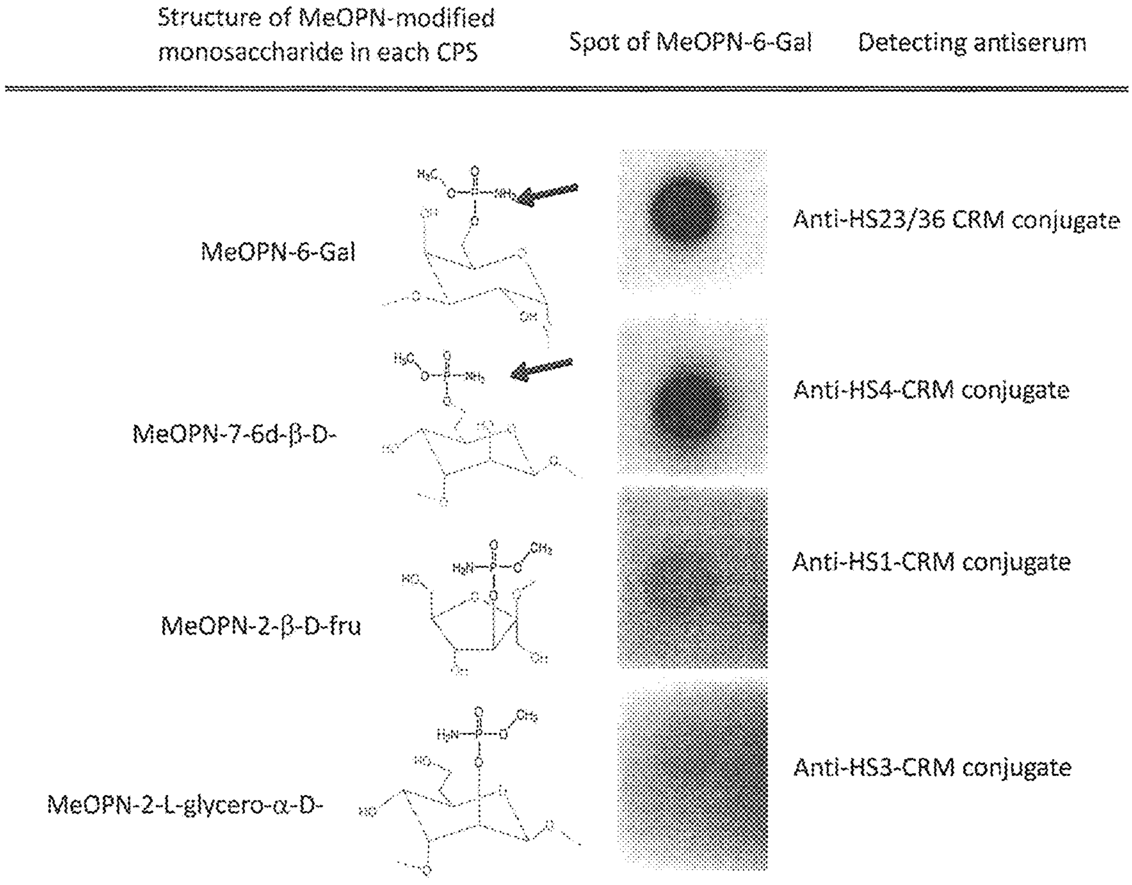
FIG. 8. Capsule cross-reactivity to 6-MeOPN-Gal with antibodies to multiple conjugate immunogenic compositions.

In one embodiment, galactose modified at the 6 carbon with O-methyl phosphoramidate (MeOPN-6-Gal) is used to induce immunity against multiple *C. jejuni* strains, even those strains not expressing MeOPN-6-Gal. As illustrated in FIG. 8, the monosaccharide construct MeOPN-6-Gal was recognized by antibody against capsule polysaccharide isolated from HS23/36, conjugated to $CRM_{197}$. Unexpectedly, antibody against polysaccharide from HS4, conjugated to $CRM_{197}$, also elicited an equivalent response, as anti-HS23/36 $CRM_{197}$ conjugate, against MeOPN-6-Gal. Also, anti-HS1-$CRM_{197}$, also reacted to MeOPN-6-Gal, although to a somewhat less extent.

The strong cross-reactivity with MeOPON-6-Gal exhibited against HS23/36 and HS4 antibody may be explained by the fact that MeOPN-6-Gal share epitopic structures with HS23/36 and HS4 capsule polysaccharides. One explanation may be that the MeOPN group in both HS23/36 and HS4 is to a primary hydroxyl. The cross reaction of MeOPN-6-Gal (HS23/36) with HS4, which contains MeOPN-7-6d-β-D-ido-Heptose, was unexpected, but may be due to the linkage of MeOPN to primary hydroxyl positions on both sugars. This feature is illustrated in FIG. 8 by the arrow.

Example 6: Immunogenic Composition Against *C. jejuni* and Enterotoxigenic *Escherichia coli* (ETEC) Using a Combined *C. jejuni* Capsule/ETEC Construct A synthetic conjugate vaccine strategy can be developed to protect against multiple enteric pathogens. Most efforts at development of vaccines against bacterial enteric pathogens are limited to a specific pathogen. The ability to combine vaccines against multiple, antigenically variable pathogens in a single, multi-valent, injectable vaccine would greatly simplify approaches to prevent acquisition and transmission of these pathogens worldwide. Globally, ETEC and *C. jejuni* are among the leading causes of bacterial diarrheal disease. In addition CJ has been causally linked to several serious sequelae including Guillain Barré Syndrome, irritable bowel syndrome, and reactive arthritis. Moreover, recent studies have indicated an association between CJ infections and malnutrition and growth stunting in young children in resource-limited settings.

Using conventional methods, we have developed conjugate vaccines containing CJ polysaccharide capsules that have proven to be immunogenic in multiple animal species and to confer protection against *C. jejuni* diarrhea in NHP. The newer synthetic approach is based on recent data that the immunodominant epitope on CJ polysaccharide capsule conjugate vaccines is the MeOPN modification found on different sugars in different capsule types.

Therefore, an immunogenic platform against both *C. jejuni* and ETEC can be created by linking synthetic MeOPN-sugars to different ETEC protein antigens. The approach could also be extended to include *Shigella* lipopolysaccharides (synthetic or detoxified) conjugated to ETEC proteins. Thus, this platform could form the basis of a multivalent vaccine against three major bacterial diarrheal pathogens. Conjugation can also serve as a protein carrier to enhance immunogenicity of the *Campylobacter* construct.

It is envisioned to conjugate the construct of Examples 3-5 to an ETEC construct. The overall method of conjugating includes oxidizing *C. jejuni* CPS, for example, with $NaIO_4$ in sodium acetate (pH 4.0). Oxidized CPSs were desalted with a 5 kDa cutoff membrane by stirred ultrafiltration, which is subsequently lypholized. ETEC proteins are then added. The stoichiometery protein to CPS can vary, however, a typical ratio is 1:2 protein to CPS by mass. The concentration of components can be by any method. However, for example, polysaccharide concentration was determined by antrhone assay and protein concentration was determined by Pierce 660 protein assay or the BCA assay. $NaCNBH_3$ is then added. The conjugates can then be subsequently desalted by ultrafiltration and lyophilized. CPS, ETEC proteins and conjugates were analyzed, for example by SEC-HPLC or by SDS polyacrylaminde gel electrophoresis (PAGE), or other methods.

Example 7: Non-Human Primate Response

The immunogenicity of CfaE-HS23/36 and CfaEB-HS23/36 conjugates was observed in mice, as well as induction of hemagglutination inhibition (HAI) titers against CfaI in mice. The amino acid sequence of the dscCfaE construct used is SEQ ID No. 138 (nucleotide sequence is SEQ ID No. 139). The $dsc_{19}$CfaE amino acid sequence is SEQ ID No. 143 (nucleotide sequence is SEQ ID No. 142). The amino acid sequence for $dsc_{19}$CfaEB is SEQ ID No. 141 (nucleotide sequence is SEQ ID No. 140).

The CfaEB-HS23/36 conjugate was down-selected in order to proceed to studies in *Aotus nancymaae*. This non-human primate (NHP) model was selected because it has been used as a diarrheal disease model for both ETEC and *C. jejuni*. We synthesized a lot of the CfaEB-HS23/36 vaccine that was sufficient in size for three NHP studies by reductive amination. The first such study, which is the only one that has been completed, was a dose finding study followed by a *C. jejuni* challenge.

The design of this NHP study is shown in Table 7. Animals (6 per group) were immunized three times at days 0, 42, and 84. The CfaEB-HS23/36 vaccine was given subcutaneously at either 0.5 ug or 3.5 ug polysaccharide (PS) adjuvanted with aluminum hydroxide. The ratio of PS to protein in the vaccine was roughly 1:1 so this was equivalent to 0.5 or 3.5 ug of CfaEB per dose. The 3.5 ug dose was also given intradermally (ID) with poly-IC as adjuvant. This was done to bridge to previous work done using ID immunizations with CfaEB alone. Similarly, another group was given HS23/36-CRM197 subcutaneously to bridge to previous work with the same capsule conjugated to another protein. Finally, the control group was immunized with PBS. On day 148 the animals were all challenged with $4\times10^{11}$ CFU of CG8421, an HS23/36 strain.

TABLE 7

Design of NHP study

| Group | Route | CfaEB-CPS | CPS-CRM197 | Alum (ug) | Poly IC (ug) | PBS |
|---|---|---|---|---|---|---|
| 1 | SC | 0.5 | – | 300 | – | – |
| 2 | SC | 3.5 | – | 300 | – | – |
| 3 | ID | 3.5 | – | – | 100 | – |
| 4 | SC | – | 3.5 | 300 | – | – |
| 5 | SC | – | – | – | – | + |

Animals were observed for diarrheal disease daily for 10 days following challenge. Diarrhea was defined as two or more days of consecutive of stools that were ≥grade 3. The results are summarized in Table 8. Only 3/5 animals in the PBS group developed diarrhea for an attack rate of 60%. Note that one animal was eliminated because it developed diarrhea prior to challenge. The mean time to onset of disease in this negative control group was 2.3 days and the mean duration of illness was 5.3 days. The attack rate in the animals immunized with the HS23/36-CRM197 vaccine was 33% (2/6), with a mean onset of disease of 2 days and a mean duration of illness of 4 days (45% efficacy). Animals that were immunized with CfaEB-HS23/36 intradermally with poly IC also showed an attack rate of 33% with a mean onset of 1.5 days and a duration of two days (45% efficacy). The animals immunized subcutaneously with CfaEB-CPS showed between 67-100% efficacy against diarrheal disease. The attack rate in the group immunized with 0.5 ug of the vaccine was 0 (0/5, with one animal that vomited after challenge being eliminated) and the attack rate in the group immunized with 3.5 ug of the vaccine was 20% (1/5, with one animal being eliminated due to diarrhea prior to challenge). The single animal in this group that did develop diarrhea had a later onset of disease (day 9). There were no significant differences among the control group and any of the immunized animals due to the small numbers of animals per group.

TABLE 8

Results of challenge with *C. jejuni* CG8421.

| Group | Vaccine | #ill/ total | Attack rate (%) | Mean days to onset of diarrhea (range) | Mean days of illness (range) | Protective efficacy |
|---|---|---|---|---|---|---|
| 1 | CfaEB-CPS (0.5 ug) + alum | 0/5* | 0 | 0 | 0 | 100 |
| 2 | CfaEB-CPS (3.5 ug) + alum | 1/5** | 20 | 9 | 2 | 67 |
| 3 | CfaEB-CPS (3.5 ug) + poly IC | 2/6 | 33 | 1.5 (1-4) | 2 (2-4) | 45 |
| 4 | CRM-CPS + alum | 2/6 | 33 | 2 (1-3) | 4 (2-6) | 45 |
| 5 | PBS | 3/5** | 60 | 2.3 (1-6) | 5.3 (2-10) | — |

*One animal vomited after challenge and was excluded

**Animals were excluded from analyses due to diarrheal onset prior to challenge

Figure 9:
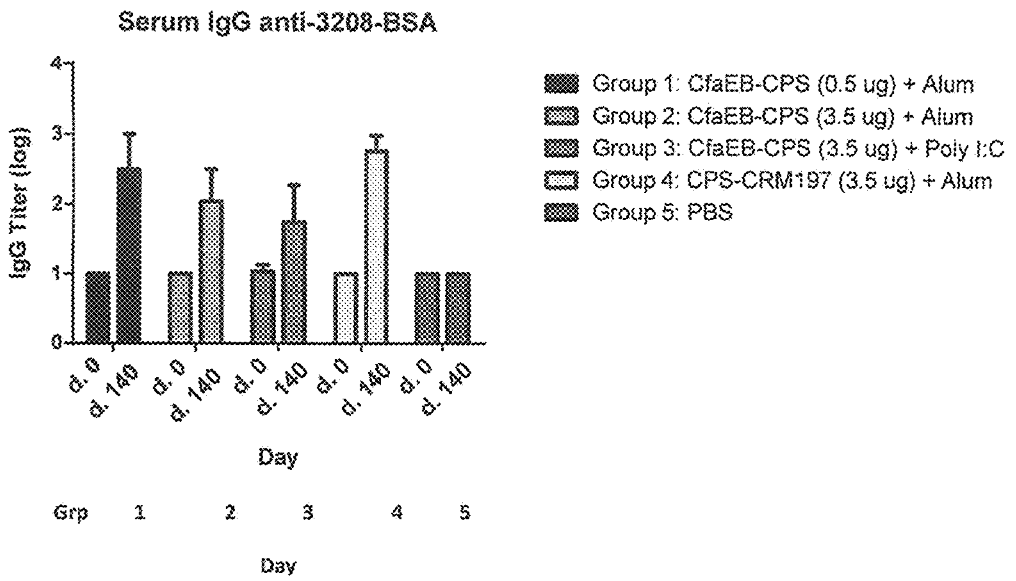
FIG. 9. Serology of *A. nancymaae* immunized with CfaEB-HS23-36 construct. Day 0 verses day 140.
Figure 9:
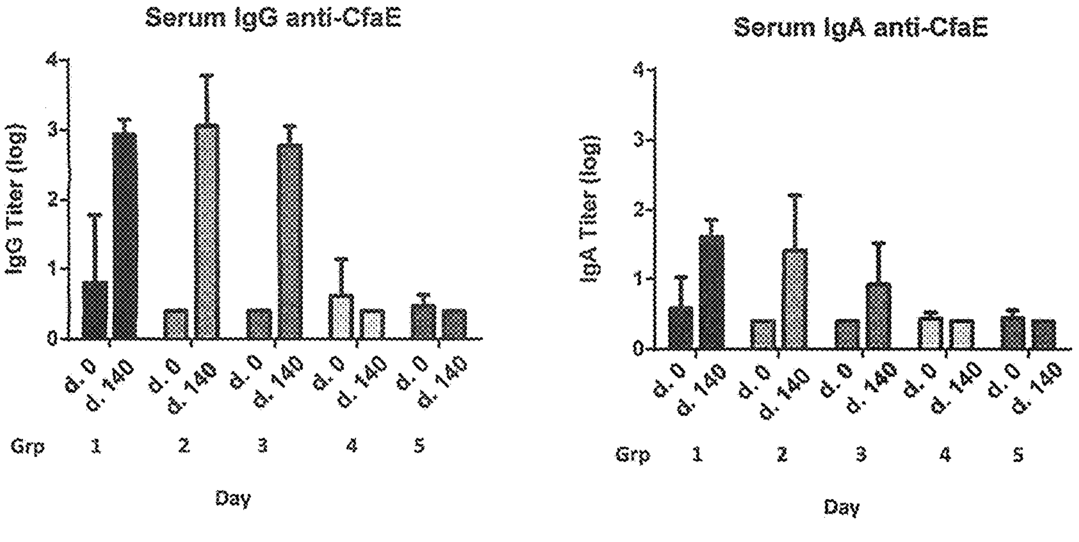
Figure 10:
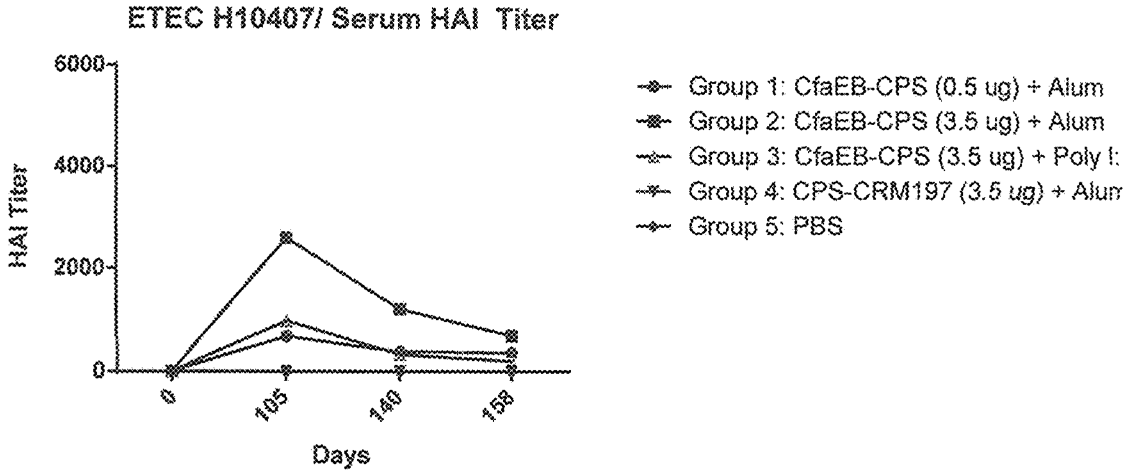
FIG. 10. HAI titers of *A. nanacymaae* against ETEC strain H10407 expressing Cfa 1.

Serology results are shown in FIG. 9. Immune responses to CPS and to CfaE were measured by ELISA. Animals in groups 1, 2 and 3 displayed IgG responses to both antigens and IgA response to CfaE. Hemagglutination inhibition (HAI) titers against ETEC strain H10407 expressing CfaI fimbriae were determined and are shown in FIG. 10. The results indicate that HAI titers were detected in animals in groups 1, 2 and 3, with group 2 showing the highest titers.

Example 8: Synthesis and Immunogenicity of Additional Combinations of ETEC-*Campylobacter* Capsule Conjugates CssBA-HS3 vaccine. CssBA is a recombinant form of the two subunits of CS6 that are fused together. This protein was conjugated to capsule from an HS3 strain by TEMPO oxidation. The conjugates were analyzed by SDS-PAGE and immunoblotting. Purified CssBA has a predicted Mr of 31.8 kDa. The conjugate of CssBA-HS3 CPS runs as two bands, one slightly smaller than CssBA and one that runs at approximately 60 kDa. The bands in the conjugate react with both anti-CssBA antiserum and antibodies to whole cells of HS3, indicating that polysaccharide has been conjugated to the protein.

Figure 11:
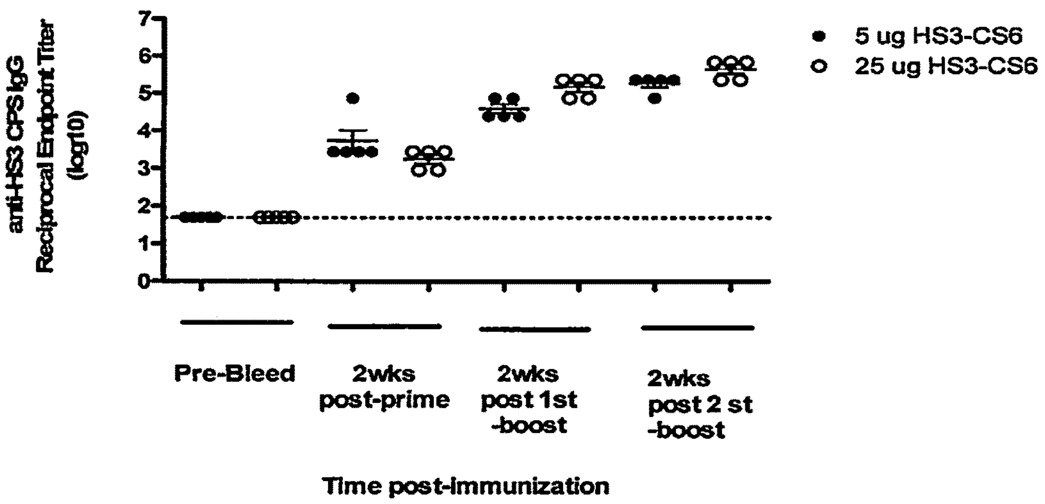
FIG. 11. Immune response of mice against HS3 capsule (top panel) and against CS6 (bottom panel) following immunization with an CssBA-HS3 conjugate vaccine. The vaccine was administered at two doses, either 5 μg or 25 μg by weight.
Figure 11:
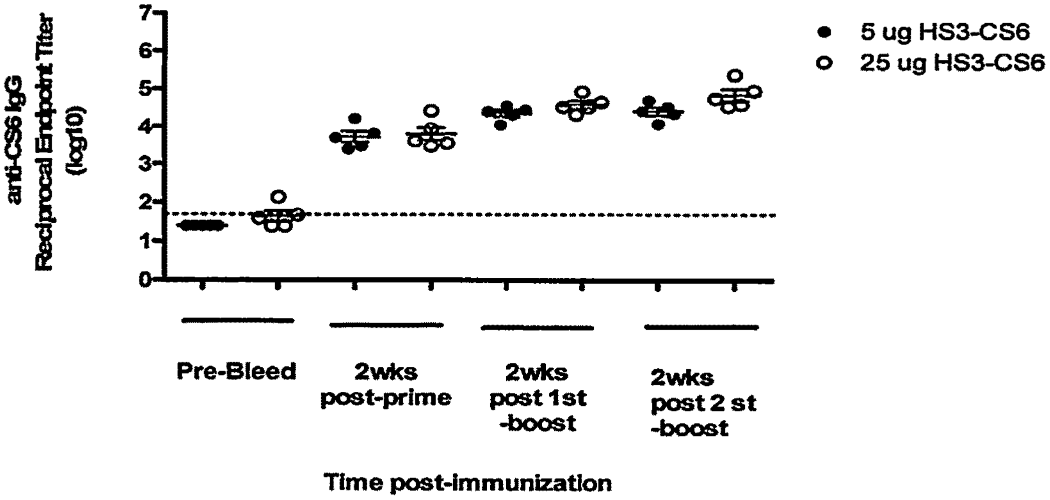

Mice were immunized subcutaneously with three doses of the vaccine given at 4 week intervals. Doses were 5 ug by weight or 25 ug by weight. Animals were bled at day 0 and two weeks after each immunization and the response to CssBA and to CPS were determined by ELISA. The results, shown in FIG. 11, indicate that there was a robust response to both the protein and the polysaccharide at both doses.

LTB-HS4 Vaccine.

Figure 12:
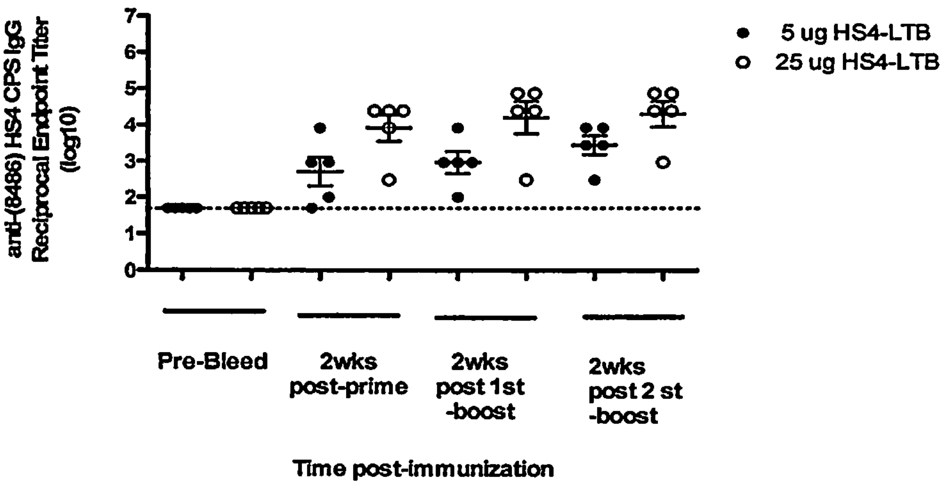
FIG. 12. Immune response of mice to HS4 capsule (top panel) and to LTB (bottom panel) following immunization with an LTB-HS4 conjugate vaccine. The vaccine was administered at two doses, 5 ug or 25 ug by weight.
Figure 12:
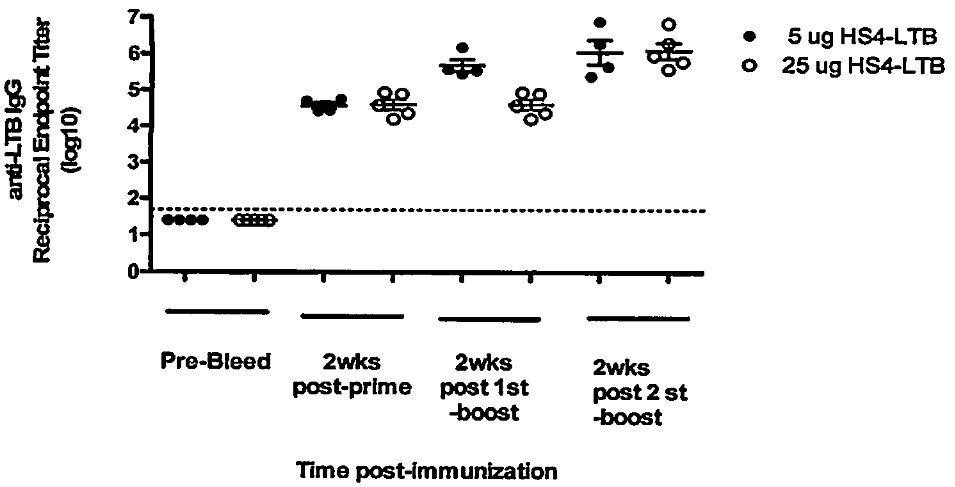

LTB is the binding component of the heat labile enterotoxin of ETEC. Recombinant LTB, which is not toxic, was conjugated to the polysaccharide capsule of an HS4 strain by reductive amination. The conjugate was analyzed by immunoblotting as shown in FIG. 12. Immunodetection with anti-LTB antiserum revealed a single band for LTB at approximately 10 kDa. The conjugate contained 4 major bands ranging from ~20 kDa→75 kDa that were reactive with both anti-LTB and anti-HS4 antiserum, indicating successful conjugation.

Mice were immunized with three doses of either 5 or 25 ug (by weight) of the LTB-HS4 conjugate subcutaneously at 4 week intervals and the serum immune response was determined. The results, shown in FIG. 12, indicate that there was a robust immune response to both the HS4 capsule and to LTB at both doses.

Example 9: Conjugation to *Shigella* Lipopolysaccharide (LPS)

There are four species of *Shigella*, a human pathogen cause diseases such as diarrhea and bacillary dysentaery: *Shigella dysenteriae, Shigella flexneri, Shigella boydii* and *Shigella sonnei* are important enteropathogens Strains of *Shigella* spp. Express long-chain lipopolysaccharides. The chemical structures for many strains has been determined (see Liu, et al., FEMS Microbiol. Rev. 32: 627-653 (2008)).

An object of this invention, is a *Shigella* LPS-ETEC construct. The construct comprises an ETEC construct, as the above examples, conjugated, to a *Shigella* LPS, as an alternative or in addition to *C. jejuni* capsule polysaccharide. It is envisioned that any of the *Shigella* spp. can be conjugated to the ETEC construct. As an example, the *Shigella flexneri* 2a LPS is illustrated, as a potential LPS structure that can be conjugated to an ETEC construct, as follows:

α-D-Glc(1-4)
|
-2)-α-L-Rhap-(1-2)-α-L-Rhap-(1-3)-α-L-Rhap-(1-3)-β-D-GlcNAcp(1-.

What is claimed is:

1. A multi-agent immunogenic construct, comprising a *Campylobacter jejuni* capsule polysaccharide conjugated to a protein carrier, wherein said protein carrier comprises an *Escherichia coli* enterotoxigenic recombinant polypeptide construct, wherein said *Escherichia coli* recombinant polypeptide construct comprises a minor or major subunit connected to one or more major fimbrial subunits or immunogenic fragments, thereof, of the same fimbrial type, via a polypeptide linker, are also connected to each other via a polypeptide linker wherein the C-terminal *Escherichia coli* fimbrial major subunit is connected, via a linker, to a C-terminal donor β strand derived from a major *Escherichia coli* fimbrial subunit that is homologous or heterologous to the immediately N-terminal major subunit, wherein said donor β strand contains 12 to 16 amino acids from the N-terminal region of said one or more major fimbrial subunits, and wherein said recombinant polypeptide construct can be connected to one or more additional recombinant polypeptide constructs, wherein each of the constructs contain fimibrial subunits derived from a different fimbrial type than any of the other constructs and wherein the recombinant polypeptide construct can contain a C-terminal histidine tag at the C-terminus, wherein said minor or major *Escherichia coli* fimbrial subunits are derived from ETEC strains selected from the group consisting of Class 5, CS3 and CS6.

2. The multi-agent immunogenic construct of claim 1, wherein the multi-agent immunogenic construct comprises *Shigella* lipopolysaccharide in place of or in addition to the *Campylobacter jejuni* capsule polysaccharide.

3. The multi-agent immunogenic construct of claim 1, wherein said molar ratio of *Campylobacter jejuni* or *Shigella* spp. lipopolysaccharide to *Escherichia coli* recombinant protein carrier is 1:1 to 5:1.

4. The multi-agent immunogenic construct of claim 1, wherein the *Escherichia coli* recombinant polypeptide construct comprises the amino acid sequence selected from the group consisting of SEQ ID Nos. 108 and 110.

5. The multi-agent immunogenic construct of claim 1, wherein the *Escherichia coli* recombinant polypeptide construct is encoded by the nucleotide sequence of SEQ ID Nos. 105 and 109.

6. The multi-agent immunogenic construct of claim 1, wherein said *Campylobacter jejuni* polysaccharide is a repeating trisaccharide structure having the formula selected from the group consisting of:

[→3)-α-D-Gal-(1→2)-6d-α-D-altro-Me-Hep-(1→3)-β-D-GlcNAc-(1→]$_n$;

[→3)-β-6-deoxy-D-ido-Heptose(1→4)-β-D-GlcNAc (1→]$_n$;

selected from the group consisting of:

[→3)-α-Araf-(1→3)-6-d-α-gulo-Hepp-(1→]$_n$;

```
[→3)-β-GalpNAc-(1→]n;        3    ;
              4              ↑
              ↑            MeOPN
      6-d-α-gal-Hep
```

```
                MeOPN
                  ↓
                  7
[→4)-β-Glcp-(1→3)-6-d-α-ido-Hepp]n;
```

```
            MeOPN
              ↓
              7
[→4)-β-Glcp-(1→3)-LD-ido-Hepp]n;
```

```
[→4)-α-D-Galp-(1→2)-Gro(1→P→]n
             3     2
             ↑     ↑
             1     1
   [MeOPN]→3)-Fruf   Fruf-(3←[MeOPN];
```

[→2)-D-glycero-α-D-manno-Hepp-(1→4)-α-D-Glcp-(1→]$_n$;

```
      [→4)-α-D-Galp-(1→2)-Gro(1→P→]n
              3     2
              ↑     ↑
              1     1
[MeOPN]→3)-Fruf   Fruf-(3←[MeOPN];
```

[→3)-L-beta-ido-Hep-(1→4)-beta-D-Glc-(1→]$_n$, with non-stoichiometric substitution of O-methyl-phosphoramidate at position 2 of L-glycero-beta-D-ido-heptose;

[→3)-6d-beta-ido-Hep-(1→4)-beta-D-Glc-(1→]$_n$, derived from HS13, with non-stoichiometric substitution of O-methyl-phosphoramidate at position 2 or/and 7 of 6-deoxy-beta-D-ido-heptose;

[→3)-L-beta-D-ido-Hep-(1→4)-beta-D-Glc-(1→]$_n$;

[→3)-L-alpha-D-ido-Hep-(1→4)-alpha-Gal-(1→]$_n$, with non-stoichiometric substitution of O-methyl-phosphoramidate at position 2 of 6-deoxy-alpha-D-ido-heptose;

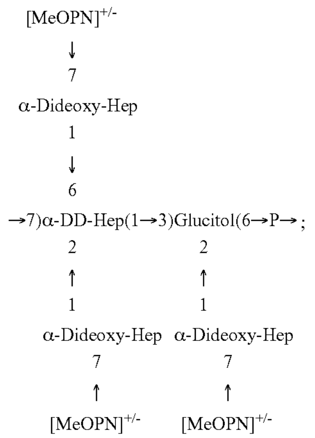

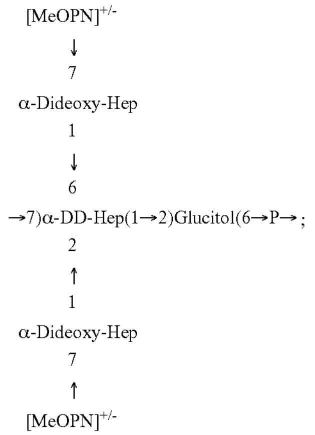

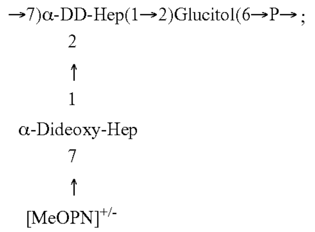

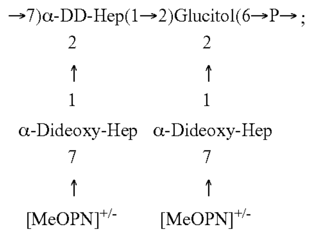

and

[→3)-6d-alpha-D-ido-Hep-(1→4)-alpha-Gal-(1→]$_n$, derived from HS3, HS13 and HS50 with non-stoichiometric substitution of O-methyl-phosphoramidate at position 2 of L-glycero-alpha-D-ido-heptose, wherein "n" is 1 to 100.

7. The multi-agent immunogenic construct of claim 2, wherein said *Shigella* lipopolysaccharide has the structure:

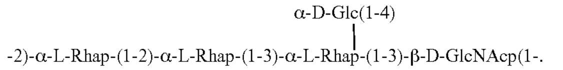

8. The multi-agent immunogenic construct of claim 1, wherein said N-terminus of said minor or major subunit contains an 18-22 amino acid signal peptide.

9. The multi-agent immunogenic construct of claim 1, wherein the amino acid sequence of said polypeptide linker is the amino acid sequence of SEQ ID No. 5 or a tri-glycine.

10. The multi-agent immunogenic construct of claim 1, wherein one or more major subunits contain a deletion of the 14 to 18 N-terminal amino acids.

11. The multi-agent Immunogenic construct of claim 1, wherein said amino acid sequence of said *Escherichia coli* fimbrial minor subunit is selected from the group consisting of SEQ ID Nos. 46, 52 and 58, or derivatives thereof, and wherein said amino acid sequence of said *Escherichia coli* fimbrial major subunit is selected from the group consisting of SEQ ID Nos. 55 and 61, or derivatives thereof.

12. A method of inducing an immune response against *C. jejuni* strains, wherein said method induces an immune response against one or more enterobacteria selected from the group consisting of *C. jejuni* strains, *Escherichia coli*, and *Shigella*, comprising the steps: a. administering the multi-agent immunogenic composition of claim 1 at a dose range of 0.1 μg to 10 mg per dose; b. administering a boosting dose of said capsule polysaccharide composition as in section a) at a dose range of 0.1 μg to 10 mg per dose.

13. The method of claim 12, wherein said *Campylobacter jejuni* capsule polysaccharide comprises the polysaccharide structures of claim 6.

14. The method of claim 12, wherein said multi-agent immunogenic composition comprises the construct of claim 2.

15. The method of claim 12, wherein said *Escherichia coli* enterotoxigenic recombinant polypeptide construct wherein said *Escherichia coli* fimbrial minor subunit is selected from the group consisting of SEQ ID Nos. 46 and 58 or derivatives thereof, and wherein said amino acid sequence of said *Escherichia coli* fimbrial major subunit is selected from the group consisting of SEQ ID Nos. 49, 55 and 61, or derivatives thereof.

16. The method of claim 12, wherein the *Escherichia coli* recombinant polypeptide construct comprises the amino acid sequence selected from the group consisting of SEQ ID Nos. 108 and 110.

17. The method of claim 12, wherein the *Escherichia coli* recombinant polypeptide construct is encoded by the nucleotide sequence of SEQ ID Nos. 105 and 109.

18. The method of claim 12, wherein said N-terminus of said minor or major subunit contains an 18-22 amino acid signal peptide.

19. The method of claim 12, wherein the amino acid sequence of said polypeptide linker is the amino acid sequence of SEQ ID No. 5 or a tri-glyicine.

20. The method of claim 12, wherein one or more major subunits contain a deletion of the 14 to 18 N-terminal amino acids.

* * * * *

SEQUENCE LISTING

```
<160> NUMBER OF SEQ ID NOS: 143

<210> SEQ ID NO 1
<211> LENGTH: 414
<212> TYPE: PRT
<213> ORGANISM: Escherichia coli

<400> SEQUENCE: 1

Ala Thr Gly Ala Gly Ala Ala Cys Ala Gly Ala Ala Ala Thr Ala Gly
1               5                   10                  15

Cys Gly Ala Cys Thr Ala Ala Ala Ala Ala Cys Thr Thr Cys Cys Cys
            20                  25                  30

Ala Gly Thr Ala Thr Cys Ala Ala Cys Gly Ala Cys Thr Ala Thr Thr
        35                  40                  45

Thr Cys Ala Ala Ala Ala Ala Gly Thr Thr Thr Thr Thr Thr Thr Gly
    50                  55                  60

Cys Gly Cys Cys Thr Gly Ala Ala Cys Cys Ala Cys Ala Ala Ala Thr
65                  70                  75                  80

Cys Cys Ala Gly Cys Cys Thr Thr Cys Thr Thr Thr Thr Gly Gly Thr
                85                  90                  95

Ala Ala Ala Ala Ala Thr Gly Thr Thr Gly Gly Ala Ala Ala Gly Gly
            100                 105                 110

Ala Ala Gly Gly Ala Gly Ala Thr Thr Thr Ala Thr Thr Ala Thr Thr
        115                 120                 125

Thr Ala Gly Thr Gly Thr Gly Ala Gly Cys Thr Thr Ala Ala Thr Thr
    130                 135                 140

Gly Thr Thr Cys Cys Thr Gly Ala Ala Ala Ala Thr Gly Thr Ala Thr
145                 150                 155                 160

Cys Cys Cys Ala Gly Gly Thr Ala Ala Cys Gly Gly Thr Cys Thr Ala
                165                 170                 175

Cys Cys Cys Thr Gly Thr Thr Thr Ala Thr Gly Ala Thr Gly Ala Ala
            180                 185                 190

Gly Ala Thr Thr Ala Thr Gly Gly Ala Thr Thr Ala Gly Gly Ala Cys
        195                 200                 205

Gly Ala Cys Thr Cys Gly Thr Ala Ala Ala Thr Ala Cys Cys Gly Cys
    210                 215                 220

Thr Gly Ala Thr Gly Ala Thr Thr Cys Cys Cys Ala Ala Thr Cys Ala
225                 230                 235                 240

Ala Thr Ala Ala Thr Cys Thr Ala Cys Cys Ala Gly Ala Thr Thr Gly
                245                 250                 255
```

-continued

```
Thr Thr Gly Ala Thr Gly Ala Thr Ala Ala Ala Gly Gly Gly Ala Ala
            260                 265                 270

Ala Ala Ala Ala Ala Thr Gly Thr Thr Ala Ala Ala Ala Gly Ala Thr
        275                 280                 285

Cys Ala Thr Gly Gly Thr Ala Cys Ala Gly Ala Gly Gly Thr Thr Ala
    290                 295                 300

Cys Gly Cys Cys Thr Ala Ala Thr Cys Ala Ala Cys Ala Ala Ala Thr
305                 310                 315                 320

Ala Ala Cys Thr Thr Thr Thr Ala Ala Ala Gly Cys Gly Cys Thr Gly
                325                 330                 335

Ala Ala Thr Thr Ala Thr Ala Cys Thr Ala Gly Cys Gly Gly Ala Gly
            340                 345                 350

Ala Thr Ala Ala Ala Gly Ala Ala Ala Thr Ala Cys Cys Thr Cys Cys
        355                 360                 365

Thr Gly Gly Gly Ala Thr Ala Thr Ala Thr Ala Ala Cys Gly Ala Thr
    370                 375                 380

Cys Ala Gly Gly Thr Thr Ala Thr Gly Gly Thr Thr Gly Gly Thr Thr
385                 390                 395                 400

Ala Cys Thr Ala Thr Gly Thr Ala Ala Ala Cys Thr Ala Ala
                405                 410


<210> SEQ ID NO 2
<211> LENGTH: 137
<212> TYPE: PRT
<213> ORGANISM: Escherichia coli

<400> SEQUENCE: 2

Met Arg Thr Glu Ile Ala Thr Lys Asn Phe Pro Val Ser Thr Thr Ile
1               5                   10                  15

Ser Lys Ser Phe Phe Ala Pro Glu Pro Gln Ile Gln Pro Ser Phe Gly
            20                  25                  30

Lys Asn Val Gly Lys Glu Gly Asp Leu Leu Phe Ser Val Ser Leu Ile
        35                  40                  45

Val Pro Glu Asn Val Ser Gln Val Thr Val Tyr Pro Val Tyr Asp Glu
    50                  55                  60

Asp Tyr Gly Leu Gly Arg Leu Val Asn Thr Ala Asp Asp Ser Gln Ser
65                  70                  75                  80

Ile Ile Tyr Gln Ile Val Asp Asp Lys Gly Lys Lys Met Leu Lys Asp
                85                  90                  95

His Gly Thr Glu Val Thr Pro Asn Gln Gln Ile Thr Phe Lys Ala Leu
            100                 105                 110

Asn Tyr Thr Ser Gly Asp Lys Glu Ile Pro Pro Gly Ile Tyr Asn Asp
        115                 120                 125

Gln Val Met Val Gly Tyr Tyr Val Asn
    130                 135


<210> SEQ ID NO 3
<211> LENGTH: 444
<212> TYPE: PRT
<213> ORGANISM: Escherichia coli

<400> SEQUENCE: 3

Ala Thr Gly Gly Gly Ala Ala Ala Cys Thr Gly Gly Cys Ala Ala Thr
1               5                   10                  15

Ala Thr Ala Ala Ala Thr Cys Thr Cys Thr Gly Gly Ala Thr Gly Thr
            20                  25                  30
```

-continued

```
Ala Ala Ala Thr Gly Thr Ala Ala Ala Thr Ala Thr Thr Gly Ala Gly
        35                  40                  45

Cys Ala Ala Ala Ala Thr Thr Thr Thr Ala Thr Thr Cys Cys Ala Gly
    50                  55                  60

Ala Thr Ala Thr Thr Gly Ala Thr Thr Cys Cys Gly Cys Thr Gly Thr
65                  70                  75                  80

Thr Cys Gly Thr Ala Thr Ala Ala Thr Ala Cys Cys Thr Gly Thr Thr
                85                  90                  95

Ala Ala Thr Thr Ala Cys Gly Ala Thr Thr Cys Gly Gly Ala Thr Cys
            100                 105                 110

Cys Gly Ala Ala Ala Cys Thr Gly Ala Ala Thr Thr Cys Ala Cys Ala
        115                 120                 125

Gly Thr Thr Ala Thr Ala Thr Ala Cys Gly Gly Thr Thr Gly Ala Gly
    130                 135                 140

Ala Thr Gly Ala Cys Gly Ala Thr Cys Cys Cys Thr Gly Cys Ala Gly
145                 150                 155                 160

Gly Thr Gly Thr Ala Ala Gly Cys Gly Cys Ala Gly Thr Thr Ala Ala
                165                 170                 175

Ala Ala Thr Cys Gly Thr Ala Cys Cys Ala Ala Cys Ala Gly Ala Thr
            180                 185                 190

Ala Gly Thr Cys Thr Gly Ala Cys Ala Thr Cys Thr Thr Cys Thr Gly
        195                 200                 205

Gly Ala Cys Ala Gly Cys Ala Gly Ala Thr Cys Gly Gly Ala Ala Ala
    210                 215                 220

Gly Cys Thr Gly Gly Thr Thr Ala Ala Thr Gly Thr Ala Ala Ala Cys
225                 230                 235                 240

Ala Ala Thr Cys Cys Ala Gly Ala Thr Cys Ala Ala Ala Ala Thr Ala
                245                 250                 255

Thr Gly Ala Ala Thr Thr Ala Thr Thr Ala Thr Ala Thr Cys Ala Gly
            260                 265                 270

Ala Ala Ala Gly Gly Ala Thr Thr Cys Thr Gly Gly Cys Gly Cys Thr
        275                 280                 285

Gly Gly Thr Ala Ala Gly Thr Thr Thr Ala Thr Gly Gly Cys Ala Gly
    290                 295                 300

Gly Gly Cys Ala Ala Ala Ala Ala Gly Gly Ala Thr Cys Cys Thr Thr
305                 310                 315                 320

Thr Thr Cys Thr Gly Thr Cys Ala Ala Ala Gly Ala Gly Ala Ala Thr
                325                 330                 335

Ala Cys Gly Thr Cys Ala Thr Ala Cys Ala Cys Ala Thr Thr Cys Thr
            340                 345                 350

Cys Ala Gly Cys Ala Ala Thr Thr Thr Ala Thr Ala Cys Thr Gly Gly
        355                 360                 365

Thr Gly Gly Cys Gly Ala Ala Thr Ala Cys Cys Cys Thr Ala Ala Thr
    370                 375                 380

Ala Gly Cys Gly Gly Ala Thr Ala Thr Thr Cys Gly Thr Cys Thr Gly
385                 390                 395                 400

Gly Thr Ala Cys Thr Thr Ala Thr Gly Cys Ala Gly Gly Ala Cys Ala
                405                 410                 415

Thr Thr Thr Gly Ala Cys Thr Gly Thr Ala Thr Cys Ala Thr Thr Thr
            420                 425                 430

Thr Ala Cys Ala Gly Cys Ala Ala Thr Thr Ala Ala
        435                 440
```

-continued

<210> SEQ ID NO 4
<211> LENGTH: 147
<212> TYPE: PRT
<213> ORGANISM: Escherichia coli

<400> SEQUENCE: 4

```
Met Gly Asn Trp Gln Tyr Lys Ser Leu Asp Val Asn Val Asn Ile Glu
1               5                   10                  15

Gln Asn Phe Ile Pro Asp Ile Asp Ser Ala Val Arg Ile Ile Pro Val
            20                  25                  30

Asn Tyr Asp Ser Asp Pro Lys Leu Asn Ser Gln Leu Tyr Thr Val Glu
        35                  40                  45

Met Thr Ile Pro Ala Gly Val Ser Ala Val Lys Ile Val Pro Thr Asp
    50                  55                  60

Ser Leu Thr Ser Ser Gly Gln Gln Ile Gly Lys Leu Val Asn Val Asn
65                  70                  75                  80

Asn Pro Asp Gln Asn Met Asn Tyr Tyr Ile Arg Lys Asp Ser Gly Ala
                85                  90                  95

Gly Lys Phe Met Ala Gly Gln Lys Gly Ser Phe Ser Val Lys Glu Asn
            100                 105                 110

Thr Ser Tyr Thr Phe Ser Ala Ile Tyr Thr Gly Gly Glu Tyr Pro Asn
        115                 120                 125

Ser Gly Tyr Ser Ser Gly Thr Tyr Ala Gly His Leu Thr Val Ser Phe
    130                 135                 140

Tyr Ser Asn
145
```

<210> SEQ ID NO 5
<211> LENGTH: 4
<212> TYPE: PRT
<213> ORGANISM: Escherichia coli

<400> SEQUENCE: 5

```
Asp Asn Lys Gln
1
```

<210> SEQ ID NO 6
<211> LENGTH: 2502
<212> TYPE: DNA
<213> ORGANISM: Escherichia coli

<400> SEQUENCE: 6

```
atgaataaaa ttttatttat ttttacattg tttttttctt cagggttttt tacatttgcc     60

gtatcggcag ataaaaatcc cggaagtgaa aacatgacta atactattgg tccccatgac    120

agggggggat cttcccccat atataatatc ttaaattcct atcttacagc atacaatgga    180

agccatcatc tgtatgatag gatgagtttt ttatgtttgt cttctcaaaa tacactgaat    240

ggagcatgcc caagcagtga tgcccctggc actgctacaa ttgatggcga aacaaatata    300

acattacaat ttacggaaaa aagaagtcta attaaaagag aactgcaaat taaaggctat    360

aaacaatttt tgttcaaaaa tgctaattgc ccatctaaac tagcacttaa ctcatctcat    420

tttcaatgta atagagaaca agcttcaggt gctactttat cgttatacat accagctggt    480

gaattaaata aattaccttt tgggggggtc tggaatgccg ttctgaagct aaatgtaaaa    540

agacgatatg atacaaccta tgggacttac actataaaca tcacagttaa tttaactgat    600

aagggaaata ttcagatatg gttaccacag ttcaaaagta acgctcgtgt cgatcttaac    660

ttgcgtccaa ctggtggtgg tacatatatc ggaagaaatt ctgttgatat gtgcttttat    720
```

-continued

```
gatggatata gtactaacag cagctcttta gagataagat ttcaggatga taattctaaa    780

tctgatggaa aattttatct aaagaaaata aatgatgact ccaaagaact tgtatacact    840

ttgtcacttc tcctggcagg taaaaattta acaccaacaa atggacaggc attaaatatt    900

aacactgctt ctctggaaac aaactggaat agaattacag ctgtcaccat gccagaaatc    960

agtgttccgg tgttgtgttg gcctggacgt ttgcaattgg atgcaaaagt gaaaaatccc   1020

gaggctggac aatatatggg gaatattaaa attactttca caccaagtag tcaaacactc   1080

gacaataaac aagtagagaa aaatattact gtaacagcta gtgttgatcc tgcaattgat   1140

cttttgcaag ctgatggcaa tgctctgcca tcagctgtaa agttagctta ttctcccgca   1200

tcaaaaactt ttgaaagtta cagagtaatg actcaagttc atacaaacga tgcaactaaa   1260

aaagtaattg ttaaacttgc tgatacacca cagcttacag atgttctgaa ttcaactgtt   1320

caaatgccta tcagtgtgtc atggggagga caagtattat ctacaacagc caaagaattt   1380

gaagctgctg ctttgggata ttctgcatcc ggtgtaaatg gcgtatcatc ttctcaagag   1440

ttagtaatta gcgctgcacc taaaactgcc ggtaccgccc caactgcagg aaactattca   1500

ggagtagtat ctcttgtaat gactttggga tccgacaata aacaagtaga gaaaaatatt   1560

actgtaacag ctagtgtcga ccctgcaggg acattagcta ttgattttac gcctattgaa   1620

aatatttatg taggtgccaa ttatggtaaa gatattggaa cccttgtttt cacaacaaat   1680

gatttaacag atattacatt gatgtcatct cgcagcgttg ttgatggtcg ccagactggt   1740

tttttacct tcatggactc atcagccact tacaaaatta gtacaaaact gggatcatcg    1800

aatgatgtaa acattcaaga aattactcaa ggagctaaaa ttactcctgt tagtggagag   1860

aaaactttgc ctaaaaaatt cactcttaag ctacatgcac acaggagtag cagtacagtt   1920

ccaggtacgt atactgttgg tcttaacgta accagtaacg ttattgataa caagcaggca   1980

gcggggccca ctctaaccaa agaactggca ttaaatgtgc tttctcctgc agctctggat   2040

gcaacttggg ctcctcagga taatttaaca ttatccaata ctggcgtttc taatactttg   2100

gtgggtgttt tgactctttc aaataccagt attgatacag ttagcattgc gagtacaaat   2160

gtttctgata catctaagaa tggtacagta acttttgcac atgagacaaa taactctgct   2220

agctttgcca ccaccatttc aacagataat gccaacatta cgttggataa aaatgctgga   2280

aatacgattg ttaaaactac aaatgggagt cagttgccaa ctaatttacc acttaagttt   2340

attaccactg aaggtaacga acatttagtt tcaggtaatt accgtgcaaa tataacaatt   2400

acttcgacaa ttaaagataa caagcaggcg gcaggtccaa ccctgactaa ggagttagcg   2460

ctgaacgttc tgagcctcga gcaccaccac caccaccact ga                      2502
```

<210> SEQ ID NO 7
<211> LENGTH: 833
<212> TYPE: PRT
<213> ORGANISM: Escherichia coli

<400> SEQUENCE: 7

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
```

-continued

```
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480
```

```
Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Thr Leu Ala Ile Asp Phe Thr Pro Ile Glu Asn Ile Tyr Val
    530                 535                 540

Gly Ala Asn Tyr Gly Lys Asp Ile Gly Thr Leu Val Phe Thr Thr Asn
545                 550                 555                 560

Asp Leu Thr Asp Ile Thr Leu Met Ser Ser Arg Ser Val Val Asp Gly
                565                 570                 575

Arg Gln Thr Gly Phe Phe Thr Phe Met Asp Ser Ser Ala Thr Tyr Lys
            580                 585                 590

Ile Ser Thr Lys Leu Gly Ser Ser Asn Asp Val Asn Ile Gln Glu Ile
        595                 600                 605

Thr Gln Gly Ala Lys Ile Thr Pro Val Ser Gly Glu Lys Thr Leu Pro
    610                 615                 620

Lys Lys Phe Thr Leu Lys Leu His Ala His Arg Ser Ser Ser Thr Val
625                 630                 635                 640

Pro Gly Thr Tyr Thr Val Gly Leu Asn Val Thr Ser Asn Val Ile Asp
                645                 650                 655

Asn Lys Gln Ala Ala Gly Pro Thr Leu Thr Lys Glu Leu Ala Leu Asn
            660                 665                 670

Val Leu Ser Pro Ala Ala Leu Asp Ala Thr Trp Ala Pro Gln Asp Asn
        675                 680                 685

Leu Thr Leu Ser Asn Thr Gly Val Ser Asn Thr Leu Val Gly Val Leu
    690                 695                 700

Thr Leu Ser Asn Thr Ser Ile Asp Thr Val Ser Ile Ala Ser Thr Asn
705                 710                 715                 720

Val Ser Asp Thr Ser Lys Asn Gly Thr Val Thr Phe Ala His Glu Thr
                725                 730                 735

Asn Asn Ser Ala Ser Phe Ala Thr Thr Ile Ser Thr Asp Asn Ala Asn
            740                 745                 750

Ile Thr Leu Asp Lys Asn Ala Gly Asn Thr Ile Val Lys Thr Thr Asn
        755                 760                 765

Gly Ser Gln Leu Pro Thr Asn Leu Pro Leu Lys Phe Ile Thr Thr Glu
    770                 775                 780

Gly Asn Glu His Leu Val Ser Gly Asn Tyr Arg Ala Asn Ile Thr Ile
785                 790                 795                 800

Thr Ser Thr Ile Lys Asp Asn Lys Gln Ala Ala Gly Pro Thr Leu Thr
                805                 810                 815

Lys Glu Leu Ala Leu Asn Val Leu Ser Leu Glu His His His His His
            820                 825                 830

His
```

<210> SEQ ID NO 8
<211> LENGTH: 3414
<212> TYPE: DNA
<213> ORGANISM: Escherichia coli

<400> SEQUENCE: 8

```
atgaataaaa ttttatttat ttttacattg ttttttttctt cagggttttt tacatttgcc      60
```

-continued

```
gtatcggcag ataaaaatcc cggaagtgaa aacatgacta atactattgg tccccatgac    120
aggggggggat cttcccccat atataatatc ttaaattcct atcttacagc atacaatgga    180
agccatcatc tgtatgatag gatgagtttt ttatgtttgt cttctcaaaa tacactgaat    240
ggagcatgcc caagcagtga tgcccctggc actgctacaa ttgatggcga aacaaatata    300
acattacaat ttacggaaaa aagaagtcta attaaaagag aactgcaaat taaaggctat    360
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattaccttt tgggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt ttgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caaagaattt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaaatatt   1560
actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accggaacgg caggtgtttc gaatagtaaa gaattagtaa ttggagcaac tacatccgga   1920
actgcaccaa gtgcaggtaa gtatcaaggc gtcgtttcca ttgtaatgac tcaatcgacc   1980
gacacagccg cgcctgttcc tgacaataaa caagtagaga aaaatattac tgtgacagcc   2040
agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
```

-continued gaaaaaaata tcactgtaac agctagtgtt gatcctacgg gcacattagc tattgatttt 2520
acgcctattg aaaatattta tgtaggtgcc aattatggta aagatattgg aacccttgtt 2580
ttcacaacaa atgatttaac agatattaca ttgatgtcat ctcgcagcgt tgttgatggt 2640
cgccagactg gtttttttac cttcatggac tcatcagcca cttacaaaat tagtacaaaa 2700
ctgggatcat cgaatgatgt aaacattcaa gaaattactc aaggagctaa aattactcct 2760
gttagtggag agaaaacttt gcctaaaaaa ttcactctta agctacatgc acacaggagt 2820
agcagtacag ttccaggtac gtatactgtt ggtcttaacg taaccagtaa cgttattgat 2880
aacaagcagg cagcggggcc cactctaacc aaagaactgg cattaaatgt gctttctcct 2940
gcagctctgg atgcaacttg ggctcctcag gataatttaa cattatccaa tactggcgtt 3000
tctaatactt tggtgggtgt tttgactctt tcaaatacca gtattgatac agttagcatt 3060
gcgagtacaa atgtttctga tacatctaag aatggtacag taacttttgc acatgagaca 3120
aataactctg ctagctttgc caccaccatt tcaacagata atgccaacat tacgttggat 3180
aaaaatgctg gaaatacgat tgttaaaact acaaatggga gtcagttgcc aactaattta 3240
ccacttaagt ttattaccac tgaaggtaac gaacatttag tttcaggtaa ttaccgtgca 3300
aatataacaa ttacttcgac aattaaagat aacaagcagg cggcaggtcc aaccctgact 3360
aaggagttag cgctgaacgt tctgagcctc gagcaccacc accaccacca ctga 3414

<210> SEQ ID NO 9
<211> LENGTH: 1137
<212> TYPE: PRT
<213> ORGANISM: Escherichia coli

<400> SEQUENCE: 9

Met Asn Lys Ile Leu Phe Ile Phe Thr Leu Phe Phe Ser Ser Gly Phe
1 5 10 15

Phe Thr Phe Ala Val Ser Ala Asp Lys Asn Pro Gly Ser Glu Asn Met
20 25 30

Thr Asn Thr Ile Gly Pro His Asp Arg Gly Gly Ser Ser Pro Ile Tyr
35 40 45

Asn Ile Leu Asn Ser Tyr Leu Thr Ala Tyr Asn Gly Ser His His Leu
50 55 60

Tyr Asp Arg Met Ser Phe Leu Cys Leu Ser Ser Gln Asn Thr Leu Asn
65 70 75 80

Gly Ala Cys Pro Ser Ser Asp Ala Pro Gly Thr Ala Thr Ile Asp Gly
85 90 95

Glu Thr Asn Ile Thr Leu Gln Phe Thr Glu Lys Arg Ser Leu Ile Lys
100 105 110

Arg Glu Leu Gln Ile Lys Gly Tyr Lys Gln Phe Leu Phe Lys Asn Ala
115 120 125

Asn Cys Pro Ser Lys Leu Ala Leu Asn Ser Ser His Phe Gln Cys Asn
130 135 140

Arg Glu Gln Ala Ser Gly Ala Thr Leu Ser Leu Tyr Ile Pro Ala Gly
145 150 155 160

Glu Leu Asn Lys Leu Pro Phe Gly Gly Val Trp Asn Ala Val Leu Lys
165 170 175

Leu Asn Val Lys Arg Arg Tyr Asp Thr Thr Tyr Gly Thr Tyr Thr Ile
180 185 190

Asn Ile Thr Val Asn Leu Thr Asp Lys Gly Asn Ile Gln Ile Trp Leu
195 200 205

```
Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Thr Ile Asp Ile Leu Gln Ala Asn Gly Ser Ala Leu Pro Thr Ala Val
    530                 535                 540

Asp Leu Thr Tyr Leu Pro Gly Ala Lys Thr Phe Glu Asn Tyr Ser Val
545                 550                 555                 560

Leu Thr Gln Ile Tyr Thr Asn Asp Pro Ser Lys Gly Leu Asp Val Arg
                565                 570                 575

Leu Val Asp Thr Pro Lys Leu Thr Asn Ile Leu Gln Pro Thr Ser Thr
            580                 585                 590

Ile Pro Leu Thr Val Ser Trp Ala Gly Lys Thr Leu Ser Thr Ser Ala
        595                 600                 605

Gln Lys Ile Ala Val Gly Asp Leu Gly Phe Gly Ser Thr Gly Thr Ala
    610                 615                 620
```

-continued

```
Gly Val Ser Asn Ser Lys Glu Leu Val Ile Gly Ala Thr Thr Ser Gly
625                 630                 635                 640

Thr Ala Pro Ser Ala Gly Lys Tyr Gln Gly Val Val Ser Ile Val Met
                645                 650                 655

Thr Gln Ser Thr Asp Thr Ala Ala Pro Val Pro Asp Asn Lys Gln Val
            660                 665                 670

Glu Lys Asn Ile Thr Val Thr Ala Ser Val Asp Pro Thr Ile Asp Ile
        675                 680                 685

Leu Gln Ala Asp Gly Ser Ser Leu Pro Thr Ala Val Glu Leu Thr Tyr
    690                 695                 700

Ser Pro Ala Ala Ser Arg Phe Glu Asn Tyr Lys Ile Ala Thr Lys Val
705                 710                 715                 720

His Thr Asn Val Ile Asn Lys Asn Val Leu Val Lys Leu Val Asn Asp
                725                 730                 735

Pro Lys Leu Thr Asn Val Leu Asp Ser Thr Lys Gln Leu Pro Ile Thr
            740                 745                 750

Val Ser Tyr Gly Gly Lys Thr Leu Ser Thr Ala Asp Val Thr Phe Glu
        755                 760                 765

Pro Ala Glu Leu Asn Phe Gly Thr Ser Gly Val Thr Gly Val Ser Ser
    770                 775                 780

Ser Gln Asp Leu Val Ile Gly Ala Thr Thr Ala Gln Ala Pro Thr Ala
785                 790                 795                 800

Gly Asn Tyr Ser Gly Val Val Ser Ile Leu Met Thr Leu Ala Ser Asp
                805                 810                 815

Asn Lys Gln Val Glu Lys Asn Ile Thr Val Thr Ala Ser Val Asp Pro
            820                 825                 830

Thr Gly Thr Leu Ala Ile Asp Phe Thr Pro Ile Glu Asn Ile Tyr Val
        835                 840                 845

Gly Ala Asn Tyr Gly Lys Asp Ile Gly Thr Leu Val Phe Thr Thr Asn
    850                 855                 860

Asp Leu Thr Asp Ile Thr Leu Met Ser Ser Arg Ser Val Val Asp Gly
865                 870                 875                 880

Arg Gln Thr Gly Phe Phe Thr Phe Met Asp Ser Ser Ala Thr Tyr Lys
                885                 890                 895

Ile Ser Thr Lys Leu Gly Ser Ser Asn Asp Val Asn Ile Gln Glu Ile
            900                 905                 910

Thr Gln Gly Ala Lys Ile Thr Pro Val Ser Gly Glu Lys Thr Leu Pro
        915                 920                 925

Lys Lys Phe Thr Leu Lys Leu His Ala His Arg Ser Ser Ser Thr Val
    930                 935                 940

Pro Gly Thr Tyr Thr Val Gly Leu Asn Val Thr Ser Asn Val Ile Asp
945                 950                 955                 960

Asn Lys Gln Ala Ala Gly Pro Thr Leu Thr Lys Glu Leu Ala Leu Asn
                965                 970                 975

Val Leu Ser Pro Ala Ala Leu Asp Ala Thr Trp Ala Pro Gln Asp Asn
            980                 985                 990

Leu Thr Leu Ser Asn Thr Gly Val  Ser Asn Thr Leu Val  Gly Val Leu
        995                 1000                1005

Thr Leu  Ser Asn Thr Ser Ile  Asp Thr Val Ser Ile  Ala Ser Thr
    1010                1015                1020

Asn Val  Ser Asp Thr Ser Lys  Asn Gly Thr Val Thr  Phe Ala His
    1025                1030                1035

Glu Thr  Asn Asn Ser Ala Ser  Phe Ala Thr Thr Ile  Ser Thr Asp
```

-continued 1040 1045 1050

Asn Ala Asn Ile Thr Leu Asp Lys Asn Ala Gly Asn Thr Ile Val
1055 1060 1065

Lys Thr Thr Asn Gly Ser Gln Leu Pro Thr Asn Leu Pro Leu Lys
1070 1075 1080

Phe Ile Thr Thr Glu Gly Asn Glu His Leu Val Ser Gly Asn Tyr
1085 1090 1095

Arg Ala Asn Ile Thr Ile Thr Ser Thr Ile Lys Asp Asn Lys Gln
1100 1105 1110

Ala Ala Gly Pro Thr Leu Thr Lys Glu Leu Ala Leu Asn Val Leu
1115 1120 1125

Ser Leu Glu His His His His His His
1130 1135

<210> SEQ ID NO 10
<211> LENGTH: 2952
<212> TYPE: DNA
<213> ORGANISM: Escherichia coli

<400> SEQUENCE: 10
atgaaaaaga tatttatttt tttgtctatc atattttctg cggtggtcag tgccgggcga 60
tacccggaaa ctacagtagg taatctgacg aagagttttc aagcccctcg tcaggataga 120
agcgtacaat caccaatata taacatcttt acgaatcatg tggctggata tagtttgagt 180
cataacttat atgacaggat tgttttttta tgtacatcct cgtcgaatcc ggttaatggt 240
gcttgcccaa ccattggaac atctggagtt caatacggta ctacaaccat aaccttgcag 300
tttacagaaa aaagaagtct gataaaaaga aatattaatc ttgcaggtaa taagaaacca 360
atatgggaga atcagagttg cgacactagc aatctaatgg tgttgaattc gaagtcttgg 420
tcctgtgggg cttacggaaa tgctaacgga acacttctaa atctgtatat ccctgcagga 480
gaaatcaaca aattgccttt tggagggata tgggaggcaa ctctgatctt acgcttatca 540
agatatggcg aagtcagtag cacccattac ggcaattata ccgtaaatat tacggttgat 600
ttaactgata aaggtaatat tcaggtatgg cttccagggt ttcacagcaa cccgcgtgta 660
gacctgaatc tgcaccctat cggtaattat aaatatagtg gtagtaattc actcgacatg 720
tgtttctatg atggatatag tacaaacagt gatagcatgg taataaagtt ccaggatgat 780
aatcctacct attcatctga atataatctt tataagatag ggggcactga aaaattaccc 840
tatgctgttt cactgcttat gggagaaaaa atattttatc cagtgaatgg tcaatcattt 900
actatcaatg acagtagtgt actcgaaaca aactggaatc gagtaaccgc agttgctatg 960
ccggaagtta atgttccagt attatgctgg ccagcaagat tgctattaaa tgctgatgta 1020
aatgctcccg atgcaggaca gtattcagga cagatatata taacatttac acccagtgtc 1080
gaaaatttag gcggtggagt cgaaaaaaat attactgtga gggcaagtgt tgaccctaaa 1140
cttgatcttc tgcaagcaga tggaacttca ctgccggact ctatcgcatt aacctattct 1200
tcggcttcaa ataattttga agtttactct cttaatactg ctattcatac aaatgacaaa 1260
agcaagggag ttgtagtgaa gctgtcagct tcaccagttc tgtccaatat tatgaagcca 1320
aactcgcaaa ttccgatgaa agtgactttg gggggggaaga cgctgaatac aactgatact 1380
gagtttactg ttgatactct gaactttggt acatctggtg ttgaaaacgt ttcttccact 1440
caacagctta cgattcatgc agacacacaa ggaactgcgc ctgaggcagg caattaccaa 1500
ggtattattt ctcttatcat gactcaaaaa acagggggcg gtgtcgaaaa aaatattact 1560

-continued

```
gtgagggcaa gtgtcgaccc taaacttgac cttctgcaat ctgatggctc tgcgctgccg   1620

aactctgtcg cattaaccta ttctccggct gtaaataatt ttgaagctca caccatcaac   1680

accgttgttc atacaaatga ctcagataaa ggtgttgttg tgaagctgtc agcagatcca   1740

gtcctgtcca atgttctgaa tccaaccctg caaattcctg tttctgtgaa tttcgcagga   1800

aaaccactga gcacaacagg cattaccatc gactccaatg atctgaactt tgcttcgagt   1860

ggtgttaata aagtttcttc tacgcagaaa ctttcaatcc atgcagatgc tactcgggta   1920

actggcggcg cactaacagc tggtcaatat cagggactcg tatcaattat cctgactaag   1980

tcaacggggg gcggtgtcga gaagaccatt agcgttacgg cgagtgttga cccgacgggc   2040

acattagcta ttgattttac gcctattgaa aatatttatg taggtgccaa ttatggtaaa   2100

gatattggaa cccttgtttt cacaacaaat gatttaacag atattacatt gatgtcatct   2160

cgcagcgttg ttgatggtcg ccagactggt ttttttacct tcatggactc atcagccact   2220

tacaaaatta gtacaaaact gggatcatcg aatgatgtaa acattcaaga aattactcaa   2280

ggagctaaaa ttactcctgt tagtggagag aaaactttgc ctaaaaaatt cactcttaag   2340

ctacatgcac acaggagtag cagtacagtt ccaggtacgt atactgttgg tcttaacgta   2400

accagtaacg ttattgataa caagcaggca gcgggggccca ctctaaccaa agaactggca   2460

ttaaatgtgc tttctcctgc agctctggat gcaacttggg ctcctcagga taatttaaca   2520

ttatccaata ctggcgtttc taatactttg gtgggtgttt tgactctttc aaataccagt   2580

attgatacag ttagcattgc gagtacaaat gtttctgata catctaagaa tggtacagta   2640

acttttgcac atgagacaaa taactctgct agctttgcca ccaccatttc aacagataat   2700

gccaacatta cgttggataa aaatgctgga aatacgattg ttaaaactac aaatgggagt   2760

cagttgccaa ctaatttacc acttaagttt attaccactg aaggtaacga acatttagtt   2820

tcaggtaatt accgtgcaaa tataacaatt acttcgacaa ttaaagataa caagcaggcg   2880

gcaggtccaa ccctgactaa ggagttagcg ctgaacgttc tgagcctcga gcaccaccac   2940

caccaccact ga                                                       2952
```

<210> SEQ ID NO 11
<211> LENGTH: 983
<212> TYPE: PRT
<213> ORGANISM: Escherichia coli

<400> SEQUENCE: 11

```
Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
```

-continued

```
        115                 120                 125

Thr Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu Gly Gly Gly Val Glu
        355                 360                 365

Lys Asn Ile Thr Val Arg Ala Ser Val Asp Pro Lys Leu Asp Leu Leu
    370                 375                 380

Gln Ala Asp Gly Thr Ser Leu Pro Asp Ser Ile Ala Leu Thr Tyr Ser
385                 390                 395                 400

Ser Ala Ser Asn Asn Phe Glu Val Tyr Ser Leu Asn Thr Ala Ile His
                405                 410                 415

Thr Asn Asp Lys Ser Lys Gly Val Val Val Lys Leu Ser Ala Ser Pro
            420                 425                 430

Val Leu Ser Asn Ile Met Lys Pro Asn Ser Gln Ile Pro Met Lys Val
        435                 440                 445

Thr Leu Gly Gly Lys Thr Leu Asn Thr Thr Asp Thr Glu Phe Thr Val
    450                 455                 460

Asp Thr Leu Asn Phe Gly Thr Ser Gly Val Glu Asn Val Ser Ser Thr
465                 470                 475                 480

Gln Gln Leu Thr Ile His Ala Asp Thr Gln Gly Thr Ala Pro Glu Ala
                485                 490                 495

Gly Asn Tyr Gln Gly Ile Ile Ser Leu Ile Met Thr Gln Lys Thr Gly
            500                 505                 510

Gly Gly Val Glu Lys Asn Ile Thr Val Arg Ala Ser Val Asp Pro Lys
        515                 520                 525

Leu Asp Leu Leu Gln Ser Asp Gly Ser Ala Leu Pro Asn Ser Val Ala
    530                 535                 540
```

-continued

```
Leu Thr Tyr Ser Pro Ala Val Asn Asn Phe Glu Ala His Thr Ile Asn
545                 550                 555                 560

Thr Val Val His Thr Asn Asp Ser Asp Lys Gly Val Val Val Lys Leu
                565                 570                 575

Ser Ala Asp Pro Val Leu Ser Asn Val Leu Asn Pro Thr Leu Gln Ile
            580                 585                 590

Pro Val Ser Val Asn Phe Ala Gly Lys Pro Leu Ser Thr Thr Gly Ile
        595                 600                 605

Thr Ile Asp Ser Asn Asp Leu Asn Phe Ala Ser Ser Gly Val Asn Lys
    610                 615                 620

Val Ser Ser Thr Gln Lys Leu Ser Ile His Ala Asp Ala Thr Arg Val
625                 630                 635                 640

Thr Gly Gly Ala Leu Thr Ala Gly Gln Tyr Gln Gly Leu Val Ser Ile
                645                 650                 655

Ile Leu Thr Lys Ser Thr Gly Gly Gly Val Glu Lys Thr Ile Ser Val
            660                 665                 670

Thr Ala Ser Val Asp Pro Thr Gly Thr Leu Ala Ile Asp Phe Thr Pro
        675                 680                 685

Ile Glu Asn Ile Tyr Val Gly Ala Asn Tyr Gly Lys Asp Ile Gly Thr
    690                 695                 700

Leu Val Phe Thr Thr Asn Asp Leu Thr Asp Ile Thr Leu Met Ser Ser
705                 710                 715                 720

Arg Ser Val Val Asp Gly Arg Gln Thr Gly Phe Phe Thr Phe Met Asp
                725                 730                 735

Ser Ser Ala Thr Tyr Lys Ile Ser Thr Lys Leu Gly Ser Ser Asn Asp
            740                 745                 750

Val Asn Ile Gln Glu Ile Thr Gln Gly Ala Lys Ile Thr Pro Val Ser
        755                 760                 765

Gly Glu Lys Thr Leu Pro Lys Lys Phe Thr Leu Lys Leu His Ala His
    770                 775                 780

Arg Ser Ser Ser Thr Val Pro Gly Thr Tyr Thr Val Gly Leu Asn Val
785                 790                 795                 800

Thr Ser Asn Val Ile Asp Asn Lys Gln Ala Ala Gly Pro Thr Leu Thr
                805                 810                 815

Lys Glu Leu Ala Leu Asn Val Leu Ser Pro Ala Ala Leu Asp Ala Thr
            820                 825                 830

Trp Ala Pro Gln Asp Asn Leu Thr Leu Ser Asn Thr Gly Val Ser Asn
        835                 840                 845

Thr Leu Val Gly Val Leu Thr Leu Ser Asn Thr Ser Ile Asp Thr Val
    850                 855                 860

Ser Ile Ala Ser Thr Asn Val Ser Asp Thr Ser Lys Asn Gly Thr Val
865                 870                 875                 880

Thr Phe Ala His Glu Thr Asn Asn Ser Ala Ser Phe Ala Thr Thr Ile
                885                 890                 895

Ser Thr Asp Asn Ala Asn Ile Thr Leu Asp Lys Asn Ala Gly Asn Thr
            900                 905                 910

Ile Val Lys Thr Thr Asn Gly Ser Gln Leu Pro Thr Asn Leu Pro Leu
        915                 920                 925

Lys Phe Ile Thr Thr Glu Gly Asn Glu His Leu Val Ser Gly Asn Tyr
    930                 935                 940

Arg Ala Asn Ile Thr Ile Thr Ser Thr Ile Lys Asp Asn Lys Gln Ala
945                 950                 955                 960
```

-continued

```
Ala Gly Pro Thr Leu Thr Lys Glu Leu Ala Leu Asn Val Leu Ser Leu
                965                 970                 975

Glu His His His His His His
            980


<210> SEQ ID NO 12
<211> LENGTH: 2514
<212> TYPE: DNA
<213> ORGANISM: Escherichia coli

<400> SEQUENCE: 12

atgaaaaaag tgatttttgt tttatccatg tttctatgtt ctcaggttta cgggcaatca     60

tggcatacga acgtagaggc tggttcaata aataaaacag agtcgatagg ccccatagac    120

cgaagtgctg ctgcatcgta tcctgctcat tatatatttc atgaacatgt tgctggttac    180

aataaagatc actctctttt tgacaggatg acgtttttat gtatgtcatc aacagatgca    240

tctaaaggtg catgtccgac aggagaaaac tccaaatcct ctcaagggga gactaatatt    300

aagctaatat ttactgaaaa gaaaagtctg gccagaaaaa cattaaactt aaaaggatat    360

aagagatttt tatatgaatc agatagatgc attcattatg tcgataaaat gaatctcaat    420

tctcatactg ttaaatgtgt aggttcattc acaagaggag tagatttcac tttatatatc    480

ccacaaggtg aaattgatgg gcttctaact ggaggtatat gggaggcaac actagagtta    540

cgagtcaaaa ggcattacga ctataatcat ggtacttaca aagttaatat cacagttgat    600

ttgacagaca aaggaaatat tcaggtctgg acaccaaagt ttcatagcga tcctagaatt    660

gatctgaatt tacgtcctga aggtaatggt aaatattctg gtagtaacgt gcttgagatg    720

tgtctctatg atggctatag tacacatagt caaagtatag aaatgaggtt tcaggatgac    780

tcacaaacag gaaataatga atataatctt ataaaaactg gagagccatt aaaaaaattg    840

ccatataaac tttctcttct tttaggagga cgagagtttt atccaaataa tggagaggct    900

tttactatta atgatacttc gtcattgttt ataaactgga atcgtattaa gtctgtatcc    960

ttaccacaga ttagtattcc agtactatgc tggccagcaa acttgacatt tatgtcagag   1020

ctaaataatc cagaagcggg tgagtattca ggaatactta acgtaacatt tactcctagt   1080

agttcaagcc tagacaataa acaagccgag aaaaatatca ctgtaactgc tagcgttgat   1140

ccaactatcg atctgatgca atctgatggc acagcgttac caagtgcagt taatattgca   1200

tatcttccag gagagaaaag atttgaatct gctcgtatca atacccaagt tcataccaat   1260

aataaaacta agggtattca gataaagctt actaatgata atgtggtaat gactaactta   1320

tctgatccaa gcaagactat tcctttagag gtttcattcg ctggcactaa gctgagcaca   1380

gctgcaacat ctattactgc cgatcaatta aattttggcg cagctggtgt agagacagtt   1440

tctgcaacta aggaactcgt tattaatgca ggaagcaccc agcaaactaa tattgtagct   1500

ggtaactatc aaggattggt gtcaattgtg cttactcaag aacctgacaa taaacaagcc   1560

gagaaaaata tcactgtaac tgctagcgtt gatccgacgg gcacattagc tattgatttt   1620

acgcctattg aaaatattta tgtaggtgcc aattatggta aagatattgg aacccttgtt   1680

ttcacaacaa atgatttaac agatattaca ttgatgtcat ctcgcagcgt tgttgatggt   1740

cgccagactg gtttttttac cttcatggac tcatcagcca cttacaaaat tagtacaaaa   1800

ctgggatcat cgaatgatgt aaacattcaa gaaattactc aaggagctaa aattactcct   1860

gttagtggag agaaaacttt gcctaaaaaa ttcactctta agctacatgc acacaggagt   1920

agcagtacag ttccaggtac gtatactgtt ggtcttaacg taaccagtaa cgttattgat   1980
```

```
aacaagcagg cagcggggcc cactctaacc aaagaactgg cattaaatgt gctttctcct   2040

gcagctctgg atgcaacttg ggctcctcag gataatttaa cattatccaa tactggcgtt   2100

tctaatactt tggtgggtgt tttgactctt tcaaatacca gtattgatac agttagcatt   2160

gcgagtacaa atgtttctga tacatctaag aatggtacag taacttttgc acatgagaca   2220

aataactctg ctagctttgc caccaccatt tcaacagata atgccaacat tacgttggat   2280

aaaaatgctg gaaatacgat tgttaaaact acaaatggga gtcagttgcc aactaattta   2340

ccacttaagt ttattaccac tgaaggtaac gaacatttag tttcaggtaa ttaccgtgca   2400

aatataacaa ttacttcgac aattaaagat aacaagcagg cggcaggtcc aaccctgact   2460

aaggagttag cgctgaacgt tctgagcctc gagcaccacc accaccacca ctga         2514
```

<210> SEQ ID NO 13
<211> LENGTH: 837
<212> TYPE: PRT
<213> ORGANISM: Escherichia coli

<400> SEQUENCE: 13

```
Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Asp Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
```

-continued

```
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Ser Leu Asp Asn Lys Gln
        355                 360                 365

Ala Glu Lys Asn Ile Thr Val Thr Ala Ser Val Asp Pro Thr Ile Asp
    370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
            420                 425                 430

Asp Asn Val Val Met Thr Asn Leu Ser Asp Pro Ser Lys Thr Ile Pro
        435                 440                 445

Leu Glu Val Ser Phe Ala Gly Thr Lys Leu Ser Thr Ala Ala Thr Ser
    450                 455                 460

Ile Thr Ala Asp Gln Leu Asn Phe Gly Ala Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
            500                 505                 510

Gln Glu Pro Asp Asn Lys Gln Ala Glu Lys Asn Ile Thr Val Thr Ala
        515                 520                 525

Ser Val Asp Pro Thr Gly Thr Leu Ala Ile Asp Phe Thr Pro Ile Glu
    530                 535                 540

Asn Ile Tyr Val Gly Ala Asn Tyr Gly Lys Asp Ile Gly Thr Leu Val
545                 550                 555                 560

Phe Thr Thr Asn Asp Leu Thr Asp Ile Thr Leu Met Ser Ser Arg Ser
                565                 570                 575

Val Val Asp Gly Arg Gln Thr Gly Phe Phe Thr Phe Met Asp Ser Ser
            580                 585                 590

Ala Thr Tyr Lys Ile Ser Thr Lys Leu Gly Ser Ser Asn Asp Val Asn
        595                 600                 605

Ile Gln Glu Ile Thr Gln Gly Ala Lys Ile Thr Pro Val Ser Gly Glu
    610                 615                 620

Lys Thr Leu Pro Lys Lys Phe Thr Leu Lys Leu His Ala His Arg Ser
625                 630                 635                 640

Ser Ser Thr Val Pro Gly Thr Tyr Thr Val Gly Leu Asn Val Thr Ser
                645                 650                 655

Asn Val Ile Asp Asn Lys Gln Ala Ala Gly Pro Thr Leu Thr Lys Glu
            660                 665                 670

Leu Ala Leu Asn Val Leu Ser Pro Ala Ala Leu Asp Ala Thr Trp Ala
        675                 680                 685

Pro Gln Asp Asn Leu Thr Leu Ser Asn Thr Gly Val Ser Asn Thr Leu
    690                 695                 700
```

Val Gly Val Leu Thr Leu Ser Asn Thr Ser Ile Asp Thr Val Ser Ile
705 710 715 720

Ala Ser Thr Asn Val Ser Asp Thr Ser Lys Asn Gly Thr Val Thr Phe
725 730 735

Ala His Glu Thr Asn Asn Ser Ala Ser Phe Ala Thr Thr Ile Ser Thr
740 745 750

Asp Asn Ala Asn Ile Thr Leu Asp Lys Asn Ala Gly Asn Thr Ile Val
755 760 765

Lys Thr Thr Asn Gly Ser Gln Leu Pro Thr Asn Leu Pro Leu Lys Phe
770 775 780

Ile Thr Thr Glu Gly Asn Glu His Leu Val Ser Gly Asn Tyr Arg Ala
785 790 795 800

Asn Ile Thr Ile Thr Ser Thr Ile Lys Asp Asn Lys Gln Ala Ala Gly
805 810 815

Pro Thr Leu Thr Lys Glu Leu Ala Leu Asn Val Leu Ser Leu Glu His
820 825 830

His His His His His
835

<210> SEQ ID NO 14
<211> LENGTH: 1845
<212> TYPE: DNA
<213> ORGANISM: Escherichia coli

<400> SEQUENCE: 14
atggcagtgg gcccaacgaa agatatgagt ttaggtgcaa atttaacttc agagcctaca 60
ttagctattg attttacgcc tattgaaaat atttatgtag gtgccaatta tggtaaagat 120
attggaaccc ttgttttcac aacaaatgat ttaacagata ttacattgat gtcatctcgc 180
agcgttgttg atggtcgcca gactggtttt tttaccttca tggactcatc agccacttac 240
aaaattagta caaaactggg atcatcgaat gatgtaaaca ttcaagaaat tactcaagga 300
gctaaaatta ctcctgttag tggagagaaa actttgccta aaaaattcac tcttaagcta 360
catgcacaca ggagtagcag tacagttcca ggtacgtata ctgttggtct taacgtaacc 420
agtaacgtta ttgataacaa gcaggcagcg gggcccactc taaccaaaga actggcatta 480
aatgtgcttt ctcctgcagc tctggatgca acttgggctc ctcaggataa tttaacatta 540
tccaatactg gcgtttctaa tactttggtg ggtgttttga ctctttcaaa taccagtatt 600
gatacagtta gcattgcgag tacaaatgtt tctgatacat ctaagaatgg tacagtaact 660
tttgcacatg agacaaataa ctctgctagc tttgccacca ccatttcaac agataatgcc 720
aacattacgt tggataaaaa tgctggaaat acgattgtta aaactacaaa tgggagtcag 780
ttgccaacta atttaccact taagtttatt accactgaag gtaacgaaca tttagtttca 840
ggtaattacc gtgcaaatat aacaattact tcgacaatta aagataacaa gcaggcggca 900
ggtccaaccc tgactaagga gttagcgctg aacgttttaa gcggctcaaa aagttttttt 960
gcacctgaac cacgaataca gccttctttt ggtgaaaatg ttggaaagga aggagcttta 1020
ttatttagtg tgaacttaac tgttcctgaa aatgtatccc aggtaacggt ctaccctgtt 1080
tatgatgaag attatgggtt aggacgacta gtaaataccg ctgatgcttc ccaatcaata 1140
atctaccaga ttgttgatga gaaagggaaa aaaatgttaa aagatcatgg tgcagaggtt 1200
acacctaatc aacaaataac ttttaaagcg ctgaattata ctagcgggga aaaaaaaata 1260
tctcctggaa tatataacga tcaggttatg gttggttact acgtcaacga caataaacaa 1320

```
ggaaactggc aatataaatc tctggatgta aatgtaaata ttgagcaaaa ttttattcca   1380

gatattgatt ccgctgttcg tataatacct gttaattacg attcggaccc gaaactggat   1440

tcacagttat atacggttga gatgacgatc cctgcaggtg taagcgcagt taaaatcgca   1500

ccaacagata gtctgacatc ttctggacag cagatcggaa agctggttaa tgtaaacaat   1560

ccagatcaaa atatgaatta ttatatcaga aaggattctg gcgctggtaa ctttatggca   1620

ggacaaaaag gatcctttcc tgtcaaagag aatacgtcat acacattctc agcaatttat   1680

actggtggcg aataccctaa tagcggatat tcgtctggta cttatgcagg aaatttgact   1740

gtatcatttt acagcaatga caataaacaa agaacagaaa tagcgactaa aaacttccca   1800

gtatcaacga ctatttcact cgagcaccac caccaccacc actga                   1845
```

```
<210> SEQ ID NO 15
<211> LENGTH: 614
<212> TYPE: PRT
<213> ORGANISM: Escherichia coli

<400> SEQUENCE: 15

Met Ala Val Gly Pro Thr Lys Asp Met Ser Leu Gly Ala Asn Leu Thr
1               5                   10                  15

Ser Glu Pro Thr Leu Ala Ile Asp Phe Thr Pro Ile Glu Asn Ile Tyr
            20                  25                  30

Val Gly Ala Asn Tyr Gly Lys Asp Ile Gly Thr Leu Val Phe Thr Thr
        35                  40                  45

Asn Asp Leu Thr Asp Ile Thr Leu Met Ser Ser Arg Ser Val Val Asp
    50                  55                  60

Gly Arg Gln Thr Gly Phe Phe Thr Phe Met Asp Ser Ser Ala Thr Tyr
65                  70                  75                  80

Lys Ile Ser Thr Lys Leu Gly Ser Ser Asn Asp Val Asn Ile Gln Glu
                85                  90                  95

Ile Thr Gln Gly Ala Lys Ile Thr Pro Val Ser Gly Glu Lys Thr Leu
            100                 105                 110

Pro Lys Lys Phe Thr Leu Lys Leu His Ala His Arg Ser Ser Ser Thr
        115                 120                 125

Val Pro Gly Thr Tyr Thr Val Gly Leu Asn Val Thr Ser Asn Val Ile
    130                 135                 140

Asp Asn Lys Gln Ala Ala Gly Pro Thr Leu Thr Lys Glu Leu Ala Leu
145                 150                 155                 160

Asn Val Leu Ser Pro Ala Ala Leu Asp Ala Thr Trp Ala Pro Gln Asp
                165                 170                 175

Asn Leu Thr Leu Ser Asn Thr Gly Val Ser Asn Thr Leu Val Gly Val
            180                 185                 190

Leu Thr Leu Ser Asn Thr Ser Ile Asp Thr Val Ser Ile Ala Ser Thr
        195                 200                 205

Asn Val Ser Asp Thr Ser Lys Asn Gly Thr Val Thr Phe Ala His Glu
    210                 215                 220

Thr Asn Asn Ser Ala Ser Phe Ala Thr Thr Ile Ser Thr Asp Asn Ala
225                 230                 235                 240

Asn Ile Thr Leu Asp Lys Asn Ala Gly Asn Thr Ile Val Lys Thr Thr
                245                 250                 255

Asn Gly Ser Gln Leu Pro Thr Asn Leu Pro Leu Lys Phe Ile Thr Thr
            260                 265                 270

Glu Gly Asn Glu His Leu Val Ser Gly Asn Tyr Arg Ala Asn Ile Thr
```

-continued

```
        275                 280                 285

Ile Thr Ser Thr Ile Lys Asp Asn Lys Gln Ala Ala Gly Pro Thr Leu
    290                 295                 300

Thr Lys Glu Leu Ala Leu Asn Val Leu Ser Gly Ser Lys Ser Phe Phe
305                 310                 315                 320

Ala Pro Glu Pro Arg Ile Gln Pro Ser Phe Gly Glu Asn Val Gly Lys
                325                 330                 335

Glu Gly Ala Leu Leu Phe Ser Val Asn Leu Thr Val Pro Glu Asn Val
            340                 345                 350

Ser Gln Val Thr Val Tyr Pro Val Tyr Asp Glu Asp Tyr Gly Leu Gly
        355                 360                 365

Arg Leu Val Asn Thr Ala Asp Ala Ser Gln Ser Ile Ile Tyr Gln Ile
    370                 375                 380

Val Asp Glu Lys Gly Lys Lys Met Leu Lys Asp His Gly Ala Glu Val
385                 390                 395                 400

Thr Pro Asn Gln Gln Ile Thr Phe Lys Ala Leu Asn Tyr Thr Ser Gly
                405                 410                 415

Glu Lys Lys Ile Ser Pro Gly Ile Tyr Asn Asp Gln Val Met Val Gly
            420                 425                 430

Tyr Tyr Val Asn Asp Asn Lys Gln Gly Asn Trp Gln Tyr Lys Ser Leu
        435                 440                 445

Asp Val Asn Val Asn Ile Glu Gln Asn Phe Ile Pro Asp Ile Asp Ser
    450                 455                 460

Ala Val Arg Ile Ile Pro Val Asn Tyr Asp Ser Asp Pro Lys Leu Asp
465                 470                 475                 480

Ser Gln Leu Tyr Thr Val Glu Met Thr Ile Pro Ala Gly Val Ser Ala
                485                 490                 495

Val Lys Ile Ala Pro Thr Asp Ser Leu Thr Ser Ser Gly Gln Gln Ile
            500                 505                 510

Gly Lys Leu Val Asn Val Asn Asn Pro Asp Gln Asn Met Asn Tyr Tyr
        515                 520                 525

Ile Arg Lys Asp Ser Gly Ala Gly Asn Phe Met Ala Gly Gln Lys Gly
    530                 535                 540

Ser Phe Pro Val Lys Glu Asn Thr Ser Tyr Thr Phe Ser Ala Ile Tyr
545                 550                 555                 560

Thr Gly Gly Glu Tyr Pro Asn Ser Gly Tyr Ser Ser Gly Thr Tyr Ala
                565                 570                 575

Gly Asn Leu Thr Val Ser Phe Tyr Ser Asn Asp Asn Lys Gln Arg Thr
            580                 585                 590

Glu Ile Ala Thr Lys Asn Phe Pro Val Ser Thr Thr Ile Ser Leu Glu
        595                 600                 605

His His His His His His
    610


<210> SEQ ID NO 16
<211> LENGTH: 2487
<212> TYPE: DNA
<213> ORGANISM: Escherichia coli

<400> SEQUENCE: 16

atgaataaaa ttttatttat ttttacattg ttttttttctt cagggttttt tacatttgcc      60

gtatcggcag ataaaaatcc cggaagtgaa aacatgacta atactattgg tccccatgac     120

aggggggat cttcccccat atataatatc ttaaattcct atcttacagc atacaatgga     180
```

-continued

```
agccatcatc tgtatgatag gatgagtttt ttatgtttgt cttctcaaaa tacactgaat    240
ggagcatgcc caagcagtga tgcccctggc actgctacaa ttgatggcga aacaaatata    300
acattacaat ttacggaaaa aagaagtcta attaaaagag aactgcaaat taaaggctat    360
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattaccttt tgggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt ttgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caaagaattt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaaatatt   1560
actgtaacag ctagtgtcga ccctgcaggg aattttattc cagatattga ttccgctgtt   1620
cgtataatac ctgttaatta cgattcggac ccgaaactgg attcacagtt atatacggtt   1680
gagatgacga tccctgcagg tgtaagcgca gttaaaatcg caccaacaga tagtctgaca   1740
tcttctggac agcagatcgg aaagctggtt aatgtaaaca atccagatca aaatatgaat   1800
tattatatca gaaaggattc tggcgctggt aactttatgg caggacaaaa aggatccttt   1860
cctgtcaaag agaatacgtc atacacattc tcagcaattt atactggtgg cgaataccct   1920
aatagcggat attcgtctgg tacttatgca ggaaatttga ctgtatcatt ttacagcaat   1980
gacaataaac aaagaacaga aatagcgact aaaaacttcc cagtatcaac gactatttca   2040
aaaagttttt ttgcacctga accacgaata cagccttctt ttggtgaaaa tgttggaaag   2100
gaaggagctt tattatttag tgtgaactta actgttcctg aaaatgtatc ccaggtaacg   2160
gtctaccctg tttatgatga agattatggg ttaggacgac tagtaaatac cgctgatgct   2220
tcccaatcaa taatctacca gattgttgat gagaaaggga aaaaaatgtt aaaagatcat   2280
ggtgcagagg ttacacctaa tcaacaaata acttttaaag cgctgaatta tactagcggg   2340
gaaaaaaaaa tatctcctgg aatatataac gatcaggtta tggttggtta ctacgtaaac   2400
gacaataaac aacgtaccga gattgccacc aagaattttc cggtgagcac caccatcagc   2460
ctcgagcacc accaccacca ccactga                                        2487
```

-continued

<210> SEQ ID NO 17
<211> LENGTH: 828
<212> TYPE: PRT
<213> ORGANISM: Escherichia coli

<400> SEQUENCE: 17

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380
```

-continued

```
Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Asn Phe Ile Pro Asp Ile Asp Ser Ala Val Arg Ile Ile Pro
    530                 535                 540

Val Asn Tyr Asp Ser Asp Pro Lys Leu Asp Ser Gln Leu Tyr Thr Val
545                 550                 555                 560

Glu Met Thr Ile Pro Ala Gly Val Ser Ala Val Lys Ile Ala Pro Thr
                565                 570                 575

Asp Ser Leu Thr Ser Ser Gly Gln Gln Ile Gly Lys Leu Val Asn Val
            580                 585                 590

Asn Asn Pro Asp Gln Asn Met Asn Tyr Tyr Ile Arg Lys Asp Ser Gly
        595                 600                 605

Ala Gly Asn Phe Met Ala Gly Gln Lys Gly Ser Phe Pro Val Lys Glu
    610                 615                 620

Asn Thr Ser Tyr Thr Phe Ser Ala Ile Tyr Thr Gly Gly Glu Tyr Pro
625                 630                 635                 640

Asn Ser Gly Tyr Ser Ser Gly Thr Tyr Ala Gly Asn Leu Thr Val Ser
                645                 650                 655

Phe Tyr Ser Asn Asp Asn Lys Gln Arg Thr Glu Ile Ala Thr Lys Asn
            660                 665                 670

Phe Pro Val Ser Thr Thr Ile Ser Lys Ser Phe Phe Ala Pro Glu Pro
        675                 680                 685

Arg Ile Gln Pro Ser Phe Gly Glu Asn Val Gly Lys Glu Gly Ala Leu
    690                 695                 700

Leu Phe Ser Val Asn Leu Thr Val Pro Glu Asn Val Ser Gln Val Thr
705                 710                 715                 720

Val Tyr Pro Val Tyr Asp Glu Asp Tyr Gly Leu Gly Arg Leu Val Asn
                725                 730                 735

Thr Ala Asp Ala Ser Gln Ser Ile Ile Tyr Gln Ile Val Asp Glu Lys
            740                 745                 750

Gly Lys Lys Met Leu Lys Asp His Gly Ala Glu Val Thr Pro Asn Gln
        755                 760                 765

Gln Ile Thr Phe Lys Ala Leu Asn Tyr Thr Ser Gly Glu Lys Lys Ile
    770                 775                 780

Ser Pro Gly Ile Tyr Asn Asp Gln Val Met Val Gly Tyr Tyr Val Asn
785                 790                 795                 800

Asp Asn Lys Gln Arg Thr Glu Ile Ala Thr Lys Asn Phe Pro Val Ser
```

805 810 815

Thr Thr Ile Ser Leu Glu His His His His His His
820 825

<210> SEQ ID NO 18
<211> LENGTH: 2490
<212> TYPE: DNA
<213> ORGANISM: Escherichia coli

<400> SEQUENCE: 18
atgaataaaa ttttatttat ttttacattg ttttttttctt cagggttttt tacatttgcc 60
gtatcggcag ataaaaatcc cggaagtgaa aacatgacta atactattgg tccccatgac 120
agggggggat cttcccccat atataatatc ttaaattcct atcttacagc atacaatgga 180
agccatcatc tgtatgatag gatgagtttt ttatgtttgt cttctcaaaa tacactgaat 240
ggagcatgcc caagcagtga tgcccctggc actgctacaa ttgatggcga aacaaatata 300
acattacaat ttacggaaaa aagaagtcta attaaaagag aactgcaaat taaaggctat 360
aaacaatttt tgttcaaaaa tgctaattgc ccatctaaac tagcacttaa ctcatctcat 420
tttcaatgta atagagaaca agcttcaggt gctactttat cgttatacat accagctggt 480
gaattaaata aattaccttt tgggggggtc tggaatgccg ttctgaagct aaatgtaaaa 540
agacgatatg atacaaccta tgggacttac actataaaca tcacagttaa tttaactgat 600
aagggaaata ttcagatatg gttaccacag ttcaaaagta acgctcgtgt cgatcttaac 660
ttgcgtccaa ctggtggtgg tacatatatc ggaagaaatt ctgttgatat gtgcttttat 720
gatggatata gtactaacag cagctcttta gagataagat ttcaggatga taattctaaa 780
tctgatggaa aattttatct aaagaaaata aatgatgact ccaaagaact tgtatacact 840
ttgtcacttc tcctggcagg taaaaattta acaccaacaa atggacaggc attaaatatt 900
aacactgctt ctctggaaac aaactggaat agaattacag ctgtcaccat gccagaaatc 960
agtgttccgg tgttgtgttg gcctggacgt ttgcaattgg atgcaaaagt gaaaaatccc 1020
gaggctggac aatatatggg gaatattaaa attactttca caccaagtag tcaaacactc 1080
gacaataaac aagtagagaa aaatattact gtaacagcta gtgttgatcc tgcaattgat 1140
cttttgcaag ctgatggcaa tgctctgcca tcagctgtaa agttagctta ttctcccgca 1200
tcaaaaactt ttgaaagtta cagagtaatg actcaagttc atacaaacga tgcaactaaa 1260
aaagtaattg ttaaacttgc tgatacacca cagcttacag atgttctgaa ttcaactgtt 1320
caaatgccta tcagtgtgtc atggggagga caagtattat ctacaacagc caaagaattt 1380
gaagctgctg ctttgggata ttctgcatcc ggtgtaaatg gcgtatcatc ttctcaagag 1440
ttagtaatta gcgctgcacc taaaactgcc ggtaccgccc caactgcagg aaactattca 1500
ggagtagtat ctcttgtaat gactttggga tccgacaata aacaagtaga gaaaaatatt 1560
actgtaacag ctagtgtcga ccctgcaggg tcaaaaagtt tttttgcacc tgaaccacga 1620
atacagcctt cttttggtga aaatgttgga aaggaaggag ctttattatt tagtgtgaac 1680
ttaactgttc ctgaaaatgt atcccaggta acggtctacc ctgtttatga tgaagattat 1740
gggttaggac gactagtaaa taccgctgat gcttcccaat caataatcta ccagattgtt 1800
gatgagaaag ggaaaaaaat gttaaaagat catggtgcag aggttacacc taatcaacaa 1860
ataactttta aagcgctgaa ttatactagc ggggaaaaaa aaatatctcc tggaatatat 1920
aacgatcagg ttatggttgg ttactacgtc aacgacaata aacaaggaaa ctggcaatat 1980

-continued

```
aaatctctgg atgtaaatgt aaatattgag caaaatttta ttccagatat tgattccgct   2040

gttcgtataa tacctgttaa ttacgattcg gacccgaaac tggattcaca gttatatacg   2100

gttgagatga cgatccctgc aggtgtaagc gcagttaaaa tcgcaccaac agatagtctg   2160

acatcttctg gacagcagat cggaaagctg gttaatgtaa acaatccaga tcaaaatatg   2220

aattattata tcagaaagga ttctggcgct ggtaacttta tggcaggaca aaaaggatcc   2280

tttcctgtca aagagaatac gtcatacaca ttctcagcaa tttatactgg tggcgaatac   2340

cctaatagcg gatattcgtc tggtacttat gcaggaaatt tgactgtatc attttacagc   2400

aatgacaata aacaaggcaa ttggcagtac aagagcctcg acgtgaacgt gaacatcgaa   2460

cagctcgagc accaccacca ccaccactga                                   2490
```

<210> SEQ ID NO 19
<211> LENGTH: 829
<212> TYPE: PRT
<213> ORGANISM: Escherichia coli

<400> SEQUENCE: 19

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285
```

-continued

```
Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Ser Lys Ser Phe Phe Ala Pro Glu Pro Arg Ile Gln Pro Ser
    530                 535                 540

Phe Gly Glu Asn Val Gly Lys Glu Gly Ala Leu Leu Phe Ser Val Asn
545                 550                 555                 560

Leu Thr Val Pro Glu Asn Val Ser Gln Val Thr Val Tyr Pro Val Tyr
                565                 570                 575

Asp Glu Asp Tyr Gly Leu Gly Arg Leu Val Asn Thr Ala Asp Ala Ser
            580                 585                 590

Gln Ser Ile Ile Tyr Gln Ile Val Asp Glu Lys Gly Lys Lys Met Leu
        595                 600                 605

Lys Asp His Gly Ala Glu Val Thr Pro Asn Gln Gln Ile Thr Phe Lys
    610                 615                 620

Ala Leu Asn Tyr Thr Ser Gly Glu Lys Lys Ile Ser Pro Gly Ile Tyr
625                 630                 635                 640

Asn Asp Gln Val Met Val Gly Tyr Tyr Val Asn Asp Asn Lys Gln Gly
                645                 650                 655

Asn Trp Gln Tyr Lys Ser Leu Asp Val Asn Val Asn Ile Glu Gln Asn
            660                 665                 670

Phe Ile Pro Asp Ile Asp Ser Ala Val Arg Ile Ile Pro Val Asn Tyr
        675                 680                 685

Asp Ser Asp Pro Lys Leu Asp Ser Gln Leu Tyr Thr Val Glu Met Thr
    690                 695                 700
```

```
Ile Pro Ala Gly Val Ser Ala Val Lys Ile Ala Pro Thr Asp Ser Leu
705                 710                 715                 720

Thr Ser Ser Gly Gln Gln Ile Gly Lys Leu Val Asn Val Asn Asn Pro
                725                 730                 735

Asp Gln Asn Met Asn Tyr Tyr Ile Arg Lys Asp Ser Gly Ala Gly Asn
            740                 745                 750

Phe Met Ala Gly Gln Lys Gly Ser Phe Pro Val Lys Glu Asn Thr Ser
        755                 760                 765

Tyr Thr Phe Ser Ala Ile Tyr Thr Gly Gly Glu Tyr Pro Asn Ser Gly
    770                 775                 780

Tyr Ser Ser Gly Thr Tyr Ala Gly Asn Leu Thr Val Ser Phe Tyr Ser
785                 790                 795                 800

Asn Asp Asn Lys Gln Gly Asn Trp Gln Tyr Lys Ser Leu Asp Val Asn
                805                 810                 815

Val Asn Ile Glu Gln Leu Glu His His His His His His
            820                 825


<210> SEQ ID NO 20
<211> LENGTH: 3405
<212> TYPE: DNA
<213> ORGANISM: Escherichia coli

<400> SEQUENCE: 20

atgaataaaa ttttatttat ttttacattg tttttttctt cagggttttt tacatttgcc      60

gtatcggcag ataaaaatcc cggaagtgaa aacatgacta atactattgg tccccatgac     120

aggggggggat cttcccccat atataatatc ttaaattcct atcttacagc atacaatgga    180

agccatcatc tgtatgatag gatgagtttt ttatgtttgt cttctcaaaa tacactgaat     240

ggagcatgcc caagcagtga tgcccctggc actgctacaa ttgatggcga aacaaatata     300

acattacaat ttacggaaaa aagaagtcta attaaaagag aactgcaaat taaaggctat     360

aaacaatttt tgttcaaaaa tgctaattgc ccatctaaac tagcacttaa ctcatctcat     420

tttcaatgta atagagaaca agcttcaggt gctactttat cgttatacat accagctggt     480

gaattaaata aattaccttt tgggggggtc tggaatgccg ttctgaagct aaatgtaaaa     540

agacgatatg atacaaccta tgggacttac actataaaca tcacagttaa tttaactgat     600

aagggaaata ttcagatatg gttaccacag ttcaaaagta acgctcgtgt cgatcttaac     660

ttgcgtccaa ctggtggtgg tacatatatc ggaagaaatt ctgttgatat gtgcttttat     720

gatggatata gtactaacag cagctcttta gagataagat ttcaggatga taattctaaa     780

tctgatggaa aattttatct aaagaaaata aatgatgact ccaaagaact tgtatacact     840

ttgtcacttc tcctggcagg taaaaattta acaccaacaa atggacaggc attaaatatt     900

aacactgctt ctctggaaac aaactggaat agaattacag ctgtcaccat gccagaaatc     960

agtgttccgg tgttgtgttg gcctggacgt ttgcaattgg atgcaaaagt gaaaaatccc    1020

gaggctggac aatatatggg gaatattaaa attactttca caccaagtag tcaaacactc    1080

gacaataaac aagtagagaa aaatattact gtaacagcta gtgttgatcc tgcaattgat    1140

cttttgcaag ctgatggcaa tgctctgcca tcagctgtaa agttagctta ttctcccgca    1200

tcaaaaactt ttgaaagtta cagagtaatg actcaagttc atacaaacga tgcaactaaa    1260

aaagtaattg ttaaacttgc tgatacacca cagcttacag atgttctgaa ttcaactgtt    1320

caaatgccta tcagtgtgtc atggggagga caagtattat ctacaacagc caaagaattt    1380

gaagctgctg ctttgggata ttctgcatcc ggtgtaaatg gcgtatcatc ttctcaagag    1440
```

-continued

```
ttagtaatta gcgctgcacc taaaactgcc ggtaccgccc caactgcagg aaactattca   1500
ggagtagtat ctcttgtaat gactttggga tccgacaata aacaagtaga gaaaaatatt   1560
actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accggaacgg caggtgtttc gaatagtaaa gaattagtaa ttggagcaac tacatccgga   1920
actgcaccaa gtgcaggtaa gtatcaaggc gtcgtttcca ttgtaatgac tcaatcgacc   1980
gacacagccg cgcctgttcc tgacaataaa caagtagaga aaaatattac tgtgacagcc   2040
agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
gaaaaaaata tcactgtaac agctagtgtt gatcctacgg gcgagcaaaa ttttattcca   2520
gatattgatt ccgctgttcg tataatacct gttaattacg attcggatcc gaaactgaat   2580
tcacagttat atacggttga gatgacgatc cctgcaggtg taagcgcagt taaaatcgta   2640
ccaacagata gtctgacatc ttctggacag cagatcggaa agctggttaa tgtaaacaat   2700
ccagatcaaa atatgaatta ttatatcaga aaggattctg gcgctggtaa gtttatggca   2760
gggcaaaaag gatccttttc tgtcaaagag aatacgtcat acacattctc agcaatttat   2820
actggtggcg aataccctaa tagcggatat tcgtctggta cttatgcagg acatttgact   2880
gtatcatttt acagcaatga caataaacaa agaacagaaa tagcgactaa aaacttccca   2940
gtatcaacga ctatttcaaa aagttttttt gcgcctgaac cacaaatcca gccttctttt   3000
ggtaaaaatg ttggaaagga aggagattta ttatttagtg tgagcttaat tgttcctgaa   3060
aatgtatccc aggtaacggt ctaccctgtt tatgatgaag attatggatt aggacgactc   3120
gtaaataccg ctgatgattc ccaatcaata atctaccaga ttgttgatga taaagggaaa   3180
aaaatgttaa aagatcatgg tacagaggtt acgcctaatc aacaaataac ttttaaagcg   3240
ctgaattata ctagcggaga taaagaaata cctcctggga tatataacga tcaggttatg   3300
gttggttact acgtaaacga caataaacaa ggaaactggc aatataaatc tctggatgta   3360
aatgtaaata ttgagcaact cgagcaccac caccaccacc actga                  3405
```

<210> SEQ ID NO 21
<211> LENGTH: 1134
<212> TYPE: PRT
<213> ORGANISM: Escherichia coli

<400> SEQUENCE: 21

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
```

-continued

```
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445
```

-continued

```
Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Thr Ile Asp Ile Leu Gln Ala Asn Gly Ser Ala Leu Pro Thr Ala Val
    530                 535                 540

Asp Leu Thr Tyr Leu Pro Gly Ala Lys Thr Phe Glu Asn Tyr Ser Val
545                 550                 555                 560

Leu Thr Gln Ile Tyr Thr Asn Asp Pro Ser Lys Gly Leu Asp Val Arg
                565                 570                 575

Leu Val Asp Thr Pro Lys Leu Thr Asn Ile Leu Gln Pro Thr Ser Thr
            580                 585                 590

Ile Pro Leu Thr Val Ser Trp Ala Gly Lys Thr Leu Ser Thr Ser Ala
        595                 600                 605

Gln Lys Ile Ala Val Gly Asp Leu Gly Phe Gly Ser Thr Gly Thr Ala
    610                 615                 620

Gly Val Ser Asn Ser Lys Glu Leu Val Ile Gly Ala Thr Thr Ser Gly
625                 630                 635                 640

Thr Ala Pro Ser Ala Gly Lys Tyr Gln Gly Val Val Ser Ile Val Met
                645                 650                 655

Thr Gln Ser Thr Asp Thr Ala Ala Pro Val Pro Asp Asn Lys Gln Val
            660                 665                 670

Glu Lys Asn Ile Thr Val Thr Ala Ser Val Asp Pro Thr Ile Asp Ile
        675                 680                 685

Leu Gln Ala Asp Gly Ser Ser Leu Pro Thr Ala Val Glu Leu Thr Tyr
    690                 695                 700

Ser Pro Ala Ala Ser Arg Phe Glu Asn Tyr Lys Ile Ala Thr Lys Val
705                 710                 715                 720

His Thr Asn Val Ile Asn Lys Asn Val Leu Val Lys Leu Val Asn Asp
                725                 730                 735

Pro Lys Leu Thr Asn Val Leu Asp Ser Thr Lys Gln Leu Pro Ile Thr
            740                 745                 750

Val Ser Tyr Gly Gly Lys Thr Leu Ser Thr Ala Asp Val Thr Phe Glu
        755                 760                 765

Pro Ala Glu Leu Asn Phe Gly Thr Ser Gly Val Thr Gly Val Ser Ser
    770                 775                 780

Ser Gln Asp Leu Val Ile Gly Ala Thr Thr Ala Gln Ala Pro Thr Ala
785                 790                 795                 800

Gly Asn Tyr Ser Gly Val Val Ser Ile Leu Met Thr Leu Ala Ser Asp
                805                 810                 815

Asn Lys Gln Val Glu Lys Asn Ile Thr Val Thr Ala Ser Val Asp Pro
            820                 825                 830

Thr Gly Glu Gln Asn Phe Ile Pro Asp Ile Asp Ser Ala Val Arg Ile
        835                 840                 845

Ile Pro Val Asn Tyr Asp Ser Asp Pro Lys Leu Asn Ser Gln Leu Tyr
    850                 855                 860
```

-continued

```
Thr Val Glu Met Thr Ile Pro Ala Gly Val Ser Ala Val Lys Ile Val
865                 870                 875                 880

Pro Thr Asp Ser Leu Thr Ser Ser Gly Gln Gln Ile Gly Lys Leu Val
                885                 890                 895

Asn Val Asn Asn Pro Asp Gln Asn Met Asn Tyr Tyr Ile Arg Lys Asp
            900                 905                 910

Ser Gly Ala Gly Lys Phe Met Ala Gly Gln Lys Gly Ser Phe Ser Val
        915                 920                 925

Lys Glu Asn Thr Ser Tyr Thr Phe Ser Ala Ile Tyr Thr Gly Gly Glu
    930                 935                 940

Tyr Pro Asn Ser Gly Tyr Ser Ser Gly Thr Tyr Ala Gly His Leu Thr
945                 950                 955                 960

Val Ser Phe Tyr Ser Asn Asp Asn Lys Gln Arg Thr Glu Ile Ala Thr
                965                 970                 975

Lys Asn Phe Pro Val Ser Thr Thr Ile Ser Lys Ser Phe Phe Ala Pro
            980                 985                 990

Glu Pro Gln Ile Gln Pro Ser Phe  Gly Lys Asn Val Gly  Lys Glu Gly
        995                 1000                 1005

Asp Leu  Leu Phe Ser Val Ser  Leu Ile Val Pro Glu  Asn Val Ser
    1010                 1015                 1020

Gln Val  Thr Val Tyr Pro Val  Tyr Asp Glu Asp Tyr  Gly Leu Gly
    1025                 1030                 1035

Arg Leu  Val Asn Thr Ala Asp  Asp Ser Gln Ser Ile  Ile Tyr Gln
    1040                 1045                 1050

Ile Val  Asp Asp Lys Gly Lys  Lys Met Leu Lys Asp  His Gly Thr
    1055                 1060                 1065

Glu Val  Thr Pro Asn Gln Gln  Ile Thr Phe Lys Ala  Leu Asn Tyr
    1070                 1075                 1080

Thr Ser  Gly Asp Lys Glu Ile  Pro Pro Gly Ile Tyr  Asn Asp Gln
    1085                 1090                 1095

Val Met  Val Gly Tyr Tyr Val  Asn Asp Asn Lys Gln  Gly Asn Trp
    1100                 1105                 1110

Gln Tyr  Lys Ser Leu Asp Val  Asn Val Asn Ile Glu  Gln Leu Glu
    1115                 1120                 1125

His His  His His His His
    1130
```

<210> SEQ ID NO 22
<211> LENGTH: 3342
<212> TYPE: DNA
<213> ORGANISM: Escherichia coli

<400> SEQUENCE: 22

```
atggcagata aaaatcccgg aagtgaaaac atgactaata ctattggtcc ccatgacagg      60

gggggatctt cccccatata taatatctta aattcctatc ttacagcata caatggaagc     120

catcatctgt atgataggat gagtttttta tgtttgtctt ctcaaaatac actgaatgga     180

gcatgcccaa gcagtgatgc ccctggcact gctacaattg atggcgaaac aaatataaca     240

ttacaattta cggaaaaaag aagtctaatt aaaagagaac tgcaaattaa aggctataaa     300

caatttttgt tcaaaaatgc taattgccca tctaaactag cacttaactc atctcatttt     360

caatgtaata gagaacaagc ttcaggtgct actttatcgt tatacatacc agctggtgaa     420

ttaaataaat taccttttgg gggggtctgg aatgccgttc tgaagctaaa tgtaaaaaga     480

cgatatgata caacctatgg gacttacact ataaacatca cagttaattt aactgataag     540
```

```
ggaaatattc agatatggtt accacagttc aaaagtaacg ctcgtgtcga tcttaacttg    600
cgtccaactg gtggtggtac atatatcgga agaaattctg ttgatatgtg cttttatgat    660
ggatatagta ctaacagcag ctctttagag ataagatttc aggatgataa ttctaaatct    720
gatggaaaat tttatctaaa gaaaataaat gatgactcca aagaacttgt atacactttg    780
tcacttctcc tggcaggtaa aaatttaaca ccaacaaatg gacaggcatt aaatattaac    840
actgcttctc tggaaacaaa ctggaataga attacagctg tcaccatgcc agaaatcagt    900
gttccggtgt tgtgttggcc tggacgtttg caattggatg caaaagtgaa aaatcccgag    960
gctggacaat atatggggaa tattaaaatt actttcacac caagtagtca aacactcgac   1020
aataaacaag tagagaaaaa tattactgta acagctagtg ttgatcctgc aattgatctt   1080
ttgcaagctg atggcaatgc tctgccatca gctgtaaagt tagcttattc tcccgcatca   1140
aaaacttttg aaagttacag agtaatgact caagttcata caaacgatgc aactaaaaaa   1200
gtaattgtta aacttgctga tacaccacag cttacagatg ttctgaattc aactgttcaa   1260
atgcctatca gtgtgtcatg gggaggacaa gtattatcta caacagccaa agaatttgaa   1320
gctgctgctt tgggatattc tgcatccggt gtaaatggcg tatcatcttc tcaagagtta   1380
gtaattagcg ctgcacctaa aactgccggt accgccccaa ctgcaggaaa ctattcagga   1440
gtagtatctc ttgtaatgac tttgggatcc gacaataaac aagtagagaa aaatattact   1500
gtaacagcta gtgtcgaccc tactattgat attcttcaag caaatggttc tgcgctaccg   1560
acagctgtag atttaactta tctacctggt gcaaaaactt ttgaaaatta cagtgttcta   1620
acccagattt acacaaatga cccttcaaaa ggtttagatg ttcgactggt tgatacaccg   1680
aaacttacaa atattttgca accgacatct accattcctc ttactgtctc atgggcaggg   1740
aagacattaa gtacaagtgc tcagaagatt gcagttggcg atctgggttt tggttccacc   1800
ggaacggcag gtgtttcgaa tagtaaagaa ttagtaattg gagcaactac atccggaact   1860
gcaccaagtg caggtaagta tcaaggcgtc gtttccattg taatgactca atcgaccgac   1920
acagccgcgc ctgttcctga caataaacaa gtagagaaaa atattactgt gacagccagt   1980
gttgatccta ctattgacat tttgcaagct gatggtagta gtttacctac tgctgtagaa   2040
ttaacctatt cacctgcggc aagtcgtttt gaaaattata aaatcgcaac taaagttcat   2100
acaaatgtta taaataaaaa tgtactagtt aagcttgtaa atgatccaaa acttacaaat   2160
gttttggatt ctacaaaaca actccccatt actgtatcat atggaggaaa gactctatca   2220
accgcagatg tgacttttga acctgcagaa ttaaattttg gaacgtcagg tgtaactggt   2280
gtatcttctt cccaagattt agtgattggt gcgactacag cacaagcacc aacggcggga   2340
aattatagtg gggtcgtttc tatcttaatg accttagcat cagacaataa acaagtggaa   2400
aaaaatatca ctgtaacagc tagtgttgat cctacgggcg agcaaaattt tattccagat   2460
attgattccg ctgttcgtat aatacctgtt aattacgatt cggatccgaa actgaattca   2520
cagttatata cggttgagat gacgatccct gcaggtgtaa gcgcagttaa aatcgtacca   2580
acagatagtc tgacatcttc tggacagcag atcggaaagc tggttaatgt aaacaatcca   2640
gatcaaaata tgaattatta tatcagaaag gattctggcg ctggtaagtt tatggcaggg   2700
caaaaaggat ccttttctgt caaagagaat acgtcataca cattctcagc aatttatact   2760
ggtggcgaat accctaatag cggatattcg tctggtactt atgcaggaca tttgactgta   2820
tcattttaca gcaatgacaa taaacaaaga acagaaatag cgactaaaaa cttcccagta   2880
```

```
tcaacgacta tttcaaaaag tttttttgcg cctgaaccac aaatccagcc ttcttttggt   2940

aaaaatgttg gaaaggaagg agatttatta tttagtgtga gcttaattgt tcctgaaaat   3000

gtatcccagg taacggtcta ccctgtttat gatgaagatt atggattagg acgactcgta   3060

aataccgctg atgattccca atcaataatc taccagattg ttgatgataa agggaaaaaa   3120

atgttaaaag atcatggtac agaggttacg cctaatcaac aaataacttt taaagcgctg   3180

aattatacta gcggagataa agaaatacct cctgggatat ataacgatca ggttatggtt   3240

ggttactacg taaacgacaa taaacaagga aactggcaat ataaatctct ggatgtaaat   3300

gtaaatattg agcaactcga gcaccaccac caccaccact ga                      3342


<210> SEQ ID NO 23
<211> LENGTH: 1113
<212> TYPE: PRT
<213> ORGANISM: Escherichia coli

<400> SEQUENCE: 23

Met Ala Asp Lys Asn Pro Gly Ser Glu Asn Met Thr Asn Thr Ile Gly
1               5                   10                  15

Pro His Asp Arg Gly Gly Ser Ser Pro Ile Tyr Asn Ile Leu Asn Ser
            20                  25                  30

Tyr Leu Thr Ala Tyr Asn Gly Ser His His Leu Tyr Asp Arg Met Ser
        35                  40                  45

Phe Leu Cys Leu Ser Ser Gln Asn Thr Leu Asn Gly Ala Cys Pro Ser
    50                  55                  60

Ser Asp Ala Pro Gly Thr Ala Thr Ile Asp Gly Glu Thr Asn Ile Thr
65                  70                  75                  80

Leu Gln Phe Thr Glu Lys Arg Ser Leu Ile Lys Arg Glu Leu Gln Ile
                85                  90                  95

Lys Gly Tyr Lys Gln Phe Leu Phe Lys Asn Ala Asn Cys Pro Ser Lys
            100                 105                 110

Leu Ala Leu Asn Ser Ser His Phe Gln Cys Asn Arg Glu Gln Ala Ser
        115                 120                 125

Gly Ala Thr Leu Ser Leu Tyr Ile Pro Ala Gly Glu Leu Asn Lys Leu
    130                 135                 140

Pro Phe Gly Gly Val Trp Asn Ala Val Leu Lys Leu Asn Val Lys Arg
145                 150                 155                 160

Arg Tyr Asp Thr Thr Tyr Gly Thr Tyr Thr Ile Asn Ile Thr Val Asn
                165                 170                 175

Leu Thr Asp Lys Gly Asn Ile Gln Ile Trp Leu Pro Gln Phe Lys Ser
            180                 185                 190

Asn Ala Arg Val Asp Leu Asn Leu Arg Pro Thr Gly Gly Gly Thr Tyr
        195                 200                 205

Ile Gly Arg Asn Ser Val Asp Met Cys Phe Tyr Asp Gly Tyr Ser Thr
    210                 215                 220

Asn Ser Ser Ser Leu Glu Ile Arg Phe Gln Asp Asp Asn Ser Lys Ser
225                 230                 235                 240

Asp Gly Lys Phe Tyr Leu Lys Lys Ile Asn Asp Asp Ser Lys Glu Leu
                245                 250                 255

Val Tyr Thr Leu Ser Leu Leu Leu Ala Gly Lys Asn Leu Thr Pro Thr
            260                 265                 270

Asn Gly Gln Ala Leu Asn Ile Asn Thr Ala Ser Leu Glu Thr Asn Trp
        275                 280                 285

Asn Arg Ile Thr Ala Val Thr Met Pro Glu Ile Ser Val Pro Val Leu
```

-continued

```
    290                 295                 300

Cys Trp Pro Gly Arg Leu Gln Leu Asp Ala Lys Val Lys Asn Pro Glu
305                 310                 315                 320

Ala Gly Gln Tyr Met Gly Asn Ile Lys Ile Thr Phe Thr Pro Ser Ser
                325                 330                 335

Gln Thr Leu Asp Asn Lys Gln Val Glu Lys Asn Ile Thr Val Thr Ala
            340                 345                 350

Ser Val Asp Pro Ala Ile Asp Leu Leu Gln Ala Asp Gly Asn Ala Leu
        355                 360                 365

Pro Ser Ala Val Lys Leu Ala Tyr Ser Pro Ala Ser Lys Thr Phe Glu
    370                 375                 380

Ser Tyr Arg Val Met Thr Gln Val His Thr Asn Asp Ala Thr Lys Lys
385                 390                 395                 400

Val Ile Val Lys Leu Ala Asp Thr Pro Gln Leu Thr Asp Val Leu Asn
                405                 410                 415

Ser Thr Val Gln Met Pro Ile Ser Val Ser Trp Gly Gly Gln Val Leu
            420                 425                 430

Ser Thr Thr Ala Lys Glu Phe Glu Ala Ala Ala Leu Gly Tyr Ser Ala
        435                 440                 445

Ser Gly Val Asn Gly Val Ser Ser Ser Gln Glu Leu Val Ile Ser Ala
    450                 455                 460

Ala Pro Lys Thr Ala Gly Thr Ala Pro Thr Ala Gly Asn Tyr Ser Gly
465                 470                 475                 480

Val Val Ser Leu Val Met Thr Leu Gly Ser Asp Asn Lys Gln Val Glu
                485                 490                 495

Lys Asn Ile Thr Val Thr Ala Ser Val Asp Pro Thr Ile Asp Ile Leu
            500                 505                 510

Gln Ala Asn Gly Ser Ala Leu Pro Thr Ala Val Asp Leu Thr Tyr Leu
        515                 520                 525

Pro Gly Ala Lys Thr Phe Glu Asn Tyr Ser Val Leu Thr Gln Ile Tyr
    530                 535                 540

Thr Asn Asp Pro Ser Lys Gly Leu Asp Val Arg Leu Val Asp Thr Pro
545                 550                 555                 560

Lys Leu Thr Asn Ile Leu Gln Pro Thr Ser Thr Ile Pro Leu Thr Val
                565                 570                 575

Ser Trp Ala Gly Lys Thr Leu Ser Thr Ser Ala Gln Lys Ile Ala Val
            580                 585                 590

Gly Asp Leu Gly Phe Gly Ser Thr Gly Thr Ala Gly Val Ser Asn Ser
        595                 600                 605

Lys Glu Leu Val Ile Gly Ala Thr Thr Ser Gly Thr Ala Pro Ser Ala
    610                 615                 620

Gly Lys Tyr Gln Gly Val Val Ser Ile Val Met Thr Gln Ser Thr Asp
625                 630                 635                 640

Thr Ala Ala Pro Val Pro Asp Asn Lys Gln Val Glu Lys Asn Ile Thr
                645                 650                 655

Val Thr Ala Ser Val Asp Pro Thr Ile Asp Ile Leu Gln Ala Asp Gly
            660                 665                 670

Ser Ser Leu Pro Thr Ala Val Glu Leu Thr Tyr Ser Pro Ala Ala Ser
        675                 680                 685

Arg Phe Glu Asn Tyr Lys Ile Ala Thr Lys Val His Thr Asn Val Ile
    690                 695                 700

Asn Lys Asn Val Leu Val Lys Leu Val Asn Asp Pro Lys Leu Thr Asn
705                 710                 715                 720
```

```
Val Leu Asp Ser Thr Lys Gln Leu Pro Ile Thr Val Ser Tyr Gly Gly
                725                 730                 735

Lys Thr Leu Ser Thr Ala Asp Val Thr Phe Glu Pro Ala Glu Leu Asn
            740                 745                 750

Phe Gly Thr Ser Gly Val Thr Gly Val Ser Ser Ser Gln Asp Leu Val
        755                 760                 765

Ile Gly Ala Thr Thr Ala Gln Ala Pro Thr Ala Gly Asn Tyr Ser Gly
    770                 775                 780

Val Val Ser Ile Leu Met Thr Leu Ala Ser Asp Asn Lys Gln Val Glu
785                 790                 795                 800

Lys Asn Ile Thr Val Thr Ala Ser Val Asp Pro Thr Gly Glu Gln Asn
                805                 810                 815

Phe Ile Pro Asp Ile Asp Ser Ala Val Arg Ile Ile Pro Val Asn Tyr
            820                 825                 830

Asp Ser Asp Pro Lys Leu Asn Ser Gln Leu Tyr Thr Val Glu Met Thr
        835                 840                 845

Ile Pro Ala Gly Val Ser Ala Val Lys Ile Val Pro Thr Asp Ser Leu
    850                 855                 860

Thr Ser Ser Gly Gln Gln Ile Gly Lys Leu Val Asn Val Asn Asn Pro
865                 870                 875                 880

Asp Gln Asn Met Asn Tyr Tyr Ile Arg Lys Asp Ser Gly Ala Gly Lys
                885                 890                 895

Phe Met Ala Gly Gln Lys Gly Ser Phe Ser Val Lys Glu Asn Thr Ser
            900                 905                 910

Tyr Thr Phe Ser Ala Ile Tyr Thr Gly Gly Glu Tyr Pro Asn Ser Gly
        915                 920                 925

Tyr Ser Ser Gly Thr Tyr Ala Gly His Leu Thr Val Ser Phe Tyr Ser
    930                 935                 940

Asn Asp Asn Lys Gln Arg Thr Glu Ile Ala Thr Lys Asn Phe Pro Val
945                 950                 955                 960

Ser Thr Thr Ile Ser Lys Ser Phe Phe Ala Pro Glu Pro Gln Ile Gln
                965                 970                 975

Pro Ser Phe Gly Lys Asn Val Gly Lys Glu Gly Asp Leu Leu Phe Ser
            980                 985                 990

Val Ser Leu Ile Val Pro Glu Asn  Val Ser Gln Val Thr  Val Tyr Pro
        995                 1000                1005

Val Tyr  Asp Glu Asp Tyr Gly  Leu Gly Arg Leu Val  Asn Thr Ala
    1010                1015                1020

Asp Asp  Ser Gln Ser Ile Ile  Tyr Gln Ile Val Asp  Asp Lys Gly
    1025                1030                1035

Lys Lys  Met Leu Lys Asp His  Gly Thr Glu Val Thr  Pro Asn Gln
    1040                1045                1050

Gln Ile  Thr Phe Lys Ala Leu  Asn Tyr Thr Ser Gly  Asp Lys Glu
    1055                1060                1065

Ile Pro  Pro Gly Ile Tyr Asn  Asp Gln Val Met Val  Gly Tyr Tyr
    1070                1075                1080

Val Asn  Asp Asn Lys Gln Gly  Asn Trp Gln Tyr Lys  Ser Leu Asp
    1085                1090                1095

Val Asn  Val Asn Ile Glu Gln  Leu Glu His His His  His His His
    1100                1105                1110
```

<210> SEQ ID NO 24
<211> LENGTH: 2943

<212> TYPE: DNA
<213> ORGANISM: Escherichia coli

<400> SEQUENCE: 24
atgaaaaaga tatttatttt tttgtctatc atattttctg cggtggtcag tgccgggcga 60
tacccggaaa ctacagtagg taatctgacg aagagttttc aagcccctcg tcaggataga 120
agcgtacaat caccaatata taacatcttt acgaatcatg tggctggata tagtttgagt 180
cataacttat atgacaggat tgttttttta tgtacatcct cgtcgaatcc ggttaatggt 240
gcttgcccaa ccattggaac atctggagtt caatacggta ctacaaccat aaccttgcag 300
tttacagaaa aaagaagtct gataaaaaga aatattaatc ttgcaggtaa taagaaacca 360
atatgggaga atcagagttg cgacactagc aatctaatgg tgttgaattc gaagtcttgg 420
tcctgtgggg cttacggaaa tgctaacgga acacttctaa atctgtatat ccctgcagga 480
gaaatcaaca aattgccttt tggagggata tgggaggcaa ctctgatctt acgcttatca 540
agatatggcg aagtcagtag cacccattac ggcaattata ccgtaaatat tacggttgat 600
ttaactgata aaggtaatat tcaggtatgg cttccagggt ttcacagcaa cccgcgtgta 660
gacctgaatc tgcaccctat cggtaattat aaatatagtg gtagtaattc actcgacatg 720
tgtttctatg atggatatag tacaaacagt gatagcatgg taataaagtt ccaggatgat 780
aatcctacct attcatctga atataatctt tataagatag ggggcactga aaaattaccc 840
tatgctgttt cactgcttat gggagaaaaa atattttatc cagtgaatgg tcaatcattt 900
actatcaatg acagtagtgt actcgaaaca aactggaatc gagtaaccgc agttgctatg 960
ccggaagtta atgttccagt attatgctgg ccagcaagat tgctattaaa tgctgatgta 1020
aatgctcccg atgcaggaca gtattcagga cagatatata taacatttac acccagtgtc 1080
gaaaatttag gcggtggagt cgaaaaaaat attactgtga gggcaagtgt tgaccctaaa 1140
cttgatcttc tgcaagcaga tggaacttca ctgccggact ctatcgcatt aacctattct 1200
tcggcttcaa ataattttga agtttactct cttaatactg ctattcatac aaatgacaaa 1260
agcaagggag ttgtagtgaa gctgtcagct tcaccagttc tgtccaatat tatgaagcca 1320
aactcgcaaa ttccgatgaa agtgactttg gggggggaaga cgctgaatac aactgatact 1380
gagtttactg ttgatactct gaactttggt acatctggtg ttgaaaacgt ttcttccact 1440
caacagctta cgattcatgc agacacacaa ggaactgcgc ctgaggcagg caattaccaa 1500
ggtattattt ctcttatcat gactcaaaaa acagggggcg gtgtcgaaaa aaatattact 1560
gtgagggcaa gtgtcgaccc taaacttgac cttctgcaat ctgatggctc tgcgctgccg 1620
aactctgtcg cattaaccta ttctccggct gtaaataatt ttgaagctca caccatcaac 1680
accgttgttc atacaaatga ctcagataaa ggtgttgttg tgaagctgtc agcagatcca 1740
gtcctgtcca atgttctgaa tccaaccctg caaattcctg tttctgtgaa tttcgcagga 1800
aaaccactga gcacaacagg cattaccatc gactccaatg atctgaactt tgcttcgagt 1860
ggtgttaata aagtttcttc tacgcagaaa ctttcaatcc atgcagatgc tactcgggta 1920
actggcggcg cactaacagc tggtcaatat cagggactcg tatcaattat cctgactaag 1980
tcaacggggg gcggtgtcga gaagaccatt agcgttacgg cgagtgttga cccgacgggc 2040
gagcaaaatt ttattccaga tattgattcc gctgttcgta taatacctgt taattacgat 2100
tcggatccga aactgaattc acagttatat acggttgaga tgacgatccc tgcaggtgta 2160
agcgcagtta aaatcgtacc aacagatagt ctgacatctt ctggacagca gatcggaaag 2220

-continued

```
ctggttaatg taaacaatcc agatcaaaat atgaattatt atatcagaaa ggattctggc   2280

gctggtaagt ttatggcagg gcaaaaagga tccttttctg tcaaagagaa tacgtcatac   2340

acattctcag caatttatac tggtggcgaa taccctaata gcggatattc gtctggtact   2400

tatgcaggac atttgactgt atcattttac agcaatgaca ataaacaaag aacagaaata   2460

gcgactaaaa acttcccagt atcaacgact atttcaaaaa gtttttttgc gcctgaacca   2520

caaatccagc cttcttttgg taaaaatgtt ggaaaggaag gagatttatt atttagtgtg   2580

agcttaattg ttcctgaaaa tgtatcccag gtaacggtct accctgttta tgatgaagat   2640

tatggattag gacgactcgt aaataccgct gatgattccc aatcaataat ctaccagatt   2700

gttgatgata aagggaaaaa aatgttaaaa gatcatggta cagaggttac gcctaatcaa   2760

caaataactt ttaaagcgct gaattatact agcggagata aagaaatacc tcctgggata   2820

tataacgatc aggttatggt tggttactac gtaaacgaca ataaacaagg aaactggcaa   2880

tataaatctc tggatgtaaa tgtaaatatt gagcaactcg agcaccacca ccaccaccac   2940

tga                                                                 2943
```

<210> SEQ ID NO 25
<211> LENGTH: 980
<212> TYPE: PRT
<213> ORGANISM: Escherichia coli

<400> SEQUENCE: 25

```
Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240
```

-continued

```
Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu Gly Gly Gly Val Glu
        355                 360                 365

Lys Asn Ile Thr Val Arg Ala Ser Val Asp Pro Lys Leu Asp Leu Leu
    370                 375                 380

Gln Ala Asp Gly Thr Ser Leu Pro Asp Ser Ile Ala Leu Thr Tyr Ser
385                 390                 395                 400

Ser Ala Ser Asn Asn Phe Glu Val Tyr Ser Leu Asn Thr Ala Ile His
                405                 410                 415

Thr Asn Asp Lys Ser Lys Gly Val Val Val Lys Leu Ser Ala Ser Pro
            420                 425                 430

Val Leu Ser Asn Ile Met Lys Pro Asn Ser Gln Ile Pro Met Lys Val
        435                 440                 445

Thr Leu Gly Gly Lys Thr Leu Asn Thr Thr Asp Thr Glu Phe Thr Val
    450                 455                 460

Asp Thr Leu Asn Phe Gly Thr Ser Gly Val Glu Asn Val Ser Ser Thr
465                 470                 475                 480

Gln Gln Leu Thr Ile His Ala Asp Thr Gln Gly Thr Ala Pro Glu Ala
                485                 490                 495

Gly Asn Tyr Gln Gly Ile Ile Ser Leu Ile Met Thr Gln Lys Thr Gly
            500                 505                 510

Gly Gly Val Glu Lys Asn Ile Thr Val Arg Ala Ser Val Asp Pro Lys
        515                 520                 525

Leu Asp Leu Leu Gln Ser Asp Gly Ser Ala Leu Pro Asn Ser Val Ala
    530                 535                 540

Leu Thr Tyr Ser Pro Ala Val Asn Asn Phe Glu Ala His Thr Ile Asn
545                 550                 555                 560

Thr Val Val His Thr Asn Asp Ser Asp Lys Gly Val Val Val Lys Leu
                565                 570                 575

Ser Ala Asp Pro Val Leu Ser Asn Val Leu Asn Pro Thr Leu Gln Ile
            580                 585                 590

Pro Val Ser Val Asn Phe Ala Gly Lys Pro Leu Ser Thr Thr Gly Ile
        595                 600                 605

Thr Ile Asp Ser Asn Asp Leu Asn Phe Ala Ser Ser Gly Val Asn Lys
    610                 615                 620

Val Ser Ser Thr Gln Lys Leu Ser Ile His Ala Asp Ala Thr Arg Val
625                 630                 635                 640

Thr Gly Gly Ala Leu Thr Ala Gly Gln Tyr Gln Gly Leu Val Ser Ile
                645                 650                 655

Ile Leu Thr Lys Ser Thr Gly Gly Gly Val Glu Lys Thr Ile Ser Val
```

```
            660                 665                 670

Thr Ala Ser Val Asp Pro Thr Gly Glu Gln Asn Phe Ile Pro Asp Ile
        675                 680                 685

Asp Ser Ala Val Arg Ile Ile Pro Val Asn Tyr Asp Ser Asp Pro Lys
    690                 695                 700

Leu Asn Ser Gln Leu Tyr Thr Val Glu Met Thr Ile Pro Ala Gly Val
705                 710                 715                 720

Ser Ala Val Lys Ile Val Pro Thr Asp Ser Leu Thr Ser Ser Gly Gln
                725                 730                 735

Gln Ile Gly Lys Leu Val Asn Val Asn Asn Pro Asp Gln Asn Met Asn
            740                 745                 750

Tyr Tyr Ile Arg Lys Asp Ser Gly Ala Gly Lys Phe Met Ala Gly Gln
        755                 760                 765

Lys Gly Ser Phe Ser Val Lys Glu Asn Thr Ser Tyr Thr Phe Ser Ala
    770                 775                 780

Ile Tyr Thr Gly Gly Glu Tyr Pro Asn Ser Gly Tyr Ser Ser Gly Thr
785                 790                 795                 800

Tyr Ala Gly His Leu Thr Val Ser Phe Tyr Ser Asn Asp Asn Lys Gln
                805                 810                 815

Arg Thr Glu Ile Ala Thr Lys Asn Phe Pro Val Ser Thr Thr Ile Ser
            820                 825                 830

Lys Ser Phe Phe Ala Pro Glu Pro Gln Ile Gln Pro Ser Phe Gly Lys
        835                 840                 845

Asn Val Gly Lys Glu Gly Asp Leu Leu Phe Ser Val Ser Leu Ile Val
    850                 855                 860

Pro Glu Asn Val Ser Gln Val Thr Val Tyr Pro Val Tyr Asp Glu Asp
865                 870                 875                 880

Tyr Gly Leu Gly Arg Leu Val Asn Thr Ala Asp Asp Ser Gln Ser Ile
                885                 890                 895

Ile Tyr Gln Ile Val Asp Asp Lys Gly Lys Lys Met Leu Lys Asp His
            900                 905                 910

Gly Thr Glu Val Thr Pro Asn Gln Gln Ile Thr Phe Lys Ala Leu Asn
        915                 920                 925

Tyr Thr Ser Gly Asp Lys Glu Ile Pro Pro Gly Ile Tyr Asn Asp Gln
    930                 935                 940

Val Met Val Gly Tyr Tyr Val Asn Asp Asn Lys Gln Gly Asn Trp Gln
945                 950                 955                 960

Tyr Lys Ser Leu Asp Val Asn Val Asn Ile Glu Gln Leu Glu His His
                965                 970                 975

His His His His
            980


<210> SEQ ID NO 26
<211> LENGTH: 2795
<212> TYPE: DNA
<213> ORGANISM: Escherichia coli

<400> SEQUENCE: 26

ttacgaatca tgtggctgga tatagtttga gtcataactt atatgacagg attgtttttt      60

tatgtacatc ctcgtcgaat ccggttaatg gtgcttgccc aaccattgga acatctggag     120

ttcaatacgg tactacaacc ataaccttgc agtttacaga aaaaagaagt ctgataaaaa     180

gaaatattaa tcttgcaggt aataagaaac caatatggga gaatcagagt tgcgacacta     240

gcaatctaat ggtgttgaat tcgaagtctt ggtcctgtgg ggcttacgga aatgctaacg     300
```

-continued

```
gaacacttct aaatctgtat atccctgcag gagaaatcaa caaattgcct tttggaggga    360
tatgggaggc aactctgatc ttacgcttat caagatatgg cgaagtcagt agcacccatt    420
acggcaatta taccgtaaat attacggttg atttaactga taaaggtaat attcaggtat    480
ggcttccagg gtttcacagc aacccgcgtg tagacctgaa tctgcaccct atcggtaatt    540
ataaatatag tggtagtaat tcactcgaca tgtgtttcta tgatggatat agtacaaaca    600
gtgatagcat ggtaataaag ttccaggatg ataatcctac ctattcatct gaatataatc    660
tttataagat agggggcact gaaaaattac cctatgctgt ttcactgctt atgggagaaa    720
aaatatttta tccagtgaat ggtcaatcat ttactatcaa tgacagtagt gtactcgaaa    780
caaactggaa tcgagtaacc gcagttgcta tgccggaagt taatgttcca gtattatgct    840
ggccagcaag attgctatta aatgctgatg taaatgctcc cgatgcagga cagtattcag    900
gacagatata tataacattt acacccagtg tcgaaaattt aggcggtgga gtcgaaaaaa    960
atattactgt gagggcaagt gttgacccta aacttgatct tctgcaagca gatggaactt   1020
cactgccgga ctctatcgca ttaacctatt cttcggcttc aaataatttt gaagtttact   1080
ctcttaatac tgctattcat acaaatgaca aaagcaaggg agttgtagtg aagctgtcag   1140
cttcaccagt tctgtccaat attatgaagc caaactcgca aattccgatg aaagtgactt   1200
tgggggggaa gacgctgaat acaactgata ctgagtttac tgttgatact ctgaactttg   1260
gtacatctgg tgttgaaaac gtttcttcca ctcaacagct tacgattcat gcagacacac   1320
aaggaactgc gcctgaggca ggcaattacc aaggtattat ttctcttatc atgactcaaa   1380
aaacaggggg cggtgtcgaa aaaaatatta ctgtgagggc aagtgtcgac cctaaacttg   1440
accttctgca atctgatggc tctgcgctgc cgaactctgt cgcattaacc tattctccgg   1500
ctgtaaataa ttttgaagct cacaccatca acaccgttgt tcatacaaat gactcagata   1560
aaggtgttgt tgtgaagctg tcagcagatc cagtcctgtc caatgttctg aatccaaccc   1620
tgcaaattcc tgtttctgtg aatttcgcag gaaaaccact gagcacaaca ggcattacca   1680
tcgactccaa tgatctgaac tttgcttcga gtggtgttaa taaagtttct tctacgcaga   1740
aactttcaat ccatgcagat gctactcggg taactggcgg cgcactaaca gctggtcaat   1800
atcagggact cgtatcaatt atcctgacta agtcaacggg gggcggtgtc gagaagacca   1860
ttagcgttac ggcgagtgtt gacccgacgg gcgagcaaaa ttttattcca gatattgatt   1920
ccgctgttcg tataatacct gttaattacg attcggatcc gaaactgaat tcacagttat   1980
atacggttga gatgacgatc cctgcaggtg taagcgcagt taaaatcgta ccaacagata   2040
gtctgacatc ttctggacag cagatcggaa agctggttaa tgtaaacaat ccagatcaaa   2100
atatgaatta ttatatcaga aaggattctg gcgctggtaa gtttatggca gggcaaaaag   2160
gatccttttc tgtcaaagag aatacgtcat acacattctc agcaatttat actggtggcg   2220
aataccctaa tagcggatat tcgtctggta cttatgcagg acatttgact gtatcatttt   2280
acagcaatga caataaacaa agaacagaaa tagcgactaa aaacttccca gtatcaacga   2340
ctatttcaaa aagttttttt gcgcctgaac cacaaatcca gccttctttt ggtaaaaatg   2400
ttggaaagga aggagattta ttatttagtg tgagcttaat tgttcctgaa aatgtatccc   2460
aggtaacggt ctaccctgtt tatgatgaag attatggatt aggacgactc gtaaataccg   2520
ctgatgattc ccaatcaata atctaccaga ttgttgatga taaagggaaa aaaatgttaa   2580
aagatcatgg tacagaggtt acgcctaatc aacaaataac ttttaaagcg ctgaattata   2640
```

```
ctagcggaga taaagaaata cctcctggga tatataacga tcaggttatg gttggttact   2700

acgtaaacga caataaacaa ggaaactggc aatataaatc tctggatgta aatgtaaata   2760

ttgagcaact cgagcaccac caccaccacc actga                              2795


<210> SEQ ID NO 27
<211> LENGTH: 963
<212> TYPE: PRT
<213> ORGANISM: Escherichia coli

<400> SEQUENCE: 27

Met Gly Arg Tyr Pro Glu Thr Thr Val Gly Asn Leu Thr Lys Ser Phe
1               5                   10                  15

Gln Ala Pro Arg Gln Asp Arg Ser Val Gln Ser Pro Ile Tyr Asn Ile
            20                  25                  30

Phe Thr Asn His Val Ala Gly Tyr Ser Leu Ser His Asn Leu Tyr Asp
        35                  40                  45

Arg Ile Val Phe Leu Cys Thr Ser Ser Ser Asn Pro Val Asn Gly Ala
    50                  55                  60

Cys Pro Thr Ile Gly Thr Ser Gly Val Gln Tyr Gly Thr Thr Thr Ile
65                  70                  75                  80

Thr Leu Gln Phe Thr Glu Lys Arg Ser Leu Ile Lys Arg Asn Ile Asn
                85                  90                  95

Leu Ala Gly Asn Lys Lys Pro Ile Trp Glu Asn Gln Ser Cys Asp Thr
            100                 105                 110

Ser Asn Leu Met Val Leu Asn Ser Lys Ser Trp Ser Cys Gly Ala Tyr
        115                 120                 125

Gly Asn Ala Asn Gly Thr Leu Leu Asn Leu Tyr Ile Pro Ala Gly Glu
    130                 135                 140

Ile Asn Lys Leu Pro Phe Gly Gly Ile Trp Glu Ala Thr Leu Ile Leu
145                 150                 155                 160

Arg Leu Ser Arg Tyr Gly Glu Val Ser Ser Thr His Tyr Gly Asn Tyr
                165                 170                 175

Thr Val Asn Ile Thr Val Asp Leu Thr Asp Lys Gly Asn Ile Gln Val
            180                 185                 190

Trp Leu Pro Gly Phe His Ser Asn Pro Arg Val Asp Leu Asn Leu His
        195                 200                 205

Pro Ile Gly Asn Tyr Lys Tyr Ser Gly Ser Asn Ser Leu Asp Met Cys
    210                 215                 220

Phe Tyr Asp Gly Tyr Ser Thr Asn Ser Asp Ser Met Val Ile Lys Phe
225                 230                 235                 240

Gln Asp Asp Asn Pro Thr Tyr Ser Ser Glu Tyr Asn Leu Tyr Lys Ile
                245                 250                 255

Gly Gly Thr Glu Lys Leu Pro Tyr Ala Val Ser Leu Leu Met Gly Glu
            260                 265                 270

Lys Ile Phe Tyr Pro Val Asn Gly Gln Ser Phe Thr Ile Asn Asp Ser
        275                 280                 285

Ser Val Leu Glu Thr Asn Trp Asn Arg Val Thr Ala Val Ala Met Pro
    290                 295                 300

Glu Val Asn Val Pro Val Leu Cys Trp Pro Ala Arg Leu Leu Leu Asn
305                 310                 315                 320

Ala Asp Val Asn Ala Pro Asp Ala Gly Gln Tyr Ser Gly Gln Ile Tyr
                325                 330                 335

Ile Thr Phe Thr Pro Ser Val Glu Asn Leu Gly Gly Gly Val Glu Lys
            340                 345                 350
```

```
Asn Ile Thr Val Arg Ala Ser Val Asp Pro Lys Leu Asp Leu Leu Gln
        355                 360                 365

Ala Asp Gly Thr Ser Leu Pro Asp Ser Ile Ala Leu Thr Tyr Ser Ser
    370                 375                 380

Ala Ser Asn Asn Phe Glu Val Tyr Ser Leu Asn Thr Ala Ile His Thr
385                 390                 395                 400

Asn Asp Lys Ser Lys Gly Val Val Val Lys Leu Ser Ala Ser Pro Val
                405                 410                 415

Leu Ser Asn Ile Met Lys Pro Asn Ser Gln Ile Pro Met Lys Val Thr
            420                 425                 430

Leu Gly Gly Lys Thr Leu Asn Thr Thr Asp Thr Glu Phe Thr Val Asp
        435                 440                 445

Thr Leu Asn Phe Gly Thr Ser Gly Val Glu Asn Val Ser Ser Thr Gln
    450                 455                 460

Gln Leu Thr Ile His Ala Asp Thr Gln Gly Thr Ala Pro Glu Ala Gly
465                 470                 475                 480

Asn Tyr Gln Gly Ile Ile Ser Leu Ile Met Thr Gln Lys Thr Gly Gly
                485                 490                 495

Gly Val Glu Lys Asn Ile Thr Val Arg Ala Ser Val Asp Pro Lys Leu
            500                 505                 510

Asp Leu Leu Gln Ser Asp Gly Ser Ala Leu Pro Asn Ser Val Ala Leu
        515                 520                 525

Thr Tyr Ser Pro Ala Val Asn Asn Phe Glu Ala His Thr Ile Asn Thr
    530                 535                 540

Val Val His Thr Asn Asp Ser Asp Lys Gly Val Val Val Lys Leu Ser
545                 550                 555                 560

Ala Asp Pro Val Leu Ser Asn Val Leu Asn Pro Thr Leu Gln Ile Pro
                565                 570                 575

Val Ser Val Asn Phe Ala Gly Lys Pro Leu Ser Thr Thr Gly Ile Thr
            580                 585                 590

Ile Asp Ser Asn Asp Leu Asn Phe Ala Ser Ser Gly Val Asn Lys Val
        595                 600                 605

Ser Ser Thr Gln Lys Leu Ser Ile His Ala Asp Ala Thr Arg Val Thr
    610                 615                 620

Gly Gly Ala Leu Thr Ala Gly Gln Tyr Gln Gly Leu Val Ser Ile Ile
625                 630                 635                 640

Leu Thr Lys Ser Thr Gly Gly Gly Val Glu Lys Thr Ile Ser Val Thr
                645                 650                 655

Ala Ser Val Asp Pro Thr Gly Glu Gln Asn Phe Ile Pro Asp Ile Asp
            660                 665                 670

Ser Ala Val Arg Ile Ile Pro Val Asn Tyr Asp Ser Asp Pro Lys Leu
        675                 680                 685

Asn Ser Gln Leu Tyr Thr Val Glu Met Thr Ile Pro Ala Gly Val Ser
    690                 695                 700

Ala Val Lys Ile Val Pro Thr Asp Ser Leu Thr Ser Ser Gly Gln Gln
705                 710                 715                 720

Ile Gly Lys Leu Val Asn Val Asn Asn Pro Asp Gln Asn Met Asn Tyr
                725                 730                 735

Tyr Ile Arg Lys Asp Ser Gly Ala Gly Lys Phe Met Ala Gly Gln Lys
            740                 745                 750

Gly Ser Phe Ser Val Lys Glu Asn Thr Ser Tyr Thr Phe Ser Ala Ile
        755                 760                 765
```

```
Tyr Thr Gly Gly Glu Tyr Pro Asn Ser Gly Tyr Ser Ser Gly Thr Tyr
    770                 775                 780

Ala Gly His Leu Thr Val Ser Phe Tyr Ser Asn Asp Asn Lys Gln Arg
785                 790                 795                 800

Thr Glu Ile Ala Thr Lys Asn Phe Pro Val Ser Thr Thr Ile Ser Lys
                805                 810                 815

Ser Phe Phe Ala Pro Glu Pro Gln Ile Gln Pro Ser Phe Gly Lys Asn
            820                 825                 830

Val Gly Lys Glu Gly Asp Leu Leu Phe Ser Val Ser Leu Ile Val Pro
        835                 840                 845

Glu Asn Val Ser Gln Val Thr Val Tyr Pro Val Tyr Asp Glu Asp Tyr
    850                 855                 860

Gly Leu Gly Arg Leu Val Asn Thr Ala Asp Asp Ser Gln Ser Ile Ile
865                 870                 875                 880

Tyr Gln Ile Val Asp Asp Lys Gly Lys Lys Met Leu Lys Asp His Gly
                885                 890                 895

Thr Glu Val Thr Pro Asn Gln Gln Ile Thr Phe Lys Ala Leu Asn Tyr
            900                 905                 910

Thr Ser Gly Asp Lys Glu Ile Pro Pro Gly Ile Tyr Asn Asp Gln Val
        915                 920                 925

Met Val Gly Tyr Tyr Val Asn Asp Asn Lys Gln Gly Asn Trp Gln Tyr
    930                 935                 940

Lys Ser Leu Asp Val Asn Val Asn Ile Glu Gln Leu Glu His His His
945                 950                 955                 960

His His His


<210> SEQ ID NO 28
<211> LENGTH: 2505
<212> TYPE: DNA
<213> ORGANISM: Escherichia coli

<400> SEQUENCE: 28

atgaaaaaag tgatttttgt tttatccatg tttctatgtt ctcaggttta cgggcaatca      60

tggcatacga acgtagaggc tggttcaata aataaaacag agtcgatagg ccccatagac     120

cgaagtgctg ctgcatcgta tcctgctcat tatatatttc atgaacatgt tgctggttac     180

aataaagatc actctctttt tgacaggatg acgtttttat gtatgtcatc aacagatgca     240

tctaaaggtg catgtccgac aggagaaaac tccaaatcct ctcaagggga gactaatatt     300

aagctaatat ttactgaaaa gaaaagtctg gccagaaaaa cattaaactt aaaaggatat     360

aagagatttt tatatgaatc agatagatgc attcattatg tcgataaaat gaatctcaat     420

tctcatactg ttaaatgtgt aggttcattc acaagaggag tagatttcac tttatatatc     480

ccacaaggtg aaattgatgg gcttctaact ggaggtatat gggaggcaac actagagtta     540

cgagtcaaaa ggcattacga ctataatcat ggtacttaca aagttaatat cacagttgat     600

ttgacagaca aaggaaatat tcaggtctgg acaccaaagt ttcatagcga tcctagaatt     660

gatctgaatt tacgtcctga aggtaatggt aaatattctg gtagtaacgt gcttgagatg     720

tgtctctatg atggctatag tacacatagt caaagtatag aaatgaggtt tcaggatgac     780

tcacaaacag gaaataatga atataatctt ataaaaactg gagagccatt aaaaaaattg     840

ccatataaac tttctcttct tttaggagga cgagagtttt atccaaataa tggagaggct     900

tttactatta atgatacttc gtcattgttt ataaactgga atcgtattaa gtctgtatcc     960

ttaccacaga ttagtattcc agtactatgc tggccagcaa acttgacatt tatgtcagag    1020
```

```
ctaaataatc cagaagcggg tgagtattca ggaatactta acgtaacatt tactcctagt   1080

agttcaagcc tagacaataa acaagccgag aaaaatatca ctgtaactgc tagcgttgat   1140

ccaactatcg atctgatgca atctgatggc acagcgttac caagtgcagt taatattgca   1200

tatcttccag gagagaaaag atttgaatct gctcgtatca atacccaagt tcataccaat   1260

aataaaacta agggtattca gataaagctt actaatgata atgtggtaat gactaactta   1320

tctgatccaa gcaagactat tcctttagag gtttcattcg ctggcactaa gctgagcaca   1380

gctgcaacat ctattactgc cgatcaatta aattttggcg cagctggtgt agagacagtt   1440

tctgcaacta aggaactcgt tattaatgca ggaagcaccc agcaaactaa tattgtagct   1500

ggtaactatc aaggattggt gtcaattgtg cttactcaag aacctgacaa taaacaagcc   1560

gagaaaaata tcactgtaac tgctagcgtt gatccgacgg gcgagcaaaa ttttattcca   1620

gatattgatt ccgctgttcg tataatacct gttaattacg attcggatcc gaaactgaat   1680

tcacagttat atacggttga gatgacgatc cctgcaggtg taagcgcagt taaaatcgta   1740

ccaacagata gtctgacatc ttctggacag cagatcggaa agctggttaa tgtaaacaat   1800

ccagatcaaa atatgaatta ttatatcaga aaggattctg gcgctggtaa gtttatggca   1860

gggcaaaaag gatccttttc tgtcaaagag aatacgtcat acacattctc agcaatttat   1920

actggtggcg aataccctaa tagcggatat tcgtctggta cttatgcagg acatttgact   1980

gtatcatttt acagcaatga caataaacaa agaacagaaa tagcgactaa aaacttccca   2040

gtatcaacga ctatttcaaa aagttttttt gcgcctgaac cacaaatcca gccttctttt   2100

ggtaaaaatg ttggaaagga aggagattta ttatttagtg tgagcttaat tgttcctgaa   2160

aatgtatccc aggtaacggt ctaccctgtt tatgatgaag attatggatt aggacgactc   2220

gtaaataccg ctgatgattc ccaatcaata atctaccaga ttgttgatga taaagggaaa   2280

aaaatgttaa aagatcatgg tacagaggtt acgcctaatc aacaaataac ttttaaagcg   2340

ctgaattata ctagcggaga taaagaaata cctcctggga tatataacga tcaggttatg   2400

gttggttact acgtaaacga caataaacaa ggaaactggc aatataaatc tctggatgta   2460

aatgtaaata ttgagcaact cgagcaccac caccaccacc actga                    2505
```

```
<210> SEQ ID NO 29
<211> LENGTH: 834
<212> TYPE: PRT
<213> ORGANISM: Escherichia coli

<400> SEQUENCE: 29

Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110
```

-continued

```
Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Asp Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Ser Leu Asp Asn Lys Gln
        355                 360                 365

Ala Glu Lys Asn Ile Thr Val Thr Ala Ser Val Asp Pro Thr Ile Asp
    370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
            420                 425                 430

Asp Asn Val Val Met Thr Asn Leu Ser Asp Pro Ser Lys Thr Ile Pro
        435                 440                 445

Leu Glu Val Ser Phe Ala Gly Thr Lys Leu Ser Thr Ala Ala Thr Ser
    450                 455                 460

Ile Thr Ala Asp Gln Leu Asn Phe Gly Ala Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
            500                 505                 510

Gln Glu Pro Asp Asn Lys Gln Ala Glu Lys Asn Ile Thr Val Thr Ala
        515                 520                 525
```

```
Ser Val Asp Pro Thr Gly Glu Gln Asn Phe Ile Pro Asp Ile Asp Ser
    530                 535                 540

Ala Val Arg Ile Ile Pro Val Asn Tyr Asp Ser Asp Pro Lys Leu Asn
545                 550                 555                 560

Ser Gln Leu Tyr Thr Val Glu Met Thr Ile Pro Ala Gly Val Ser Ala
                565                 570                 575

Val Lys Ile Val Pro Thr Asp Ser Leu Thr Ser Ser Gly Gln Gln Ile
            580                 585                 590

Gly Lys Leu Val Asn Val Asn Asn Pro Asp Gln Asn Met Asn Tyr Tyr
        595                 600                 605

Ile Arg Lys Asp Ser Gly Ala Gly Lys Phe Met Ala Gly Gln Lys Gly
    610                 615                 620

Ser Phe Ser Val Lys Glu Asn Thr Ser Tyr Thr Phe Ser Ala Ile Tyr
625                 630                 635                 640

Thr Gly Gly Glu Tyr Pro Asn Ser Gly Tyr Ser Ser Gly Thr Tyr Ala
                645                 650                 655

Gly His Leu Thr Val Ser Phe Tyr Ser Asn Asp Asn Lys Gln Arg Thr
            660                 665                 670

Glu Ile Ala Thr Lys Asn Phe Pro Val Ser Thr Thr Ile Ser Lys Ser
        675                 680                 685

Phe Phe Ala Pro Glu Pro Gln Ile Gln Pro Ser Phe Gly Lys Asn Val
    690                 695                 700

Gly Lys Glu Gly Asp Leu Leu Phe Ser Val Ser Leu Ile Val Pro Glu
705                 710                 715                 720

Asn Val Ser Gln Val Thr Val Tyr Pro Val Tyr Asp Glu Asp Tyr Gly
                725                 730                 735

Leu Gly Arg Leu Val Asn Thr Ala Asp Asp Ser Gln Ser Ile Ile Tyr
            740                 745                 750

Gln Ile Val Asp Asp Lys Gly Lys Lys Met Leu Lys Asp His Gly Thr
        755                 760                 765

Glu Val Thr Pro Asn Gln Gln Ile Thr Phe Lys Ala Leu Asn Tyr Thr
    770                 775                 780

Ser Gly Asp Lys Glu Ile Pro Pro Gly Ile Tyr Asn Asp Gln Val Met
785                 790                 795                 800

Val Gly Tyr Tyr Val Asn Asp Asn Lys Gln Gly Asn Trp Gln Tyr Lys
                805                 810                 815

Ser Leu Asp Val Asn Val Asn Ile Glu Gln Leu Glu His His His His
            820                 825                 830

His His
```

<210> SEQ ID NO 30
<211> LENGTH: 2454
<212> TYPE: DNA
<213> ORGANISM: Escherichia coli

<400> SEQUENCE: 30

```
atgcaatcat ggcatacgaa cgtagaggct ggttcaataa ataaaacaga gtcgataggc      60

cccatagacc gaagtgctgc tgcatcgtat cctgctcatt atatatttca tgaacatgtt     120

gctggttaca ataaagatca ctctcttttt gacaggatga cgtttttatg tatgtcatca     180

acagatgcat ctaaaggtgc atgtccgaca ggagaaaact ccaaatcctc tcaaggggag     240

actaatatta agctaatatt tactgaaaag aaaagtctgg ccagaaaaac attaaactta     300

aaaggatata agagattttt atatgaatca gatagatgca ttcattatgt cgataaaatg     360
```

```
aatctcaatt ctcatactgt taaatgtgta ggttcattca caagaggagt agatttcact    420
ttatatatcc cacaaggtga aattgatggg cttctaactg gaggtatatg ggaggcaaca    480
ctagagttac gagtcaaaag gcattacgac tataatcatg gtacttacaa agttaatatc    540
acagttgatt tgacagacaa aggaaatatt caggtctgga caccaaagtt tcatagcgat    600
cctagaattg atctgaattt acgtcctgaa ggtaatggta aatattctgg tagtaacgtg    660
cttgagatgt gtctctatga tggctatagt acacatagtc aaagtataga aatgaggttt    720
caggatgact cacaaacagg aaataatgaa tataatctta taaaaactgg agagccatta    780
aaaaaattgc catataaact ttctcttctt ttaggaggac gagagtttta tccaaataat    840
ggagaggctt ttactattaa tgatacttcg tcattgttta taaactggaa tcgtattaag    900
tctgtatcct taccacagat tagtattcca gtactatgct ggccagcaaa cttgacattt    960
atgtcagagc taaataatcc agaagcgggt gagtattcag gaatacttaa cgtaacattt   1020
actcctagta gttcaagcct agacaataaa caagccgaga aaaatatcac tgtaactgct   1080
agcgttgatc caactatcga tctgatgcaa tctgatggca cagcgttacc aagtgcagtt   1140
aatattgcat atcttccagg agagaaaaga tttgaatctg ctcgtatcaa tacccaagtt   1200
cataccaata ataaaactaa gggtattcag ataaagctta ctaatgataa tgtggtaatg   1260
actaacttat ctgatccaag caagactatt cctttagagg tttcattcgc tggcactaag   1320
ctgagcacag ctgcaacatc tattactgcc gatcaattaa attttggcgc agctggtgta   1380
gagacagttt ctgcaactaa ggaactcgtt attaatgcag gaagcaccca gcaaactaat   1440
attgtagctg gtaactatca aggattggtg tcaattgtgc ttactcaaga acctgacaat   1500
aaacaagccg agaaaaatat cactgtaact gctagcgttg atccgacggg cgagcaaaat   1560
tttattccag atattgattc cgctgttcgt ataatacctg ttaattacga ttcggatccg   1620
aaactgaatt cacagttata tacggttgag atgacgatcc ctgcaggtgt aagcgcagtt   1680
aaaatcgtac caacagatag tctgacatct tctggacagc agatcggaaa gctggttaat   1740
gtaaacaatc cagatcaaaa tatgaattat tatatcagaa aggattctgg cgctggtaag   1800
tttatggcag ggcaaaaagg atccttttct gtcaaagaga atacgtcata cacattctca   1860
gcaatttata ctggtggcga ataccctaat agcggatatt cgtctggtac ttatgcagga   1920
catttgactg tatcatttta cagcaatgac aataaacaaa gaacagaaat agcgactaaa   1980
aacttcccag tatcaacgac tatttcaaaa agtttttttg cgcctgaacc acaaatccag   2040
ccttcttttg gtaaaaatgt tggaaaggaa ggagatttat tatttagtgt gagcttaatt   2100
gttcctgaaa atgtatccca ggtaacggtc taccctgttt atgatgaaga ttatggatta   2160
ggacgactcg taaataccgc tgatgattcc caatcaataa tctaccagat tgttgatgat   2220
aaagggaaaa aaatgttaaa agatcatggt acagaggtta cgcctaatca acaaataact   2280
tttaaagcgc tgaattatac tagcggagat aaagaaatac ctcctgggat atataacgat   2340
caggttatgg ttggttacta cgtaaacgac aataaacaag gaaactggca atataaatct   2400
ctggatgtaa atgtaaatat tgagcaactc gagcaccacc accaccacca ctga         2454
```

<210> SEQ ID NO 31
<211> LENGTH: 817
<212> TYPE: PRT
<213> ORGANISM: Escherichia coli

<400> SEQUENCE: 31

Met Gln Ser Trp His Thr Asn Val Glu Ala Gly Ser Ile Asn Lys Thr

-continued

```
1               5                   10                  15

Glu Ser Ile Gly Pro Ile Asp Arg Ser Ala Ala Ala Ser Tyr Pro Ala
            20                  25                  30

His Tyr Ile Phe His Glu His Val Ala Gly Tyr Asn Lys Asp His Ser
        35                  40                  45

Leu Phe Asp Arg Met Thr Phe Leu Cys Met Ser Ser Thr Asp Ala Ser
    50                  55                  60

Lys Gly Ala Cys Pro Thr Gly Glu Asn Ser Lys Ser Ser Gln Gly Glu
65                  70                  75                  80

Thr Asn Ile Lys Leu Ile Phe Thr Glu Lys Lys Ser Leu Ala Arg Lys
                85                  90                  95

Thr Leu Asn Leu Lys Gly Tyr Lys Arg Phe Leu Tyr Glu Ser Asp Arg
            100                 105                 110

Cys Ile His Tyr Val Asp Lys Met Asn Leu Asn Ser His Thr Val Lys
        115                 120                 125

Cys Val Gly Ser Phe Thr Arg Gly Val Asp Phe Thr Leu Tyr Ile Pro
    130                 135                 140

Gln Gly Glu Ile Asp Gly Leu Leu Thr Gly Gly Ile Trp Glu Ala Thr
145                 150                 155                 160

Leu Glu Leu Arg Val Lys Arg His Tyr Asp Tyr Asn His Gly Thr Tyr
                165                 170                 175

Lys Val Asn Ile Thr Val Asp Leu Thr Asp Lys Gly Asn Ile Gln Val
            180                 185                 190

Trp Thr Pro Lys Phe His Ser Asp Pro Arg Ile Asp Leu Asn Leu Arg
        195                 200                 205

Pro Glu Gly Asn Gly Lys Tyr Ser Gly Ser Asn Val Leu Glu Met Cys
    210                 215                 220

Leu Tyr Asp Gly Tyr Ser Thr His Ser Gln Ser Ile Glu Met Arg Phe
225                 230                 235                 240

Gln Asp Asp Ser Gln Thr Gly Asn Asn Glu Tyr Asn Leu Ile Lys Thr
                245                 250                 255

Gly Glu Pro Leu Lys Lys Leu Pro Tyr Lys Leu Ser Leu Leu Leu Gly
            260                 265                 270

Gly Arg Glu Phe Tyr Pro Asn Asn Gly Glu Ala Phe Thr Ile Asn Asp
        275                 280                 285

Thr Ser Ser Leu Phe Ile Asn Trp Asn Arg Ile Lys Ser Val Ser Leu
    290                 295                 300

Pro Gln Ile Ser Ile Pro Val Leu Cys Trp Pro Ala Asn Leu Thr Phe
305                 310                 315                 320

Met Ser Glu Leu Asn Asn Pro Glu Ala Gly Glu Tyr Ser Gly Ile Leu
                325                 330                 335

Asn Val Thr Phe Thr Pro Ser Ser Ser Ser Leu Asp Asn Lys Gln Ala
            340                 345                 350

Glu Lys Asn Ile Thr Val Thr Ala Ser Val Asp Pro Thr Ile Asp Leu
        355                 360                 365

Met Gln Ser Asp Gly Thr Ala Leu Pro Ser Ala Val Asn Ile Ala Tyr
    370                 375                 380

Leu Pro Gly Glu Lys Arg Phe Glu Ser Ala Arg Ile Asn Thr Gln Val
385                 390                 395                 400

His Thr Asn Asn Lys Thr Lys Gly Ile Gln Ile Lys Leu Thr Asn Asp
                405                 410                 415

Asn Val Val Met Thr Asn Leu Ser Asp Pro Ser Lys Thr Ile Pro Leu
            420                 425                 430
```

-continued

Glu Val Ser Phe Ala Gly Thr Lys Leu Ser Thr Ala Ala Thr Ser Ile
435 440 445

Thr Ala Asp Gln Leu Asn Phe Gly Ala Ala Gly Val Glu Thr Val Ser
450 455 460

Ala Thr Lys Glu Leu Val Ile Asn Ala Gly Ser Thr Gln Gln Thr Asn
465 470 475 480

Ile Val Ala Gly Asn Tyr Gln Gly Leu Val Ser Ile Val Leu Thr Gln
485 490 495

Glu Pro Asp Asn Lys Gln Ala Glu Lys Asn Ile Thr Val Thr Ala Ser
500 505 510

Val Asp Pro Thr Gly Glu Gln Asn Phe Ile Pro Asp Ile Asp Ser Ala
515 520 525

Val Arg Ile Ile Pro Val Asn Tyr Asp Ser Asp Pro Lys Leu Asn Ser
530 535 540

Gln Leu Tyr Thr Val Glu Met Thr Ile Pro Ala Gly Val Ser Ala Val
545 550 555 560

Lys Ile Val Pro Thr Asp Ser Leu Thr Ser Ser Gly Gln Gln Ile Gly
565 570 575

Lys Leu Val Asn Val Asn Asn Pro Asp Gln Asn Met Asn Tyr Tyr Ile
580 585 590

Arg Lys Asp Ser Gly Ala Gly Lys Phe Met Ala Gly Gln Lys Gly Ser
595 600 605

Phe Ser Val Lys Glu Asn Thr Ser Tyr Thr Phe Ser Ala Ile Tyr Thr
610 615 620

Gly Gly Glu Tyr Pro Asn Ser Gly Tyr Ser Ser Gly Thr Tyr Ala Gly
625 630 635 640

His Leu Thr Val Ser Phe Tyr Ser Asn Asp Asn Lys Gln Arg Thr Glu
645 650 655

Ile Ala Thr Lys Asn Phe Pro Val Ser Thr Thr Ile Ser Lys Ser Phe
660 665 670

Phe Ala Pro Glu Pro Gln Ile Gln Pro Ser Phe Gly Lys Asn Val Gly
675 680 685

Lys Glu Gly Asp Leu Leu Phe Ser Val Ser Leu Ile Val Pro Glu Asn
690 695 700

Val Ser Gln Val Thr Val Tyr Pro Val Tyr Asp Glu Asp Tyr Gly Leu
705 710 715 720

Gly Arg Leu Val Asn Thr Ala Asp Asp Ser Gln Ser Ile Ile Tyr Gln
725 730 735

Ile Val Asp Asp Lys Gly Lys Lys Met Leu Lys Asp His Gly Thr Glu
740 745 750

Val Thr Pro Asn Gln Gln Ile Thr Phe Lys Ala Leu Asn Tyr Thr Ser
755 760 765

Gly Asp Lys Glu Ile Pro Pro Gly Ile Tyr Asn Asp Gln Val Met Val
770 775 780

Gly Tyr Tyr Val Asn Asp Asn Lys Gln Gly Asn Trp Gln Tyr Lys Ser
785 790 795 800

Leu Asp Val Asn Val Asn Ile Glu Gln Leu Glu His His His His His
805 810 815

His

<210> SEQ ID NO 32
<211> LENGTH: 1848
<212> TYPE: DNA

<213> ORGANISM: Escherichia coli

<400> SEQUENCE: 32
atggcagtgg gcccaacgaa agatatgagt ttaggtgcaa atttaacttc agagcctaca 60
ttagctattg attttacgcc tattgaaaat atttatgtag gtgccaatta tggtaaagat 120
attggaaccc ttgttttcac aacaaatgat ttaacagata ttacattgat gtcatctcgc 180
agcgttgttg atggtcgcca gactggtttt tttaccttca tggactcatc agccacttac 240
aaaattagta caaaactggg atcatcgaat gatgtaaaca ttcaagaaat tactcaagga 300
gctaaaatta ctcctgttag tggagagaaa actttgccta aaaaattcac tcttaagcta 360
catgcacaca ggagtagcag tacagttcca ggtacgtata ctgttggtct taacgtaacc 420
agtaacgtta ttgataacaa gcaggcagcg gggcccactc taaccaaaga actggcatta 480
aatgtgcttt ctcctgcagc tctggatgca acttgggctc ctcaggataa tttaacatta 540
tccaatactg gcgtttctaa tactttggtg ggtgttttga ctctttcaaa taccagtatt 600
gatacagtta gcattgcgag tacaaatgtt tctgatacat ctaagaatgg tacagtaact 660
tttgcacatg agacaaataa ctctgctagc tttgccacca ccatttcaac agataatgcc 720
aacattacgt tggataaaaa tgctggaaat acgattgtta aaactacaaa tgggagtcag 780
ttgccaacta atttaccact taagtttatt accactgaag gtaacgaaca tttagtttca 840
ggtaattacc gtgcaaatat aacaattact tcgacaatta aagataacaa gcaggcggca 900
ggtccaaccc tgactaagga gttagcgctg aacgttttaa gcggcgagca aaattttatt 960
ccagatattg attccgctgt tcgtataata cctgttaatt acgattcgga tccgaaactg 1020
aattcacagt tatatacggt tgagatgacg atccctgcag gtgtaagcgc agttaaaatc 1080
gtaccaacag atagtctgac atcttctgga cagcagatcg gaaagctggt taatgtaaac 1140
aatccagatc aaaatatgaa ttattatatc agaaaggatt ctggcgctgg taagtttatg 1200
gcagggcaaa aaggatcctt ttctgtcaaa gagaatacgt catacacatt ctcagcaatt 1260
tatactggtg gcgaataccc taatagcgga tattcgtctg gtacttatgc aggacatttg 1320
actgtatcat tttacagcaa tgacaataaa caaagaacag aaatagcgac taaaaacttc 1380
ccagtatcaa cgactatttc aaaaagtttt tttgcgcctg aaccacaaat ccagccttct 1440
tttggtaaaa atgttggaaa ggaaggagat ttattattta gtgtgagctt aattgttcct 1500
gaaaatgtat cccaggtaac ggtctaccct gtttatgatg aagattatgg attaggacga 1560
ctcgtaaata ccgctgatga ttcccaatca ataatctacc agattgttga tgataaaggg 1620
aaaaaaatgt taaaagatca tggtacagag gttacgccta atcaacaaat aacttttaaa 1680
gcgctgaatt atactagcgg agataaagaa atacctcctg ggatatataa cgatcaggtt 1740
atggttggtt actacgtaaa cgacaataaa caaggaaact ggcaatataa atctctggat 1800
gtaaatgtaa atattgagca actcgagcac caccaccacc accactga 1848

<210> SEQ ID NO 33
<211> LENGTH: 615
<212> TYPE: PRT
<213> ORGANISM: Escherichia coli

<400> SEQUENCE: 33

Met Ala Val Gly Pro Thr Lys Asp Met Ser Leu Gly Ala Asn Leu Thr
1 5 10 15

Ser Glu Pro Thr Leu Ala Ile Asp Phe Thr Pro Ile Glu Asn Ile Tyr
20 25 30

```
Val Gly Ala Asn Tyr Gly Lys Asp Ile Gly Thr Leu Val Phe Thr Thr
        35                  40                  45

Asn Asp Leu Thr Asp Ile Thr Leu Met Ser Ser Arg Ser Val Val Asp
    50                  55                  60

Gly Arg Gln Thr Gly Phe Phe Thr Phe Met Asp Ser Ser Ala Thr Tyr
65                  70                  75                  80

Lys Ile Ser Thr Lys Leu Gly Ser Ser Asn Asp Val Asn Ile Gln Glu
                85                  90                  95

Ile Thr Gln Gly Ala Lys Ile Thr Pro Val Ser Gly Glu Lys Thr Leu
            100                 105                 110

Pro Lys Lys Phe Thr Leu Lys Leu His Ala His Arg Ser Ser Ser Thr
        115                 120                 125

Val Pro Gly Thr Tyr Thr Val Gly Leu Asn Val Thr Ser Asn Val Ile
    130                 135                 140

Asp Asn Lys Gln Ala Ala Gly Pro Thr Leu Thr Lys Glu Leu Ala Leu
145                 150                 155                 160

Asn Val Leu Ser Pro Ala Ala Leu Asp Ala Thr Trp Ala Pro Gln Asp
                165                 170                 175

Asn Leu Thr Leu Ser Asn Thr Gly Val Ser Asn Thr Leu Val Gly Val
            180                 185                 190

Leu Thr Leu Ser Asn Thr Ser Ile Asp Thr Val Ser Ile Ala Ser Thr
        195                 200                 205

Asn Val Ser Asp Thr Ser Lys Asn Gly Thr Val Thr Phe Ala His Glu
    210                 215                 220

Thr Asn Asn Ser Ala Ser Phe Ala Thr Thr Ile Ser Thr Asp Asn Ala
225                 230                 235                 240

Asn Ile Thr Leu Asp Lys Asn Ala Gly Asn Thr Ile Val Lys Thr Thr
                245                 250                 255

Asn Gly Ser Gln Leu Pro Thr Asn Leu Pro Leu Lys Phe Ile Thr Thr
            260                 265                 270

Glu Gly Asn Glu His Leu Val Ser Gly Asn Tyr Arg Ala Asn Ile Thr
        275                 280                 285

Ile Thr Ser Thr Ile Lys Asp Asn Lys Gln Ala Ala Gly Pro Thr Leu
    290                 295                 300

Thr Lys Glu Leu Ala Leu Asn Val Leu Ser Gly Glu Gln Asn Phe Ile
305                 310                 315                 320

Pro Asp Ile Asp Ser Ala Val Arg Ile Ile Pro Val Asn Tyr Asp Ser
                325                 330                 335

Asp Pro Lys Leu Asn Ser Gln Leu Tyr Thr Val Glu Met Thr Ile Pro
            340                 345                 350

Ala Gly Val Ser Ala Val Lys Ile Val Pro Thr Asp Ser Leu Thr Ser
        355                 360                 365

Ser Gly Gln Gln Ile Gly Lys Leu Val Asn Val Asn Asn Pro Asp Gln
    370                 375                 380

Asn Met Asn Tyr Tyr Ile Arg Lys Asp Ser Gly Ala Gly Lys Phe Met
385                 390                 395                 400

Ala Gly Gln Lys Gly Ser Phe Ser Val Lys Glu Asn Thr Ser Tyr Thr
                405                 410                 415

Phe Ser Ala Ile Tyr Thr Gly Gly Glu Tyr Pro Asn Ser Gly Tyr Ser
            420                 425                 430

Ser Gly Thr Tyr Ala Gly His Leu Thr Val Ser Phe Tyr Ser Asn Asp
        435                 440                 445
```

-continued

```
Asn Lys Gln Arg Thr Glu Ile Ala Thr Lys Asn Phe Pro Val Ser Thr
    450                 455                 460

Thr Ile Ser Lys Ser Phe Phe Ala Pro Glu Pro Gln Ile Gln Pro Ser
465                 470                 475                 480

Phe Gly Lys Asn Val Gly Lys Glu Gly Asp Leu Leu Phe Ser Val Ser
                485                 490                 495

Leu Ile Val Pro Glu Asn Val Ser Gln Val Thr Val Tyr Pro Val Tyr
            500                 505                 510

Asp Glu Asp Tyr Gly Leu Gly Arg Leu Val Asn Thr Ala Asp Asp Ser
        515                 520                 525

Gln Ser Ile Ile Tyr Gln Ile Val Asp Asp Lys Gly Lys Lys Met Leu
    530                 535                 540

Lys Asp His Gly Thr Glu Val Thr Pro Asn Gln Gln Ile Thr Phe Lys
545                 550                 555                 560

Ala Leu Asn Tyr Thr Ser Gly Asp Lys Glu Ile Pro Pro Gly Ile Tyr
                565                 570                 575

Asn Asp Gln Val Met Val Gly Tyr Tyr Val Asn Asp Asn Lys Gln Gly
            580                 585                 590

Asn Trp Gln Tyr Lys Ser Leu Asp Val Asn Val Asn Ile Glu Gln Leu
        595                 600                 605

Glu His His His His His His
    610                 615


<210> SEQ ID NO 34
<211> LENGTH: 1794
<212> TYPE: DNA
<213> ORGANISM: Escherichia coli

<400> SEQUENCE: 34

atggagcaaa attttattcc agatattgat tccgctgttc gtataatacc tgttaattac      60

gattcggatc cgaaactgaa ttcacagtta tatacggttg agatgacgat ccctgcaggt     120

gtaagcgcag ttaaaatcgt accaacagat agtctgacat cttctggaca gcagatcgga     180

aagctggtta atgtaaacaa tccagatcaa aatatgaatt attatatcag aaaggattct     240

ggcgctggta agtttatggc agggcaaaaa ggatcctttt ctgtcaaaga gaatacgtca     300

tacacattct cagcaattta tactggtggc gaatacccta atagcggata ttcgtctggt     360

acttatgcag gacatttgac tgtatcattt tacagcaatg acaataaaca aagaacagaa     420

atagcgacta aaaacttccc agtatcaacg actatttcaa aaagtttttt tgcgcctgaa     480

ccacaaatcc agccttcttt tggtaaaaat gttggaaagg aaggagattt attatttagt     540

gtgagcttaa ttgttcctga aaatgtatcc caggtaacgg tctaccctgt ttatgatgaa     600

gattatggat taggacgact cgtaaatacc gctgatgatt cccaatcaat aatctaccag     660

attgttgatg ataaagggaa aaaaatgtta aaagatcatg gtacagaggt tacgcctaat     720

caacaaataa cttttaaagc gctgaattat actagcggag ataaagaaat acctcctggg     780

atatataacg atcaggttat ggttggttac tacgtaaacg acaataaaca aggaaactgg     840

caatataaat ctctggacgt gaatgtaaat attgagcaag gcacattagc tattgatttt     900

acgcctattg aaaatattta tgtaggtgcc aattatggta aagatattgg aacccttgtt     960

ttcacaacaa atgatttaac agatattaca ttgatgtcat ctcgcagcgt tgttgatggt    1020

cgccagactg gtttttttac cttcatggac tcatcagcca cttacaaaat tagtacaaaa    1080

ctgggatcat cgaatgatgt aaacattcaa gaaattactc aaggagctaa aattactcct    1140
```

-continued

```
gttagtggag agaaaacttt gcctaaaaaa ttcactctta agctacatgc acacaggagt   1200

agcagtacag ttccaggtac gtatactgtt ggtcttaacg taaccagtaa cgttattgat   1260

aacaagcagg cagcggggcc cactctaacc aaagaactgg cattaaatgt gctttctcct   1320

gcagctctgg atgcaacttg ggctcctcag gataatttaa cattatccaa tactggcgtt   1380

tctaatactt tggtgggtgt tttgactctt tcaaatacca gtattgatac agttagcatt   1440

gcgagtacaa atgtttctga tacatctaag aatggtacag taacttttgc acatgagaca   1500

aataactctg ctagctttgc caccaccatt tcaacagata atgccaacat tacgttggat   1560

aaaaatgctg gaaatacgat tgttaaaact acaaatggga gtcagttgcc aactaattta   1620

ccacttaagt ttattaccac tgaaggtaac gaacatttag tttcaggtaa ttaccgtgca   1680

aatataacaa ttacttcgac aattaaagat aacaagcagg cggcaggtcc aaccctgact   1740

aaggagttag cgctgaacgt tctgagcctc gagcaccacc accaccacca ctga         1794
```

<210> SEQ ID NO 35
<211> LENGTH: 597
<212> TYPE: PRT
<213> ORGANISM: Escherichia coli

<400> SEQUENCE: 35

```
Met Glu Gln Asn Phe Ile Pro Asp Ile Asp Ser Ala Val Arg Ile Ile
1               5                   10                  15

Pro Val Asn Tyr Asp Ser Asp Pro Lys Leu Asn Ser Gln Leu Tyr Thr
            20                  25                  30

Val Glu Met Thr Ile Pro Ala Gly Val Ser Ala Val Lys Ile Val Pro
        35                  40                  45

Thr Asp Ser Leu Thr Ser Ser Gly Gln Gln Ile Gly Lys Leu Val Asn
    50                  55                  60

Val Asn Asn Pro Asp Gln Asn Met Asn Tyr Tyr Ile Arg Lys Asp Ser
65                  70                  75                  80

Gly Ala Gly Lys Phe Met Ala Gly Gln Lys Gly Ser Phe Ser Val Lys
                85                  90                  95

Glu Asn Thr Ser Tyr Thr Phe Ser Ala Ile Tyr Thr Gly Gly Glu Tyr
            100                 105                 110

Pro Asn Ser Gly Tyr Ser Ser Gly Thr Tyr Ala Gly His Leu Thr Val
        115                 120                 125

Ser Phe Tyr Ser Asn Asp Asn Lys Gln Arg Thr Glu Ile Ala Thr Lys
    130                 135                 140

Asn Phe Pro Val Ser Thr Thr Ile Ser Lys Ser Phe Phe Ala Pro Glu
145                 150                 155                 160

Pro Gln Ile Gln Pro Ser Phe Gly Lys Asn Val Gly Lys Glu Gly Asp
                165                 170                 175

Leu Leu Phe Ser Val Ser Leu Ile Val Pro Glu Asn Val Ser Gln Val
            180                 185                 190

Thr Val Tyr Pro Val Tyr Asp Glu Asp Tyr Gly Leu Gly Arg Leu Val
        195                 200                 205

Asn Thr Ala Asp Asp Ser Gln Ser Ile Ile Tyr Gln Ile Val Asp Asp
    210                 215                 220

Lys Gly Lys Lys Met Leu Lys Asp His Gly Thr Glu Val Thr Pro Asn
225                 230                 235                 240

Gln Gln Ile Thr Phe Lys Ala Leu Asn Tyr Thr Ser Gly Asp Lys Glu
                245                 250                 255

Ile Pro Pro Gly Ile Tyr Asn Asp Gln Val Met Val Gly Tyr Tyr Val
```

-continued

```
            260                 265                 270

Asn Asp Asn Lys Gln Gly Asn Trp Gln Tyr Lys Ser Leu Asp Val Asn
        275                 280                 285

Val Asn Ile Glu Gln Gly Thr Leu Ala Ile Asp Phe Thr Pro Ile Glu
    290                 295                 300

Asn Ile Tyr Val Gly Ala Asn Tyr Gly Lys Asp Ile Gly Thr Leu Val
305                 310                 315                 320

Phe Thr Thr Asn Asp Leu Thr Asp Ile Thr Leu Met Ser Ser Arg Ser
                325                 330                 335

Val Val Asp Gly Arg Gln Thr Gly Phe Phe Thr Phe Met Asp Ser Ser
            340                 345                 350

Ala Thr Tyr Lys Ile Ser Thr Lys Leu Gly Ser Ser Asn Asp Val Asn
        355                 360                 365

Ile Gln Glu Ile Thr Gln Gly Ala Lys Ile Thr Pro Val Ser Gly Glu
    370                 375                 380

Lys Thr Leu Pro Lys Lys Phe Thr Leu Lys Leu His Ala His Arg Ser
385                 390                 395                 400

Ser Ser Thr Val Pro Gly Thr Tyr Thr Val Gly Leu Asn Val Thr Ser
                405                 410                 415

Asn Val Ile Asp Asn Lys Gln Ala Ala Gly Pro Thr Leu Thr Lys Glu
            420                 425                 430

Leu Ala Leu Asn Val Leu Ser Pro Ala Ala Leu Asp Ala Thr Trp Ala
        435                 440                 445

Pro Gln Asp Asn Leu Thr Leu Ser Asn Thr Gly Val Ser Asn Thr Leu
    450                 455                 460

Val Gly Val Leu Thr Leu Ser Asn Thr Ser Ile Asp Thr Val Ser Ile
465                 470                 475                 480

Ala Ser Thr Asn Val Ser Asp Thr Ser Lys Asn Gly Thr Val Thr Phe
                485                 490                 495

Ala His Glu Thr Asn Asn Ser Ala Ser Phe Ala Thr Thr Ile Ser Thr
            500                 505                 510

Asp Asn Ala Asn Ile Thr Leu Asp Lys Asn Ala Gly Asn Thr Ile Val
        515                 520                 525

Lys Thr Thr Asn Gly Ser Gln Leu Pro Thr Asn Leu Pro Leu Lys Phe
    530                 535                 540

Ile Thr Thr Glu Gly Asn Glu His Leu Val Ser Gly Asn Tyr Arg Ala
545                 550                 555                 560

Asn Ile Thr Ile Thr Ser Thr Ile Lys Asp Asn Lys Gln Ala Ala Gly
                565                 570                 575

Pro Thr Leu Thr Lys Glu Leu Ala Leu Asn Val Leu Ser Leu Glu His
            580                 585                 590

His His His His His
        595
```

<210> SEQ ID NO 36
<211> LENGTH: 1104
<212> TYPE: DNA
<213> ORGANISM: Escherichia coli

<400> SEQUENCE: 36

```
atgaaatacc tgctgccgac cgctgctgct ggtctgctgc tcctcgctgc ccagccggcg     60

atggccatgg cagtgggccc aacgaaagat atgagtttag gtgcaaattt aacttcagag    120

cctacattag ctattgattt tacgcctatt gaaaatattt atgtaggtgc caattatggt    180
```

-continued

```
aaagatattg gaacccttgt tttcacaaca aatgatttaa cagatattac attgatgtca    240

tctcgcagcg ttgttgatgg tcgccagact ggttttttta ccttcatgga ctcatcagcc    300

acttacaaaa ttagtacaaa actgggatca tcgaatgatg taaacattca agaaattact    360

caaggagcta aaattactcc tgttagtgga gagaaaactt tgcctaaaaa attcactctt    420

aagctacatg cacacaggag tagcagtaca gttccaggta cgtatactgt tggtcttaac    480

gtaaccagta acgttattga taacaagcag gcagcggggc ccactctaac caaagaactg    540

gcattaaatg tgctttctcc tgcagctctg gatgcaactt gggctcctca ggataattta    600

acattatcca atactggcgt ttctaatact ttggtgggtg ttttgactct ttcaaatacc    660

agtattgata cagttagcat tgcgagtaca aatgtttctg atacatctaa gaatggtaca    720

gtaacttttg cacatgagac aaataactct gctagctttg ccaccaccat ttcaacagat    780

aatgccaaca ttacgttgga taaaaatgct ggaaatacga ttgttaaaac tacaaatggg    840

agtcagttgc caactaattt accacttaag tttattacca ctgaaggtaa cgaacattta    900

gtttcaggta attaccgtgc aaatataaca attacttcga caattaaaga taacaagcag    960

gcggcaggtc caaccctgac taaggagtta gcgctgaacg ttctatcgat acttgacgaa   1020

taccaatcta aagttaaaag acaaatattt tcaggctatc aatctgatat tgatacacat   1080

aatagaatta aggatgaatt atga                                          1104
```

<210> SEQ ID NO 37
<211> LENGTH: 367
<212> TYPE: PRT
<213> ORGANISM: Escherichia coli

<400> SEQUENCE: 37

```
Met Lys Tyr Leu Leu Pro Thr Ala Ala Ala Gly Leu Leu Leu Leu Ala
1               5                   10                  15

Ala Gln Pro Ala Met Ala Met Ala Val Gly Pro Thr Lys Asp Met Ser
            20                  25                  30

Leu Gly Ala Asn Leu Thr Ser Glu Pro Thr Leu Ala Ile Asp Phe Thr
        35                  40                  45

Pro Ile Glu Asn Ile Tyr Val Gly Ala Asn Tyr Gly Lys Asp Ile Gly
    50                  55                  60

Thr Leu Val Phe Thr Thr Asn Asp Leu Thr Asp Ile Thr Leu Met Ser
65                  70                  75                  80

Ser Arg Ser Val Val Asp Gly Arg Gln Thr Gly Phe Phe Thr Phe Met
                85                  90                  95

Asp Ser Ser Ala Thr Tyr Lys Ile Ser Thr Lys Leu Gly Ser Ser Asn
            100                 105                 110

Asp Val Asn Ile Gln Glu Ile Thr Gln Gly Ala Lys Ile Thr Pro Val
        115                 120                 125

Ser Gly Glu Lys Thr Leu Pro Lys Lys Phe Thr Leu Lys Leu His Ala
    130                 135                 140

His Arg Ser Ser Ser Thr Val Pro Gly Thr Tyr Thr Val Gly Leu Asn
145                 150                 155                 160

Val Thr Ser Asn Val Ile Asp Asn Lys Gln Ala Ala Gly Pro Thr Leu
                165                 170                 175

Thr Lys Glu Leu Ala Leu Asn Val Leu Ser Pro Ala Ala Leu Asp Ala
            180                 185                 190

Thr Trp Ala Pro Gln Asp Asn Leu Thr Leu Ser Asn Thr Gly Val Ser
        195                 200                 205
```

```
Asn Thr Leu Val Gly Val Leu Thr Leu Ser Asn Thr Ser Ile Asp Thr
    210                 215                 220

Val Ser Ile Ala Ser Thr Asn Val Ser Asp Thr Ser Lys Asn Gly Thr
225                 230                 235                 240

Val Thr Phe Ala His Glu Thr Asn Asn Ser Ala Ser Phe Ala Thr Thr
                245                 250                 255

Ile Ser Thr Asp Asn Ala Asn Ile Thr Leu Asp Lys Asn Ala Gly Asn
            260                 265                 270

Thr Ile Val Lys Thr Thr Asn Gly Ser Gln Leu Pro Thr Asn Leu Pro
        275                 280                 285

Leu Lys Phe Ile Thr Thr Glu Gly Asn Glu His Leu Val Ser Gly Asn
    290                 295                 300

Tyr Arg Ala Asn Ile Thr Ile Thr Ser Thr Ile Lys Asp Asn Lys Gln
305                 310                 315                 320

Ala Ala Gly Pro Thr Leu Thr Lys Glu Leu Ala Leu Asn Val Leu Ser
                325                 330                 335

Ile Leu Asp Glu Tyr Gln Ser Lys Val Lys Arg Gln Ile Phe Ser Gly
            340                 345                 350

Tyr Gln Ser Asp Ile Asp Thr His Asn Arg Ile Lys Asp Glu Leu
        355                 360                 365


<210> SEQ ID NO 38
<211> LENGTH: 381
<212> TYPE: DNA
<213> ORGANISM: Escherichia coli

<400> SEQUENCE: 38

atgagcttta agaaaattat caaggcattt gttatcatgg ctgctttggt atctgttcag      60

gcgcatgccg ctccccagtc tattacagaa ctatgttcgg aatatcacaa cacacaaata     120

tatacgataa atgacaagat actatcatat acggaatcca tggcaggcaa aagagaaatg     180

gttatcatta catttaagag cggcgcaaca tttcaggtcg aagtcccggg cagtcaacat     240

atagactccc aaaaaaaagc cattgaaagg atgaaggaca cattaagaat cgcatatctg     300

accgagacca aaattgataa attatgtgta tggaataata aaaccccgca ttcaattgcg     360

gcaatcagta tggaaaacta a                                               381


<210> SEQ ID NO 39
<211> LENGTH: 126
<212> TYPE: PRT
<213> ORGANISM: Escherichia coli

<400> SEQUENCE: 39

Met Ser Phe Lys Lys Ile Ile Lys Ala Phe Val Ile Met Ala Ala Leu
1               5                   10                  15

Val Ser Val Gln Ala His Ala Ala Pro Gln Ser Ile Thr Glu Leu Cys
            20                  25                  30

Ser Glu Tyr His Asn Thr Gln Ile Tyr Thr Ile Asn Asp Lys Ile Leu
        35                  40                  45

Ser Tyr Thr Glu Ser Met Ala Gly Lys Arg Glu Met Val Ile Ile Thr
    50                  55                  60

Phe Lys Ser Gly Ala Thr Phe Gln Val Glu Val Pro Gly Ser Gln His
65                  70                  75                  80

Ile Asp Ser Gln Lys Lys Ala Ile Glu Arg Met Lys Asp Thr Leu Arg
                85                  90                  95

Ile Ala Tyr Leu Thr Glu Thr Lys Ile Asp Lys Leu Cys Val Trp Asn
```

```
            100                 105                 110

Asn Lys Thr Pro His Ser Ile Ala Ala Ile Ser Met Glu Asn
        115                 120                 125


<210> SEQ ID NO 40
<211> LENGTH: 1038
<212> TYPE: DNA
<213> ORGANISM: Escherichia coli

<400> SEQUENCE: 40

atgaaatacc tgctgccgac cgctgctgct ggtctgctgc tcctcgctgc ccagccggcg     60

atggccatgt caaaaagttt ttttgcacct gaaccacgaa tacagccttc ttttggtgaa    120

aatgttggaa aggaaggagc tttattattt agtgtgaact taactgttcc tgaaaatgta    180

tcccaggtaa cggtctaccc tgtttatgat gaagattatg ggttaggacg actagtaaat    240

accgctgatg cttcccaatc aataatctac cagattgttg atgagaaagg gaaaaaaatg    300

ttaaaagatc atggtgcaga ggttacacct aatcaacaaa taacttttaa agcgctgaat    360

tatactagcg gggaaaaaaa aatatctcct ggaatatata acgatcaggt tatggttggt    420

tactacgtca acgacaataa acaaggaaac tggcaatata aatctctgga tgtaaatgta    480

aatattgagc aaaattttat tccagatatt gattccgctg ttcgtataat acctgttaat    540

tacgattcgg acccgaaact ggattcacag ttatatacgg ttgagatgac gatccctgca    600

ggtgtaagcg cagttaaaat cgcaccaaca gatagtctga catcttctgg acagcagatc    660

ggaaagctgg ttaatgtaaa caatccagat caaaatatga attattatat cagaaaggat    720

tctggcgctg gtaactttat ggcaggacaa aaaggatcct ttcctgtcaa agagaatacg    780

tcatacacat tctcagcaat ttatactggt ggcgaatacc ctaatagcgg atattcgtct    840

ggtacttatg caggaaattt gactgtatca ttttacagca atgacaataa acaaagaaca    900

gaaatagcga ctaaaaactt cccagtatca acgactatat cgatacttga cgaataccaa    960

tctaaagtta aaagacaaat attttcaggc tatcaatctg atattgatac acataataga   1020

attaaggatg aattatga                                                 1038


<210> SEQ ID NO 41
<211> LENGTH: 347
<212> TYPE: PRT
<213> ORGANISM: Escherichia coli

<400> SEQUENCE: 41

Met Lys Tyr Leu Leu Pro Thr Ala Ala Ala Gly Leu Leu Leu Leu Ala
1               5                   10                  15

Ala Gln Pro Ala Met Ala Met Glu Gln Asn Phe Ile Pro Asp Ile Asp
            20                  25                  30

Ser Ala Val Arg Ile Ile Pro Val Asn Tyr Asp Ser Asp Pro Lys Leu
        35                  40                  45

Asn Ser Gln Leu Tyr Thr Val Glu Met Thr Ile Pro Ala Gly Val Ser
    50                  55                  60

Ala Val Lys Ile Val Pro Thr Asp Ser Leu Thr Ser Ser Gly Gln Gln
65                  70                  75                  80

Ile Gly Lys Leu Val Asn Val Asn Asn Pro Asp Gln Asn Met Asn Tyr
                85                  90                  95

Tyr Ile Arg Lys Asp Ser Gly Ala Gly Lys Phe Met Ala Gly Gln Lys
            100                 105                 110

Gly Ser Phe Ser Val Lys Glu Asn Thr Ser Tyr Thr Phe Ser Ala Ile
```

-continued

```
        115                 120                 125

Tyr Thr Gly Gly Glu Tyr Pro Asn Ser Gly Tyr Ser Ser Gly Thr Tyr
    130                 135                 140

Ala Gly His Leu Thr Val Ser Phe Tyr Ser Asn Asp Asn Lys Gln Arg
145                 150                 155                 160

Thr Glu Ile Ala Thr Lys Asn Phe Pro Val Ser Thr Thr Ile Ser Lys
                165                 170                 175

Ser Phe Phe Ala Pro Glu Pro Gln Ile Gln Pro Ser Phe Gly Lys Asn
            180                 185                 190

Val Gly Lys Glu Gly Asp Leu Leu Phe Ser Val Ser Leu Ile Val Pro
        195                 200                 205

Glu Asn Val Ser Gln Val Thr Val Tyr Pro Val Tyr Asp Glu Asp Tyr
    210                 215                 220

Gly Leu Gly Arg Leu Val Asn Thr Ala Asp Asp Ser Gln Ser Ile Ile
225                 230                 235                 240

Tyr Gln Ile Val Asp Asp Lys Gly Lys Lys Met Leu Lys Asp His Gly
                245                 250                 255

Thr Glu Val Thr Pro Asn Gln Gln Ile Thr Phe Lys Ala Leu Asn Tyr
            260                 265                 270

Thr Ser Gly Asp Lys Glu Ile Pro Pro Gly Ile Tyr Asn Asp Gln Val
        275                 280                 285

Met Val Gly Tyr Tyr Val Asn Asp Asn Lys Gln Gly Asn Trp Gln Tyr
    290                 295                 300

Lys Ser Leu Asp Val Asn Val Asn Ile Glu Gln Ser Ile Leu Asp Glu
305                 310                 315                 320

Tyr Gln Ser Lys Val Lys Arg Gln Ile Phe Ser Gly Tyr Gln Ser Asp
                325                 330                 335

Ile Asp Thr His Asn Arg Ile Lys Asp Glu Leu
            340                 345
```

<210> SEQ ID NO 42
<211> LENGTH: 1038
<212> TYPE: DNA
<213> ORGANISM: Escherichia coli

<400> SEQUENCE: 42

```
atgaaatacc tgctgccgac cgctgctgct ggtctgctgc tcctcgctgc ccagccggcg     60

atggccatgt caaaaagttt ttttgcacct gaaccacgaa tacagccttc ttttggtgaa    120

aatgttggaa aggaaggagc tttattattt agtgtgaact taactgttcc tgaaaatgta    180

tcccaggtaa cggtctaccc tgtttatgat gaagattatg ggttaggacg actagtaaat    240

accgctgatg cttcccaatc aataatctac cagattgttg atgagaaagg gaaaaaaatg    300

ttaaaagatc atggtgcaga ggttacacct aatcaacaaa taactttaa agcgctgaat    360

tatactagcg gggaaaaaaa aatatctcct ggaatatata acgatcaggt tatggttggt    420

tactacgtca acgacaataa acaaggaaac tggcaatata aatctctgga tgtaaatgta    480

aatattgagc aaaattttat tccagatatt gattccgctg ttcgtataat acctgttaat    540

tacgattcgg acccgaaact ggattcacag ttatatacgg ttgagatgac gatccctgca    600

ggtgtaagcg cagttaaaat cgcaccaaca gatagtctga catcttctgg acagcagatc    660

ggaaagctgg ttaatgtaaa caatccagat caaaatatga attattatat cagaaaggat    720

tctggcgctg gtaactttat ggcaggacaa aaaggatcct ttcctgtcaa agagaatacg    780

tcatacacat tctcagcaat ttatactggt ggcgaatacc ctaatagcgg atattcgtct    840
```

-continued

```
ggtacttatg caggaaattt gactgtatca ttttacagca atgacaataa acaaagaaca    900

gaaatagcga ctaaaaactt cccagtatca acgactatat cgatacttga cgaataccaa    960

tctaaagtta aaagacaaat attttcaggc tatcaatctg atattgatac acataataga   1020

attaaggatg aattatga                                                 1038


<210> SEQ ID NO 43
<211> LENGTH: 345
<212> TYPE: PRT
<213> ORGANISM: Escherichia coli

<400> SEQUENCE: 43

Met Lys Tyr Leu Leu Pro Thr Ala Ala Ala Gly Leu Leu Leu Leu Ala
1               5                   10                  15

Ala Gln Pro Ala Met Ala Met Ser Lys Ser Phe Phe Ala Pro Glu Pro
            20                  25                  30

Arg Ile Gln Pro Ser Phe Gly Glu Asn Val Gly Lys Glu Gly Ala Leu
        35                  40                  45

Leu Phe Ser Val Asn Leu Thr Val Pro Glu Asn Val Ser Gln Val Thr
    50                  55                  60

Val Tyr Pro Val Tyr Asp Glu Asp Tyr Gly Leu Gly Arg Leu Val Asn
65                  70                  75                  80

Thr Ala Asp Ala Ser Gln Ser Ile Ile Tyr Gln Ile Val Asp Glu Lys
                85                  90                  95

Gly Lys Lys Met Leu Lys Asp His Gly Ala Glu Val Thr Pro Asn Gln
            100                 105                 110

Gln Ile Thr Phe Lys Ala Leu Asn Tyr Thr Ser Gly Glu Lys Lys Ile
        115                 120                 125

Ser Pro Gly Ile Tyr Asn Asp Gln Val Met Val Gly Tyr Tyr Val Asn
    130                 135                 140

Asp Asn Lys Gln Gly Asn Trp Gln Tyr Lys Ser Leu Asp Val Asn Val
145                 150                 155                 160

Asn Ile Glu Gln Asn Phe Ile Pro Asp Ile Asp Ser Ala Val Arg Ile
                165                 170                 175

Ile Pro Val Asn Tyr Asp Ser Asp Pro Lys Leu Asp Ser Gln Leu Tyr
            180                 185                 190

Thr Val Glu Met Thr Ile Pro Ala Gly Val Ser Ala Val Lys Ile Ala
        195                 200                 205

Pro Thr Asp Ser Leu Thr Ser Ser Gly Gln Gln Ile Gly Lys Leu Val
    210                 215                 220

Asn Val Asn Asn Pro Asp Gln Asn Met Asn Tyr Tyr Ile Arg Lys Asp
225                 230                 235                 240

Ser Gly Ala Gly Asn Phe Met Ala Gly Gln Lys Gly Ser Phe Pro Val
                245                 250                 255

Lys Glu Asn Thr Ser Tyr Thr Phe Ser Ala Ile Tyr Thr Gly Gly Glu
            260                 265                 270

Tyr Pro Asn Ser Gly Tyr Ser Ser Gly Thr Tyr Ala Gly Asn Leu Thr
        275                 280                 285

Val Ser Phe Tyr Ser Asn Asp Asn Lys Gln Arg Thr Glu Ile Ala Thr
    290                 295                 300

Lys Asn Phe Pro Val Ser Thr Thr Ile Ser Ile Leu Asp Glu Tyr Gln
305                 310                 315                 320

Ser Lys Val Lys Arg Gln Ile Phe Ser Gly Tyr Gln Ser Asp Ile Asp
                325                 330                 335
```

-continued

```
Thr His Asn Arg Ile Lys Asp Glu Leu
            340                 345


<210> SEQ ID NO 44
<211> LENGTH: 1092
<212> TYPE: DNA
<213> ORGANISM: Escherichia coli

<400> SEQUENCE: 44

atgaaaaaga tatttatttt tttgtctatc atattttctg cggtggtcag tgccgggcga     60

tacccggaaa ctacagtagg taatctgacg aagagttttc aagcccctcg tcaggataga    120

agcgtacaat caccaatata taacatcttt acgaatcatg tggctggata tagtttgagt    180

cataacttat atgacaggat tgttttttta tgtacatcct cgtcgaatcc ggttaatggt    240

gcttgcccaa ccattggaac atctggagtt caatacggta ctacaaccat aaccttgcag    300

tttacagaaa aaagaagtct gataaaaaga aatattaatc ttgcaggtaa taagaaacca    360

atatgggaga atcagagttg cgacactagc aatctaatgg tgttgaattc gaagtcttgg    420

tcctgtgggg cttacggaaa tgctaacgga acacttctaa atctgtatat ccctgcagga    480

gaaatcaaca aattgccttt tggagggata tgggaggcaa ctctgatctt acgcttatca    540

agatatggcg aagtcagtag cacccattac ggcaattata ccgtaaatat tacggttgat    600

ttaactgata aaggtaatat tcaggtatgg cttccagggt ttcacagcaa cccgcgtgta    660

gacctgaatc tgcaccctat cggtaattat aaatatagtg gtagtaattc actcgacatg    720

tgtttctatg atggatatag tacaaacagt gatagcatgg taataaagtt ccaggatgat    780

aatcctacct attcatctga atataatctt tataagatag gggcactgaa aaaattacca    840

tatgctgttt cactgcttat gggagaaaaa atattttatc cagtgaatgg tcaatcattt    900

actatcaatg acagtagtgt actcgaaaca aactggaatc gagtaaccgc agttgctatg    960

ccggaagtta atgttccagt attatgctgg ccagcaagat tgctattaaa tgctgatgta   1020

aatgctcccg atgcaggaca gtattcagga cagatatata taacatttac acccagtgtc   1080

gaaaatttat ga                                                        1092


<210> SEQ ID NO 45
<211> LENGTH: 363
<212> TYPE: PRT
<213> ORGANISM: Escherichia coli

<400> SEQUENCE: 45

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110
```

Asn Leu Ala Gly Asn Lys Lys Pro Ile Trp Glu Asn Gln Ser Cys Asp
115 120 125

Thr Ser Asn Leu Met Val Leu Asn Ser Lys Ser Trp Ser Cys Gly Ala
130 135 140

Tyr Gly Asn Ala Asn Gly Thr Leu Leu Asn Leu Tyr Ile Pro Ala Gly
145 150 155 160

Glu Ile Asn Lys Leu Pro Phe Gly Gly Ile Trp Glu Ala Thr Leu Ile
165 170 175

Leu Arg Leu Ser Arg Tyr Gly Glu Val Ser Ser Thr His Tyr Gly Asn
180 185 190

Tyr Thr Val Asn Ile Thr Val Asp Leu Thr Asp Lys Gly Asn Ile Gln
195 200 205

Val Trp Leu Pro Gly Phe His Ser Asn Pro Arg Val Asp Leu Asn Leu
210 215 220

His Pro Ile Gly Asn Tyr Lys Tyr Ser Gly Ser Asn Ser Leu Asp Met
225 230 235 240

Cys Phe Tyr Asp Gly Tyr Ser Thr Asn Ser Asp Ser Met Val Ile Lys
245 250 255

Phe Gln Asp Asp Asn Pro Thr Tyr Ser Ser Glu Tyr Asn Leu Tyr Lys
260 265 270

Ile Gly Gly Thr Glu Lys Leu Pro Tyr Ala Val Ser Leu Leu Met Gly
275 280 285

Glu Lys Ile Phe Tyr Pro Val Asn Gly Gln Ser Phe Thr Ile Asn Asp
290 295 300

Ser Ser Val Leu Glu Thr Asn Trp Asn Arg Val Thr Ala Val Ala Met
305 310 315 320

Pro Glu Val Asn Val Pro Val Leu Cys Trp Pro Ala Arg Leu Leu Leu
325 330 335

Asn Ala Asp Val Asn Ala Pro Asp Ala Gly Gln Tyr Ser Gly Gln Ile
340 345 350

Tyr Ile Thr Phe Thr Pro Ser Val Glu Asn Leu
355 360

<210> SEQ ID NO 46
<211> LENGTH: 345
<212> TYPE: PRT
<213> ORGANISM: Escherichia coli

<400> SEQUENCE: 46

Gly Arg Tyr Pro Glu Thr Thr Val Gly Asn Leu Thr Lys Ser Phe Gln
1 5 10 15

Ala Pro Arg Gln Asp Arg Ser Val Gln Ser Pro Ile Tyr Asn Ile Phe
20 25 30

Thr Asn His Val Ala Gly Tyr Ser Leu Ser His Asn Leu Tyr Asp Arg
35 40 45

Ile Val Phe Leu Cys Thr Ser Ser Ser Asn Pro Val Asn Gly Ala Cys
50 55 60

Pro Thr Ile Gly Thr Ser Gly Val Gln Tyr Gly Thr Thr Thr Ile Thr
65 70 75 80

Leu Gln Phe Thr Glu Lys Arg Ser Leu Ile Lys Arg Asn Ile Asn Leu
85 90 95

Ala Gly Asn Lys Lys Pro Ile Trp Glu Asn Gln Ser Cys Asp Thr Ser
100 105 110

Asn Leu Met Val Leu Asn Ser Lys Ser Trp Ser Cys Gly Ala Tyr Gly
115 120 125

```
Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu His Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Tyr Ser Ser Glu Tyr Asn Leu Tyr Lys Ile Gly
                245                 250                 255

Gly Thr Glu Lys Leu Pro Tyr Ala Val Ser Leu Leu Met Gly Glu Lys
            260                 265                 270

Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345


<210> SEQ ID NO 47
<211> LENGTH: 507
<212> TYPE: DNA
<213> ORGANISM: Escherichia coli

<400> SEQUENCE: 47

atgaaactga agaaaacaat tggcgcaatg gctatggcga ctctgtttgc caccatggct      60

gcctctgcag tcgaaaaaaa tattactgtg agggcaagtg ttgaccctaa acttgatctt     120

ctgcaagcag atggaacttc actgccggac tctatcgcat taacctattc ttcggcttca     180

aataattttg aagtttactc tcttaatact gctattcata caaatgacaa aagcaaggga     240

gttgtagtga agctgtcagc ttcaccagtt ctgtccaata ttatgaagcc aaactcgcaa     300

attccgatga aagtgacttt ggggggggaag acgctgaata caactgatac tgagtttact     360

gttgatactc tgaactttgg tacatctggt gttgaaaacg tttcttccac tcaacagctt     420

acgattcatg cagacacaca aggaactgcg cctgaggcag gcaattacca aggtattatt     480

tctcttatca tgactcaaaa aacttaa                                         507


<210> SEQ ID NO 48
<211> LENGTH: 168
<212> TYPE: PRT
<213> ORGANISM: Escherichia coli

<400> SEQUENCE: 48

Met Lys Leu Lys Lys Thr Ile Gly Ala Met Ala Met Ala Thr Leu Phe
1               5                   10                  15
```

```
Ala Thr Met Ala Ala Ser Ala Val Glu Lys Asn Ile Thr Val Arg Ala
            20                  25                  30

Ser Val Asp Pro Lys Leu Asp Leu Leu Gln Ala Asp Gly Thr Ser Leu
        35                  40                  45

Pro Asp Ser Ile Ala Leu Thr Tyr Ser Ser Ala Ser Asn Asn Phe Glu
    50                  55                  60

Val Tyr Ser Leu Asn Thr Ala Ile His Thr Asn Asp Lys Ser Lys Gly
65                  70                  75                  80

Val Val Val Lys Leu Ser Ala Ser Pro Val Leu Ser Asn Ile Met Lys
                85                  90                  95

Pro Asn Ser Gln Ile Pro Met Lys Val Thr Leu Gly Gly Lys Thr Leu
            100                 105                 110

Asn Thr Thr Asp Thr Glu Phe Thr Val Asp Thr Leu Asn Phe Gly Thr
        115                 120                 125

Ser Gly Val Glu Asn Val Ser Ser Thr Gln Gln Leu Thr Ile His Ala
    130                 135                 140

Asp Thr Gln Gly Thr Ala Pro Glu Ala Gly Asn Tyr Gln Gly Ile Ile
145                 150                 155                 160

Ser Leu Ile Met Thr Gln Lys Thr
                165
```

<210> SEQ ID NO 49
<211> LENGTH: 145
<212> TYPE: PRT
<213> ORGANISM: Escherichia coli

<400> SEQUENCE: 49

```
Val Glu Lys Asn Ile Thr Val Arg Ala Ser Val Asp Pro Lys Leu Asp
1               5                   10                  15

Leu Leu Gln Ala Asp Gly Thr Ser Leu Pro Asp Ser Ile Ala Leu Thr
            20                  25                  30

Tyr Ser Ser Ala Ser Asn Asn Phe Glu Val Tyr Ser Leu Asn Thr Ala
        35                  40                  45

Ile His Thr Asn Asp Lys Ser Lys Gly Val Val Val Lys Leu Ser Ala
    50                  55                  60

Ser Pro Val Leu Ser Asn Ile Met Lys Pro Asn Ser Gln Ile Pro Met
65                  70                  75                  80

Lys Val Thr Leu Gly Gly Lys Thr Leu Asn Thr Thr Asp Thr Glu Phe
                85                  90                  95

Thr Val Asp Thr Leu Asn Phe Gly Thr Ser Gly Val Glu Asn Val Ser
            100                 105                 110

Ser Thr Gln Gln Leu Thr Ile His Ala Asp Thr Gln Gly Thr Ala Pro
        115                 120                 125

Glu Ala Gly Asn Tyr Gln Gly Ile Ile Ser Leu Ile Met Thr Gln Lys
    130                 135                 140

Thr
145
```

<210> SEQ ID NO 50
<211> LENGTH: 1095
<212> TYPE: DNA
<213> ORGANISM: Escherichia coli

<400> SEQUENCE: 50

```
ttgaaaaaag tgatttttgt tttatccatg tttctatgtt ctcaggttta cgggcaatca     60
```

```
tggcatacga acgtagaggc tggttcaata aataaaacag agtcgatagg ccccatagac    120

cgaagtgctg ctgcatcgta tcctgctcat tatatatttc atgaacatgt tgctggttac    180

aataaagatc actctctttt tgacaggatg acgtttttat gtatgtcatc aacagatgca    240

tctaaaggtg catgtccgac aggagaaaac tccaaatcct ctcaagggga gactaatatt    300

aagctaatat ttactgaaaa gaaaagtctg gccagaaaaa cattaaactt aaaaggatat    360

aagagatttt tatatgaatc agatagatgc attcattatg tcgataaaat gaatctcaat    420

tctcatactg ttaaatgtgt aggttcattc acaagaggag tagatttcac tttatatatc    480

ccacaaggtg aaattgatgg gcttctaact ggaggtatat gggaggcaac actagagtta    540

cgagtcaaaa ggcattacga ctataatcat ggtacttaca aagttaatat cacagttgat    600

ttgacagaca aaggaaatat tcaggtctgg acaccaaagt ttcatagcga tcctagaatt    660

gatctgaatt tacgtcctga aggtaatggt aaatattctg gtagtaacgt gcttgagatg    720

tgtctctatg atggctatag tacacatagt caaagtatag aaatgaggtt tcaggatgac    780

tcacaaacag gaaataatga atataatctt ataaaaactg gagagccatt aaaaaaattg    840

ccatataaac tttctcttct tttaggagga cgagagtttt atccaaataa tggagaggct    900

tttactatta atgatacttc gtcattgttt ataaactgga atcgtattaa gtctgtatcc    960

ttaccacaga ttagtattcc agtactatgc tggccagcaa acttgacatt tatgtcagag   1020

ctaaataatc cagaagcggg tgagtattca ggaatactta acgtaacatt tactcctagt   1080

agttcaagtc tgtaa                                                    1095
```

<210> SEQ ID NO 51
<211> LENGTH: 364
<212> TYPE: PRT
<213> ORGANISM: Escherichia coli

<400> SEQUENCE: 51

```
Leu Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190
```

```
Tyr Lys Val Asn Ile Thr Val Asp Leu Thr Asp Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Ser Leu
        355                 360


<210> SEQ ID NO 52
<211> LENGTH: 346
<212> TYPE: PRT
<213> ORGANISM: Escherichia coli

<400> SEQUENCE: 52

Gln Ser Trp His Thr Asn Val Glu Ala Gly Ser Ile Asn Lys Thr Glu
1               5                   10                  15

Ser Ile Gly Pro Ile Asp Arg Ser Ala Ala Ala Ser Tyr Pro Ala His
            20                  25                  30

Tyr Ile Phe His Glu His Val Ala Gly Tyr Asn Lys Asp His Ser Leu
        35                  40                  45

Phe Asp Arg Met Thr Phe Leu Cys Met Ser Ser Thr Asp Ala Ser Lys
    50                  55                  60

Gly Ala Cys Pro Thr Gly Glu Asn Ser Lys Ser Ser Gln Gly Glu Thr
65                  70                  75                  80

Asn Ile Lys Leu Ile Phe Thr Glu Lys Lys Ser Leu Ala Arg Lys Thr
                85                  90                  95

Leu Asn Leu Lys Gly Tyr Lys Arg Phe Leu Tyr Glu Ser Asp Arg Cys
            100                 105                 110

Ile His Tyr Val Asp Lys Met Asn Leu Asn Ser His Thr Val Lys Cys
        115                 120                 125

Val Gly Ser Phe Thr Arg Gly Val Asp Phe Thr Leu Tyr Ile Pro Gln
    130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175

Val Asn Ile Thr Val Asp Leu Thr Asp Lys Gly Asn Ile Gln Val Trp
            180                 185                 190

Thr Pro Lys Phe His Ser Asp Pro Arg Ile Asp Leu Asn Leu Arg Pro
```

```
        195                 200                 205

Glu Gly Asn Gly Lys Tyr Ser Gly Ser Asn Val Leu Glu Met Cys Leu
    210                 215                 220

Tyr Asp Gly Tyr Ser Thr His Ser Gln Ser Ile Glu Met Arg Phe Gln
225                 230                 235                 240

Asp Asp Ser Gln Thr Gly Asn Asn Glu Tyr Asn Leu Ile Lys Thr Gly
                245                 250                 255

Glu Pro Leu Lys Lys Leu Pro Tyr Lys Leu Ser Leu Leu Leu Gly Gly
            260                 265                 270

Arg Glu Phe Tyr Pro Asn Asn Gly Glu Ala Phe Thr Ile Asn Asp Thr
        275                 280                 285

Ser Ser Leu Phe Ile Asn Trp Asn Arg Ile Lys Ser Val Ser Leu Pro
    290                 295                 300

Gln Ile Ser Ile Pro Val Leu Cys Trp Pro Ala Asn Leu Thr Phe Met
305                 310                 315                 320

Ser Glu Leu Asn Asn Pro Glu Ala Gly Glu Tyr Ser Gly Ile Leu Asn
                325                 330                 335

Val Thr Phe Thr Pro Ser Ser Ser Ser Leu
            340                 345
```

<210> SEQ ID NO 53
<211> LENGTH: 513
<212> TYPE: DNA
<213> ORGANISM: Escherichia coli

<400> SEQUENCE: 53

```
atgaaactca ataagattat tggagcatta gttctttcat ctacatttgt tagcatgggg     60

gcttctgctg ccgagaaaaa tatcactgta actgctagcg ttgatccaac tatcgatctg    120

atgcaatctg atggcacagc gttaccaagt gcagttaata ttgcatatct tccaggagag    180

aaaagatttg aatctgctcg tatcaatacc caagttcata ccaataataa aactaagggt    240

attcagataa agcttactaa tgataatgtg gtaatgacta acttatctga tccaagcaag    300

actattcctt tagaggtttc attcgctggc actaagctga gcacagctgc aacatctatt    360

actgccgatc aattaaattt tggcgcagct ggtgtagaga cagtttctgc aactaaggaa    420

ctcgttatta atgcaggaag cacccagcaa actaatattg tagctggtaa ctatcaagga    480

ttggtgtcaa ttgtgcttac tcaagaacct taa                                 513
```

<210> SEQ ID NO 54
<211> LENGTH: 170
<212> TYPE: PRT
<213> ORGANISM: Escherichia coli

<400> SEQUENCE: 54

```
Met Lys Leu Asn Lys Ile Ile Gly Ala Leu Val Leu Ser Ser Thr Phe
1               5                   10                  15

Val Ser Met Gly Ala Ser Ala Ala Glu Lys Asn Ile Thr Val Thr Ala
            20                  25                  30

Ser Val Asp Pro Thr Ile Asp Leu Met Gln Ser Asp Gly Thr Ala Leu
        35                  40                  45

Pro Ser Ala Val Asn Ile Ala Tyr Leu Pro Gly Glu Lys Arg Phe Glu
    50                  55                  60

Ser Ala Arg Ile Asn Thr Gln Val His Thr Asn Asn Lys Thr Lys Gly
65                  70                  75                  80

Ile Gln Ile Lys Leu Thr Asn Asp Asn Val Val Met Thr Asn Leu Ser
```

```
            85                  90                  95

Asp Pro Ser Lys Thr Ile Pro Leu Glu Val Ser Phe Ala Gly Thr Lys
            100                 105                 110

Leu Ser Thr Ala Ala Thr Ser Ile Thr Ala Asp Gln Leu Asn Phe Gly
        115                 120                 125

Ala Ala Gly Val Glu Thr Val Ser Ala Thr Lys Glu Leu Val Ile Asn
    130                 135                 140

Ala Gly Ser Thr Gln Gln Thr Asn Ile Val Ala Gly Asn Tyr Gln Gly
145                 150                 155                 160

Leu Val Ser Ile Val Leu Thr Gln Glu Pro
                165                 170


<210> SEQ ID NO 55
<211> LENGTH: 147
<212> TYPE: PRT
<213> ORGANISM: Escherichia coli

<400> SEQUENCE: 55

Ala Glu Lys Asn Ile Thr Val Thr Ala Ser Val Asp Pro Thr Ile Asp
1               5                   10                  15

Leu Met Gln Ser Asp Gly Thr Ala Leu Pro Ser Ala Val Asn Ile Ala
            20                  25                  30

Tyr Leu Pro Gly Glu Lys Arg Phe Glu Ser Ala Arg Ile Asn Thr Gln
        35                  40                  45

Val His Thr Asn Asn Lys Thr Lys Gly Ile Gln Ile Lys Leu Thr Asn
    50                  55                  60

Asp Asn Val Val Met Thr Asn Leu Ser Asp Pro Ser Lys Thr Ile Pro
65                  70                  75                  80

Leu Glu Val Ser Phe Ala Gly Thr Lys Leu Ser Thr Ala Ala Thr Ser
                85                  90                  95

Ile Thr Ala Asp Gln Leu Asn Phe Gly Ala Ala Gly Val Glu Thr Val
            100                 105                 110

Ser Ala Thr Lys Glu Leu Val Ile Asn Ala Gly Ser Thr Gln Gln Thr
        115                 120                 125

Asn Ile Val Ala Gly Asn Tyr Gln Gly Leu Val Ser Ile Val Leu Thr
    130                 135                 140

Gln Glu Pro
145


<210> SEQ ID NO 56
<211> LENGTH: 1083
<212> TYPE: DNA
<213> ORGANISM: Escherichia coli

<400> SEQUENCE: 56

atgaataaaa ttttatttat ttttacattg tttttttctt cagggttttt tacatttgcc      60

gtatcggcag ataaaaatcc cggaagtgaa aacatgacta atactattgg tccccatgac     120

agggggggat cttcccccat atataatatc ttaaattcct atcttacagc atacaatgga     180

agccatcatc tgtatgatag gatgagtttt ttatgtttgt cttctcaaaa tacactgaat     240

ggagcatgcc caagcagtga tgcccctggc actgctacaa ttgatggcga aacaaatata     300

acattacaat ttacggaaaa aagaagtcta attaaaagag aactgcaaat taaaggctat     360

aaacaatttt tgttcaaaaa tgctaattgc ccatctaaac tagcacttaa ctcatctcat     420

tttcaatgta atagagaaca agcttcaggt gctactttat cgttatacat accagctggt     480
```

-continued

```
gaattaaata aattaccttt tgggggggtc tggaatgccg ttctgaagct aaatgtaaaa    540

agacgatatg atacaaccta tgggacttac actataaaca tcacagttaa tttaactgat    600

aagggaaata ttcagatatg gttaccacag ttcaaaagta acgctcgtgt cgatcttaac    660

ttgcgtccaa ctggtggtgg tacatatatc ggaagaaatt ctgttgatat gtgcttttat    720

gatggatata gtactaacag cagctctttg gagataagat ttcaggatga taattctaaa    780

tctgatggaa aattttatct aaagaaaata aatgatgact ccaaagaact tgtatacact    840

ttgtcacttc tcctggcagg taaaaattta acaccaacaa atggacaggc attaaatatt    900

aacactgctt ctctggaaac aaactggaat agaattacag ctgtcaccat gccagaaatc    960

agtgttccgg tgttgtgttg gcctggacgt ttgcaattgg atgcaaaagt gaaaaatccc   1020

gaggctggac aatatatggg gaatattaaa attactttca caccaagtag tcaaacactc   1080

tag                                                                 1083
```

<210> SEQ ID NO 57
<211> LENGTH: 360
<212> TYPE: PRT
<213> ORGANISM: Escherichia coli

<400> SEQUENCE: 57

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
```

```
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu
        355                 360


<210> SEQ ID NO 58
<211> LENGTH: 338
<212> TYPE: PRT
<213> ORGANISM: Escherichia coli

<400> SEQUENCE: 58

Ala Asp Lys Asn Pro Gly Ser Glu Asn Met Thr Asn Thr Ile Gly Pro
1               5                   10                  15

His Asp Arg Gly Gly Ser Ser Pro Ile Tyr Asn Ile Leu Asn Ser Tyr
            20                  25                  30

Leu Thr Ala Tyr Asn Gly Ser His His Leu Tyr Asp Arg Met Ser Phe
        35                  40                  45

Leu Cys Leu Ser Ser Gln Asn Thr Leu Asn Gly Ala Cys Pro Ser Ser
    50                  55                  60

Asp Ala Pro Gly Thr Ala Thr Ile Asp Gly Glu Thr Asn Ile Thr Leu
65                  70                  75                  80

Gln Phe Thr Glu Lys Arg Ser Leu Ile Lys Arg Glu Leu Gln Ile Lys
                85                  90                  95

Gly Tyr Lys Gln Phe Leu Phe Lys Asn Ala Asn Cys Pro Ser Lys Leu
            100                 105                 110

Ala Leu Asn Ser Ser His Phe Gln Cys Asn Arg Glu Gln Ala Ser Gly
        115                 120                 125

Ala Thr Leu Ser Leu Tyr Ile Pro Ala Gly Glu Leu Asn Lys Leu Pro
    130                 135                 140

Phe Gly Gly Val Trp Asn Ala Val Leu Lys Leu Asn Val Lys Arg Arg
145                 150                 155                 160

Tyr Asp Thr Thr Tyr Gly Thr Tyr Thr Ile Asn Ile Thr Val Asn Leu
                165                 170                 175

Thr Asp Lys Gly Asn Ile Gln Ile Trp Leu Pro Gln Phe Lys Ser Asn
            180                 185                 190

Ala Arg Val Asp Leu Asn Leu Arg Pro Thr Gly Gly Gly Thr Tyr Ile
        195                 200                 205

Gly Arg Asn Ser Val Asp Met Cys Phe Tyr Asp Gly Tyr Ser Thr Asn
    210                 215                 220

Ser Ser Ser Leu Glu Ile Arg Phe Gln Asp Asp Asn Ser Lys Ser Asp
225                 230                 235                 240

Gly Lys Phe Tyr Leu Lys Lys Ile Asn Asp Asp Ser Lys Glu Leu Val
                245                 250                 255

Tyr Thr Leu Ser Leu Leu Leu Ala Gly Lys Asn Leu Thr Pro Thr Asn
            260                 265                 270
```

```
Gly Gln Ala Leu Asn Ile Asn Thr Ala Ser Leu Glu Thr Asn Trp Asn
        275                 280                 285

Arg Ile Thr Ala Val Thr Met Pro Glu Ile Ser Val Pro Val Leu Cys
    290                 295                 300

Trp Pro Gly Arg Leu Gln Leu Asp Ala Lys Val Lys Asn Pro Glu Ala
305                 310                 315                 320

Gly Gln Tyr Met Gly Asn Ile Lys Ile Thr Phe Thr Pro Ser Ser Gln
                325                 330                 335

Thr Leu


<210> SEQ ID NO 59
<211> LENGTH: 513
<212> TYPE: DNA
<213> ORGANISM: Escherichia coli

<400> SEQUENCE: 59

atgaaattta aaaaaactat tggtgcaatg gctctgacca caatgtttgt agcagtgagt      60

gcttcagcag tagagaaaaa tattactgta acagctagtg ttgatcctgc aattgatctt     120

ttgcaagctg atggcaatgc tctgccatca gctgtaaagt tagcttattc tcccgcatca     180

aaaacttttg aaagttacag agtaatgact caagttcata caaacgatgc aactaaaaaa     240

gtaattgtta aacttgctga tacaccacag cttacagatg ttctgaattc aactgttcaa     300

atgcctatca gtgtgtcatg gggaggacaa gtattatcta caacagccaa agaatttgaa     360

gctgctgctt tgggatattc tgcatccggt gtaaatggcg tatcatcttc tcaagagtta     420

gtaattagcg ctgcacctaa aactgccggt accgccccaa ctgcaggaaa ctattcagga     480

gtagtatctc ttgtaatgac tttgggatcc tga                                  513


<210> SEQ ID NO 60
<211> LENGTH: 170
<212> TYPE: PRT
<213> ORGANISM: Escherichia coli

<400> SEQUENCE: 60

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
            20                  25                  30

Ser Val Asp Pro Ala Ile Asp Leu Leu Gln Ala Asp Gly Asn Ala Leu
        35                  40                  45

Pro Ser Ala Val Lys Leu Ala Tyr Ser Pro Ala Ser Lys Thr Phe Glu
    50                  55                  60

Ser Tyr Arg Val Met Thr Gln Val His Thr Asn Asp Ala Thr Lys Lys
65                  70                  75                  80

Val Ile Val Lys Leu Ala Asp Thr Pro Gln Leu Thr Asp Val Leu Asn
                85                  90                  95

Ser Thr Val Gln Met Pro Ile Ser Val Ser Trp Gly Gly Gln Val Leu
            100                 105                 110

Ser Thr Thr Ala Lys Glu Phe Glu Ala Ala Ala Leu Gly Tyr Ser Ala
        115                 120                 125

Ser Gly Val Asn Gly Val Ser Ser Ser Gln Glu Leu Val Ile Ser Ala
    130                 135                 140

Ala Pro Lys Thr Ala Gly Thr Ala Pro Thr Ala Gly Asn Tyr Ser Gly
145                 150                 155                 160

Val Val Ser Leu Val Met Thr Leu Gly Ser
```

165 170

<210> SEQ ID NO 61
<211> LENGTH: 147
<212> TYPE: PRT
<213> ORGANISM: Escherichia coli

<400> SEQUENCE: 61

Val Glu Lys Asn Ile Thr Val Thr Ala Ser Val Asp Pro Ala Ile Asp
1 5 10 15

Leu Leu Gln Ala Asp Gly Asn Ala Leu Pro Ser Ala Val Lys Leu Ala
20 25 30

Tyr Ser Pro Ala Ser Lys Thr Phe Glu Ser Tyr Arg Val Met Thr Gln
35 40 45

Val His Thr Asn Asp Ala Thr Lys Lys Val Ile Val Lys Leu Ala Asp
50 55 60

Thr Pro Gln Leu Thr Asp Val Leu Asn Ser Thr Val Gln Met Pro Ile
65 70 75 80

Ser Val Ser Trp Gly Gly Gln Val Leu Ser Thr Thr Ala Lys Glu Phe
85 90 95

Glu Ala Ala Ala Leu Gly Tyr Ser Ala Ser Gly Val Asn Gly Val Ser
100 105 110

Ser Ser Gln Glu Leu Val Ile Ser Ala Ala Pro Lys Thr Ala Gly Thr
115 120 125

Ala Pro Thr Ala Gly Asn Tyr Ser Gly Val Val Ser Leu Val Met Thr
130 135 140

Leu Gly Ser
145

<210> SEQ ID NO 62
<211> LENGTH: 504
<212> TYPE: DNA
<213> ORGANISM: Escherichia coli

<400> SEQUENCE: 62
atgaaattaa aaaaaactat tggtgcaatg gcactgacca caatgtttgt agctatgagt 60
gcttctgcag tagagaaaaa tatcactgta acagctagtg ttgatcctac aattgatatt 120
ttgcaagctg atggtagtag tttacctact gctgtagaat taacctattc acctgcggca 180
agtcgttttg aaaattataa aatcgcaact aaagttcata caaatgttat aaataaaaat 240
gtactagtta agcttgtaaa tgatccaaaa cttacaaatg ttttggattc tacaaaacaa 300
ctccccatta ctgtatcata tggaggaaag actctatcaa ccgcagatgt gacttttgaa 360
cctgcagaat taaattttgg aacgtcaggt gtaactggtg tatcttcttc ccaagattta 420
gtgattggtg cgactacagc acaagcacca acggcgggaa attatagtgg ggtcgtttct 480
atcttaatga ccttagcatc ataa 504

<210> SEQ ID NO 63
<211> LENGTH: 167
<212> TYPE: PRT
<213> ORGANISM: Escherichia coli

<400> SEQUENCE: 63

Met Lys Leu Lys Lys Thr Ile Gly Ala Met Ala Leu Thr Thr Met Phe
1 5 10 15

Val Ala Met Ser Ala Ser Ala Val Glu Lys Asn Ile Thr Val Thr Ala
20 25 30

```
Ser Val Asp Pro Thr Ile Asp Ile Leu Gln Ala Asp Gly Ser Ser Leu
        35                  40                  45

Pro Thr Ala Val Glu Leu Thr Tyr Ser Pro Ala Ala Ser Arg Phe Glu
    50                  55                  60

Asn Tyr Lys Ile Ala Thr Lys Val His Thr Asn Val Ile Asn Lys Asn
65                  70                  75                  80

Val Leu Val Lys Leu Val Asn Asp Pro Lys Leu Thr Asn Val Leu Asp
                85                  90                  95

Ser Thr Lys Gln Leu Pro Ile Thr Val Ser Tyr Gly Gly Lys Thr Leu
            100                 105                 110

Ser Thr Ala Asp Val Thr Phe Glu Pro Ala Glu Leu Asn Phe Gly Thr
        115                 120                 125

Ser Gly Val Thr Gly Val Ser Ser Ser Gln Asp Leu Val Ile Gly Ala
    130                 135                 140

Thr Thr Ala Gln Ala Pro Thr Ala Gly Asn Tyr Ser Gly Val Val Ser
145                 150                 155                 160

Ile Leu Met Thr Leu Ala Ser
                165
```

<210> SEQ ID NO 64
<211> LENGTH: 1086
<212> TYPE: DNA
<213> ORGANISM: Escherichia coli

<400> SEQUENCE: 64

```
atgaataaga ttttatttat ttttacattg tttttctctt cagtactttt tacatttgct     60

gtatcggcag ataaaattcc cggagatgaa agcataacta atatttttgg cccgcgtgac    120

aggaacgaat cttcccccaa acataatata ttaaataacc atattacagc atacagtgaa    180

agtcatactc tgtatgatag gatgactttt ttatgtttgt cttctcacaa tacacttaat    240

ggagcatgtc caaccagtga gaatcctagc agttcatcgg tcagcggtga aacaaatata    300

acattacaat ttacggaaaa aagaagttta ataaaaagag agctacaaat taaaggctat    360

aaacaattat tgttcaaaag tgttaactgc ccatccggcc taacacttaa ctcagctcat    420

tttaactgta ataaaaacgc ggcttcaggt gcaagtttat atttatatat tcctgctggc    480

gaactaaaaa atttgccttt tggtggtatc tgggatgcta ctctgaagtt aagagtaaaa    540

agacgatata gtgagaccta tggaacttac actataaata tcactattaa attaactgat    600

aagggaaata ttcagatatg gttacctcag ttcaaaagtg acgctcgcgt cgatcttaac    660

ttgcgtccaa ctggtggggg cacatatatt ggaagaaatt ctgttgatat gtgcttttat    720

gatggatata gtactaacag cagctctttg gagataagat ttcaggataa caatcctaaa    780

tctgatggga aattttatct aaggaaaata aatgatgaca ccaaagaaat tgcatatact    840

ttgtcacttc tcttggcggg taaaagttta actccaacaa atggaacgtc attaaatatt    900

gctgacgcag cttctctgga aacaaactgg aatagaatta cagctgtcac catgccagaa    960

atcagtgttc cggtgttgtg ttggcctgga cgtttgcaat tggatgcaaa agtggaaaat   1020

cccgaggctg gacaatatat gggtaatatt aatgttactt tcacaccaag tagtcaaaca   1080

ctctag                                                               1086
```

<210> SEQ ID NO 65
<211> LENGTH: 361
<212> TYPE: PRT
<213> ORGANISM: Escherichia coli

<400> SEQUENCE: 65

Met Asn Lys Ile Leu Phe Ile Phe Thr Leu Phe Phe Ser Ser Val Leu
1 5 10 15

Phe Thr Phe Ala Val Ser Ala Asp Lys Ile Pro Gly Asp Glu Ser Ile
20 25 30

Thr Asn Ile Phe Gly Pro Arg Asp Arg Asn Glu Ser Ser Pro Lys His
35 40 45

Asn Ile Leu Asn Asn His Ile Thr Ala Tyr Ser Glu Ser His Thr Leu
50 55 60

Tyr Asp Arg Met Thr Phe Leu Cys Leu Ser Ser His Asn Thr Leu Asn
65 70 75 80

Gly Ala Cys Pro Thr Ser Glu Asn Pro Ser Ser Ser Ser Val Ser Gly
85 90 95

Glu Thr Asn Ile Thr Leu Gln Phe Thr Glu Lys Arg Ser Leu Ile Lys
100 105 110

Arg Glu Leu Gln Ile Lys Gly Tyr Lys Gln Leu Leu Phe Lys Ser Val
115 120 125

Asn Cys Pro Ser Gly Leu Thr Leu Asn Ser Ala His Phe Asn Cys Asn
130 135 140

Lys Asn Ala Ala Ser Gly Ala Ser Leu Tyr Leu Tyr Ile Pro Ala Gly
145 150 155 160

Glu Leu Lys Asn Leu Pro Phe Gly Gly Ile Trp Asp Ala Thr Leu Lys
165 170 175

Leu Arg Val Lys Arg Arg Tyr Ser Glu Thr Tyr Gly Thr Tyr Thr Ile
180 185 190

Asn Ile Thr Ile Lys Leu Thr Asp Lys Gly Asn Ile Gln Ile Trp Leu
195 200 205

Pro Gln Phe Lys Ser Asp Ala Arg Val Asp Leu Asn Leu Arg Pro Thr
210 215 220

Gly Gly Gly Thr Tyr Ile Gly Arg Asn Ser Val Asp Met Cys Phe Tyr
225 230 235 240

Asp Gly Tyr Ser Thr Asn Ser Ser Ser Leu Glu Ile Arg Phe Gln Asp
245 250 255

Asn Asn Pro Lys Ser Asp Gly Lys Phe Tyr Leu Arg Lys Ile Asn Asp
260 265 270

Asp Thr Lys Glu Ile Ala Tyr Thr Leu Ser Leu Leu Leu Ala Gly Lys
275 280 285

Ser Leu Thr Pro Thr Asn Gly Thr Ser Leu Asn Ile Ala Asp Ala Ala
290 295 300

Ser Leu Glu Thr Asn Trp Asn Arg Ile Thr Ala Val Thr Met Pro Glu
305 310 315 320

Ile Ser Val Pro Val Leu Cys Trp Pro Gly Arg Leu Gln Leu Asp Ala
325 330 335

Lys Val Glu Asn Pro Glu Ala Gly Gln Tyr Met Gly Asn Ile Asn Val
340 345 350

Thr Phe Thr Pro Ser Ser Gln Thr Leu
355 360

<210> SEQ ID NO 66
<211> LENGTH: 510
<212> TYPE: DNA
<213> ORGANISM: Escherichia coli

<400> SEQUENCE: 66
atgaaattaa aaaaaactat tggcgcaatg gctctgagca caatatttgt agcggtgagt 60
gcttcagcag tagagaaaaa tattactgtg acagccagtg ttgatcctac tattgatatt 120
cttcaagcaa atggttctgc gctaccgaca gctgtagatt taacttatct acctggtgca 180
aaaacttttg aaaattacag tgttctaacc cagatttaca caaatgaccc ttcaaaaggt 240
ttagatgttc gactggttga tacaccgaaa cttacaaata ttttgcaacc gacatctacc 300
attcctctta ctgtctcatg ggcagggagg acattaagta caagtgctca gaagatcgca 360
gttggcgatc tgggttttgg ttccaccgga acggcaggtg tttcgaatag taaagaatta 420
gtaattggag caactacatc cggaactgca ccaagtgcag gtaagtatca aggcgtcgtt 480
tccattgtaa tgactcaatc gacaaactaa 510

<210> SEQ ID NO 67
<211> LENGTH: 169
<212> TYPE: PRT
<213> ORGANISM: Escherichia coli

<400> SEQUENCE: 67

Met Lys Leu Lys Lys Thr Ile Gly Ala Met Ala Leu Ser Thr Ile Phe
1 5 10 15

Val Ala Val Ser Ala Ser Ala Val Glu Lys Asn Ile Thr Val Thr Ala
20 25 30

Ser Val Asp Pro Thr Ile Asp Ile Leu Gln Ala Asn Gly Ser Ala Leu
35 40 45

Pro Thr Ala Val Asp Leu Thr Tyr Leu Pro Gly Ala Lys Thr Phe Glu
50 55 60

Asn Tyr Ser Val Leu Thr Gln Ile Tyr Thr Asn Asp Pro Ser Lys Gly
65 70 75 80

Leu Asp Val Arg Leu Val Asp Thr Pro Lys Leu Thr Asn Ile Leu Gln
85 90 95

Pro Thr Ser Thr Ile Pro Leu Thr Val Ser Trp Ala Gly Arg Thr Leu
100 105 110

Ser Thr Ser Ala Gln Lys Ile Ala Val Gly Asp Leu Gly Phe Gly Ser
115 120 125

Thr Gly Thr Ala Gly Val Ser Asn Ser Lys Glu Leu Val Ile Gly Ala
130 135 140

Thr Thr Ser Gly Thr Ala Pro Ser Ala Gly Lys Tyr Gln Gly Val Val
145 150 155 160

Ser Ile Val Met Thr Gln Ser Thr Asn
165

<210> SEQ ID NO 68
<211> LENGTH: 528
<212> TYPE: DNA
<213> ORGANISM: Escherichia coli

<400> SEQUENCE: 68
atgaaattaa aaaaaactat tggcgcaatg gctctgagca caatgtttgt agcggtgagt 60
gcttcagcag tagagaaaaa tattactgtg acagccagtg ttgatcctac tattgatatt 120
cttcaagcaa atggttctgc gctaccgaca gctgtagatt taacttatct acctggtgca 180
aaaacttttg aaaattacag tgttctaacc cagatttaca caaatgaccc ttcaaaaggt 240
ttagatgttc gactggttga tacaccgaaa cttacaaata ttttgcaacc gacatctacc 300
attcctctta ctgtctcatg ggcagggaag acattaagta caagtgctca gaagattgca 360
gttggcgatc tgggttttgg ttccaccgga acggcaggtg tttcgaatag taaagaatta 420
gtaattggag caactacatc cggaactgca ccaagtgcag gtaagtatca aggcgtcgtt 480
tccattgtaa tgactcaatc gacagacaca gccgcgcctg ttccttaa 528

<210> SEQ ID NO 69
<211> LENGTH: 175
<212> TYPE: PRT
<213> ORGANISM: Escherichia coli

<400> SEQUENCE: 69

Met Lys Leu Lys Lys Thr Ile Gly Ala Met Ala Leu Ser Thr Met Phe
1 5 10 15

Val Ala Val Ser Ala Ser Ala Val Glu Lys Asn Ile Thr Val Thr Ala
20 25 30

Ser Val Asp Pro Thr Ile Asp Ile Leu Gln Ala Asn Gly Ser Ala Leu
35 40 45

Pro Thr Ala Val Asp Leu Thr Tyr Leu Pro Gly Ala Lys Thr Phe Glu
50 55 60

Asn Tyr Ser Val Leu Thr Gln Ile Tyr Thr Asn Asp Pro Ser Lys Gly
65 70 75 80

Leu Asp Val Arg Leu Val Asp Thr Pro Lys Leu Thr Asn Ile Leu Gln
85 90 95

Pro Thr Ser Thr Ile Pro Leu Thr Val Ser Trp Ala Gly Lys Thr Leu
100 105 110

Ser Thr Ser Ala Gln Lys Ile Ala Val Gly Asp Leu Gly Phe Gly Ser
115 120 125

Thr Gly Thr Ala Gly Val Ser Asn Ser Lys Glu Leu Val Ile Gly Ala
130 135 140

Thr Thr Ser Gly Thr Ala Pro Ser Ala Gly Lys Tyr Gln Gly Val Val
145 150 155 160

Ser Ile Val Met Thr Gln Ser Thr Asp Thr Ala Ala Pro Val Pro
165 170 175

<210> SEQ ID NO 70
<211> LENGTH: 1086
<212> TYPE: DNA
<213> ORGANISM: Escherichia coli

<400> SEQUENCE: 70
atgaataaga ttttatttat ttttacattg tttttctctt cagtactttt tacatttgct 60
gtatcggcag ataaaattcc cggagatgag aatataacta atatttttgg cccgcgtgac 120
aggaacgaat cttcccccaa acataatata ttaaatgact atattacagc atacagtgaa 180
agtcatactc tgtatgatag gatgattttt ttatgtttgt cttctcaaaa tacacttaat 240
ggagcatgtc caaccagtga gaatcctagc agttcatcgg tcagtggcga aacaaatata 300
acattacaat ttacggaaaa aagaagttta attaaaagag agctacaaat taaaggctat 360
aaacgattat tgttcaaagg tgctaactgc ccatcctacc taacacttaa ctcagctcat 420
tatacctgca atagaaactc ggcttcaggt gcaagtttat atttatatat tcctgctggc 480
gaactaaaaa atttaccttt tggtggtatc tgggatgcta ctctgaagtt aagagtaaaa 540
agacgatatg atcagaccta tggaacttac actataaata tcactgttaa attaactgat 600
aagggaaata ttcagatatg gttacctcag ttcaaaagtg acgctcgcgt cgatcttaac 660
ttgcgtccaa ctggtggggg cacatatatt ggaagaaatt ctgttgatat gtgcttttat 720

-continued gatggatata gtactaacag cagctctttg gagctaagat ttcaggataa caatcctaaa 780
tctgatggga aattttatct aaggaaaata aatgatgaca ccaaagaaat tgcatatact 840
ttgtcacttc tcttggcggg taaaagttta actccaacaa atggaacgtc attaaatatt 900
gctgacgcag cttctctgga aataaactgg aatagaatta cagctgtcac catgccagaa 960
atcagtgttc cggtgttgtg ttggcctgga cgtttgcaat tggatgcaaa agtggaaaat 1020
cccgaggccg gacaatatat gggtaatatt aatattactt tcacaccaag tagtcaaaca 1080
ctctag 1086

<210> SEQ ID NO 71
<211> LENGTH: 361
<212> TYPE: PRT
<213> ORGANISM: Escherichia coli

<400> SEQUENCE: 71

Met Asn Lys Ile Leu Phe Ile Phe Thr Leu Phe Phe Ser Ser Val Leu
1 5 10 15

Phe Thr Phe Ala Val Ser Ala Asp Lys Ile Pro Gly Asp Glu Asn Ile
20 25 30

Thr Asn Ile Phe Gly Pro Arg Asp Arg Asn Glu Ser Ser Pro Lys His
35 40 45

Asn Ile Leu Asn Asp Tyr Ile Thr Ala Tyr Ser Glu Ser His Thr Leu
50 55 60

Tyr Asp Arg Met Ile Phe Leu Cys Leu Ser Ser Gln Asn Thr Leu Asn
65 70 75 80

Gly Ala Cys Pro Thr Ser Glu Asn Pro Ser Ser Ser Ser Val Ser Gly
85 90 95

Glu Thr Asn Ile Thr Leu Gln Phe Thr Glu Lys Arg Ser Leu Ile Lys
100 105 110

Arg Glu Leu Gln Ile Lys Gly Tyr Lys Arg Leu Leu Phe Lys Gly Ala
115 120 125

Asn Cys Pro Ser Tyr Leu Thr Leu Asn Ser Ala His Tyr Thr Cys Asn
130 135 140

Arg Asn Ser Ala Ser Gly Ala Ser Leu Tyr Leu Tyr Ile Pro Ala Gly
145 150 155 160

Glu Leu Lys Asn Leu Pro Phe Gly Gly Ile Trp Asp Ala Thr Leu Lys
165 170 175

Leu Arg Val Lys Arg Arg Tyr Asp Gln Thr Tyr Gly Thr Tyr Thr Ile
180 185 190

Asn Ile Thr Val Lys Leu Thr Asp Lys Gly Asn Ile Gln Ile Trp Leu
195 200 205

Pro Gln Phe Lys Ser Asp Ala Arg Val Asp Leu Asn Leu Arg Pro Thr
210 215 220

Gly Gly Gly Thr Tyr Ile Gly Arg Asn Ser Val Asp Met Cys Phe Tyr
225 230 235 240

Asp Gly Tyr Ser Thr Asn Ser Ser Ser Leu Glu Leu Arg Phe Gln Asp
245 250 255

Asn Asn Pro Lys Ser Asp Gly Lys Phe Tyr Leu Arg Lys Ile Asn Asp
260 265 270

Asp Thr Lys Glu Ile Ala Tyr Thr Leu Ser Leu Leu Leu Ala Gly Lys
275 280 285

Ser Leu Thr Pro Thr Asn Gly Thr Ser Leu Asn Ile Ala Asp Ala Ala
290 295 300

-continued

Ser Leu Glu Ile Asn Trp Asn Arg Ile Thr Ala Val Thr Met Pro Glu
305 310 315 320

Ile Ser Val Pro Val Leu Cys Trp Pro Gly Arg Leu Gln Leu Asp Ala
325 330 335

Lys Val Glu Asn Pro Glu Ala Gly Gln Tyr Met Gly Asn Ile Asn Ile
340 345 350

Thr Phe Thr Pro Ser Ser Gln Thr Leu
355 360

<210> SEQ ID NO 72
<211> LENGTH: 516
<212> TYPE: DNA
<213> ORGANISM: Escherichia coli

<400> SEQUENCE: 72
atgaaactaa agaaaaacaat tggcgcaatg gctctggcga cattatttgc aactatggga 60
gcatctgcgg tcgagaagac cattagcgtt acggcgagtg ttgacccgac tgttgacctt 120
ctgcaatctg atggctctgc gctgccgaac tctgtcgcat taacctattc tccggctgta 180
aataattttg aagctcacac catcaacacc gttgttcata caaatgactc agataaaggt 240
gttgttgtga agctgtcagc agatccagtc ctgtccaatg ttctgaatcc aaccctgcaa 300
attcctgttt ctgtgaattt cgcaggaaaa ccactgagca caacaggcat taccatcgac 360
tccaatgatc tgaactttgc ttcgagtggt gttaataaag tttcttctac gcagaaactt 420
tcaatccatg cagatgctac tcgggtaact ggcggcgcac taacagctgg tcaatatcag 480
ggactcgtat caattatcct gactaagtca acgtaa 516

<210> SEQ ID NO 73
<211> LENGTH: 171
<212> TYPE: PRT
<213> ORGANISM: Escherichia coli

<400> SEQUENCE: 73

Met Lys Leu Lys Lys Thr Ile Gly Ala Met Ala Leu Ala Thr Leu Phe
1 5 10 15

Ala Thr Met Gly Ala Ser Ala Val Glu Lys Thr Ile Ser Val Thr Ala
20 25 30

Ser Val Asp Pro Thr Val Asp Leu Leu Gln Ser Asp Gly Ser Ala Leu
35 40 45

Pro Asn Ser Val Ala Leu Thr Tyr Ser Pro Ala Val Asn Asn Phe Glu
50 55 60

Ala His Thr Ile Asn Thr Val Val His Thr Asn Asp Ser Asp Lys Gly
65 70 75 80

Val Val Val Lys Leu Ser Ala Asp Pro Val Leu Ser Asn Val Leu Asn
85 90 95

Pro Thr Leu Gln Ile Pro Val Ser Val Asn Phe Ala Gly Lys Pro Leu
100 105 110

Ser Thr Thr Gly Ile Thr Ile Asp Ser Asn Asp Leu Asn Phe Ala Ser
115 120 125

Ser Gly Val Asn Lys Val Ser Ser Thr Gln Lys Leu Ser Ile His Ala
130 135 140

Asp Ala Thr Arg Val Thr Gly Gly Ala Leu Thr Ala Gly Gln Tyr Gln
145 150 155 160

Gly Leu Val Ser Ile Ile Leu Thr Lys Ser Thr
165 170

<210> SEQ ID NO 74
<211> LENGTH: 1092
<212> TYPE: DNA
<213> ORGANISM: Escherichia coli

<400> SEQUENCE: 74
atgaaaaaga tatttatttt tttgtctatc atattttctg cggtggtcag tgccgggcga 60
tacccggaaa ctacagtagg taatctgacg aagagttttc aagcccctcg tctggataga 120
agcgtacaat caccaatata taacatcttt acgaatcatg tggctggata tagtttgagt 180
catagcttat atgacaggat tgttttttta tgtacatcct cgtcgaatcc ggttaatggt 240
gcttgcccaa ccattggaac atctggagtt caatacggta ctacaaccat aaccttgcag 300
tttacagaaa aaagaagtct gataaaaaga aatattaatc ttgcaggtaa taagaaacca 360
atatgggaga atcagagttg cgactttagc aatctaatgg tgttgaattc gaagtcttgg 420
agctgtgggg cttacggaaa tgctaacgga acacttctaa atctgtatat ccctgcagga 480
gaaatcaaca aattgccttt tggagggata tgggaggcaa ctctgatctt acgcttatca 540
agatatggcg aagtcagtag cacccattac ggcaattata ccgtaaatat tacggttgat 600
ttaactgata aaggtaatat tcaggtatgg cttccagggt ttcacagcaa cccgcgtgta 660
gacctgaatc tgcgccctat cggtaattat aaatatagtg gtagtaattc actcgacatg 720
tgtttctatg atggatatag tacaaacagt gatagcatgg taataaagtt ccaggatgat 780
aatcctacca attcatctga atataatctt tataagatag ggggcactga aaaattacca 840
tatgctgttt cactgcttat gggagaaaaa atattttatc cagtgaatgg tcaatcattt 900
actatcaatg acagtagtgt actcgaaaca aactggaatc gagtaaccgc agttgctatg 960
ccggaagtta atgttccagt attatgctgg ccagcaagat tgctattaaa tgctgatgta 1020
aatgctcccg atgcaggaca gtattcagga cagatatata taacatttac acccagtgtc 1080
gaaaatttat ga 1092

<210> SEQ ID NO 75
<211> LENGTH: 363
<212> TYPE: PRT
<213> ORGANISM: Escherichia coli

<400> SEQUENCE: 75

Met Lys Lys Ile Phe Ile Phe Leu Ser Ile Ile Phe Ser Ala Val Val
1 5 10 15

Ser Ala Gly Arg Tyr Pro Glu Thr Thr Val Gly Asn Leu Thr Lys Ser
20 25 30

Phe Gln Ala Pro Arg Leu Asp Arg Ser Val Gln Ser Pro Ile Tyr Asn
35 40 45

Ile Phe Thr Asn His Val Ala Gly Tyr Ser Leu Ser His Ser Leu Tyr
50 55 60

Asp Arg Ile Val Phe Leu Cys Thr Ser Ser Ser Asn Pro Val Asn Gly
65 70 75 80

Ala Cys Pro Thr Ile Gly Thr Ser Gly Val Gln Tyr Gly Thr Thr Thr
85 90 95

Ile Thr Leu Gln Phe Thr Glu Lys Arg Ser Leu Ile Lys Arg Asn Ile
100 105 110

Asn Leu Ala Gly Asn Lys Lys Pro Ile Trp Glu Asn Gln Ser Cys Asp
115 120 125

-continued

```
Phe Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

Arg Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360


<210> SEQ ID NO 76
<211> LENGTH: 501
<212> TYPE: DNA
<213> ORGANISM: Escherichia coli

<400> SEQUENCE: 76

atgaaactga agaaaacaat tggcgcaatg gctatggcga ctctgtttgc caccatggct     60

gcctctgcag tcgaaaaaaa tattactgtg agggcaagtg ttgaccctaa acttgatctt    120

ctgcaagcag atggaacttc actgccggac tctatcgcat taacctattc ttcggcttca    180

aataattttg aagtttactc tcttaatact gctattcata caaatgacaa aaccaaggca    240

gttgtagtga agctgtcagc tccagcagtt ctgtccaata ttatgaagcc aagctcgcaa    300

attccgatga aagtgacttt ggggggaag acgctgagta cagctgatgc tgagtttgct    360

gctgatactc tgaactttgg tgcatctggt gttgaaaacg tttcttccgt tcaacagctt    420

acgattcatg cagaagctgc tccgcctgag gcaggtaatt accaaggtgt tatttctctt    480

atcatgactc aaaaaactta a                                              501


<210> SEQ ID NO 77
<211> LENGTH: 166
<212> TYPE: PRT
<213> ORGANISM: Escherichia coli

<400> SEQUENCE: 77
```

```
Met Lys Leu Lys Lys Thr Ile Gly Ala Met Ala Met Ala Thr Leu Phe
1               5                   10                  15

Ala Thr Met Ala Ala Ser Ala Val Glu Lys Asn Ile Thr Val Arg Ala
            20                  25                  30

Ser Val Asp Pro Lys Leu Asp Leu Leu Gln Ala Asp Gly Thr Ser Leu
        35                  40                  45

Pro Asp Ser Ile Ala Leu Thr Tyr Ser Ser Ala Ser Asn Asn Phe Glu
    50                  55                  60

Val Tyr Ser Leu Asn Thr Ala Ile His Thr Asn Asp Lys Thr Lys Ala
65                  70                  75                  80

Val Val Val Lys Leu Ser Ala Pro Ala Val Leu Ser Asn Ile Met Lys
                85                  90                  95

Pro Ser Ser Gln Ile Pro Met Lys Val Thr Leu Gly Gly Lys Thr Leu
            100                 105                 110

Ser Thr Ala Asp Ala Glu Phe Ala Ala Asp Thr Leu Asn Phe Gly Ala
        115                 120                 125

Ser Gly Val Glu Asn Val Ser Ser Val Gln Gln Leu Thr Ile His Ala
    130                 135                 140

Glu Ala Ala Pro Pro Glu Ala Gly Asn Tyr Gln Gly Val Ile Ser Leu
145                 150                 155                 160

Ile Met Thr Gln Lys Thr
                165


<210> SEQ ID NO 78
<211> LENGTH: 1092
<212> TYPE: DNA
<213> ORGANISM: Escherichia coli

<400> SEQUENCE: 78

atgaaaaaga tatttatttt tttgtctatc atattttctg cggtggtcag tgccgggcga      60

tacccggaaa ctacagtagg taatctgacg aagagttttc aagcccctcg tctggataga     120

agcgtacaat caccaatata taacatcttt acgaatcatg tggctggata tagtttgagt     180

catagattat atgacaggat tgtttttgta tgtacatcct cgtcgaatcc ggttaatggt     240

gcttgcccaa ccattggaac atctagagtt gaatacggta ctacaaccat aaccttgcag     300

tttacagaaa aaagaagtct gataaaaaga aatattaatc ttgcaggtaa taagaaacca     360

atatgggaga atcagagttg cgacactagc aatctaatgg tgttgaattc gaagtcttgg     420

tcctgtgggg ctctaggaaa tgctaacgga acacttctaa atctgtatat ccctgcagga     480

gaaatcaaca aattgccttt tggagggata tgggaggcaa ctctgatctt acgcttatca     540

agatatggcg aagtcagtag cacccattac ggcaattata ccgtaaatat tacggttgat     600

ttaactgata aaggtaatat tcaggtatgg cttccagggt ttcacagcaa cccgcgtgta     660

gacctgaatc tgcaccctat cggtaattat aaatatagtg gtagtaattc actcgacatg     720

tgtttctatg atggatatag tacaaacagt gatagcatgg taataaagtt ccaggatgat     780

aatcctacca attcatctga atataatctt tataagatag ggggcactga aaaattacca     840

tatgctgttt cactgcttat gggaggaaaa atattttatc cagtgaatgg tcaatcattt     900

actatcaatg acagtagtgt actcgaaaca aactggaatc gagtaaccgc agttgctatg     960

ccggaagtta atgttccagt attatgctgg ccagcaagat tgctattaaa tgctgatgta    1020

aatgctcccg atgcaggaca gtattcagga cagatatata taacatttac acccagtgtc    1080

gaaaatttat ga                                                        1092
```

<210> SEQ ID NO 79
<211> LENGTH: 363
<212> TYPE: PRT
<213> ORGANISM: Escherichia coli

<400> SEQUENCE: 79

Met Lys Lys Ile Phe Ile Phe Leu Ser Ile Ile Phe Ser Ala Val Val
1 5 10 15

Ser Ala Gly Arg Tyr Pro Glu Thr Thr Val Gly Asn Leu Thr Lys Ser
20 25 30

Phe Gln Ala Pro Arg Leu Asp Arg Ser Val Gln Ser Pro Ile Tyr Asn
35 40 45

Ile Phe Thr Asn His Val Ala Gly Tyr Ser Leu Ser His Arg Leu Tyr
50 55 60

Asp Arg Ile Val Phe Val Cys Thr Ser Ser Ser Asn Pro Val Asn Gly
65 70 75 80

Ala Cys Pro Thr Ile Gly Thr Ser Arg Val Glu Tyr Gly Thr Thr Thr
85 90 95

Ile Thr Leu Gln Phe Thr Glu Lys Arg Ser Leu Ile Lys Arg Asn Ile
100 105 110

Asn Leu Ala Gly Asn Lys Lys Pro Ile Trp Glu Asn Gln Ser Cys Asp
115 120 125

Thr Ser Asn Leu Met Val Leu Asn Ser Lys Ser Trp Ser Cys Gly Ala
130 135 140

Leu Gly Asn Ala Asn Gly Thr Leu Leu Asn Leu Tyr Ile Pro Ala Gly
145 150 155 160

Glu Ile Asn Lys Leu Pro Phe Gly Gly Ile Trp Glu Ala Thr Leu Ile
165 170 175

Leu Arg Leu Ser Arg Tyr Gly Glu Val Ser Ser Thr His Tyr Gly Asn
180 185 190

Tyr Thr Val Asn Ile Thr Val Asp Leu Thr Asp Lys Gly Asn Ile Gln
195 200 205

Val Trp Leu Pro Gly Phe His Ser Asn Pro Arg Val Asp Leu Asn Leu
210 215 220

His Pro Ile Gly Asn Tyr Lys Tyr Ser Gly Ser Asn Ser Leu Asp Met
225 230 235 240

Cys Phe Tyr Asp Gly Tyr Ser Thr Asn Ser Asp Ser Met Val Ile Lys
245 250 255

Phe Gln Asp Asp Asn Pro Thr Asn Ser Ser Glu Tyr Asn Leu Tyr Lys
260 265 270

Ile Gly Gly Thr Glu Lys Leu Pro Tyr Ala Val Ser Leu Leu Met Gly
275 280 285

Gly Lys Ile Phe Tyr Pro Val Asn Gly Gln Ser Phe Thr Ile Asn Asp
290 295 300

Ser Ser Val Leu Glu Thr Asn Trp Asn Arg Val Thr Ala Val Ala Met
305 310 315 320

Pro Glu Val Asn Val Pro Val Leu Cys Trp Pro Ala Arg Leu Leu Leu
325 330 335

Asn Ala Asp Val Asn Ala Pro Asp Ala Gly Gln Tyr Ser Gly Gln Ile
340 345 350

Tyr Ile Thr Phe Thr Pro Ser Val Glu Asn Leu
355 360

<210> SEQ ID NO 80

-continued

<211> LENGTH: 513
<212> TYPE: DNA
<213> ORGANISM: Escherichia coli

<400> SEQUENCE: 80

```
atgaaactaa agaaaacaat tggcgcaatg gctctggcga cattatttgc aaccatggga     60

gcatctgcgg tcgagaagac cattagcgtt acggcgagtg ttgacccgac tgttgacctt    120

ctgcaatctg atggctctgc gctgccgaac tctgtcgcat taacctattc tccggctgta    180

gggggttttg aagctcacac catcaacacc gttgttcata caaatgaccc agctaaaggt    240

gttattgtga agctgtcagc agaaccagtc ctgtccaatg tactgaatcc aaccctgcaa    300

attcctgttt ctgtgaattt cgcaggaaaa aaactgacca caacaggcac taccatcgaa    360

tccaataaac tgaactttgc ttcgagtggt gttgataaag tttcttctac gcagaaactt    420

tcaatccatg cagatactac tcaggtaact ggcggactaa cagctggtca atatcagggg    480

ctcgtatcaa ttatcctgac tcagtcaacg taa                                 513
```

<210> SEQ ID NO 81
<211> LENGTH: 170
<212> TYPE: PRT
<213> ORGANISM: Escherichia coli

<400> SEQUENCE: 81

```
Met Lys Leu Lys Lys Thr Ile Gly Ala Met Ala Leu Ala Thr Leu Phe
1               5                   10                  15

Ala Thr Met Gly Ala Ser Ala Val Glu Lys Thr Ile Ser Val Thr Ala
            20                  25                  30

Ser Val Asp Pro Thr Val Asp Leu Leu Gln Ser Asp Gly Ser Ala Leu
        35                  40                  45

Pro Asn Ser Val Ala Leu Thr Tyr Ser Pro Ala Val Gly Gly Phe Glu
    50                  55                  60

Ala His Thr Ile Asn Thr Val Val His Thr Asn Asp Pro Ala Lys Gly
65                  70                  75                  80

Val Ile Val Lys Leu Ser Ala Glu Pro Val Leu Ser Asn Val Leu Asn
                85                  90                  95

Pro Thr Leu Gln Ile Pro Val Ser Val Asn Phe Ala Gly Lys Lys Leu
            100                 105                 110

Thr Thr Thr Gly Thr Thr Ile Glu Ser Asn Lys Leu Asn Phe Ala Ser
        115                 120                 125

Ser Gly Val Asp Lys Val Ser Ser Thr Gln Lys Leu Ser Ile His Ala
    130                 135                 140

Asp Thr Thr Gln Val Thr Gly Gly Leu Thr Ala Gly Gln Tyr Gln Gly
145                 150                 155                 160

Leu Val Ser Ile Ile Leu Thr Gln Ser Thr
                165                 170
```

<210> SEQ ID NO 82
<211> LENGTH: 1092
<212> TYPE: DNA
<213> ORGANISM: Escherichia coli

<400> SEQUENCE: 82

```
atgaaaaaga tatttatttt tttgtctatc atattttctg cggtggtcag tgccgggcga     60

tacccggaaa ctacagtagg taatctgacg aagagttttc aagcccctcg tctggataga    120

agcgtacaat caccaatata taacatcttt acgaatcatg tggctggata tagtttgagt    180
```

-continued

```
catagattat atgacaggat tgtttttgta tgtacatcct cgtcgaatcc ggttaatggt    240
gcttgcccaa ccattggaac atctggagtt gaatacggta ctacaaccat aaccttgcag    300
tttacagaaa aaagaagtct gataaaaaga aatattaatc ttgcaggtaa taagaaacca    360
atatgggaga atcagagttg cgactttagc aatctaatgg tgttgaattc gaagtcttgg    420
tcctgtgggg ctcaaggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacca attcatctga atataatctt tataagagag ggggcactga aaaattacca    840
tatgctgttt cactgcttat gggaggaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                       1092
```

<210> SEQ ID NO 83
<211> LENGTH: 363
<212> TYPE: PRT
<213> ORGANISM: Escherichia coli

<400> SEQUENCE: 83

```
Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Leu Asp Arg Ser Val Gln Ser Pro Ile Tyr Asn
        35                  40                  45

Ile Phe Thr Asn His Val Ala Gly Tyr Ser Leu Ser His Arg Leu Tyr
    50                  55                  60

Asp Arg Ile Val Phe Val Cys Thr Ser Ser Ser Asn Pro Val Asn Gly
65                  70                  75                  80

Ala Cys Pro Thr Ile Gly Thr Ser Gly Val Glu Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

Gln Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205
```

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Arg Gly Gly Thr Glu Lys Leu Pro Tyr Ala Val Ser Leu Leu Met Gly
        275                 280                 285

Gly Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 84
<211> LENGTH: 507
<212> TYPE: DNA
<213> ORGANISM: Escherichia coli

<400> SEQUENCE: 84
atgttaaaaa taaaatactt attaataggt ctttcactgt cagctatgag ttcatactca 60
ctagctgcag cggggcccac tctaaccaaa gaactggcat taaatgtgct ttctcctgca 120
gctctggatg caacttgggc tcctcaggat aatttaacat tatccaatac tggcgtttct 180
aatactttgg tgggtgtttt gactctttca aataccagta ttgatacagt tagcattgcg 240
agtacaaatg tttctgatac atctaagaat ggtacagtaa cttttgcaca tgagacaaat 300
aactctgcta gctttgccac caccatttca acagataatg ccaacattac gttggataaa 360
aatgctggaa atacgattgt taaaactaca aatgggagtc agttgccaac taatttacca 420
cttaagttta ttaccactga aggtaacgaa catttagttt caggtaatta ccgtgcaaat 480
ataacaatta cttcgacaat taaataa 507

<210> SEQ ID NO 85
<211> LENGTH: 168
<212> TYPE: PRT
<213> ORGANISM: Escherichia coli

<400> SEQUENCE: 85

Met Leu Lys Ile Lys Tyr Leu Leu Ile Gly Leu Ser Leu Ser Ala Met
1               5                   10                  15

Ser Ser Tyr Ser Leu Ala Ala Ala Gly Pro Thr Leu Thr Lys Glu Leu
            20                  25                  30

Ala Leu Asn Val Leu Ser Pro Ala Ala Leu Asp Ala Thr Trp Ala Pro
        35                  40                  45

Gln Asp Asn Leu Thr Leu Ser Asn Thr Gly Val Ser Asn Thr Leu Val
    50                  55                  60

Gly Val Leu Thr Leu Ser Asn Thr Ser Ile Asp Thr Val Ser Ile Ala
65                  70                  75                  80

```
Ser Thr Asn Val Ser Asp Thr Ser Lys Asn Gly Thr Val Thr Phe Ala
                85                  90                  95

His Glu Thr Asn Asn Ser Ala Ser Phe Ala Thr Thr Ile Ser Thr Asp
            100                 105                 110

Asn Ala Asn Ile Thr Leu Asp Lys Asn Ala Gly Asn Thr Ile Val Lys
        115                 120                 125

Thr Thr Asn Gly Ser Gln Leu Pro Thr Asn Leu Pro Leu Lys Phe Ile
    130                 135                 140

Thr Thr Glu Gly Asn Glu His Leu Val Ser Gly Asn Tyr Arg Ala Asn
145                 150                 155                 160

Ile Thr Ile Thr Ser Thr Ile Lys
                165


<210> SEQ ID NO 86
<211> LENGTH: 480
<212> TYPE: DNA
<213> ORGANISM: Escherichia coli

<400> SEQUENCE: 86

atgattttag cattgacttt gatgtcggtg tggggaggtg cgtttgccgc agtgggccca      60

acgaaagata tgagtttagg tgcaaattta acttcagagc ctacattagc tattgatttt     120

acgcctattg aaaatattta tgtaggtgcc aattatggta aagatattgg aacccttgtt     180

ttcacaacaa atgatttaac agatattaca ttgatgtcat ctcgcagcgt tgttgatggt     240

cgccagactg gtttttttac cttcatggac tcatcagcca cttacaaaat tagtacaaaa     300

ctgggatcat cgaatgatgt aaacattcaa gaaattactc aaggagctaa aattactcct     360

gttagtggag agaaaacttt gcctaaaaaa ttcactctta agctacatgc acacaggagt     420

agcagtacag ttccaggtac gtatactgtt ggtcttaacg taaccagtaa tgttatttaa     480


<210> SEQ ID NO 87
<211> LENGTH: 159
<212> TYPE: PRT
<213> ORGANISM: Escherichia coli

<400> SEQUENCE: 87

Met Ile Leu Ala Leu Thr Leu Met Ser Val Trp Gly Gly Ala Phe Ala
1               5                   10                  15

Ala Val Gly Pro Thr Lys Asp Met Ser Leu Gly Ala Asn Leu Thr Ser
            20                  25                  30

Glu Pro Thr Leu Ala Ile Asp Phe Thr Pro Ile Glu Asn Ile Tyr Val
        35                  40                  45

Gly Ala Asn Tyr Gly Lys Asp Ile Gly Thr Leu Val Phe Thr Thr Asn
    50                  55                  60

Asp Leu Thr Asp Ile Thr Leu Met Ser Ser Arg Ser Val Val Asp Gly
65                  70                  75                  80

Arg Gln Thr Gly Phe Phe Thr Phe Met Asp Ser Ser Ala Thr Tyr Lys
                85                  90                  95

Ile Ser Thr Lys Leu Gly Ser Ser Asn Asp Val Asn Ile Gln Glu Ile
            100                 105                 110

Thr Gln Gly Ala Lys Ile Thr Pro Val Ser Gly Glu Lys Thr Leu Pro
        115                 120                 125

Lys Lys Phe Thr Leu Lys Leu His Ala His Arg Ser Ser Ser Thr Val
    130                 135                 140

Pro Gly Thr Tyr Thr Val Gly Leu Asn Val Thr Ser Asn Val Ile
145                 150                 155
```

<210> SEQ ID NO 88
<211> LENGTH: 339
<212> TYPE: PRT
<213> ORGANISM: Escherichia coli

<400> SEQUENCE: 88

Ala Asp Lys Ile Pro Gly Asp Glu Ser Ile Thr Asn Ile Phe Gly Pro
1 5 10 15

Arg Asp Arg Asn Glu Ser Ser Pro Lys His Asn Ile Leu Asn Asn His
20 25 30

Ile Thr Ala Tyr Ser Glu Ser His Thr Leu Tyr Asp Arg Met Thr Phe
35 40 45

Leu Cys Leu Ser Ser His Asn Thr Leu Asn Gly Ala Cys Pro Thr Ser
50 55 60

Glu Asn Pro Ser Ser Ser Ser Val Ser Gly Glu Thr Asn Ile Thr Leu
65 70 75 80

Gln Phe Thr Glu Lys Arg Ser Leu Ile Lys Arg Glu Leu Gln Ile Lys
85 90 95

Gly Tyr Lys Gln Leu Leu Phe Lys Ser Val Asn Cys Pro Ser Gly Leu
100 105 110

Thr Leu Asn Ser Ala His Phe Asn Cys Asn Lys Asn Ala Ala Ser Gly
115 120 125

Ala Ser Leu Tyr Leu Tyr Ile Pro Ala Gly Glu Leu Lys Asn Leu Pro
130 135 140

Phe Gly Gly Ile Trp Asp Ala Thr Leu Lys Leu Arg Val Lys Arg Arg
145 150 155 160

Tyr Ser Glu Thr Tyr Gly Thr Tyr Thr Ile Asn Ile Thr Ile Lys Leu
165 170 175

Thr Asp Lys Gly Asn Ile Gln Ile Trp Leu Pro Gln Phe Lys Ser Asp
180 185 190

Ala Arg Val Asp Leu Asn Leu Arg Pro Thr Gly Gly Gly Thr Tyr Ile
195 200 205

Gly Arg Asn Ser Val Asp Met Cys Phe Tyr Asp Gly Tyr Ser Thr Asn
210 215 220

Ser Ser Ser Leu Glu Ile Arg Phe Gln Asp Asn Asn Pro Lys Ser Asp
225 230 235 240

Gly Lys Phe Tyr Leu Arg Lys Ile Asn Asp Asp Thr Lys Glu Ile Ala
245 250 255

Tyr Thr Leu Ser Leu Leu Leu Ala Gly Lys Ser Leu Thr Pro Thr Asn
260 265 270

Gly Thr Ser Leu Asn Ile Ala Asp Ala Ala Ser Leu Glu Thr Asn Trp
275 280 285

Asn Arg Ile Thr Ala Val Thr Met Pro Glu Ile Ser Val Pro Val Leu
290 295 300

Cys Trp Pro Gly Arg Leu Gln Leu Asp Ala Lys Val Glu Asn Pro Glu
305 310 315 320

Ala Gly Gln Tyr Met Gly Asn Ile Asn Val Thr Phe Thr Pro Ser Ser
325 330 335

Gln Thr Leu

<210> SEQ ID NO 89
<211> LENGTH: 144
<212> TYPE: PRT
<213> ORGANISM: Escherichia coli

<400> SEQUENCE: 89

Val Glu Lys Asn Ile Thr Val Thr Ala Ser Val Asp Pro Thr Ile Asp
1 5 10 15

Ile Leu Gln Ala Asp Gly Ser Ser Leu Pro Thr Ala Val Glu Leu Thr
20 25 30

Tyr Ser Pro Ala Ala Ser Arg Phe Glu Asn Tyr Lys Ile Ala Thr Lys
35 40 45

Val His Thr Asn Val Ile Asn Lys Asn Val Leu Val Lys Leu Val Asn
50 55 60

Asp Pro Lys Leu Thr Asn Val Leu Asp Ser Thr Lys Gln Leu Pro Ile
65 70 75 80

Thr Val Ser Tyr Gly Gly Lys Thr Leu Ser Thr Ala Asp Val Thr Phe
85 90 95

Glu Pro Ala Glu Leu Asn Phe Gly Thr Ser Gly Val Thr Gly Val Ser
100 105 110

Ser Ser Gln Asp Leu Val Ile Gly Ala Thr Thr Ala Gln Ala Pro Thr
115 120 125

Ala Gly Asn Tyr Ser Gly Val Val Ser Ile Leu Met Thr Leu Ala Ser
130 135 140

<210> SEQ ID NO 90
<211> LENGTH: 339
<212> TYPE: PRT
<213> ORGANISM: Escherichia coli

<400> SEQUENCE: 90

Ala Asp Lys Ile Pro Gly Asp Glu Asn Ile Thr Asn Ile Phe Gly Pro
1 5 10 15

Arg Asp Arg Asn Glu Ser Ser Pro Lys His Asn Ile Leu Asn Asp Tyr
20 25 30

Ile Thr Ala Tyr Ser Glu Ser His Thr Leu Tyr Asp Arg Met Ile Phe
35 40 45

Leu Cys Leu Ser Ser Gln Asn Thr Leu Asn Gly Ala Cys Pro Thr Ser
50 55 60

Glu Asn Pro Ser Ser Ser Ser Val Ser Gly Glu Thr Asn Ile Thr Leu
65 70 75 80

Gln Phe Thr Glu Lys Arg Ser Leu Ile Lys Arg Glu Leu Gln Ile Lys
85 90 95

Gly Tyr Lys Arg Leu Leu Phe Lys Gly Ala Asn Cys Pro Ser Tyr Leu
100 105 110

Thr Leu Asn Ser Ala His Tyr Thr Cys Asn Arg Asn Ser Ala Ser Gly
115 120 125

Ala Ser Leu Tyr Leu Tyr Ile Pro Ala Gly Glu Leu Lys Asn Leu Pro
130 135 140

Phe Gly Gly Ile Trp Asp Ala Thr Leu Lys Leu Arg Val Lys Arg Arg
145 150 155 160

Tyr Asp Gln Thr Tyr Gly Thr Tyr Thr Ile Asn Ile Thr Val Lys Leu
165 170 175

Thr Asp Lys Gly Asn Ile Gln Ile Trp Leu Pro Gln Phe Lys Ser Asp
180 185 190

Ala Arg Val Asp Leu Asn Leu Arg Pro Thr Gly Gly Gly Thr Tyr Ile
195 200 205

Gly Arg Asn Ser Val Asp Met Cys Phe Tyr Asp Gly Tyr Ser Thr Asn
210 215 220

```
Ser Ser Ser Leu Glu Leu Arg Phe Gln Asp Asn Asn Pro Lys Ser Asp
225                 230                 235                 240

Gly Lys Phe Tyr Leu Arg Lys Ile Asn Asp Asp Thr Lys Glu Ile Ala
                245                 250                 255

Tyr Thr Leu Ser Leu Leu Leu Ala Gly Lys Ser Leu Thr Pro Thr Asn
            260                 265                 270

Gly Thr Ser Leu Asn Ile Ala Asp Ala Ala Ser Leu Glu Ile Asn Trp
        275                 280                 285

Asn Arg Ile Thr Ala Val Thr Met Pro Glu Ile Ser Val Pro Val Leu
    290                 295                 300

Cys Trp Pro Gly Arg Leu Gln Leu Asp Ala Lys Val Glu Asn Pro Glu
305                 310                 315                 320

Ala Gly Gln Tyr Met Gly Asn Ile Asn Ile Thr Phe Thr Pro Ser Ser
                325                 330                 335

Gln Thr Leu


<210> SEQ ID NO 91
<211> LENGTH: 152
<212> TYPE: PRT
<213> ORGANISM: Escherichia coli

<400> SEQUENCE: 91

Val Glu Lys Asn Ile Thr Val Thr Ala Ser Val Asp Pro Thr Ile Asp
1               5                   10                  15

Ile Leu Gln Ala Asn Gly Ser Ala Leu Pro Thr Ala Val Asp Leu Thr
            20                  25                  30

Tyr Leu Pro Gly Ala Lys Thr Phe Glu Asn Tyr Ser Val Leu Thr Gln
        35                  40                  45

Ile Tyr Thr Asn Asp Pro Ser Lys Gly Leu Asp Val Arg Leu Val Asp
    50                  55                  60

Thr Pro Lys Leu Thr Asn Ile Leu Gln Pro Thr Ser Thr Ile Pro Leu
65                  70                  75                  80

Thr Val Ser Trp Ala Gly Lys Thr Leu Ser Thr Ser Ala Gln Lys Ile
                85                  90                  95

Ala Val Gly Asp Leu Gly Phe Gly Ser Thr Gly Thr Ala Gly Val Ser
            100                 105                 110

Asn Ser Lys Glu Leu Val Ile Gly Ala Thr Thr Ser Gly Thr Ala Pro
        115                 120                 125

Ser Ala Gly Lys Tyr Gln Gly Val Val Ser Ile Val Met Thr Gln Ser
    130                 135                 140

Thr Asp Thr Ala Ala Pro Val Pro
145                 150


<210> SEQ ID NO 92
<211> LENGTH: 146
<212> TYPE: PRT
<213> ORGANISM: Escherichia coli

<400> SEQUENCE: 92

Val Glu Lys Asn Ile Thr Val Thr Ala Ser Val Asp Pro Thr Ile Asp
1               5                   10                  15

Ile Leu Gln Ala Asn Gly Ser Ala Leu Pro Thr Ala Val Asp Leu Thr
            20                  25                  30

Tyr Leu Pro Gly Ala Lys Thr Phe Glu Asn Tyr Ser Val Leu Thr Gln
        35                  40                  45
```

```
Ile Tyr Thr Asn Asp Pro Ser Lys Gly Leu Asp Val Arg Leu Val Asp
    50                  55                  60

Thr Pro Lys Leu Thr Asn Ile Leu Gln Pro Thr Ser Thr Ile Pro Leu
65                  70                  75                  80

Thr Val Ser Trp Ala Gly Arg Thr Leu Ser Thr Ser Ala Gln Lys Ile
                85                  90                  95

Ala Val Gly Asp Leu Gly Phe Gly Ser Thr Gly Thr Ala Gly Val Ser
            100                 105                 110

Asn Ser Lys Glu Leu Val Ile Gly Ala Thr Thr Ser Gly Thr Ala Pro
        115                 120                 125

Ser Ala Gly Lys Tyr Gln Gly Val Val Ser Ile Val Met Thr Gln Ser
    130                 135                 140

Thr Asn
145


<210> SEQ ID NO 93
<211> LENGTH: 345
<212> TYPE: PRT
<213> ORGANISM: Escherichia coli

<400> SEQUENCE: 93

Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
            20                  25                  30

Thr Asn His Val Ala Gly Tyr Ser Leu Ser His Ser Leu Tyr Asp Arg
        35                  40                  45

Ile Val Phe Leu Cys Thr Ser Ser Ser Asn Pro Val Asn Gly Ala Cys
    50                  55                  60

Pro Thr Ile Gly Thr Ser Gly Val Gln Tyr Gly Thr Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Phe Ser
            100                 105                 110

Asn Leu Met Val Leu Asn Ser Lys Ser Trp Ser Cys Gly Ala Tyr Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu Arg Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Asn Ser Ser Glu Tyr Asn Leu Tyr Lys Ile Gly
                245                 250                 255

Gly Thr Glu Lys Leu Pro Tyr Ala Val Ser Leu Leu Met Gly Glu Lys
            260                 265                 270
```

```
Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345


<210> SEQ ID NO 94
<211> LENGTH: 148
<212> TYPE: PRT
<213> ORGANISM: Escherichia coli

<400> SEQUENCE: 94

Val Glu Lys Thr Ile Ser Val Thr Ala Ser Val Asp Pro Thr Val Asp
1               5                   10                  15

Leu Leu Gln Ser Asp Gly Ser Ala Leu Pro Asn Ser Val Ala Leu Thr
            20                  25                  30

Tyr Ser Pro Ala Val Asn Asn Phe Glu Ala His Thr Ile Asn Thr Val
        35                  40                  45

Val His Thr Asn Asp Ser Asp Lys Gly Val Val Val Lys Leu Ser Ala
    50                  55                  60

Asp Pro Val Leu Ser Asn Val Leu Asn Pro Thr Leu Gln Ile Pro Val
65                  70                  75                  80

Ser Val Asn Phe Ala Gly Lys Pro Leu Ser Thr Thr Gly Ile Thr Ile
                85                  90                  95

Asp Ser Asn Asp Leu Asn Phe Ala Ser Ser Gly Val Asn Lys Val Ser
            100                 105                 110

Ser Thr Gln Lys Leu Ser Ile His Ala Asp Ala Thr Arg Val Thr Gly
        115                 120                 125

Gly Ala Leu Thr Ala Gly Gln Tyr Gln Gly Leu Val Ser Ile Ile Leu
    130                 135                 140

Thr Lys Ser Thr
145


<210> SEQ ID NO 95
<211> LENGTH: 345
<212> TYPE: PRT
<213> ORGANISM: Escherichia coli

<400> SEQUENCE: 95

Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
            20                  25                  30

Thr Asn His Val Ala Gly Tyr Ser Leu Ser His Arg Leu Tyr Asp Arg
        35                  40                  45

Ile Val Phe Val Cys Thr Ser Ser Ser Asn Pro Val Asn Gly Ala Cys
    50                  55                  60

Pro Thr Ile Gly Thr Ser Arg Val Glu Tyr Gly Thr Thr Thr Ile Thr
65                  70                  75                  80

Leu Gln Phe Thr Glu Lys Arg Ser Leu Ile Lys Arg Asn Ile Asn Leu
                85                  90                  95
```

```
Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly Ala Leu Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu His Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Asn Ser Ser Glu Tyr Asn Leu Tyr Lys Ile Gly
                245                 250                 255

Gly Thr Glu Lys Leu Pro Tyr Ala Val Ser Leu Leu Met Gly Gly Lys
            260                 265                 270

Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345


<210> SEQ ID NO 96
<211> LENGTH: 143
<212> TYPE: PRT
<213> ORGANISM: Escherichia coli

<400> SEQUENCE: 96

Val Glu Lys Asn Ile Thr Val Arg Ala Ser Val Asp Pro Lys Leu Asp
1               5                   10                  15

Leu Leu Gln Ala Asp Gly Thr Ser Leu Pro Asp Ser Ile Ala Leu Thr
            20                  25                  30

Tyr Ser Ser Ala Ser Asn Asn Phe Glu Val Tyr Ser Leu Asn Thr Ala
        35                  40                  45

Ile His Thr Asn Asp Lys Thr Lys Ala Val Val Val Lys Leu Ser Ala
    50                  55                  60

Pro Ala Val Leu Ser Asn Ile Met Lys Pro Ser Ser Gln Ile Pro Met
65                  70                  75                  80

Lys Val Thr Leu Gly Gly Lys Thr Leu Ser Thr Ala Asp Ala Glu Phe
                85                  90                  95

Ala Ala Asp Thr Leu Asn Phe Gly Ala Ser Gly Val Glu Asn Val Ser
            100                 105                 110

Ser Val Gln Gln Leu Thr Ile His Ala Glu Ala Ala Pro Pro Glu Ala
```

115 120 125

Gly Asn Tyr Gln Gly Val Ile Ser Leu Ile Met Thr Gln Lys Thr
130 135 140

<210> SEQ ID NO 97
<211> LENGTH: 345
<212> TYPE: PRT
<213> ORGANISM: Escherichia coli

<400> SEQUENCE: 97

Gly Arg Tyr Pro Glu Thr Thr Val Gly Asn Leu Thr Lys Ser Phe Gln
1 5 10 15

Ala Pro Arg Leu Asp Arg Ser Val Gln Ser Pro Ile Tyr Asn Ile Phe
20 25 30

Thr Asn His Val Ala Gly Tyr Ser Leu Ser His Arg Leu Tyr Asp Arg
35 40 45

Ile Val Phe Val Cys Thr Ser Ser Ser Asn Pro Val Asn Gly Ala Cys
50 55 60

Pro Thr Ile Gly Thr Ser Gly Val Glu Tyr Gly Thr Thr Thr Ile Thr
65 70 75 80

Leu Gln Phe Thr Glu Lys Arg Ser Leu Ile Lys Arg Asn Ile Asn Leu
85 90 95

Ala Gly Asn Lys Lys Pro Ile Trp Glu Asn Gln Ser Cys Asp Phe Ser
100 105 110

Asn Leu Met Val Leu Asn Ser Lys Ser Trp Ser Cys Gly Ala Gln Gly
115 120 125

Asn Ala Asn Gly Thr Leu Leu Asn Leu Tyr Ile Pro Ala Gly Glu Ile
130 135 140

Asn Lys Leu Pro Phe Gly Gly Ile Trp Glu Ala Thr Leu Ile Leu Arg
145 150 155 160

Leu Ser Arg Tyr Gly Glu Val Ser Ser Thr His Tyr Gly Asn Tyr Thr
165 170 175

Val Asn Ile Thr Val Asp Leu Thr Asp Lys Gly Asn Ile Gln Val Trp
180 185 190

Leu Pro Gly Phe His Ser Asn Pro Arg Val Asp Leu Asn Leu His Pro
195 200 205

Ile Gly Asn Tyr Lys Tyr Ser Gly Ser Asn Ser Leu Asp Met Cys Phe
210 215 220

Tyr Asp Gly Tyr Ser Thr Asn Ser Asp Ser Met Val Ile Lys Phe Gln
225 230 235 240

Asp Asp Asn Pro Thr Asn Ser Ser Glu Tyr Asn Leu Tyr Lys Arg Gly
245 250 255

Gly Thr Glu Lys Leu Pro Tyr Ala Val Ser Leu Leu Met Gly Gly Lys
260 265 270

Ile Phe Tyr Pro Val Asn Gly Gln Ser Phe Thr Ile Asn Asp Ser Ser
275 280 285

Val Leu Glu Thr Asn Trp Asn Arg Val Thr Ala Val Ala Met Pro Glu
290 295 300

Val Asn Val Pro Val Leu Cys Trp Pro Ala Arg Leu Leu Leu Asn Ala
305 310 315 320

Asp Val Asn Ala Pro Asp Ala Gly Gln Tyr Ser Gly Gln Ile Tyr Ile
325 330 335

Thr Phe Thr Pro Ser Val Glu Asn Leu
340 345

<210> SEQ ID NO 98
<211> LENGTH: 147
<212> TYPE: PRT
<213> ORGANISM: Escherichia coli

<400> SEQUENCE: 98

Val Glu Lys Thr Ile Ser Val Thr Ala Ser Val Asp Pro Thr Val Asp
1               5                   10                  15

Leu Leu Gln Ser Asp Gly Ser Ala Leu Pro Asn Ser Val Ala Leu Thr
            20                  25                  30

Tyr Ser Pro Ala Val Gly Gly Phe Glu Ala His Thr Ile Asn Thr Val
        35                  40                  45

Val His Thr Asn Asp Pro Ala Lys Gly Val Ile Val Lys Leu Ser Ala
    50                  55                  60

Glu Pro Val Leu Ser Asn Val Leu Asn Pro Thr Leu Gln Ile Pro Val
65                  70                  75                  80

Ser Val Asn Phe Ala Gly Lys Lys Leu Thr Thr Thr Gly Thr Thr Ile
                85                  90                  95

Glu Ser Asn Lys Leu Asn Phe Ala Ser Ser Gly Val Asp Lys Val Ser
            100                 105                 110

Ser Thr Gln Lys Leu Ser Ile His Ala Asp Thr Thr Gln Val Thr Gly
        115                 120                 125

Gly Leu Thr Ala Gly Gln Tyr Gln Gly Leu Val Ser Ile Ile Leu Thr
    130                 135                 140

Gln Ser Thr
145

<210> SEQ ID NO 99
<211> LENGTH: 146
<212> TYPE: PRT
<213> ORGANISM: Escherichia coli

<400> SEQUENCE: 99

Ala Ala Gly Pro Thr Leu Thr Lys Glu Leu Ala Leu Asn Val Leu Ser
1               5                   10                  15

Pro Ala Ala Leu Asp Ala Thr Trp Ala Pro Gln Asp Asn Leu Thr Leu
            20                  25                  30

Ser Asn Thr Gly Val Ser Asn Thr Leu Val Gly Val Leu Thr Leu Ser
        35                  40                  45

Asn Thr Ser Ile Asp Thr Val Ser Ile Ala Ser Thr Asn Val Ser Asp
    50                  55                  60

Thr Ser Lys Asn Gly Thr Val Thr Phe Ala His Glu Thr Asn Asn Ser
65                  70                  75                  80

Ala Ser Phe Ala Thr Thr Ile Ser Thr Asp Asn Ala Asn Ile Thr Leu
                85                  90                  95

Asp Lys Asn Ala Gly Asn Thr Ile Val Lys Thr Thr Asn Gly Ser Gln
            100                 105                 110

Leu Pro Thr Asn Leu Pro Leu Lys Phe Ile Thr Thr Glu Gly Asn Glu
        115                 120                 125

His Leu Val Ser Gly Asn Tyr Arg Ala Asn Ile Thr Ile Thr Ser Thr
    130                 135                 140

Ile Lys
145

<210> SEQ ID NO 100
<211> LENGTH: 143

<212> TYPE: PRT
<213> ORGANISM: Escherichia coli

<400> SEQUENCE: 100

```
Ala Val Gly Pro Thr Lys Asp Met Ser Leu Gly Ala Asn Leu Thr Ser
1               5                   10                  15

Glu Pro Thr Leu Ala Ile Asp Phe Thr Pro Ile Glu Asn Ile Tyr Val
            20                  25                  30

Gly Ala Asn Tyr Gly Lys Asp Ile Gly Thr Leu Val Phe Thr Thr Asn
        35                  40                  45

Asp Leu Thr Asp Ile Thr Leu Met Ser Ser Arg Ser Val Val Asp Gly
    50                  55                  60

Arg Gln Thr Gly Phe Phe Thr Phe Met Asp Ser Ser Ala Thr Tyr Lys
65                  70                  75                  80

Ile Ser Thr Lys Leu Gly Ser Ser Asn Asp Val Asn Ile Gln Glu Ile
                85                  90                  95

Thr Gln Gly Ala Lys Ile Thr Pro Val Ser Gly Glu Lys Thr Leu Pro
            100                 105                 110

Lys Lys Phe Thr Leu Lys Leu His Ala His Arg Ser Ser Ser Thr Val
        115                 120                 125

Pro Gly Thr Tyr Thr Val Gly Leu Asn Val Thr Ser Asn Val Ile
    130                 135                 140
```

<210> SEQ ID NO 101
<211> LENGTH: 1836
<212> TYPE: DNA
<213> ORGANISM: Escherichia coli

<400> SEQUENCE: 101

```
atgagaacag aaatagcgac taaaaacttc ccagtatcaa cgactatttc aaaaagtttt      60

tttgcacctg aaccacgaat acagccttct tttggtgaaa atgttggaaa ggaaggagct     120

ttattattta gtgtgaactt aactgttcct gaaaatgtat cccaggtaac ggtctaccct     180

gtttatgatg aagattatgg gttaggacga ctagtaaata ccgctgatgc ttcccaatca     240

ataatctacc agattgttga tgagaaaggg aaaaaaatgt taaaagatca tggtgcagag     300

gttacaccta atcaacaaat aacttttaaa gcgctgaatt atactagcgg ggaaaaaaaa     360

atatctcctg gaatatataa cgatcaggtt atggttggtt actacgtcaa cgacaataaa     420

caaggaaact ggcaatataa atctctggat gtaaatgtaa atattgagca aaattttatt     480

ccagatattg attccgctgt tcgtataata cctgttaatt acgattcgga cccgaaactg     540

gattcacagt tatatacggt tgagatgacg atccctgcag gtgtaagcgc agttaaaatc     600

gcaccaacag atagtctgac atcttctgga cagcagatcg gaaagctggt taatgtaaac     660

aatccagatc aaaatatgaa ttattatatc agaaaggatt ctggcgctgg taactttatg     720

gcaggacaaa aaggatcctt tcctgtcaaa gagaatacgt catacacatt ctcagcaatt     780

tatactggtg gcgaataccc taatagcgga tattcgtctg gtacttatgc aggaaatttg     840

actgtatcat tttacagcaa tgacaataaa caaagaacag aaatagcgac taaaaacttc     900

ccagtatcca cgactatttc aggcacatta gctattgatt ttacgcctat tgaaaatatt     960

tatgtaggtg ccaattatgg taaagatatt ggaacccttg ttttcacaac aaatgattta    1020

acagatatta cattgatgtc atctcgcagc gttgttgatg gtcgccagac tggttttttt    1080

accttcatgg actcatcagc cacttacaaa attagtacaa aactgggatc atcgaatgat    1140

gtaaacattc aagaaattac tcaaggagct aaaattactc ctgttagtgg agagaaaact    1200
```

```
ttgcctaaaa aattcactct taagctacat gcacacagga gtagcagtac agttccaggt   1260

acgtatactg ttggtcttaa cgtaaccagt aacgttattg ataacaagca ggcagcgggg   1320

cccactctaa ccaaagaact ggcattaaat gtgctttctc ctgcagctct ggatgcaact   1380

tgggctcctc aggataattt aacattatcc aatactggcg tttctaatac tttggtgggt   1440

gttttgactc tttcaaatac cagtattgat acagttagca ttgcgagtac aaatgtttct   1500

gatacatcta agaatggtac agtaactttt gcacatgaga caaataactc tgctagcttt   1560

gccaccacca tttcaacaga taatgccaac attacgttgg ataaaaatgc tggaaatacg   1620

attgttaaaa ctacaaatgg gagtcagttg ccaactaatt taccacttaa gtttattacc   1680

actgaaggta acgaacattt agtttcaggt aattaccgtg caaatataac aattacttcg   1740

acaattaaag ataacaagca ggcggcaggt ccaaccctga ctaaggagtt agcgctgaac   1800

gttctgagcc tcgagcacca ccaccaccac cactga                             1836
```

<210> SEQ ID NO 102
<211> LENGTH: 611
<212> TYPE: PRT
<213> ORGANISM: Escherichia coli

<400> SEQUENCE: 102

```
Met Arg Thr Glu Ile Ala Thr Lys Asn Phe Pro Val Ser Thr Thr Ile
1               5                   10                  15

Ser Lys Ser Phe Phe Ala Pro Glu Pro Arg Ile Gln Pro Ser Phe Gly
            20                  25                  30

Glu Asn Val Gly Lys Glu Gly Ala Leu Leu Phe Ser Val Asn Leu Thr
        35                  40                  45

Val Pro Glu Asn Val Ser Gln Val Thr Val Tyr Pro Val Tyr Asp Glu
    50                  55                  60

Asp Tyr Gly Leu Gly Arg Leu Val Asn Thr Ala Asp Ala Ser Gln Ser
65                  70                  75                  80

Ile Ile Tyr Gln Ile Val Asp Glu Lys Gly Lys Lys Met Leu Lys Asp
                85                  90                  95

His Gly Ala Glu Val Thr Pro Asn Gln Gln Ile Thr Phe Lys Ala Leu
            100                 105                 110

Asn Tyr Thr Ser Gly Glu Lys Lys Ile Ser Pro Gly Ile Tyr Asn Asp
        115                 120                 125

Gln Val Met Val Gly Tyr Tyr Val Asn Asp Asn Lys Gln Gly Asn Trp
    130                 135                 140

Gln Tyr Lys Ser Leu Asp Val Asn Val Asn Ile Glu Gln Asn Phe Ile
145                 150                 155                 160

Pro Asp Ile Asp Ser Ala Val Arg Ile Ile Pro Val Asn Tyr Asp Ser
                165                 170                 175

Asp Pro Lys Leu Asp Ser Gln Leu Tyr Thr Val Glu Met Thr Ile Pro
            180                 185                 190

Ala Gly Val Ser Ala Val Lys Ile Ala Pro Thr Asp Ser Leu Thr Ser
        195                 200                 205

Ser Gly Gln Gln Ile Gly Lys Leu Val Asn Val Asn Asn Pro Asp Gln
    210                 215                 220

Asn Met Asn Tyr Tyr Ile Arg Lys Asp Ser Gly Ala Gly Asn Phe Met
225                 230                 235                 240

Ala Gly Gln Lys Gly Ser Phe Pro Val Lys Glu Asn Thr Ser Tyr Thr
                245                 250                 255
```

-continued

```
Phe Ser Ala Ile Tyr Thr Gly Gly Glu Tyr Pro Asn Ser Gly Tyr Ser
            260                 265                 270

Ser Gly Thr Tyr Ala Gly Asn Leu Thr Val Ser Phe Tyr Ser Asn Asp
        275                 280                 285

Asn Lys Gln Arg Thr Glu Ile Ala Thr Lys Asn Phe Pro Val Ser Thr
    290                 295                 300

Thr Ile Ser Gly Thr Leu Ala Ile Asp Phe Thr Pro Ile Glu Asn Ile
305                 310                 315                 320

Tyr Val Gly Ala Asn Tyr Gly Lys Asp Ile Gly Thr Leu Val Phe Thr
                325                 330                 335

Thr Asn Asp Leu Thr Asp Ile Thr Leu Met Ser Ser Arg Ser Val Val
            340                 345                 350

Asp Gly Arg Gln Thr Gly Phe Phe Thr Phe Met Asp Ser Ser Ala Thr
        355                 360                 365

Tyr Lys Ile Ser Thr Lys Leu Gly Ser Ser Asn Asp Val Asn Ile Gln
    370                 375                 380

Glu Ile Thr Gln Gly Ala Lys Ile Thr Pro Val Ser Gly Glu Lys Thr
385                 390                 395                 400

Leu Pro Lys Lys Phe Thr Leu Lys Leu His Ala His Arg Ser Ser Ser
                405                 410                 415

Thr Val Pro Gly Thr Tyr Thr Val Gly Leu Asn Val Thr Ser Asn Val
            420                 425                 430

Ile Asp Asn Lys Gln Ala Ala Gly Pro Thr Leu Thr Lys Glu Leu Ala
        435                 440                 445

Leu Asn Val Leu Ser Pro Ala Ala Leu Asp Ala Thr Trp Ala Pro Gln
    450                 455                 460

Asp Asn Leu Thr Leu Ser Asn Thr Gly Val Ser Asn Thr Leu Val Gly
465                 470                 475                 480

Val Leu Thr Leu Ser Asn Thr Ser Ile Asp Thr Val Ser Ile Ala Ser
                485                 490                 495

Thr Asn Val Ser Asp Thr Ser Lys Asn Gly Thr Val Thr Phe Ala His
            500                 505                 510

Glu Thr Asn Asn Ser Ala Ser Phe Ala Thr Thr Ile Ser Thr Asp Asn
        515                 520                 525

Ala Asn Ile Thr Leu Asp Lys Asn Ala Gly Asn Thr Ile Val Lys Thr
    530                 535                 540

Thr Asn Gly Ser Gln Leu Pro Thr Asn Leu Pro Leu Lys Phe Ile Thr
545                 550                 555                 560

Thr Glu Gly Asn Glu His Leu Val Ser Gly Asn Tyr Arg Ala Asn Ile
                565                 570                 575

Thr Ile Thr Ser Thr Ile Lys Asp Asn Lys Gln Ala Ala Gly Pro Thr
            580                 585                 590

Leu Thr Lys Glu Leu Ala Leu Asn Val Leu Ser Leu Glu His His His
        595                 600                 605

His His His
    610
```

```
<210> SEQ ID NO 103
<211> LENGTH: 2526
<212> TYPE: DNA
<213> ORGANISM: Escherichia coli

<400> SEQUENCE: 103

atgaataaaa ttttatttat ttttacattg ttttttttctt cagggttttt tacatttgcc      60
```

-continued

```
gtatcggcag ataaaaatcc cggaagtgaa aacatgacta atactattgg tccccatgac    120
aggggggggat cttcccccat atataatatc ttaaattcct atcttacagc atacaatgga    180
agccatcatc tgtatgatag gatgagtttt ttatgtttgt cttctcaaaa tacactgaat    240
ggagcatgcc caagcagtga tgcccctggc actgctacaa ttgatggcga aacaaatata    300
acattacaat ttacggaaaa aagaagtcta attaaaagag aactgcaaat taaaggctat    360
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattaccttt tgggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt ttgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caaagaattt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaaatatt   1560
actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accggaacgg caggtgtttc gaatagtaaa gaattagtaa ttggagcaac tacatccgga   1920
actgcaccaa gtgcaggtaa gtatcaaggc gtcgtttcca ttgtaatgac tcaatcgacc   1980
gacacagccg cgcctgttcc tgacaataaa caagtagaga aaaatattac tgtgacagcc   2040
agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
```

```
gaaaaaaata tcactgtaac agctagtgtt gatcctacgc tcgagcacca ccaccaccac   2520

cactga                                                              2526


<210> SEQ ID NO 104
<211> LENGTH: 841
<212> TYPE: PRT
<213> ORGANISM: Escherichia coli

<400> SEQUENCE: 104

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350
```

```
Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Thr Ile Asp Ile Leu Gln Ala Asn Gly Ser Ala Leu Pro Thr Ala Val
    530                 535                 540

Asp Leu Thr Tyr Leu Pro Gly Ala Lys Thr Phe Glu Asn Tyr Ser Val
545                 550                 555                 560

Leu Thr Gln Ile Tyr Thr Asn Asp Pro Ser Lys Gly Leu Asp Val Arg
                565                 570                 575

Leu Val Asp Thr Pro Lys Leu Thr Asn Ile Leu Gln Pro Thr Ser Thr
            580                 585                 590

Ile Pro Leu Thr Val Ser Trp Ala Gly Lys Thr Leu Ser Thr Ser Ala
        595                 600                 605

Gln Lys Ile Ala Val Gly Asp Leu Gly Phe Gly Ser Thr Gly Thr Ala
    610                 615                 620

Gly Val Ser Asn Ser Lys Glu Leu Val Ile Gly Ala Thr Thr Ser Gly
625                 630                 635                 640

Thr Ala Pro Ser Ala Gly Lys Tyr Gln Gly Val Val Ser Ile Val Met
                645                 650                 655

Thr Gln Ser Thr Asp Thr Ala Ala Pro Val Pro Asp Asn Lys Gln Val
            660                 665                 670

Glu Lys Asn Ile Thr Val Thr Ala Ser Val Asp Pro Thr Ile Asp Ile
        675                 680                 685

Leu Gln Ala Asp Gly Ser Ser Leu Pro Thr Ala Val Glu Leu Thr Tyr
    690                 695                 700

Ser Pro Ala Ala Ser Arg Phe Glu Asn Tyr Lys Ile Ala Thr Lys Val
705                 710                 715                 720

His Thr Asn Val Ile Asn Lys Asn Val Leu Val Lys Leu Val Asn Asp
                725                 730                 735

Pro Lys Leu Thr Asn Val Leu Asp Ser Thr Lys Gln Leu Pro Ile Thr
            740                 745                 750

Val Ser Tyr Gly Gly Lys Thr Leu Ser Thr Ala Asp Val Thr Phe Glu
        755                 760                 765

Pro Ala Glu Leu Asn Phe Gly Thr Ser Gly Val Thr Gly Val Ser Ser
```

```
    770                 775                 780

Ser Gln Asp Leu Val Ile Gly Ala Thr Thr Ala Gln Ala Pro Thr Ala
785                 790                 795                 800

Gly Asn Tyr Ser Gly Val Val Ser Ile Leu Met Thr Leu Ala Ser Asp
                805                 810                 815

Asn Lys Gln Val Glu Lys Asn Ile Thr Val Thr Ala Ser Val Asp Pro
            820                 825                 830

Thr Leu Glu His His His His His His
        835                 840


<210> SEQ ID NO 105
<211> LENGTH: 2164
<212> TYPE: DNA
<213> ORGANISM: Escherichia coli

<400> SEQUENCE: 105

atgaaaaaga tatttatttt tttgtctatc atattttctg cggtggtcag tgccgggcga     60

tacccggaaa ctacagtagg taatctgacg aagagttttc aagcccctcg tcaggataga    120

agcgtacaat caccaatata taacatcttt acgaatcatg tggctggata tagtttgagt    180

cataacttat atgacaggat tgttttttta tgtacatcct cgtcgaatcc ggttaatggt    240

gcttgcccaa ccattggaac atctggagtt caatacggta ctacaaccat aaccttgcag    300

tttacagaaa aaagaagtct gataaaaaga aatattaatc ttgcaggtaa taagaaacca    360

atatgggaga atcagagttg cgacactagc aatctaatgg tgttgaattc gaagtcttgg    420

tcctgtgggg cttacggaaa tgctaacgga acacttctaa atctgtatat ccctgcagga    480

gaaatcaaca aattgccttt tggagggata tgggaggcaa ctctgatctt acgcttatca    540

agatatggcg aagtcagtag cacccattac ggcaattata ccgtaaatat tacggttgat    600

ttaactgata aaggtaatat tcaggtatgg cttccagggt ttcacagcaa cccgcgtgta    660

gacctgaatc tgcaccctat cggtaattat aaatatagtg gtagtaattc actcgacatg    720

tgtttctatg atggatatag tacaaacagt gatagcatgg taataaagtt ccaggatgat    780

aatcctacct attcatctga atataatctt tataagatag ggggcactga aaaattaccc    840

tatgctgttt cactgcttat gggagaaaaa atattttatc cagtgaatgg tcaatcattt    900

actatcaatg acagtagtgt actcgaaaca aactggaatc gagtaaccgc agttgctatg    960

ccggaagtta atgttccagt attatgctgg ccagcaagat tgctattaaa tgctgatgta   1020

aatgctcccg atgcaggaca gtattcagga cagatatata taacatttac acccagtgtc   1080

gaaaatttag gcggtggagt cgaaaaaaat attactgtga gggcaagtgt tgaccctaaa   1140

cttgatcttc tgcaagcaga tggaacttca ctgccggact ctatcgcatt aacctattct   1200

tcggcttcaa ataattttga agtttactct cttaatactg ctattcatac aaatgacaaa   1260

agcaagggag ttgtagtgaa gctgtcagct tcaccagttc tgtccaatat tatgaagcca   1320

aactcgcaaa ttccgatgaa agtgactttg gggggggaaga cgctgaatac aactgatact   1380

gagtttactg ttgatactct gaactttggt acatctggtg ttgaaaacgt ttcttccact   1440

caacagctta cgattcatgc agacacacaa ggaactgcgc ctgaggcagg caattaccaa   1500

ggtattattt ctcttatcat gactcaaaaa acagggggcg gtgtcgaaaa aaatattact   1560

gtgagggcaa gtgtcgaccc taaacttgac cttctgcaat ctgatggctc tgcgctgccg   1620

aactctgtcg cattaaccta ttctccggct gtaaataatt ttgaagctca caccatcaac   1680

accgttgttc atacaaatga ctcagataaa ggtgttgttg tgaagctgtc agcagatcca   1740
```

gtcctgtcca atgttctgaa tccaaccctg caaattcctg tttctgtgaa tttcgcagga 1800
aaaccactga gcacaacagg cattaccatc gactccaatg atctgaactt tgcttcgagt 1860
ggtgttaata aagtttcttc tacgcagaaa ctttcaatcc atgcagatgc tactcgggta 1920
actggcggcg cactaacagc tggtcaatat cagggactcg tatcaattat cctgactaag 1980
tcaacggggg gcggtgtcga gaagaccatt agcgttacgg cgagtgttga cccgacgggc 2040
acattagcta ttgattttac gcctattgaa aatatttatg taggtgccaa ttatggtaaa 2100
gatattggaa cccttgtttt cacaacaaat gatttaactc gagcaccacc accaccacca 2160
ctga 2164

<210> SEQ ID NO 106
<211> LENGTH: 687
<212> TYPE: PRT
<213> ORGANISM: Escherichia coli

<400> SEQUENCE: 106

Met Lys Lys Ile Phe Ile Phe Leu Ser Ile Ile Phe Ser Ala Val Val
1 5 10 15

Ser Ala Gly Arg Tyr Pro Glu Thr Thr Val Gly Asn Leu Thr Lys Ser
20 25 30

Phe Gln Ala Pro Arg Gln Asp Arg Ser Val Gln Ser Pro Ile Tyr Asn
35 40 45

Ile Phe Thr Asn His Val Ala Gly Tyr Ser Leu Ser His Asn Leu Tyr
50 55 60

Asp Arg Ile Val Phe Leu Cys Thr Ser Ser Ser Asn Pro Val Asn Gly
65 70 75 80

Ala Cys Pro Thr Ile Gly Thr Ser Gly Val Gln Tyr Gly Thr Thr Thr
85 90 95

Ile Thr Leu Gln Phe Thr Glu Lys Arg Ser Leu Ile Lys Arg Asn Ile
100 105 110

Asn Leu Ala Gly Asn Lys Lys Pro Ile Trp Glu Asn Gln Ser Cys Asp
115 120 125

Thr Ser Asn Leu Met Val Leu Asn Ser Lys Ser Trp Ser Cys Gly Ala
130 135 140

Tyr Gly Asn Ala Asn Gly Thr Leu Leu Asn Leu Tyr Ile Pro Ala Gly
145 150 155 160

Glu Ile Asn Lys Leu Pro Phe Gly Gly Ile Trp Glu Ala Thr Leu Ile
165 170 175

Leu Arg Leu Ser Arg Tyr Gly Glu Val Ser Ser Thr His Tyr Gly Asn
180 185 190

Tyr Thr Val Asn Ile Thr Val Asp Leu Thr Asp Lys Gly Asn Ile Gln
195 200 205

Val Trp Leu Pro Gly Phe His Ser Asn Pro Arg Val Asp Leu Asn Leu
210 215 220

His Pro Ile Gly Asn Tyr Lys Tyr Ser Gly Ser Asn Ser Leu Asp Met
225 230 235 240

Cys Phe Tyr Asp Gly Tyr Ser Thr Asn Ser Asp Ser Met Val Ile Lys
245 250 255

Phe Gln Asp Asp Asn Pro Thr Tyr Ser Ser Glu Tyr Asn Leu Tyr Lys
260 265 270

Ile Gly Gly Thr Glu Lys Leu Pro Tyr Ala Val Ser Leu Leu Met Gly
275 280 285

-continued

```
Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu Gly Gly Gly Val Glu
        355                 360                 365

Lys Asn Ile Thr Val Arg Ala Ser Val Asp Pro Lys Leu Asp Leu Leu
    370                 375                 380

Gln Ala Asp Gly Thr Ser Leu Pro Asp Ser Ile Ala Leu Thr Tyr Ser
385                 390                 395                 400

Ser Ala Ser Asn Asn Phe Glu Val Tyr Ser Leu Asn Thr Ala Ile His
                405                 410                 415

Thr Asn Asp Lys Ser Lys Gly Val Val Val Lys Leu Ser Ala Ser Pro
            420                 425                 430

Val Leu Ser Asn Ile Met Lys Pro Asn Ser Gln Ile Pro Met Lys Val
        435                 440                 445

Thr Leu Gly Gly Lys Thr Leu Asn Thr Thr Asp Thr Glu Phe Thr Val
    450                 455                 460

Asp Thr Leu Asn Phe Gly Thr Ser Gly Val Glu Asn Val Ser Ser Thr
465                 470                 475                 480

Gln Gln Leu Thr Ile His Ala Asp Thr Gln Gly Thr Ala Pro Glu Ala
                485                 490                 495

Gly Asn Tyr Gln Gly Ile Ile Ser Leu Ile Met Thr Gln Lys Thr Gly
            500                 505                 510

Gly Gly Val Glu Lys Asn Ile Thr Val Arg Ala Ser Val Asp Pro Lys
        515                 520                 525

Leu Asp Leu Leu Gln Ser Asp Gly Ser Ala Leu Pro Asn Ser Val Ala
    530                 535                 540

Leu Thr Tyr Ser Pro Ala Val Asn Asn Phe Glu Ala His Thr Ile Asn
545                 550                 555                 560

Thr Val Val His Thr Asn Asp Ser Asp Lys Gly Val Val Val Lys Leu
                565                 570                 575

Ser Ala Asp Pro Val Leu Ser Asn Val Leu Asn Pro Thr Leu Gln Ile
            580                 585                 590

Pro Val Ser Val Asn Phe Ala Gly Lys Pro Leu Ser Thr Thr Gly Ile
        595                 600                 605

Thr Ile Asp Ser Asn Asp Leu Asn Phe Ala Ser Ser Gly Val Asn Lys
    610                 615                 620

Val Ser Ser Thr Gln Lys Leu Ser Ile His Ala Asp Ala Thr Arg Val
625                 630                 635                 640

Thr Gly Gly Ala Leu Thr Ala Gly Gln Tyr Gln Gly Leu Val Ser Ile
                645                 650                 655

Ile Leu Thr Lys Ser Thr Gly Gly Gly Val Glu Lys Thr Ile Ser Val
            660                 665                 670

Thr Ala Ser Val Asp Pro Thr Leu Glu His His His His His His
        675                 680                 685
```

<210> SEQ ID NO 107
<211> LENGTH: 2278
<212> TYPE: DNA

<213> ORGANISM: Escherichia coli

<400> SEQUENCE: 107

```
atgaaaaaga tatttatttt tttgtctatc atattttctg cggtggtcag tgccgggcga     60
tacccggaaa ctacagtagg taatctgacg aagagttttc aagcccctcg tcaggataga    120
agcgtacaat caccaatata taacatcttt acgaatcatg tggctggata tagtttgagt    180
cataacttat atgacaggat tgttttttta tgtacatcct cgtcgaatcc ggttaatggt    240
gcttgcccaa ccattggaac atctggagtt caatacggta ctacaaccat aaccttgcag    300
tttacagaaa aaagaagtct gataaaaaga aatattaatc ttgcaggtaa taagaaacca    360
atatgggaga atcagagttg cgacactagc aatctaatgg tgttgaattc gaagtcttgg    420
tcctgtgggg cttacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag gggcactgga aaaattaccc    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttag gcggtggagt cgaaaaaaat attactgtga gggcaagtgt tgaccctaaa   1140
cttgatcttc tgcaagcaga tggaacttca ctgccggact ctatcgcatt aacctattct   1200
tcggcttcaa ataattttga agtttactct cttaatactg ctattcatac aaatgacaaa   1260
agcaagggag ttgtagtgaa gctgtcagct tcaccagttc tgtccaatat tatgaagcca   1320
aactcgcaaa ttccgatgaa agtgactttg gggggggaaga cgctgaatac aactgatact   1380
gagtttactg ttgatactct gaactttggt acatctggtg ttgaaaacgt ttcttccact   1440
caacagctta cgattcatgc agacacacaa ggaactgcgc ctgaggcagg caattaccaa   1500
ggtattattt ctcttatcat gactcaaaaa acagggggcg gtgtcgaaaa aaatattact   1560
gtgagggcaa gtgtcgaccc taaacttaaa ctaaagaaaa caattggcgc aatggctctg   1620
gcgacattat ttgcaactat gggagcatct gcggtcgaga agaccattag cgttacggcg   1680
agtgttgacc cgactgttga ccttctgcaa tctgatggct ctgcgctgcc gaactctgtc   1740
gcattaacct attctccggc tgtaaataat tttgaagctc acaccatcaa caccgttgtt   1800
catacaaatg actcagataa aggtgttgtt gtgaagctgt cagcagatcc agtcctgtcc   1860
aatgttctga atccaaccct gcaaattcct gtttctgtga atttcgcagg aaaaccactg   1920
agcacaacag gcattaccat cgactccaat gatctgaact ttgcttcgag tggtgttaat   1980
aaagtttctt ctacgcagaa actttcaatc catgcagatg ctactcgggt aactggcggc   2040
gcactaacag ctggtcaata tcagggactc gtatcaatta tcctgactaa gtcaacgtaa   2100
gggggcggtg tcgagaagac cattagcgtt acggcgagtg ttgacccgac gggcacatta   2160
gctattgatt ttacgcctat tgaaaatatt tatgtaggtg ccaattatgg taaagatatt   2220
ggaacccttg ttttcacaac aaatgattta actcgagcac caccaccacc accactga     2278
```

<210> SEQ ID NO 108
<211> LENGTH: 703
<212> TYPE: PRT
<213> ORGANISM: Escherichia coli

<400> SEQUENCE: 108

Met Lys Lys Ile Phe Ile Phe Leu Ser Ile Ile Phe Ser Ala Val Val
1 5 10 15

Ser Ala Gly Arg Tyr Pro Glu Thr Thr Val Gly Asn Leu Thr Lys Ser
20 25 30

Phe Gln Ala Pro Arg Gln Asp Arg Ser Val Gln Ser Pro Ile Tyr Asn
35 40 45

Ile Phe Thr Asn His Val Ala Gly Tyr Ser Leu Ser His Asn Leu Tyr
50 55 60

Asp Arg Ile Val Phe Leu Cys Thr Ser Ser Ser Asn Pro Val Asn Gly
65 70 75 80

Ala Cys Pro Thr Ile Gly Thr Ser Gly Val Gln Tyr Gly Thr Thr Thr
85 90 95

Ile Thr Leu Gln Phe Thr Glu Lys Arg Ser Leu Ile Lys Arg Asn Ile
100 105 110

Asn Leu Ala Gly Asn Lys Lys Pro Ile Trp Glu Asn Gln Ser Cys Asp
115 120 125

Thr Ser Asn Leu Met Val Leu Asn Ser Lys Ser Trp Ser Cys Gly Ala
130 135 140

Tyr Gly Asn Ala Asn Gly Thr Leu Leu Asn Leu Tyr Ile Pro Ala Gly
145 150 155 160

Glu Ile Asn Lys Leu Pro Phe Gly Gly Ile Trp Glu Ala Thr Leu Ile
165 170 175

Leu Arg Leu Ser Arg Tyr Gly Glu Val Ser Ser Thr His Tyr Gly Asn
180 185 190

Tyr Thr Val Asn Ile Thr Val Asp Leu Thr Asp Lys Gly Asn Ile Gln
195 200 205

Val Trp Leu Pro Gly Phe His Ser Asn Pro Arg Val Asp Leu Asn Leu
210 215 220

His Pro Ile Gly Asn Tyr Lys Tyr Ser Gly Ser Asn Ser Leu Asp Met
225 230 235 240

Cys Phe Tyr Asp Gly Tyr Ser Thr Asn Ser Asp Ser Met Val Ile Lys
245 250 255

Phe Gln Asp Asp Asn Pro Thr Tyr Ser Ser Glu Tyr Asn Leu Tyr Lys
260 265 270

Ile Gly Gly Thr Glu Lys Leu Pro Tyr Ala Val Ser Leu Leu Met Gly
275 280 285

Glu Lys Ile Phe Tyr Pro Val Asn Gly Gln Ser Phe Thr Ile Asn Asp
290 295 300

Ser Ser Val Leu Glu Thr Asn Trp Asn Arg Val Thr Ala Val Ala Met
305 310 315 320

Pro Glu Val Asn Val Pro Val Leu Cys Trp Pro Ala Arg Leu Leu Leu
325 330 335

Asn Ala Asp Val Asn Ala Pro Asp Ala Gly Gln Tyr Ser Gly Gln Ile
340 345 350

Tyr Ile Thr Phe Thr Pro Ser Val Glu Asn Leu Gly Gly Gly Val Glu
355 360 365

Lys Asn Ile Thr Val Arg Ala Ser Val Asp Pro Lys Leu Asp Leu Leu 370 375 380

Gln Ala Asp Gly Thr Ser Leu Pro Asp Ser Ile Ala Leu Thr Tyr Ser
385 390 395 400

Ser Ala Ser Asn Asn Phe Glu Val Tyr Ser Leu Asn Thr Ala Ile His
405 410 415

Thr Asn Asp Lys Ser Lys Gly Val Val Val Lys Leu Ser Ala Ser Pro
420 425 430

Val Leu Ser Asn Ile Met Lys Pro Asn Ser Gln Ile Pro Met Lys Val
435 440 445

Thr Leu Gly Gly Lys Thr Leu Asn Thr Thr Asp Thr Glu Phe Thr Val
450 455 460

Asp Thr Leu Asn Phe Gly Thr Ser Gly Val Glu Asn Val Ser Ser Thr
465 470 475 480

Gln Gln Leu Thr Ile His Ala Asp Thr Gln Gly Thr Ala Pro Glu Ala
485 490 495

Gly Asn Tyr Gln Gly Ile Ile Ser Leu Ile Met Thr Gln Lys Thr Gly
500 505 510

Gly Gly Val Glu Lys Asn Ile Thr Val Arg Ala Ser Val Asp Pro Lys
515 520 525

Leu Asp Val Glu Lys Thr Ile Ser Val Thr Ala Ser Val Asp Pro Thr
530 535 540

Val Asp Leu Leu Gln Ser Asp Gly Ser Ala Leu Pro Asn Ser Val Ala
545 550 555 560

Leu Thr Tyr Ser Pro Ala Val Asn Asn Phe Glu Ala His Thr Ile Asn
565 570 575

Thr Val Val His Thr Asn Asp Ser Asp Lys Gly Val Val Val Lys Leu
580 585 590

Ser Ala Asp Pro Val Leu Ser Asn Val Leu Asn Pro Thr Leu Gln Ile
595 600 605

Pro Val Ser Val Asn Phe Ala Gly Lys Pro Leu Ser Thr Thr Gly Ile
610 615 620

Thr Ile Asp Ser Asn Asp Leu Asn Phe Ala Ser Ser Gly Val Asn Lys
625 630 635 640

Val Ser Ser Thr Gln Lys Leu Ser Ile His Ala Asp Ala Thr Arg Val
645 650 655

Thr Gly Gly Ala Leu Thr Ala Gly Gln Tyr Gln Gly Leu Val Ser Ile
660 665 670

Ile Leu Thr Lys Ser Thr Gly Gly Gly Val Glu Lys Thr Ile Ser Val
675 680 685

Thr Ala Ser Val Asp Pro Thr Leu Glu His His His His His His
690 695 700

<210> SEQ ID NO 109
<211> LENGTH: 1620
<212> TYPE: DNA
<213> ORGANISM: Escherichia coli

<400> SEQUENCE: 109
atgaaaaaag tgatttttgt tttatccatg tttctatgtt ctcaggttta cgggcaatca 60
tggcatacga acgtagaggc tggttcaata aataaaacag agtcgatagg ccccatagac 120
cgaagtgctg ctgcatcgta tcctgctcat tatatatttc atgaacatgt tgctggttac 180
aataaagatc actctctttt tgacaggatg acgtttttat gtatgtcatc aacagatgca 240
tctaaaggtg catgtccgac aggagaaaac tccaaatcct ctcaagggga gactaatatt 300

```
aagctaatat ttactgaaaa gaaaagtctg gccagaaaaa cattaaactt aaaaggatat    360
aagagatttt tatatgaatc agatagatgc attcattatg tcgataaaat gaatctcaat    420
tctcatactg ttaaatgtgt aggttcattc acaagaggag tagatttcac tttatatatc    480
ccacaaggtg aaattgatgg gcttctaact ggaggtatat gggaggcaac actagagtta    540
cgagtcaaaa ggcattacga ctataatcat ggtacttaca aagttaatat cacagttgat    600
ttgacagaca aaggaaatat tcaggtctgg acaccaaagt ttcatagcga tcctagaatt    660
gatctgaatt tacgtcctga aggtaatggt aaatattctg gtagtaacgt gcttgagatg    720
tgtctctatg atggctatag tacacatagt caaagtatag aaatgaggtt tcaggatgac    780
tcacaaacag gaaataatga atataatctt ataaaaactg gagagccatt aaaaaaattg    840
ccatataaac tttctcttct tttaggagga cgagagtttt atccaaataa tggagaggct    900
tttactatta atgatacttc gtcattgttt ataaactgga atcgtattaa gtctgtatcc    960
ttaccacaga ttagtattcc agtactatgc tggccagcaa acttgacatt tatgtcagag   1020
ctaaataatc cagaagcggg tgagtattca ggaatactta acgtaacatt tactcctagt   1080
agttcaagcc tagacaataa acaagccgag aaaaatatca ctgtaactgc tagcgttgat   1140
ccaactatcg atctgatgca atctgatggc acagcgttac caagtgcagt taatattgca   1200
tatcttccag gagagaaaag atttgaatct gctcgtatca atacccaagt tcataccaat   1260
aataaaacta agggtattca gataaagctt actaatgata atgtggtaat gactaactta   1320
tctgatccaa gcaagactat tcctttagag gtttcattcg ctggcactaa gctgagcaca   1380
gctgcaacat ctattactgc cgatcaatta aattttggcg cagctggtgt agagacagtt   1440
tctgcaacta aggaactcgt tattaatgca ggaagcaccc agcaaactaa tattgtagct   1500
ggtaactatc aaggattggt gtcaattgtg cttactcaag aacctgacaa taaacaagcc   1560
gagaaaaata tcactgtaac tgctagcgtt gatccgacgc accaccacca ccaccactga   1620
```

<210> SEQ ID NO 110
<211> LENGTH: 539
<212> TYPE: PRT
<213> ORGANISM: Escherichia coli

<400> SEQUENCE: 110

```
Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140
```

```
Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Asp Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Ser Leu Asp Asn Lys Gln
        355                 360                 365

Ala Glu Lys Asn Ile Thr Val Thr Ala Ser Val Asp Pro Thr Ile Asp
    370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
            420                 425                 430

Asp Asn Val Val Met Thr Asn Leu Ser Asp Pro Ser Lys Thr Ile Pro
        435                 440                 445

Leu Glu Val Ser Phe Ala Gly Thr Lys Leu Ser Thr Ala Ala Thr Ser
    450                 455                 460

Ile Thr Ala Asp Gln Leu Asn Phe Gly Ala Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
            500                 505                 510

Gln Glu Pro Asp Asn Lys Gln Ala Glu Lys Asn Ile Thr Val Thr Ala
        515                 520                 525

Ser Val Asp Pro Thr His His His His His His
    530                 535
```

<210> SEQ ID NO 111
<211> LENGTH: 2490

<212> TYPE: DNA
<213> ORGANISM: Escherichia coli

<400> SEQUENCE: 111
atgaataaaa ttttatttat ttttacattg ttttttttctt cagggttttt tacatttgcc 60
gtatcggcag ataaaaatcc cggaagtgaa aacatgacta atactattgg tccccatgac 120 aggggggggat cttcccccat atataatatc ttaaattcct atcttacagc atacaatgga 180
agccatcatc tgtatgatag gatgagtttt ttatgtttgt cttctcaaaa tacactgaat 240
ggagcatgcc caagcagtga tgcccctggc actgctacaa ttgatggcga aacaaatata 300
acattacaat ttacggaaaa aagaagtcta attaaaagag aactgcaaat taaaggctat 360
aaacaatttt tgttcaaaaa tgctaattgc ccatctaaac tagcacttaa ctcatctcat 420
tttcaatgta atagagaaca agcttcaggt gctactttat cgttatacat accagctggt 480
gaattaaata aattaccttt tgggggggtc tggaatgccg ttctgaagct aaatgtaaaa 540
agacgatatg atacaaccta tgggacttac actataaaca tcacagttaa tttaactgat 600
aagggaaata ttcagatatg gttaccacag ttcaaaagta acgctcgtgt cgatcttaac 660
ttgcgtccaa ctggtggtgg tacatatatc ggaagaaatt ctgttgatat gtgcttttat 720
gatggatata gtactaacag cagctcttta gagataagat ttcaggatga taattctaaa 780
tctgatggaa aattttatct aaagaaaata aatgatgact ccaaagaact tgtatacact 840
ttgtcacttc tcctggcagg taaaaattta acaccaacaa atggacaggc attaaatatt 900
aacactgctt ctctggaaac aaactggaat agaattacag ctgtcaccat gccagaaatc 960
agtgttccgg tgttgtgttg gcctggacgt ttgcaattgg atgcaaaagt gaaaaatccc 1020
gaggctggac aatatatggg gaatattaaa attactttca caccaagtag tcaaacactc 1080
gacaataaac aagtagagaa aaatattact gtaacagcta gtgttgatcc tgcaattgat 1140
cttttgcaag ctgatggcaa tgctctgcca tcagctgtaa agttagctta ttctcccgca 1200
tcaaaaactt ttgaaagtta cagagtaatg actcaagttc atacaaacga tgcaactaaa 1260
aaagtaattg ttaaacttgc tgatacacca cagcttacag atgttctgaa ttcaactgtt 1320
caaatgccta tcagtgtgtc atggggagga caagtattat ctacaacagc caaagaattt 1380
gaagctgctg ctttgggata ttctgcatcc ggtgtaaatg gcgtatcatc ttctcaagag 1440
ttagtaatta gcgctgcacc taaaactgcc ggtaccgccc caactgcagg aaactattca 1500
ggagtagtat ctcttgtaat gactttggga tccgacaata aacaagtaga gaaaaatatt 1560
actgtaacag ctagtgtcga ccctgcaggg tcaaaaagtt tttttgcacc tgaaccacga 1620
atacagcctt cttttggtga aaatgttgga aaggaaggag ctttattatt tagtgtgaac 1680
ttaactgttc ctgaaaatgt atcccaggta acggtctacc ctgtttatga tgaagattat 1740
gggttaggac gactagtaaa taccgctgat gcttcccaat caataatcta ccagattgtt 1800
gatgagaaag ggaaaaaaat gttaaaagat catggtgcag aggttacacc taatcaacaa 1860
ataactttta aagcgctgaa ttatactagc ggggaaaaaa aaatatctcc tggaatatat 1920
aacgatcagg ttatggttgg ttactacgtc aacgacaata aacaaggaaa ctggcaatat 1980
aaatctctgg atgtaaatgt aaatattgag caaaatttta ttccagatat tgattccgct 2040
gttcgtataa tacctgttaa ttacgattcg gacccgaaac tggattcaca gttatatacg 2100
gttgagatga cgatccctgc aggtgtaagc gcagttaaaa tcgcaccaac agatagtctg 2160
acatcttctg gacagcagat cggaaagctg gttaatgtaa acaatccaga tcaaaatatg 2220
aattattata tcagaaagga ttctggcgct ggtaacttta tggcaggaca aaaaggatcc 2280
tttcctgtca aagagaatac gtcatacaca ttctcagcaa tttatactgg tggcgaatac 2340
cctaatagcg gatattcgtc tggtacttat gcaggaaatt tgactgtatc attttacagc 2400
aatgacaata aacaacgtac cgagattgcc accaagaatt ttccggtgag caccaccatc 2460
agcctcgagc accaccacca ccaccactga 2490

<210> SEQ ID NO 112
<211> LENGTH: 829
<212> TYPE: PRT
<213> ORGANISM: Escherichia coli

<400> SEQUENCE: 112

Met Asn Lys Ile Leu Phe Ile Phe Thr Leu Phe Phe Ser Ser Gly Phe
1 5 10 15

Phe Thr Phe Ala Val Ser Ala Asp Lys Asn Pro Gly Ser Glu Asn Met
20 25 30

Thr Asn Thr Ile Gly Pro His Asp Arg Gly Gly Ser Ser Pro Ile Tyr
35 40 45

Asn Ile Leu Asn Ser Tyr Leu Thr Ala Tyr Asn Gly Ser His His Leu
50 55 60

Tyr Asp Arg Met Ser Phe Leu Cys Leu Ser Ser Gln Asn Thr Leu Asn
65 70 75 80

Gly Ala Cys Pro Ser Ser Asp Ala Pro Gly Thr Ala Thr Ile Asp Gly
85 90 95

Glu Thr Asn Ile Thr Leu Gln Phe Thr Glu Lys Arg Ser Leu Ile Lys
100 105 110

Arg Glu Leu Gln Ile Lys Gly Tyr Lys Gln Phe Leu Phe Lys Asn Ala
115 120 125

Asn Cys Pro Ser Lys Leu Ala Leu Asn Ser Ser His Phe Gln Cys Asn
130 135 140

Arg Glu Gln Ala Ser Gly Ala Thr Leu Ser Leu Tyr Ile Pro Ala Gly
145 150 155 160

Glu Leu Asn Lys Leu Pro Phe Gly Gly Val Trp Asn Ala Val Leu Lys
165 170 175

Leu Asn Val Lys Arg Arg Tyr Asp Thr Thr Tyr Gly Thr Tyr Thr Ile
180 185 190

Asn Ile Thr Val Asn Leu Thr Asp Lys Gly Asn Ile Gln Ile Trp Leu
195 200 205

Pro Gln Phe Lys Ser Asn Ala Arg Val Asp Leu Asn Leu Arg Pro Thr
210 215 220

Gly Gly Gly Thr Tyr Ile Gly Arg Asn Ser Val Asp Met Cys Phe Tyr
225 230 235 240

Asp Gly Tyr Ser Thr Asn Ser Ser Ser Leu Glu Ile Arg Phe Gln Asp
245 250 255

Asp Asn Ser Lys Ser Asp Gly Lys Phe Tyr Leu Lys Lys Ile Asn Asp
260 265 270

Asp Ser Lys Glu Leu Val Tyr Thr Leu Ser Leu Leu Leu Ala Gly Lys
275 280 285

Asn Leu Thr Pro Thr Asn Gly Gln Ala Leu Asn Ile Asn Thr Ala Ser
290 295 300

Leu Glu Thr Asn Trp Asn Arg Ile Thr Ala Val Thr Met Pro Glu Ile
305 310 315 320

Ser Val Pro Val Leu Cys Trp Pro Gly Arg Leu Gln Leu Asp Ala Lys

```
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Ser Lys Ser Phe Phe Ala Pro Glu Pro Arg Ile Gln Pro Ser
    530                 535                 540

Phe Gly Glu Asn Val Gly Lys Glu Gly Ala Leu Leu Phe Ser Val Asn
545                 550                 555                 560

Leu Thr Val Pro Glu Asn Val Ser Gln Val Thr Val Tyr Pro Val Tyr
                565                 570                 575

Asp Glu Asp Tyr Gly Leu Gly Arg Leu Val Asn Thr Ala Asp Ala Ser
            580                 585                 590

Gln Ser Ile Ile Tyr Gln Ile Val Asp Glu Lys Gly Lys Lys Met Leu
        595                 600                 605

Lys Asp His Gly Ala Glu Val Thr Pro Asn Gln Gln Ile Thr Phe Lys
    610                 615                 620

Ala Leu Asn Tyr Thr Ser Gly Glu Lys Lys Ile Ser Pro Gly Ile Tyr
625                 630                 635                 640

Asn Asp Gln Val Met Val Gly Tyr Tyr Val Asn Asp Asn Lys Gln Gly
                645                 650                 655

Asn Trp Gln Tyr Lys Ser Leu Asp Val Asn Val Asn Ile Glu Gln Asn
            660                 665                 670

Phe Ile Pro Asp Ile Asp Ser Ala Val Arg Ile Ile Pro Val Asn Tyr
        675                 680                 685

Asp Ser Asp Pro Lys Leu Asp Ser Gln Leu Tyr Thr Val Glu Met Thr
    690                 695                 700

Ile Pro Ala Gly Val Ser Ala Val Lys Ile Ala Pro Thr Asp Ser Leu
705                 710                 715                 720

Thr Ser Ser Gly Gln Gln Ile Gly Lys Leu Val Asn Val Asn Asn Pro
                725                 730                 735

Asp Gln Asn Met Asn Tyr Tyr Ile Arg Lys Asp Ser Gly Ala Gly Asn
            740                 745                 750
```

Phe Met Ala Gly Gln Lys Gly Ser Phe Pro Val Lys Glu Asn Thr Ser
755 760 765

Tyr Thr Phe Ser Ala Ile Tyr Thr Gly Gly Glu Tyr Pro Asn Ser Gly
770 775 780

Tyr Ser Ser Gly Thr Tyr Ala Gly Asn Leu Thr Val Ser Phe Tyr Ser
785 790 795 800

Asn Asp Asn Lys Gln Arg Thr Glu Ile Ala Thr Lys Asn Phe Pro Val
805 810 815

Ser Thr Thr Ile Ser Leu Glu His His His His His His
820 825

<210> SEQ ID NO 113
<211> LENGTH: 2487
<212> TYPE: DNA
<213> ORGANISM: Escherichia coli

<400> SEQUENCE: 113
atgaataaaa tttatttat ttttacattg tttttttctt cagggttttt tacatttgcc 60
gtatcggcag ataaaaatcc cggaagtgaa aacatgacta atactattgg tccccatgac 120
agggggggat cttcccccat atataatatc ttaaattcct atcttacagc atacaatgga 180
agccatcatc tgtatgatag gatgagtttt ttatgtttgt cttctcaaaa tacactgaat 240
ggagcatgcc caagcagtga tgcccctggc actgctacaa ttgatggcga aacaaatata 300
acattacaat ttacggaaaa aagaagtcta attaaaagag aactgcaaat taaaggctat 360
aaacaatttt tgttcaaaaa tgctaattgc ccatctaaac tagcacttaa ctcatctcat 420
tttcaatgta atagagaaca agcttcaggt gctactttat cgttatacat accagctggt 480
gaattaaata aattaccttt tgggggggtc tggaatgccg ttctgaagct aaatgtaaaa 540
agacgatatg atacaaccta tgggacttac actataaaca tcacagttaa tttaactgat 600
aagggaaata ttcagatatg gttaccacag ttcaaaagta acgctcgtgt cgatcttaac 660
ttgcgtccaa ctggtggtgg tacatatatc ggaagaaatt ctgttgatat gtgcttttat 720
gatggatata gtactaacag cagctcttta gagataagat ttcaggatga taattctaaa 780
tctgatggaa aattttatct aaagaaaata aatgatgact ccaaagaact tgtatacact 840
ttgtcacttc tcctggcagg taaaaattta acaccaacaa atggacaggc attaaatatt 900
aacactgctt ctctggaaac aaactggaat agaattacag ctgtcaccat gccagaaatc 960
agtgttccgg tgttgtgttg gcctggacgt ttgcaattgg atgcaaaagt gaaaaatccc 1020
gaggctggac aatatatggg gaatattaaa attactttca caccaagtag tcaaacactc 1080
gacaataaac aagtagagaa aaatattact gtaacagcta gtgttgatcc tgcaattgat 1140
cttttgcaag ctgatggcaa tgctctgcca tcagctgtaa agttagctta ttctcccgca 1200
tcaaaaactt ttgaaagtta cagagtaatg actcaagttc atacaaacga tgcaactaaa 1260
aaagtaattg ttaaacttgc tgatacacca cagcttacag atgttctgaa ttcaactgtt 1320
caaatgccta tcagtgtgtc atggggagga caagtattat ctacaacagc caaagaattt 1380
gaagctgctg ctttgggata ttctgcatcc ggtgtaaatg gcgtatcatc ttctcaagag 1440
ttagtaatta gcgctgcacc taaaactgcc ggtaccgccc caactgcagg aaactattca 1500
ggagtagtat ctcttgtaat gactttggga tccgacaata aacaagtaga gaaaaatatt 1560
actgtaacag ctagtgtcga ccctgcaggg aattttattc cagatattga ttccgctgtt 1620
cgtataatac ctgttaatta cgattcggac ccgaaactgg attcacagtt atatacggtt 1680
gagatgacga tccctgcagg tgtaagcgca gttaaaatcg caccaacaga tagtctgaca 1740
tcttctggac agcagatcgg aaagctggtt aatgtaaaca atccagatca aaatatgaat 1800
tattatatca gaaaggattc tggcgctggt aactttatgg caggacaaaa aggatccttt 1860
cctgtcaaag agaatacgtc atacacattc tcagcaattt atactggtgg cgaataccct 1920
aatagcggat attcgtctgg tacttatgca ggaaatttga ctgtatcatt ttacagcaat 1980
gacaataaac aaagaacaga aatagcgact aaaaacttcc cagtatcaac gactatttca 2040
aaaagttttt ttgcacctga accacgaata cagccttctt ttggtgaaaa tgttggaaag 2100
gaaggagctt tattatttag tgtgaactta actgttcctg aaaatgtatc ccaggtaacg 2160
gtctaccctg tttatgatga agattatggg ttaggacgac tagtaaatac cgctgatgct 2220
tcccaatcaa taatctacca gattgttgat gagaaaggga aaaaaatgtt aaaagatcat 2280
ggtgcagagg ttacacctaa tcaacaaata acttttaaag cgctgaatta tactagcggg 2340
gaaaaaaaaa tatctcctgg aatatataac gatcaggtta tggttggtta ctacgtaaac 2400
gacaataaac aaaccgagat tgccaccaag aattttccgg tgagcaccac catcagcctc 2460
ctcgagcacc accaccacca ccactga 2487

<210> SEQ ID NO 114
<211> LENGTH: 828
<212> TYPE: PRT
<213> ORGANISM: Escherichia coli

<400> SEQUENCE: 114

Met Asn Lys Ile Leu Phe Ile Phe Thr Leu Phe Phe Ser Ser Gly Phe
1 5 10 15

Phe Thr Phe Ala Val Ser Ala Asp Lys Asn Pro Gly Ser Glu Asn Met
20 25 30

Thr Asn Thr Ile Gly Pro His Asp Arg Gly Gly Ser Ser Pro Ile Tyr
35 40 45

Asn Ile Leu Asn Ser Tyr Leu Thr Ala Tyr Asn Gly Ser His His Leu
50 55 60

Tyr Asp Arg Met Ser Phe Leu Cys Leu Ser Ser Gln Asn Thr Leu Asn
65 70 75 80

Gly Ala Cys Pro Ser Ser Asp Ala Pro Gly Thr Ala Thr Ile Asp Gly
85 90 95

Glu Thr Asn Ile Thr Leu Gln Phe Thr Glu Lys Arg Ser Leu Ile Lys
100 105 110

Arg Glu Leu Gln Ile Lys Gly Tyr Lys Gln Phe Leu Phe Lys Asn Ala
115 120 125

Asn Cys Pro Ser Lys Leu Ala Leu Asn Ser Ser His Phe Gln Cys Asn
130 135 140

Arg Glu Gln Ala Ser Gly Ala Thr Leu Ser Leu Tyr Ile Pro Ala Gly
145 150 155 160

Glu Leu Asn Lys Leu Pro Phe Gly Gly Val Trp Asn Ala Val Leu Lys
165 170 175

Leu Asn Val Lys Arg Arg Tyr Asp Thr Thr Tyr Gly Thr Tyr Thr Ile
180 185 190

Asn Ile Thr Val Asn Leu Thr Asp Lys Gly Asn Ile Gln Ile Trp Leu
195 200 205

Pro Gln Phe Lys Ser Asn Ala Arg Val Asp Leu Asn Leu Arg Pro Thr
210 215 220

-continued

```
Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Asn Phe Ile Pro Asp Ile Asp Ser Ala Val Arg Ile Ile Pro
    530                 535                 540

Val Asn Tyr Asp Ser Asp Pro Lys Leu Asp Ser Gln Leu Tyr Thr Val
545                 550                 555                 560

Glu Met Thr Ile Pro Ala Gly Val Ser Ala Val Lys Ile Ala Pro Thr
                565                 570                 575

Asp Ser Leu Thr Ser Ser Gly Gln Gln Ile Gly Lys Leu Val Asn Val
            580                 585                 590

Asn Asn Pro Asp Gln Asn Met Asn Tyr Tyr Ile Arg Lys Asp Ser Gly
        595                 600                 605

Ala Gly Asn Phe Met Ala Gly Gln Lys Gly Ser Phe Pro Val Lys Glu
    610                 615                 620

Asn Thr Ser Tyr Thr Phe Ser Ala Ile Tyr Thr Gly Gly Glu Tyr Pro
625                 630                 635                 640

Asn Ser Gly Tyr Ser Ser Gly Thr Tyr Ala Gly Asn Leu Thr Val Ser
```

```
                645                 650                 655

Phe Tyr Ser Asn Asp Asn Lys Gln Arg Thr Glu Ile Ala Thr Lys Asn
            660                 665                 670

Phe Pro Val Ser Thr Thr Ile Ser Lys Ser Phe Phe Ala Pro Glu Pro
        675                 680                 685

Arg Ile Gln Pro Ser Phe Gly Glu Asn Val Gly Lys Glu Gly Ala Leu
    690                 695                 700

Leu Phe Ser Val Asn Leu Thr Val Pro Glu Asn Val Ser Gln Val Thr
705                 710                 715                 720

Val Tyr Pro Val Tyr Asp Glu Asp Tyr Gly Leu Gly Arg Leu Val Asn
                725                 730                 735

Thr Ala Asp Ala Ser Gln Ser Ile Ile Tyr Gln Ile Val Asp Glu Lys
            740                 745                 750

Gly Lys Lys Met Leu Lys Asp His Gly Ala Glu Val Thr Pro Asn Gln
        755                 760                 765

Gln Ile Thr Phe Lys Ala Leu Asn Tyr Thr Ser Gly Glu Lys Lys Ile
    770                 775                 780

Ser Pro Gly Ile Tyr Asn Asp Gln Val Met Val Gly Tyr Tyr Val Asn
785                 790                 795                 800

Asp Asn Lys Gln Gly Asn Trp Gln Tyr Lys Ser Leu Asp Val Asn Val
                805                 810                 815

Asn Ile Glu Gln Leu Glu His His His His His His
            820                 825
```

<210> SEQ ID NO 115
<211> LENGTH: 1014
<212> TYPE: DNA
<213> ORGANISM: Escherichia coli

<400> SEQUENCE: 115

```
gcagataaaa atcccggaag tgaaaacatg actaatacta ttggtcccca tgacaggggg      60

ggatcttccc ccatatataa tatcttaaat tcctatctta cagcatacaa tggaagccat     120

catctgtatg ataggatgag ttttttatgt ttgtcttctc aaaatacact gaatggagca     180

tgcccaagca gtgatgcccc tggcactgct acaattgatg gcgaaacaaa tataacatta     240

caatttacgg aaaaaagaag tctaattaaa agagaactgc aaattaaagg ctataaacaa     300

tttttgttca aaaatgctaa ttgcccatct aaactagcac ttaactcatc tcattttcaa     360

tgtaatagag aacaagcttc aggtgctact ttatcgttat acataccagc tggtgaatta     420

aataaattac cttttggggg ggtctggaat gccgttctga agctaaatgt aaaaagacga     480

tatgatacaa cctatgggac ttacactata aacatcacag ttaatttaac tgataaggga     540

aatattcaga tatggttacc acagttcaaa agtaacgctc gtgtcgatct taacttgcgt     600

ccaactggtg gtggtacata tatcggaaga aattctgttg atatgtgctt ttatgatgga     660

tatagtacta acagcagctc tttagagata agatttcagg atgataattc taaatctgat     720

ggaaaatttt atctaaagaa aataaatgat gactccaaag aacttgtata cactttgtca     780

cttctcctgg caggtaaaaa tttaacacca acaaatggac aggcattaaa tattaacact     840

gcttctctgg aaacaaactg gaatagaatt acagctgtca ccatgccaga aatcagtgtt     900

ccggtgttgt gttggcctgg acgtttgcaa ttggatgcaa aagtgaaaaa tcccgaggct     960

ggacaatata tggggaatat taaaattact ttcacaccaa gtagtcaaac actc          1014
```

<210> SEQ ID NO 116

<211> LENGTH: 441
<212> TYPE: DNA
<213> ORGANISM: Escherichia coli

<400> SEQUENCE: 116
gtagagaaaa atattactgt aacagctagt gttgatcctg caattgatct tttgcaagct 60
gatggcaatg ctctgccatc agctgtaaag ttagcttatt ctcccgcatc aaaaactttt 120
gaaagttaca gagtaatgac tcaagttcat acaaacgatg caactaaaaa agtaattgtt 180
aaacttgctg atacaccaca gcttacagat gttctgaatt caactgttca aatgcctatc 240
agtgtgtcat ggggaggaca agtattatct acaacagcca aagaatttga agctgctgct 300
ttgggatatt ctgcatccgg tgtaaatggc gtatcatctt ctcaagagtt agtaattagc 360
gctgcaccta aaactgccgg taccgcccca actgcaggaa actattcagg agtagtatct 420
cttgtaatga ctttgggatc c 441

<210> SEQ ID NO 117
<211> LENGTH: 1020
<212> TYPE: DNA
<213> ORGANISM: Escherichia coli

<400> SEQUENCE: 117
gcagataaaa ttcccggaga tgaaagcata actaatattt ttggcccgcg tgacaggaac 60
gaatcttccc ccaaacataa tatattaaat aaccatatta cagcatacag tgaaagtcat 120
actctgtatg ataggatgac ttttttatgt ttgtcttctc acaatacact taatggagca 180
tgtccaacca gtgagaatcc tagcagttca tcggtcagcg gtgaaacaaa tataacatta 240
caatttacgg aaaaaagaag tttaataaaa agagagctac aaattaaagg ctataaacaa 300
ttattgttca aaagtgttaa ctgcccatcc ggcctaacac ttaactcagc tcattttaac 360
tgtaataaaa acgcggcttc aggtgcaagt ttatatttat atattcctgc tggcgaacta 420
aaaaatttgc cttttggtgg tatctgggat gctactctga agttaagagt aaaaagacga 480
tatagtgaga cctatggaac ttacactata aatatcacta ttaaattaac tgataaggga 540
aatattcaga tatggttacc tcagttcaaa agtgacgctc gcgtcgatct taacttgcgt 600
ccaactggtg ggggcacata tattggaaga aattctgttg atatgtgctt ttatgatgga 660
tatagtacta acagcagctc tttggagata agatttcagg ataacaatcc taaatctgat 720
gggaaatttt atctaaggaa aataaatgat gacaccaaag aaattgcata tactttgtca 780
cttctcttgg cgggtaaaag tttaactcca acaaatggaa cgtcattaaa tattgctgac 840
gcagcttctc tggaaacaaa ctggaataga attacagctg tcaccatgcc agaaatcagt 900
gttccggtgt tgtgttggcc tggacgtttg caattggatg caaaagtgga aaatcccgag 960
gctggacaat atatgggtaa tattaatgtt actttcacac caagtagtca aacactctag 1020

<210> SEQ ID NO 118
<211> LENGTH: 435
<212> TYPE: DNA
<213> ORGANISM: Escherichia coli

<400> SEQUENCE: 118
gtagagaaaa atatcactgt aacagctagt gttgatccta caattgatat tttgcaagct 60
gatggtagta gtttacctac tgctgtagaa ttaacctatt cacctgcggc aagtcgtttt 120
gaaaattata aaatcgcaac taaagttcat acaaatgtta taaataaaaa tgtactagtt 180
aagcttgtaa atgatccaaa acttacaaat gttttggatt ctacaaaaca actccccatt 240
actgtatcat atggaggaaa gactctatca accgcagatg tgacttttga acctgcagaa 300
ttaaattttg gaacgtcagg tgtaactggt gtatcttctt cccaagattt agtgattggt 360
gcgactacag cacaagcacc aacggcggga aattatagtg gggtcgtttc tatcttaatg 420
accttagcat cataa 435

<210> SEQ ID NO 119
<211> LENGTH: 1020
<212> TYPE: DNA
<213> ORGANISM: Escherichia coli

<400> SEQUENCE: 119
gcagataaaa ttcccggaga tgagaatata actaatattt ttggcccgcg tgacaggaac 60
gaatcttccc ccaaacataa tatattaaat gactatatta cagcatacag tgaaagtcat 120
actctgtatg ataggatgat ttttttatgt ttgtcttctc aaaatacact taatggagca 180
tgtccaacca gtgagaatcc tagcagttca tcggtcagtg gcgaaacaaa tataacatta 240
caatttacgg aaaaaagaag tttaattaaa agagagctac aaattaaagg ctataaacga 300
ttattgttca aaggtgctaa ctgcccatcc tacctaacac ttaactcagc tcattatacc 360
tgcaatagaa actcggcttc aggtgcaagt ttatatttat atattcctgc tggcgaacta 420
aaaaatttac cttttggtgg tatctgggat gctactctga agttaagagt aaaaagacga 480
tatgatcaga cctatggaac ttacactata aatatcactg ttaaattaac tgataaggga 540
aatattcaga tatggttacc tcagttcaaa agtgacgctc gcgtcgatct taacttgcgt 600
ccaactggtg gggcacata tattggaaga aattctgttg atatgtgctt ttatgatgga 660
tatagtacta acagcagctc tttggagcta agatttcagg ataacaatcc taaatctgat 720
gggaaatttt atctaaggaa aataaatgat gacaccaaag aaattgcata tactttgtca 780
cttctcttgg cgggtaaaag tttaactcca acaaatggaa cgtcattaaa tattgctgac 840
gcagcttctc tggaaataaa ctggaataga attacagctg tcaccatgcc agaaatcagt 900
gttccggtgt tgtgttggcc tggacgtttg caattggatg caaaagtgga aaatcccgag 960
gccggacaat atatgggtaa tattaatatt actttcacac caagtagtca aacactctag 1020

<210> SEQ ID NO 120
<211> LENGTH: 459
<212> TYPE: DNA
<213> ORGANISM: Escherichia coli

<400> SEQUENCE: 120
gtagagaaaa atattactgt gacagccagt gttgatccta ctattgatat tcttcaagca 60
aatggttctg cgctaccgac agctgtagat ttaacttatc tacctggtgc aaaaactttt 120
gaaaattaca gtgttctaac ccagatttac acaaatgacc cttcaaaagg tttagatgtt 180
cgactggttg atacaccgaa acttacaaat attttgcaac cgacatctac cattcctctt 240
actgtctcat gggcagggaa gacattaagt acaagtgctc agaagattgc agttggcgat 300
ctgggttttg gttccaccgg aacggcaggt gtttcgaata gtaaagaatt agtaattgga 360
gcaactacat ccggaactgc accaagtgca ggtaagtatc aaggcgtcgt ttccattgta 420
atgactcaat cgacagacac agccgcgcct gttccttaa 459

<210> SEQ ID NO 121
<211> LENGTH: 441
<212> TYPE: DNA

<213> ORGANISM: Escherichia coli

<400> SEQUENCE: 121
gtagagaaaa atattactgt gacagccagt gttgatccta ctattgatat tcttcaagca 60
aatggttctg cgctaccgac agctgtagat ttaacttatc tacctggtgc aaaaactttt 120
gaaaattaca gtgttctaac ccagatttac acaaatgacc cttcaaaagg tttagatgtt 180
cgactggttg atacaccgaa acttacaaat attttgcaac cgacatctac cattcctctt 240
actgtctcat gggcagggag gacattaagt acaagtgctc agaagatcgc agttggcgat 300
ctgggttttg gttccaccgg aacggcaggt gtttcgaata gtaaagaatt agtaattgga 360
gcaactacat ccggaactgc accaagtgca ggtaagtatc aaggcgtcgt ttccattgta 420
atgactcaat cgacaaacta a 441

<210> SEQ ID NO 122
<211> LENGTH: 1038
<212> TYPE: DNA
<213> ORGANISM: Escherichia coli

<400> SEQUENCE: 122
gggcgatacc cggaaactac agtaggtaat ctgacgaaga gttttcaagc ccctcgtctg 60
gatagaagcg tacaatcacc aatatataac atctttacga atcatgtggc tggatatagt 120
ttgagtcata gcttatatga caggattgtt tttttatgta catcctcgtc gaatccggtt 180
aatggtgctt gcccaaccat tggaacatct ggagttcaat acggtactac aaccataacc 240
ttgcagttta cagaaaaaag aagtctgata aaaagaaata ttaatcttgc aggtaataag 300
aaaccaatat gggagaatca gagttgcgac tttagcaatc taatggtgtt gaattcgaag 360
tcttggagct gtggggctta cggaaatgct aacggaacac ttctaaatct gtatatccct 420
gcaggagaaa tcaacaaatt gccttttgga gggatatggg aggcaactct gatcttacgc 480
ttatcaagat atggcgaagt cagtagcacc cattacggca attataccgt aaatattacg 540
gttgatttaa ctgataaagg taatattcag gtatggcttc cagggtttca cagcaacccg 600
cgtgtagacc tgaatctgcg ccctatcggt aattataaat atagtggtag taattcactc 660
gacatgtgtt tctatgatgg atatagtaca aacagtgata gcatggtaat aaagttccag 720
gatgataatc ctaccaattc atctgaatat aatctttata agatagggggg cactgaaaaa 780 ttaccatatg ctgtttcact gcttatggga gaaaaaatat tttatccagt gaatggtcaa 840
tcatttacta tcaatgacag tagtgtactc gaaacaaact ggaatcgagt aaccgcagtt 900
gctatgccgg aagttaatgt tccagtatta tgctggccag caagattgct attaaatgct 960
gatgtaaatg ctcccgatgc aggacagtat tcaggacaga tatatataac atttacaccc 1020
agtgtcgaaa atttatga 1038

<210> SEQ ID NO 123
<211> LENGTH: 447
<212> TYPE: DNA
<213> ORGANISM: Escherichia coli

<400> SEQUENCE: 123
gtcgagaaga ccattagcgt tacggcgagt gttgacccga ctgttgacct tctgcaatct 60
gatggctctg cgctgccgaa ctctgtcgca ttaacctatt ctccggctgt aaataatttt 120
gaagctcaca ccatcaacac cgttgttcat acaaatgact cagataaagg tgttgttgtg 180
aagctgtcag cagatccagt cctgtccaat gttctgaatc caaccctgca aattcctgtt 240

```
tctgtgaatt tcgcaggaaa accactgagc acaacaggca ttaccatcga ctccaatgat    300

ctgaactttg cttcgagtgg tgttaataaa gtttcttcta cgcagaaact ttcaatccat    360

gcagatgcta ctcgggtaac tggcggcgca ctaacagctg gtcaatatca gggactcgta    420

tcaattatcc tgactaagtc aacgtaa                                        447
```

<210> SEQ ID NO 124
<211> LENGTH: 1038
<212> TYPE: DNA
<213> ORGANISM: Escherichia coli

<400> SEQUENCE: 124

```
gggcgatacc cggaaactac agtaggtaat ctgacgaaga gttttcaagc ccctcgtctg     60

gatagaagcg tacaatcacc aatatataac atctttacga atcatgtggc tggatatagt    120

ttgagtcata gattatatga caggattgtt tttgtatgta catcctcgtc gaatccggtt    180

aatggtgctt gcccaaccat tggaacatct agagttgaat acggtactac aaccataacc    240

ttgcagttta cagaaaaaag aagtctgata aaaagaaata ttaatcttgc aggtaataag    300

aaaccaatat gggagaatca gagttgcgac actagcaatc taatggtgtt gaattcgaag    360

tcttggtcct gtggggctct aggaaatgct aacggaacac ttctaaatct gtatatccct    420

gcaggagaaa tcaacaaatt gccttttgga gggatatggg aggcaactct gatcttacgc    480

ttatcaagat atggcgaagt cagtagcacc cattacggca attataccgt aaatattacg    540

gttgatttaa ctgataaagg taatattcag gtatggcttc cagggtttca cagcaacccg    600

cgtgtagacc tgaatctgca ccctatcggt aattataaat atagtggtag taattcactc    660

gacatgtgtt tctatgatgg atatagtaca aacagtgata gcatggtaat aaagttccag    720

gatgataatc ctaccaattc atctgaatat aatctttata agataggggg cactgaaaaa    780

ttaccatatg ctgtttcact gcttatggga ggaaaaatat tttatccagt gaatggtcaa    840

tcatttacta tcaatgacag tagtgtactc gaaacaaact ggaatcgagt aaccgcagtt    900

gctatgccgg aagttaatgt tccagtatta tgctggccag caagattgct attaaatgct    960

gatgtaaatg ctcccgatgc aggacagtat tcaggacaga tatatataac atttacaccc   1020

agtgtcgaaa atttatga                                                 1038
```

<210> SEQ ID NO 125
<211> LENGTH: 432
<212> TYPE: DNA
<213> ORGANISM: Escherichia coli

<400> SEQUENCE: 125

```
gtcgaaaaaa atattactgt gagggcaagt gttgacccta aacttgatct tctgcaagca     60

gatggaactt cactgccgga ctctatcgca ttaacctatt cttcggcttc aaataatttt    120

gaagtttact ctcttaatac tgctattcat acaaatgaca aaaccaaggc agttgtagtg    180

aagctgtcag ctccagcagt tctgtccaat attatgaagc caagctcgca aattccgatg    240

aaagtgactt tggggggggaa gacgctgagt acagctgatg ctgagtttgc tgctgatact   300

ctgaactttg gtgcatctgg tgttgaaaac gtttcttccg ttcaacagct tacgattcat    360

gcagaagctg ctccgcctga ggcaggtaat taccaaggtg ttatttctct tatcatgact    420

caaaaaactt aa                                                        432
```

<210> SEQ ID NO 126

<211> LENGTH: 444
<212> TYPE: DNA
<213> ORGANISM: Escherichia coli

<400> SEQUENCE: 126
gtcgagaaga ccattagcgt tacggcgagt gttgacccga ctgttgacct tctgcaatct 60
gatggctctg cgctgccgaa ctctgtcgca ttaacctatt ctccggctgt agggggtttt 120
gaagctcaca ccatcaacac cgttgttcat acaaatgacc cagctaaagg tgttattgtg 180
aagctgtcag cagaaccagt cctgtccaat gtactgaatc caaccctgca aattcctgtt 240
tctgtgaatt tcgcaggaaa aaaactgacc acaacaggca ctaccatcga atccaataaa 300
ctgaactttg cttcgagtgg tgttgataaa gtttcttcta cgcagaaact ttcaatccat 360
gcagatacta ctcaggtaac tggcggacta acagctggtc aatatcaggg gctcgtatca 420
attatcctga ctcagtcaac gtaa 444

<210> SEQ ID NO 127
<211> LENGTH: 1038
<212> TYPE: DNA
<213> ORGANISM: Escherichia coli

<400> SEQUENCE: 127
gggcgatacc cggaaactac agtaggtaat ctgacgaaga gttttcaagc ccctcgtcag 60
gatagaagcg tacaatcacc aatatataac atctttacga atcatgtggc tggatatagt 120
ttgagtcata acttatatga caggattgtt tttttatgta catcctcgtc gaatccggtt 180
aatggtgctt gcccaaccat tggaacatct ggagttcaat acggtactac aaccataacc 240
ttgcagttta cagaaaaaag aagtctgata aaaagaaata ttaatcttgc aggtaataag 300
aaaccaatat gggagaatca gagttgcgac actagcaatc taatggtgtt gaattcgaag 360
tcttggtcct gtggggctta cggaaatgct aacggaacac ttctaaatct gtatatccct 420
gcaggagaaa tcaacaaatt gccttttgga gggatatggg aggcaactct gatcttacgc 480
ttatcaagat atggcgaagt cagtagcacc cattacggca attataccgt aaatattacg 540
gttgatttaa ctgataaagg taatattcag gtatggcttc cagggtttca cagcaacccg 600
cgtgtagacc tgaatctgca ccctatcggt aattataaat atagtggtag taattcactc 660
gacatgtgtt tctatgatgg atatagtaca aacagtgata gcatggtaat aaagttccag 720
gatgataatc ctacctattc atctgaatat aatctttata agataggggg cactgaaaaa 780
ttaccatatg ctgtttcact gcttatggga gaaaaaatat tttatccagt gaatggtcaa 840
tcatttacta tcaatgacag tagtgtactc gaaacaaact ggaatcgagt aaccgcagtt 900
gctatgccgg aagttaatgt tccagtatta tgctggccag caagattgct attaaatgct 960
gatgtaaatg ctcccgatgc aggacagtat tcaggacaga tatatataac atttacaccc 1020
agtgtcgaaa atttatga 1038

<210> SEQ ID NO 128
<211> LENGTH: 438
<212> TYPE: DNA
<213> ORGANISM: Escherichia coli

<400> SEQUENCE: 128
gtcgaaaaaa atattactgt gagggcaagt gttgacccta aacttgatct tctgcaagca 60
gatggaactt cactgccgga ctctatcgca ttaacctatt cttcggcttc aaataatttt 120
gaagtttact ctcttaatac tgctattcat acaaatgaca aaagcaaggg agttgtagtg 180

```
aagctgtcag cttcaccagt tctgtccaat attatgaagc caaactcgca aattccgatg    240

aaagtgactt tggggggaa gacgctgaat acaactgata ctgagtttac tgttgatact    300

ctgaactttg gtacatctgg tgttgaaaac gtttcttcca ctcaacagct tacgattcat    360

gcagacacac aaggaactgc gcctgaggca ggcaattacc aaggtattat ttctcttatc    420

atgactcaaa aaacttaa                                                  438
```

<210> SEQ ID NO 129
<211> LENGTH: 1041
<212> TYPE: DNA
<213> ORGANISM: Escherichia coli

<400> SEQUENCE: 129

```
caatcatggc atacgaacgt agaggctggt tcaataaata aaacagagtc gataggcccc     60

atagaccgaa gtgctgctgc atcgtatcct gctcattata tatttcatga acatgttgct    120

ggttacaata aagatcactc tctttttgac aggatgacgt ttttatgtat gtcatcaaca    180

gatgcatcta aaggtgcatg tccgacagga gaaaactcca aatcctctca aggggagact    240

aatattaagc taatatttac tgaaaagaaa agtctggcca gaaaaacatt aaacttaaaa    300

ggatataaga gatttttata tgaatcagat agatgcattc attatgtcga taaaatgaat    360

ctcaattctc atactgttaa atgtgtaggt tcattcacaa gaggagtaga tttcacttta    420

tatatcccac aaggtgaaat tgatgggctt ctaactggag gtatatggga ggcaacacta    480

gagttacgag tcaaaaggca ttacgactat aatcatggta cttacaaagt taatatcaca    540

gttgatttga cagacaaagg aaatattcag gtctggacac caaagtttca tagcgatcct    600

agaattgatc tgaatttacg tcctgaaggt aatggtaaat attctggtag taacgtgctt    660

gagatgtgtc tctatgatgg ctatagtaca catagtcaaa gtatagaaat gaggtttcag    720

gatgactcac aaacaggaaa taatgaatat aatcttataa aaactggaga gccattaaaa    780

aaattgccat ataaactttc tcttctttta ggaggacgag agttttatcc aaataatgga    840

gaggctttta ctattaatga tacttcgtca ttgtttataa actggaatcg tattaagtct    900

gtatccttac cacagattag tattccagta ctatgctggc cagcaaactt gacatttatg    960

tcagagctaa ataatccaga agcgggtgag tattcaggaa tacttaacgt aacatttact   1020

cctagtagtt caagtctgta a                                              1041
```

<210> SEQ ID NO 130
<211> LENGTH: 444
<212> TYPE: DNA
<213> ORGANISM: Escherichia coli

<400> SEQUENCE: 130

```
gccgagaaaa atatcactgt aactgctagc gttgatccaa ctatcgatct gatgcaatct     60

gatggcacag cgttaccaag tgcagttaat attgcatatc ttccaggaga gaaaagattt    120

gaatctgctc gtatcaatac ccaagttcat accaataata aaactaaggg tattcagata    180

aagcttacta atgataatgt ggtaatgact aacttatctg atccaagcaa gactattcct    240

ttagaggttt cattcgctgg cactaagctg agcacagctg caacatctat tactgccgat    300

caattaaatt ttggcgcagc tggtgtagag acagtttctg caactaagga actcgttatt    360

aatgcaggaa gcacccagca aactaatatt gtagctggta actatcaagg attggtgtca    420

attgtgctta ctcaagaacc ttaa                                           444
```

<210> SEQ ID NO 131
<211> LENGTH: 441
<212> TYPE: DNA
<213> ORGANISM: Escherichia coli

<400> SEQUENCE: 131
gcagcggggc ccactctaac caaagaactg gcattaaatg tgctttctcc tgcagctctg 60
gatgcaactt gggctcctca ggataattta acattatcca atactggcgt ttctaatact 120
ttggtgggtg ttttgactct ttcaaatacc agtattgata cagttagcat tgcgagtaca 180
aatgtttctg atacatctaa gaatggtaca gtaacttttg cacatgagac aaataactct 240
gctagctttg ccaccaccat ttcaacagat aatgccaaca ttacgttgga taaaaatgct 300
ggaaatacga ttgttaaaac tacaaatggg agtcagttgc caactaattt accacttaag 360
tttattacca ctgaaggtaa cgaacattta gtttcaggta attaccgtgc aaatataaca 420
attacttcga caattaaata a 441

<210> SEQ ID NO 132
<211> LENGTH: 432
<212> TYPE: DNA
<213> ORGANISM: Escherichia coli

<400> SEQUENCE: 132
gcagtgggcc caacgaaaga tatgagttta ggtgcaaatt taacttcaga gcctacatta 60
gctattgatt ttacgcctat tgaaaatatt tatgtaggtg ccaattatgg taaagatatt 120
ggaacccttg ttttcacaac aaatgattta acagatatta cattgatgtc atctcgcagc 180
gttgttgatg gtcgccagac tggttttttt accttcatgg actcatcagc cacttacaaa 240
attagtacaa aactgggatc atcgaatgat gtaaacattc aagaaattac tcaaggagct 300
aaaattactc ctgttagtgg agagaaaact ttgcctaaaa aattcactct taagctacat 360
gcacacagga gtagcagtac agttccaggt acgtatactg ttggtcttaa cgtaaccagt 420
aatgttattt aa 432

<210> SEQ ID NO 133
<211> LENGTH: 1038
<212> TYPE: DNA
<213> ORGANISM: Escherichia coli

<400> SEQUENCE: 133
gggcgatacc cggaaactac agtaggtaat ctgacgaaga gttttcaagc ccctcgtctg 60
gatagaagcg tacaatcacc aatatataac atctttacga atcatgtggc tggatatagt 120
ttgagtcata gattatatga caggattgtt tttgtatgta catcctcgtc gaatccggtt 180
aatggtgctt gcccaaccat tggaacatct ggagttgaat acggtactac aaccataacc 240
ttgcagttta cagaaaaaag aagtctgata aaaagaaata ttaatcttgc aggtaataag 300
aaaccaatat gggagaatca gagttgcgac tttagcaatc taatggtgtt gaattcgaag 360
tcttggtcct gtggggctca aggaaatgct aacggaacac ttctaaatct gtatatccct 420
gcaggagaaa tcaacaaatt gccttttgga gggatatggg aggcaactct gatcttacgc 480
ttatcaagat atggcgaagt cagtagcacc cattacggca attataccgt aaatattacg 540
gttgatttaa ctgataaagg taatattcag gtatggcttc cagggtttca cagcaacccg 600
cgtgtagacc tgaatctgca ccctatcggt aattataaat atagtggtag taattcactc 660
gacatgtgtt tctatgatgg atatagtaca aacagtgata gcatggtaat aaagttccag 720

-continued

```
gatgataatc ctaccaattc atctgaatat aatctttata agagaggggg cactgaaaaa    780

ttaccatatg ctgtttcact gcttatggga ggaaaaatat tttatccagt gaatggtcaa    840

tcatttacta tcaatgacag tagtgtactc gaaacaaact ggaatcgagt aaccgcagtt    900

gctatgccgg aagttaatgt tccagtatta tgctggccag caagattgct attaaatgct    960

gatgtaaatg ctcccgatgc aggacagtat tcaggacaga tatatataac atttacaccc   1020

agtgtcgaaa atttatga                                                 1038
```

<210> SEQ ID NO 134
<211> LENGTH: 465
<212> TYPE: DNA
<213> ORGANISM: Escherichia coli

<400> SEQUENCE: 134

```
atgaagaaaa caattggttt aattctaatt cttgcttcat tcggcagcca tgccagaaca     60

gaaatagcga ctaaaaactt cccagtatca acgactattt caaaaagttt ttttgcgcct    120

gaaccacaaa tccagccttc ttttggtaaa aatgttggaa aggaaggaga tttattattt    180

agtgtgagct taattgttcc tgaaaatgta tcccaggtaa cggtctaccc tgtttatgat    240

gaagattatg gattaggacg actcgtaaat accgctgatg attcccaatc aataatctac    300

cagattgttg atgataaagg gaaaaaaatg ttaaaagatc atggtacaga ggttacgcct    360

aatcaacaaa taacttttaa agcgctgaat tatactagcg gagataaaga aatacctcct    420

gggatatata acgatcaggt tatggttggt tactatgtaa actaa                    465
```

<210> SEQ ID NO 135
<211> LENGTH: 154
<212> TYPE: PRT
<213> ORGANISM: Escherichia coli

<400> SEQUENCE: 135

```
Met Lys Lys Thr Ile Gly Leu Ile Leu Ile Leu Ala Ser Phe Gly Ser
1               5                   10                  15

His Ala Arg Thr Glu Ile Ala Thr Lys Asn Phe Pro Val Ser Thr Thr
            20                  25                  30

Ile Ser Lys Ser Phe Phe Ala Pro Glu Pro Gln Ile Gln Pro Ser Phe
        35                  40                  45

Gly Lys Asn Val Gly Lys Glu Gly Asp Leu Leu Phe Ser Val Ser Leu
    50                  55                  60

Ile Val Pro Glu Asn Val Ser Gln Val Thr Val Tyr Pro Val Tyr Asp
65                  70                  75                  80

Glu Asp Tyr Gly Leu Gly Arg Leu Val Asn Thr Ala Asp Asp Ser Gln
                85                  90                  95

Ser Ile Ile Tyr Gln Ile Val Asp Asp Lys Gly Lys Lys Met Leu Lys
            100                 105                 110

Asp His Gly Thr Glu Val Thr Pro Asn Gln Gln Ile Thr Phe Lys Ala
        115                 120                 125

Leu Asn Tyr Thr Ser Gly Asp Lys Glu Ile Pro Pro Gly Ile Tyr Asn
    130                 135                 140

Asp Gln Val Met Val Gly Tyr Tyr Val Asn
145                 150
```

<210> SEQ ID NO 136
<211> LENGTH: 504
<212> TYPE: DNA

<213> ORGANISM: Escherichia coli

<400> SEQUENCE: 136
atgttgaaaa aaattattcc ggctattgca ttaattgcag gaacttccgg agtggtaaat 60
gcaggaaact ggcaatataa atctctggat gtaaatgtaa atattgagca aaattttatt 120
ccagatattg attccgctgt tcgtataata cctgttaatt acgattcgga tccgaaactg 180
aattcacagt tatatacggt tgagatgacg atccctgcag gtgtaagcgc agttaaaatc 240
gtaccaacag atagtctgac atcttctgga cagcagatcg gaaagctggt taatgtaaac 300
aatccagatc aaaatatgaa ttattatatc agaaaggatt ctggcgctgg taagtttatg 360
gcagggcaaa aaggatcctt ttctgtcaaa gagaatacgt catacacatt ctcagcaatt 420
tatactggtg gcgaataccc taatagcgga tattcgtctg gtacttatgc aggacatttg 480
actgtatcat tttacagcaa ttaa 504

<210> SEQ ID NO 137
<211> LENGTH: 167
<212> TYPE: PRT
<213> ORGANISM: Escherichia coli

<400> SEQUENCE: 137

Met Leu Lys Lys Ile Ile Pro Ala Ile Ala Leu Ile Ala Gly Thr Ser
1 5 10 15

Gly Val Val Asn Ala Gly Asn Trp Gln Tyr Lys Ser Leu Asp Val Asn
20 25 30

Val Asn Ile Glu Gln Asn Phe Ile Pro Asp Ile Asp Ser Ala Val Arg
35 40 45

Ile Ile Pro Val Asn Tyr Asp Ser Asp Pro Lys Leu Asn Ser Gln Leu
50 55 60

Tyr Thr Val Glu Met Thr Ile Pro Ala Gly Val Ser Ala Val Lys Ile
65 70 75 80

Val Pro Thr Asp Ser Leu Thr Ser Ser Gly Gln Gln Ile Gly Lys Leu
85 90 95

Val Asn Val Asn Asn Pro Asp Gln Asn Met Asn Tyr Tyr Ile Arg Lys
100 105 110

Asp Ser Gly Ala Gly Lys Phe Met Ala Gly Gln Lys Gly Ser Phe Ser
115 120 125

Val Lys Glu Asn Thr Ser Tyr Thr Phe Ser Ala Ile Tyr Thr Gly Gly
130 135 140

Glu Tyr Pro Asn Ser Gly Tyr Ser Ser Gly Thr Tyr Ala Gly His Leu
145 150 155 160

Thr Val Ser Phe Tyr Ser Asn
165

<210> SEQ ID NO 138
<211> LENGTH: 384
<212> TYPE: PRT
<213> ORGANISM: Escherichia coli

<400> SEQUENCE: 138

Met Asn Lys Ile Leu Phe Ile Phe Thr Leu Phe Phe Ser Ser Gly Phe
1 5 10 15

Phe Thr Phe Ala Val Ser Ala Asp Lys Asn Pro Gly Ser Glu Asn Met
20 25 30

Thr Asn Thr Ile Gly Pro His Asp Arg Gly Gly Ser Ser Pro Ile Tyr
35 40 45

```
Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380
```

<210> SEQ ID NO 139
<211> LENGTH: 1002
<212> TYPE: DNA
<213> ORGANISM: Escherichia coli

<400> SEQUENCE: 139

```
atgaataaaa ttttatttat ttttacattg tttttttctt cagggttttt tacatttgcc      60

gtatcggcag ataaaaatcc cggaagtgaa aacatgacta atactattgg tccccatgac     120

aggggggggat cttcccccat atataatatc ttaaattcct atcttacagc atacaatgga     180

agccatcatc tgtatgatag gatgagtttt ttatgtttgt cttctcaaaa tacactgaat     240
```

ggagcatgcc caagcagtga tgcccctggc actgctacaa ttgatggcga aacaaatata 300
acattacaat ttacggaaaa aagaagtcta attaaaagag aactgcaaat taaaggctat 360
aaacaatttt tgttcaaaaa tgctaattgc ccatctaaac tagcacttaa ctcatctcat 420
tttcaatgta atagagaaca agcttcaggt gctactttat cgttatacat accagctggt 480
gaattaaata aattaccttt tggggggggtc tggaatgccg ttctgaagct aaatgtaaaa 540
agacgatatg atacaaccta tgggacttac actataaaca tcacagttaa tttaactgat 600
aagggaaata ttcagatatg gttaccacag ttcaaaagta acgctcgtgt cgatcttaac 660
ttgcgtccaa ctggtggtgg tacatatatc ggaagaaatt ctgttgatat gtgcttttat 720
gatggatata gtactaacag cagctcttta gagataagat ttcaggatga taattctaaa 780
tctgatggaa aattttatct aaagaaaata aatgatgact ccaaagaact tgtatacact 840
ttgtcacttc tcctggcagg taaaaattta acaccaacaa atggacaggc attaaatatt 900
aacactgctt ctctggaaac aaactggaat agaattacag ctgtcaccat gccagaaatc 960
agtgttccgg tgttgtgttg gcctggacgt ttgcaattgg at 1002

<210> SEQ ID NO 140
<211> LENGTH: 1629
<212> TYPE: DNA
<213> ORGANISM: Escherichia coli

<400> SEQUENCE: 140
atgaataaaa ttttatttat ttttacattg tttttttctt cagggttttt tacatttgcc 60
gtatcggcag ataaaaatcc cggaagtgaa aacatgacta atactattgg tccccatgac 120
agggggggat cttcccccat atataatatc ttaaattcct atcttacagc atacaatgga 180
agccatcatc tgtatgatag gatgagtttt ttatgtttgt cttctcaaaa tacactgaat 240
ggagcatgcc caagcagtga tgcccctggc actgctacaa ttgatggcga aacaaatata 300
acattacaat ttacggaaaa aagaagtcta attaaaagag aactgcaaat taaaggctat 360
aaacaatttt tgttcaaaaa tgctaattgc ccatctaaac tagcacttaa ctcatctcat 420
tttcaatgta atagagaaca agcttcaggt gctactttat cgttatacat accagctggt 480
gaattaaata aattaccttt tggggggggtc tggaatgccg ttctgaagct aaatgtaaaa 540
agacgatatg atacaaccta tgggacttac actataaaca tcacagttaa tttaactgat 600
aagggaaata ttcagatatg gttaccacag ttcaaaagta acgctcgtgt cgatcttaac 660
ttgcgtccaa ctggtggtgg tacatatatc ggaagaaatt ctgttgatat gtgcttttat 720
gatggatata gtactaacag cagctcttta gagataagat ttcaggatga taattctaaa 780
tctgatggaa aattttatct aaagaaaata aatgatgact ccaaagaact tgtatacact 840
ttgtcacttc tcctggcagg taaaaattta acaccaacaa atggacaggc attaaatatt 900
aacactgctt ctctggaaac aaactggaat agaattacag ctgtcaccat gccagaaatc 960
agtgttccgg tgttgtgttg gcctggacgt ttgcaattgg atgcaaaagt gaaaaatccc 1020
gaggctggac aatatatggg gaatattaaa attactttca caccaagtag tcaaacactc 1080
gacaataaac aagtagagaa aaatattact gtaacagcta gtgttgatcc tgcaattgat 1140
cttttgcaag ctgatggcaa tgctctgcca tcagctgtaa agttagctta ttctcccgca 1200
tcaaaaactt ttgaaagtta cagagtaatg actcaagttc atacaaacga tgcaactaaa 1260
aaagtaattg ttaaacttgc tgatacacca cagcttacag atgttctgaa ttcaactgtt 1320

-continued

```
caaatgccta tcagtgtgtc atggggagga caagtattat ctacaacagc caaagaattt   1380

gaagctgctg ctttgggata ttctgcatcc ggtgtaaatg gcgtatcatc ttctcaagag   1440

ttagtaatta gcgctgcacc taaaactgcc ggtaccgccc caactgcagg aaactattca   1500

ggagtagtat ctcttgtaat gactttggga tccgacaata aacaagtaga gaaaaatatt   1560

actgtaacag ctagtgttga tcctgtgatt gatcttttgc aactcgagca ccaccaccac   1620

caccactga                                                            1629


<210> SEQ ID NO 141
<211> LENGTH: 542
<212> TYPE: PRT
<213> ORGANISM: Escherichia coli

<400> SEQUENCE: 141

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320
```

```
Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Val Ile Asp Leu Leu Gln Leu Glu His His His His His His
    530                 535                 540
```

<210> SEQ ID NO 142
<211> LENGTH: 1176
<212> TYPE: DNA
<213> ORGANISM: Escherichia coli

<400> SEQUENCE: 142

```
atgaataaaa ttttatttat ttttacattg tttttttctt cagggttttt tacatttgcc      60

gtatcggcag ataaaaatcc cggaagtgaa aacatgacta atactattgg tccccatgac     120

aggggggggat cttcccccat atataatatc ttaaattcct atcttacagc atacaatgga    180

agccatcatc tgtatgatag gatgagtttt ttatgtttgt cttctcaaaa tacactgaat     240

ggagcatgcc caagcagtga tgcccctggc actgctacaa ttgatggcga aacaaatata     300

acattacaat ttacggaaaa aagaagtcta attaaaagag aactgcaaat taaaggctat     360

aaacaatttt tgttcaaaaa tgctaattgc ccatctaaac tagcacttaa ctcatctcat     420

tttcaatgta atagagaaca agcttcaggt gctactttat cgttatacat accagctggt     480

gaattaaata aattaccttt tgggggggtc tggaatgccg ttctgaagct aaatgtaaaa     540

agacgatatg atacaaccta tgggacttac actataaaca tcacagttaa tttaactgat     600

aagggaaata ttcagatatg gttaccacag ttcaaaagta acgctcgtgt cgatcttaac     660

ttgcgtccaa ctggtggtgg tacatatatc ggaagaaatt ctgttgatat gtgcttttat     720

gatggatata gtactaacag cagctcttta gagataagat ttcaggatga taattctaaa     780

tctgatggaa aattttatct aaagaaaata aatgatgact ccaaagaact tgtatacact     840
```

```
ttgtcacttc tcctggcagg taaaaattta acaccaacaa atggacaggc attaaatatt    900

aacactgctt ctctggaaac aaactggaat agaattacag ctgtcaccat gccagaaatc    960

agtgttccgg tgttgtgttg gcctggacgt ttgcaattgg atgcaaaagt gaaaaatccc   1020

gaggctggac aatatatggg gaatattaaa attactttca caccaagtag tcaaacactc   1080

gacaataaac aagtagagaa aatattact gtaacagcta gtgttgatcc tgtgattgat   1140

cttttgcaac tcgagcacca ccaccaccac cactga                             1176


<210> SEQ ID NO 143
<211> LENGTH: 391
<212> TYPE: PRT
<213> ORGANISM: Escherichia coli

<400> SEQUENCE: 143

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320
```

-continued

```
Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Val Ile Asp Leu Leu Gln Leu
    370                 375                 380

Glu His His His His His His
385                 390
```